US009051380B2

(12) United States Patent
Hancock et al.

(10) Patent No.: US 9,051,380 B2
(45) Date of Patent: *Jun. 9, 2015

(54) MYB14 SEQUENCES AND USES THEREOF FOR FLAVONOID BIOSYNTHESIS

(75) Inventors: Kerry Ruth Hancock, Palmerston North (NZ); Margaret Greig, Palmerston North (NZ)

(73) Assignee: Grasslanz Technology Limited, Hamilton (NZ)

( * ) Notice: Subject to any disclaimer, the term of this patent is extended or adjusted under 35 U.S.C. 154(b) by 1069 days.

This patent is subject to a terminal disclaimer.

(21) Appl. No.: 12/996,117

(22) PCT Filed: Jun. 5, 2009

(86) PCT No.: PCT/NZ2009/000099
§ 371 (c)(1),
(2), (4) Date: Apr. 6, 2011

(87) PCT Pub. No.: WO2009/148336
PCT Pub. Date: Dec. 10, 2009

(65) Prior Publication Data
US 2011/0179528 A1   Jul. 21, 2011

Related U.S. Application Data

(60) Provisional application No. 61/059,691, filed on Jun. 6, 2008.

(30) Foreign Application Priority Data

Jun. 6, 2008 (NZ) ....................................... 568928

(51) Int. Cl.
| C12N 1/00 | (2006.01) |
| C12N 5/04 | (2006.01) |
| C12N 5/10 | (2006.01) |
| C07K 14/415 | (2006.01) |
| C12N 15/82 | (2006.01) |

(52) U.S. Cl.
CPC .......... *C07K 14/415* (2013.01); *C12N 15/8243* (2013.01)

(58) Field of Classification Search
USPC .......................................................... 800/278
See application file for complete search history.

(56) References Cited

U.S. PATENT DOCUMENTS

| 2006/0162006 | A9 | 7/2006 | Sherman et al. | |
| 2007/0192889 | A1* | 8/2007 | La Rosa et al. | ............... 800/278 |
| 2007/0283460 | A9 | 12/2007 | Liu et al. | |
| 2008/0148432 | A1 | 6/2008 | Abad | |
| 2010/0293669 | A2 | 11/2010 | Liu et al. | |

OTHER PUBLICATIONS

Kranz et al. (Towards functional characterisation of the members of the R2R3-MYB gene family from *Arabidopsis thaliana*, 16 Plant Journal No. 2, 263-276 (1998)).*

Terence A. Brown, Genomes Chapter 7 § 7.1.1; 7.2.1 (Oxford: Wiley-Liss) (2nd ed. 2002) available at http://www.ncbi.nlm.nih.gov/books/NBK21136/.*
Ogle et al., Plant Guide for white clover (Trifolium repens L.), Plants USDA, 1-3 (2009); available at http://plants.usda.gov/plantguide/pdf/pg_trre3.pdf.*
Bedon et al. (Apr. 23, 2007) NCBI Database Accession No. DQ399056.1, "Pinus taeda R2R3-MYB transcription factor MYB14 mRNA, complete cds," 1 p.
Hellens et al. (Jan. 24, 2006) NCBI Database Accession No. DQ074465.1, "Malus x domestica MYB14 mRNA, complete cds," 1 p.
Lin et al. (May 28, 2011) NCBI Database Accession No. NM_128674.3, "*Arabidopsis thaliana* myb domain protein 14 (MYB14) mRNA, complete cds," 2 pp.
Matus et al. (Oct. 1, 2008) NCBI Database Accession No. EU181424.1, "Vitis vinifera R2R3 Myb14 transcription factor (MYB14) mRNA, complete cds," 1 p.
Abrahams et al. (2003) "The Arabidopsis TDS4 gene encodes leucoanthocyanidin dioxygenase (LDOX) and is essential for proanthocyanidin synthesis and vacuole development," Plant Journal 35:624-636.
Abrahams et al. (2002) "Identification and Biochemical Characterization of Mutants in the Proanthocyanidin Pathway in Arabidopsis," Plant Physiology 130:561-576.
Aerts et al. (1999) "Polyphenols and agriculture: beneficial effects of proanthocyanidins in forages," Agriculture, Ecosystems and Environment 75:1-12.
Baudry et al. (2004) "TT2, TT8, and TTG1 synergistically specify the expression of Banyuls and proanthocyanidin biosynthesis in *Arabidopsis thaliana*," Plant Journal 39:366-380.
Bingham, E.T. (1991) "Registration of Alfalfa Hybrid Regen-Sy Germplasm for Tissue Culture and Transformation Research," Crop Science 31:1098.
Blaydes, D.F. (1966) "Interaction of Kinetin and Various Inhibitors in the Growth of Soybean Tissue," Physiologia Plantarum19:748-753.
Blaxter et al. (1965) "Prediction of the amount of methane produced by ruminants," British Journal of Nutrition 19:511-522.
Bogs et al. (2005) "Proanthocyanidin Synthesis and Expression of Genes Encoding Leucoanthocyanidin Reductase and Anthocyanidin Reductase in Developing Grape Berries and Grapevine Leaves," Plant Physiology 139:652-663.
Bogs et al. (2007) "The Grapevine Transcription Factor VvMYBPA1 Regulates Proanthocyanidin Synthesis During Fruit Development," Plant Physiology 143:1347-1361.

(Continued)

*Primary Examiner* — Ashwin Mehta
*Assistant Examiner* — Rebecca Coobs
(74) *Attorney, Agent, or Firm* — Lathrop & Gage LLP

(57) ABSTRACT

The invention provides a novel MYB class transcription factor gene (nucleic acid sequences, protein sequences, and variants and fragments thereof) designated MYB14 by the applicants, that is useful for manipulating the production of flavonoids, specifically condensed tannins, in plants. The invention provides the isolated nucleic acid molecules encoding proteins with at least 70% identity to any one of MYB14 polypeptide sequences of SEQ ID NO: 14 and 46 to 54. The invention also provides, constructs, vectors, host cells, plant cells and plants genetically modified to contain the polynucleotide. The invention also provides methods for producing plants with altered flavonoid, specifically condensed tannin production, making use of the MYB14 nucleic acid molecules of the invention.

13 Claims, 57 Drawing Sheets

(56) References Cited

OTHER PUBLICATIONS

Broun P. (2005) "Transcriptional control of flavonoid biosynthesis: a complex network of conserved regulators involved in multiple aspects of differentiation in *Arabidopsis*," Current Opinion in Plant Biology 8:272-279.

Burggraaf et al. (2006) "Morphology and agronomic performance of white clover with increased flowering and condensed tannin concentration," New Zealand Journal of Agricultural Research 49:147-155.

Caradus et al. (2000) "Improved Grazing Value of Pasture Cultivars for Temperate Environments," Animal Production for a Consuming World, A Supplement of the Asian-Australasian Journal of Animal Sciences 13:5-8.

Christey et al. (1997) "Regeneration of transgenic vegetable brassicas (*Brassica oleracea* and *B. campestris*) via Ri-mediated transformation," Plant Cell Reports 16:587-593.

Christey et al. (2006) "Cabbage White Butterfly and Diamond-Back Moth Resistant *Brassica oleracea* Plants Transgenic for *CRY*1BA1 or *CRY*1Ca5," Acta Horticulturae 706:247-253.

Clark, H. (Jun. 2001) "Ruminant Methane Emissions: A Review of the Methodology Used for National Inventory Estimations," A Client Report Prepared for the Ministry of Agriculture and Forestry, New Zealand.

Chorev et al. (1993) "Dozen Years of Retro-Inverso Peptidomimetics," Acc. Chem. Res. 26:266-273.

DairyInsight: Strategic Framework for New Zealand's Future Dairy Farming and Industry, 2005-2015.

Damiani et al. (1999) "The maize transcription factor Sn alters proanthocyanidin synthesis in transgenic *Lotus corniculatus* plants," Australian Journal of Plant Physiology 26:159-169.

Davies et al. (2003) "Transcriptional regulation of secondary metabolism," Functional Plant Biology 30:913-925.

De Majnik et al. (2000) "Anthocyanin regulatory gene expression in transgenic white clover can result in an altered pattern of pigmentation," Australian Journal of Plant Physiology 27:659-667.

Debeaujon et al. (2003) "Proanthocyanidin-Accumulating Cells in Arabidopsis Testa: Regulation of Differentiation and Role in Seed Development," Plant Cell 15:2514-2531.

Debeaujon et al. (2001) "The *Transparent TESTA12* Gene of Arabidopsis Encodes a Multidrug Secondary Transporter-Like Protein Required for Flavonoid Sequestration in Vacuoles of the Seed Coat Endothelium," Plant Cell 13:853-871.

Ditta, et al. (1980) "Broad host range DNA cloning system for Gram-negative bacteria: Construction of a gene bank of *Rhizobium meliloti*," PNAS 77:7347-7351.

Dixon et al. (1996) "Metabolic engineering: prospects for crop improvement through the genetic manipulation of phenylpropanoid biosynthesis and defense responses—a review," Gene 179:61-71.

Dixon et al. (2005) "Proanthocyanidins—a final frontier in flavonoid research?," New Phytologist 165:9-28.

Douglas et al. (1995) "Liveweight gain and wool production of sheep grazing *Lotus corniculatus* and lucerne (*Medicago sativa*)," New Zealand Journal of Agricultural Research 38:95-104.

Ellison et al. (2006) "Molecular phylogenetics of the clover genus (*Trifolium*-Leguminosae)," Molecular Phylogenetics and Evolution 39:688-705.

Fay et al. (1993) "Condensed tannins in *Trifolium* species and their significance for taxonomiy and plant breeding," Genetic Resources and Crop Evolution 40:7-13.

Freidinger et al. (1982) "Protected Lactam-Bridged Dipeptides for Use as Conformational Constraints in Peptides," J Org Chem 47:104-109.

Hogan Jr., J.C. (1997) "Combinatorial chemistry in drug discovery," Nature Biotechnology 15:328-330.

Gleave A.P. (1992) "A versatile binary vector system with a T-DNA organisational structure conducive to efficient integration of cloned DNA into the plant genome," Plant Molecular Biology 20:1203-1207.

Helliwell et al. (2003) "Constructs and methods for high-throughput gene silencing in plants," Methods 30:289-295.

Horsch et al. (1985) "A Simple and General Method for Transferring Genes into Plants," Science 227:1229-1231.

Jones et al. (1976) "The Condensed Tannins of Pasture Legume Species," Phytochemistry 15:1407-1409.

Kingston-Smith et al. (2003) "Strategies of plant breeding for improved rumen function," Annals of Applied Biology 142:13-24.

Li et al. (1996) "The DMACA-HCl Protocol and the Threshold Proanthocyanidin Content for Bloat Safety in Forage Legumes," J Sci Food Agric 70:89-101.

Linsmaier, et al. (1965) "Organic Growth Factor Requirements of Tobacco Tissue Cultures," Physiologia Plantarum 18:100-127.

McKenna, P.B (1994) "The occurrence of anthelmintic-resistant sheep nematodes in the southern North Island of New Zealand," NZ Veterinary Journal 42:151-152.

McMahon et al. (2000) "A review of the effects of forage condensed tannins on ruminal fermentation and bloat in grazing cattle," Canadian Journal of Plant Science 80:469-485.

Marten et al. (1987) "Performance and Photosensitization of Cattle Related to Forage Quality of Four Legumes," Crop Science 27:138-145.

Mehrtens et al. (2005) "The Arabidopsis Transcription Factor MYB12 is a Flavonol-Specific Regulator of Phenylpropanoid Biosynthesis," Physiologia Plantarum 138:1083-1096.

Miyake et al. (2003) "Isolation of a subfamily of genes for R2R3-MYB transcription factors showing up-regulated expression under nitrogen nutrient-limited conditions," Plant Molecular Biology 53:237-245.

Molan et al. (2002) "Effect of condensed tannins on egg hatching and larval development of *Trichostrongylus colobriformis* in vitro," Veterinary Record 150:65-69.

Murashige et al. (1962) "A Revised Medium for Rapid Growth and Bio Assays with Tobacco Tissue Cultures," Physiologia Plantarum 15(3):473-497.

Nagai et al. (1985) "Synthesis of a Bicyclic Dipeptide with the Shape of β-Turn Central Part," Tetrahedron Lett 26(5):647-650.

Nesi et al. (2000) "The *TT8* Gene Encodes a Basic Helix-Loop-Helix Domain Protein Required for Expression of *DFR* and *BAN* Genes in Arabidopsis Siliques," Plant Cell 12:1863-1878.

Nesi et al. (2002) "The *Transparent TESTA16* Locus Encodes the Arabidopsis Bsister MADS Domain Protein and Is Required for Proper Development and Pigmentation of the Seed Coat," Plant Cell 14:2463-2479.

Nesi et al. (2001) "The Arabidopsis *TT2* Gene Encodes an R2R3 MYB Domain Protein That Acts as a Key Determinant for Proanthocyanidin Accumulation in Developing Seed," Plant Cell 13:2099-2114.

Niezen et al. (1995) "Growth and Gastrointestinal Nematode Parasitism in Lambs Grazing Either lucerne (*Medicago sativa*) or sulla (*Hedysarum coronarium*) Which Contains Condensed Tannins," J. Agric. Sci. (Cam) 125:281-289.

Niezen et al. (1993) "Internal Parasites and Lamb Production—a Role for Plants Containing Condensed Tannins?" Proc. NZL. Soc. Anim. Prod. 53:235-238.

Olson et al. (1993) "Concepts and Progress in the Development of Peptide Mimetics," J. Med. Chem. 36(21):3039-3049.

Pang et al. (2007) "Early Steps in Proanthocyanidin Biosynthesis in the Model Legume *Medicago truncatula*," Plant Physiology 145(3):601-615.

Pfeiffer et al. (2006) "Biosynthesis of Flavan 3-ols by Leucoanthocyanidin 4-Reductases and Anthocyanidin Reductases in Leaves of Grape (*Vitis vinifera* L.), apple (*Malus x domestica* Borkh.) and Other Crops," Plant Physiology and Biochemistry 44:323-334.

Puchala et al. (2005) "The Effect of a Condensed Tannin-Containing Forage on Methane Emission by Goats," Journal of Animal Science 83:182-186.

Ray et al. (2003) "Expression of Anthocyanins and Proanthocyanidins After Transformation of Alfalfa with Maize *Lc*," Plant Physiology 132:1448-1463.

Robbins et al. (2003) "*Sn*, a Maize bHLH Gene, Modulates Anthocyanin and Condensed Tannin Pathways in *Lotus corniculatus*," Journal of Experimental Botany 54(381):239-248.

Rumbaugh, M.D. (1985) "Breeding Bloat-Safe Cultivars of Bloat-Causing Legumes," In: Barnes et al. (Eds.), Forage Legumes for

(56) References Cited

OTHER PUBLICATIONS

Energy-Efficient Animal Production. USDA, Washington. Proc. Bilateral Workshop, Palmerston North, NZ, Apr. 1984, pp. 238-245.

Samac, D.A. (1995) "Strain Specificity in Transformation of Alfalfa by *Agrobacterium tumefaciens*," Plant Cell, Tissue and Organ Culture 43:271-277.

Sanger et al. (1977) "DNA sequencing with Chain-Terminating Inhibitors," PNAS 74(12):5463-5467.

Schenk et al. (1972) "Medium and Techniques for Induction and Growth of Monocotyledonous and Dicotyledonous Plant Cell Cultures," Canadian Journal of Botany 50:199-204.

Sharma et al. (2005) "Metabolic Engineering of Proanthocyanidins by Ectopic Expression of Transcription Factors in *Arabidopsis thaliana*," Plant Journal 44:62-75.

Smythe et al. (1994) "Design and Synthesis of a Biologically Active Antibody Mimic Based on an Antibody-Antigen Crystal Structure," J. Am. Chem. Soc. 116:2725-2733.

Stracke et al. (2001) "The *R2R3-MYB* Gene Family in *Arabidopsis thaliana*," Current Opinion in Plant Biology 4:447-456.

Sykes et al. (2001) "Interaction Between Nutrition and Gastrointestinal Parasitism in Sheep," New Zealand Veterinary Journal. 49(6):222-226.

Tanner et al. (1994) "Proanthocyanidins Inhibit Hydrolysis of Leaf Proteins by Rumen Microflora In Vitro," British Journal of Nutrition 71:947-958.

Tanner et al. (2003) "Proanthocyanidin Biosynthesis in Plants— Purification of legume leucoanthocyanidin reductase and molecular cloning of its cDNA," Journal of Biological Chemistry 278(34):31647-31656.

Voisey et al. (1994) "*Agrobacterium*-Mediated Transformation of White Clover Using Direct Shoot Organogenesis," Plant Cell Reports 13:309-314.

Waghorn et al. (1998) "Forages with Condensed Tannins—Their Management and Nutritive Value for Ruminants," Proceedings of the New Zealand Grasslands Association 60:89-98.

Walker et al. (1999) "The *Transparent Testa GLABRA1* Locus, Which Regulates Trichome Differentiation and Anthocyanin Biosynthesis in Arabidopsis, Encodes a WD40 Repeat Protein," Plant Cell 11:1337-1349.

Walter et al. (1998) "Stable Transformation and Regeneration of Transgenic Plants of *Pinus radiata* D. Don," Plant Cell Reports 17:460-468.

Wei et al. (2007) "Molecular Cloning of *Brassica napus Transparent Testa 2* Gene Family Encoding Potential MYB Regulatory Proteins of Proanthocyanidin Biosynthesis," Molecular Biology Reports 34:105-120.

Winkel-Shirley, B. (2001) "Flavonoid Biosynthesis. A Colorful Model for Genetics, Biochemistry, Cell Biology, and Biotechnology," Plant Physiology 126:485-493.

Winkel-Shirley, B. (2002) "A mutational Approach to Dissection of Flavonoid Biosynthesis in *Arabidopsis*," In Recent Advances in Phytochemistry: Proceedings of the Annual Meeting of the Phytochemical Society of North America, vol. 36, J.T. Romeo, ed. (New York: Elsevier), pp. 95-110.

Woodfield et al. (1998) "Floral and Foliar Tannin Content in White Clover," Proceedings of the 15th Trifolium Conference, p. 19.

Woodward et al. (2001) "Early Indications that Feeding *Lotus* Will Reduce Methane Emission from Ruminants," Proceedings New Zealand Society of Animal Production 61:23-26.

Xie et al. (2003) "Role of Anthocyanidin Reductase, Encoded by *Banyuls* in Plant Flavonoid Biosynthesis," Science 299:396-399.

Xie et al. (2004) "Anthocyanidin Reductases from *Medicago truncatula* and *Arabidopsis thaliana*," Archives of Biochemistry and Biophysics 422:91-102.

Xie et al. (2006) "Metabolic Engineering of Proanthocyanidins Through Co-Expression of Anthocyanidin Reductase and the PAP1 MYB Transcription Factor," Plant Journal 45:895-907.

Yoshida et al. (2008) "Functional Differentiation of *Lotus japonicus* TT2s, R2R3 MYB Transcription Factors Comprising a Multigene Family," Plant Cell Physiology 49(2):157-169.

\* cited by examiner gaattcgcccttaagcagtggtatcaacgcagagtacgcgggggaagttatttaattttatctacatcaaacacttcaagagg
ttggaatacaagacagactaattaagaataacatcaatggggagaagcccttgttgtgcaaaggaaggcttgaatagaggt
gcttggacaactcaagaagacaaaatcctcactgaatacattaagctccatggtgaaggaaaatggagaaaccttccaaa
aagagcagatttaaaaagatgtggaaaaagttgtagactagatggttgaattatctaagaccagatattaagcgaggtaata
tatccccggatgaagaagaacttattatccgacttcacaaactactcggaaacagatggtctctaatagccggaagacttcc
agggcgaacagacaatgaaataaagaactactggaacacaaatttaggaaaaaaggttaaggatcttaatcaacaaaaca
ccaacaattcttctcctactaaactttctgctcaaccaaaaaatgcaaagatcaaacagaaacagatcaatcctaagccaat
gaagccaaactcaaatgttgtccgtacaaaagctaccaagtgttctaaggtattgttcataaactcactccccaactcaccaa
tgcatgatttgcagaacaaagctgaggcagagacaacaacaaagccatcaatgctggttgatggtgtggctagtgattcaa
tgagtaacaacgaaatggaacacggttatggattttttgtcattttgcgatgaagagaaagaactatccgcagatttgctagaa
gattttaacatcgcggatgatatttgcttatctgaacttttgaactctgatttctcaaatgcgtgcaatttcgattacaatgatctatt
gtcaccttgttcggaccaaactcaaatgttctctgat*gatgagattctcaagaattggaca*caatgtaactttgctgatgagac
aaatgtgtccaacaaccttcattcttttgcttcctttcttgaatccagtgaggaagtactaggagaatgataataaaaattcatttt
ccaataaaattaactactctaggtttttttttttttttttaaatttcaatttcatgttagggtggtttaataaataaatatattctatggttta
atattgcaaaaaaaaaaaaaaaaaaaaaaaaaagtactctgcgttgataccactgcttaagggcgaattcc (SEQ ID NO:13)

FIGURE 2A

MGRSPCCAKEGLNRGAWTTQEDKILTEYIKLHGEGKWRNLPKRAGLKRCGKSCRLRWLNYL
RPDIKRGNISSDEEELIIRLHKLLGNRWSLIAGRLPGRTDNEIKNYWNTNLGKKVKDLNQQNTN
NSSPTKLSAQPKNAKIKQKQINPKPMKPNSN*VVRTKATK*CSKVLFINSLPNSPMHDLQNKAEA
ETTTKPSMLVDGVASDSMSNNEMEHGYGFLSFCDEEKELSADLLEDFNIADDICLSELLNSDF
SNACNFDYNDLLSPCSDQTQMFSD*DEILKNWT*QCNFADETNVSNNLHSFASFLESSEEVLGE*
(SEQ ID NO 14)

FIGURE 2B

```
              101                                              150
LjTT2a    (1)  ------------------ .GG.AA.C........A-------A
MYB14TaF  (101) CTAATTAAGAATAACATCA..GGA.AA.C......GA-------A
MYB92Gmax (1)  -----------GCAAAAA....A.GCT.........C-------
DcMYB3    (1)  -----------GAAGA..G.AA.C.........A------A
GHMYB10   (1)  -----------------...........T------A
BnTT2-3   (43) CACAACAACAAGAGAGATC...AG.AA..AGAAAG.AC.AAGGTGAAC.
GHMYB36   (1)  -----------------..G.AA.T.A...C..C------A 151                                              200
LjTT2a    (26) A.CGC.T.....C.GT.CTG.CA..A..GG.A..C...CC.C
MYB14TaF  (145) A..AC.C....AT.AGT.C.GC.AA....A......CCTC
MYB92Gmax (33) AA.TG.G..CA..AAG.TCC.ATGGA.TC...CA.CATGC.TTGC.
DcMYB3    (31) AA.TT.GCT...A.AA.GA..CCTG.CCCA..GCT.GGA.....TTCTC
GHMYB10   (26) A...AC.CC.T...A....A..T.ACT...TTCA..A...TT.
BnTT2-3   (93) AA.GGAG.TA.A...A.CG.C..CA.CC.A..A.CA.CA..G.TCCT.
GHMYB36   (26) A..AC.AC.G.A..AA..A..ACT.T..T..A.A..ACT.

201                                              250
LjTT2a    (76) CG...C..G...TC.TC...CCA.GAA....G.A...TCTC.
MYB14TaF  (195) ..T..A.C.T.AGC.CCA...G.AAGTA..T.GA.....TT.CA.A
MYB92Gmax (83) .CA.G...C..AGCTC..A.A..GCC.G..GGA.TCA.TA.C
DcMYB3    (81) ..T..TTC....TC..T..C....GAAG.TGG.TGGA.A...T.TCCC.A
GHMYB10   (76) AA..T....CA.AG.ACAC..AAG.TCGT..GA....T.TCCC..A
BnTT2-3   (143) AA..C....CATGT.CC.CGC.AAG.A..GA.GC.CAC.CC.A.A
GHMYB36   (76) G..TCA.....TG.TC....A..CA...C.A.....CCC..A 251                                              300
LjTT2a    (126) ......T....G..AC.T....CAA.GCCT............
MYB14TaF  (245) .....C.A..TA.A..GCT.GAA.....TG..........GA
MYB92Gmax (133) ..AA...G.GC.TCT....GAA.AAG..TG.AG..TTG...GGA.A
DcMYB3    (131) .....C..G..A...GCGGAA.GA.TGCAG.GTGA...GC.GA
GHMYB10   (126) .A..T..CC.T.....A..GAA.A.TG.AGG..TCGT.G...A
BnTT2-3   (193) CCA.A.CT.C.C..A..G.CA.A.GCTGCA..G.C.G..GAAC.A
GHMYB36   (126) G.A.....G.A.....A...CAA.AG.GCA.G....G.C.A 301                                              350
LjTT2a    (176) .T...AA.AC....CAAA..C.ATA..CAGA.A.A..A
MYB14TaF  (295) .....AA.GA....TAA.CG.T.A.T...CG.GG...GAA
MYB92Gmax (183) AC.A...AAG.C..CACAA..A..G.CA.A.A.AG.AC.A.GAT
DcMYB3    (181) A.TA.T....AG.CG..A.CA.AA..GC.AA.A.T.GA..G.A.GA
GHMYB10   (176) A..A.T....AG.CT..A..CAAA.....TAA.A..GA..GAC.ACGA
BnTT2-3   (243) ACTACTT..AG.CC..GGCA.AA..CGC.GGAAAA..C.AT....GA.GA
GHMYB36   (176) G.....T...GA....TAA...GCA..CC.T.GA 351                                              400
LjTT2a    (226) .AG...ATCA.............G.C..AA...G.....CT.A.
MYB14TaF  (345) .AC..ATTAT...TT..AC.TA.TCG.AA.AG.ATGGT.CT.AT
MYB92Gmax (233) .ATC.TATAA.GA..ATGC.ATTCA.TTTGC.AA..GTGGT.CCTCA.
DcMYB3    (231) AC.TCATCATT.T.TTC.AA.CCTT.CC.GTAATAGCTGG.C..BA.T
GHMYB10   (226) .AGC.TATCAT.AA..TCC..AA.CCT.GG.AA..GT.GGT....GA.
BnTT2-3   (293) .AAC.TATAA..A.CC.AT.GT..T.CC.TCA.AA.G.TGGT.GGA
GHMYB36   (226) .AACTCATTATAA.A.TCCAT.AT.TT.T.T.CAA.AC.TGGT.C.AAT 401                                              450
LjTT2a    (276) A.G..GAAC..T...C.AA.AAC.AG.CAATGAG.TAA.AA.CT.GGA
MYB14TaF  (395) A.C..CG.AGA.A..CC...G.A.A..AG.AATGA.AT.AA.AA.AC.GGA
MYB92Gmax (283) A..AG...G..T.ACT..A.A..A..AGCAATGAG.AT.AA.AA.AC.GGA
DcMYB3    (281) A.C..GAA..CC.TG.C.GAACAG.GAATGA.ACAACAA.ACT.GGA
GHMYB10   (276) A.C..GG.AG....G.GAA.AA.AGACAATGA.AT.AA.AAT.ACTGGA
BnTT2-3   (343) A...CGGAG.......GA.A..A.GAACAG.CAATGAA.AT.AA.AA.CACTGGA
GHMYB36   (276) A..........ACC.GG..AA.AACAG.CAATGAA.AT.CAA.AA.ACTGGA
```

```
         801                                     850
LjTT2a    (647)  ░░A░G-----░C░GG-░░CTTTC░░T░░░░CC░TGT░---░---░T░
MYB14TaF  (745)  A░░A░TGGA░CACG-░░ATGG░T░T░TG░C░TTT░CG---░TGA░░
MYB92Gmax (659)  ░AAG░TCAA░C░G-░AGTG░░GT░G░A░░TG░░GA░GA░A░T░
DcMYB3    (661)  ░T░ATTTCTC░C░TT░░AAAC░C░GAT░░T░ATCACC░GG░TT░C░░C
GHMYB10   (606)  ░░CG░T---A░T░C------AG░░CC░GA░░AA░G-----░C░░C
BnTT2-3   (702)  ░░GT░░------T░░CTC░GTTTC░░C░░CGAG░TGCT░░-----G-░
GHMYB36   (640)  ░ATG░░C-----T░░T--------GA░░░CAC░CG░░░GT░░GA░T-T░

851                                     900
LjTT2a    (688)  ░A░░AC░---C░░A░G░░░░░░░░C░T░G░T░░C░A░░T░G-----T░░A
MYB14TaF  (792)  ░AA░AC░---A░░░░A░░░░░C░AGAA░░T░TAA░░C░CGGAT░
MYB92Gmax (708)  ░T░TTT░GGC░T░TCAG░GA░GA░CA░░C░░A░T░░AC░TCTC░░░
DcMYB3    (711)  ░T░░GAGCGCGT░░CTTG░░CG░░G░C░GAGAA░C░TATAATGC░
GHMYB10   (642)  C-░ATCA░ATA░░AT░G░░TACAT░░░C░CAA░░G░G----░░G
BnTT2-3   (741)  ░TTATGT░░---░░G░░░---░CT░TC░░TC░GG░TA░░CTT░░----░
GHMYB36   (679)  GA░A░TCCTATG░A░░A░CAC░TTC░G░░GG░GA░G░AAT░CTTA░░-G 901                                     950
LjTT2a    (733)  ░░T░C░░G---C░░░AA░-░░A░C░AC░░-░░T---░T-----T░░TAT░
MYB14TaF  (840)  ░░░T░C░░---░░AC-░░░░AC░T-░░A░T---░C-----T░░AAT░
MYB92Gmax (758)  ░░GAA░GC--CACTCT░-A░░TCCCA░░░A░CA-░░-----G░░ACCT
DcMYB3    (761)  ░CTG░AGG░GT░░░░GAA-░GCA░░GGAAC-C░░GTC░░-----GTTTCTA
GHMYB10   (688)  T░░T░T░░░-░░G░░TC-░░░░AT░░C-░░TTC░CGATGT░AAC░
BnTT2-3   (782)  C░░AATAG░CC░TTC░C░-░C░░TCT░░A░AGAT░░---TCTCTGG░
GHMYB36   (728)  ░░░G░TC░░CA░G░C░T░G░C░░░░TGA░░--░░GG-░░-----C░░CTGA 951                                    1000
LjTT2a    (773)  TG░░░G░C░TCAGCT░C░A-------------░░A░-TCA░GAG░░░CTAATG
MYB14TaF  (880)  CG░░░C░░░TCGATT░C░A░GATCT░░░░░░░CT░G░TCG░░CCAAA░T
MYB92Gmax (799)  ░CA░C░░G░ATGA░G░A░░------░░░TC░AGCTCT░GAAC░░GGAC░-
DcMYB3    (805)  ░C░C░░░CT░TATTTT░CCTC---░░A░AGAC░G░TTA░TGGGTGAT
GHMYB10   (734)  ░GCT░A░░ACAGCA░TGG░TTTGAT░C░░A░CC░CACCG░░CAGC░T
BnTT2-3   (828)  ░C░T░░░░G░TAGACCCT------░░C░AAA--░C░TCAT░░ATTA░G
GHMYB36   (771)  TT░░G░░CA░TGGCCTTT░TGC---░░A░░-----░GAT░ATGGC░A 1001                                   1050
LjTT2a    (811)  C---░TTTT░CCGAGA░░AC░CT░GTCC░░-----GCA░░░A-░░░CTC
MYB14TaF  (930)  CAAA░░TT░CTGATG░TG░G░T░CTCA░AATTGGA░C░A░░ACT░
MYB92Gmax (843)  ---A░░GC░AATTCGA░░TG░░T░CATT░--------░░A░C░TTAT░
DcMYB3    (852)  TGGT░░GC░░AATATGTGA░░C░GGGA░TG-----T░C░T░T░░TG░
GHMYB10   (784)  CCTA░░GAT░TCTCCG░░C░A-░GCTA░A---------░░G░GA░GGC
BnTT2-3   (870)  TC-TACCT░░GTACGA░░A░░G░ATAT░TTTATATT░T░TT░░A░GC░
GHMYB36   (814)  TGA--816---------------------------------------

1051                                   1100
LjTT2a    (853)  G░-TG░░GAA░░A░░░T░GGTAA░TA░------░TG░░TT----------
MYB14TaF  (980)  T░CTG░░GAG░░A░░C░GTCCA░CA░CCTTCA░TC░░TTGCTTCCTT░C
MYB92Gmax (883)  A░---░░TAA░AG░░A░CAACA░AG░T-----░░TG░CAGTTCA---░G
DcMYB3    (897)  T░TTC░░TTT░░TT░AC░TCCGGAA░TAAAGA░GCA░GTATCATAGT░C
GHMYB10   (825)  C░CCGCCTCC░░TC░CTGCTGTC░CC░AAGTGCGGC░░CCAATC-----░C
BnTT2-3   (919)  TCTAAT░ACA░GT░░A░CT-----938------------------------
GHMYB36   (817)  ----------------------------------------------------

1101                                   1150
LjTT2a    (886)  --------░A░░AGG░GA----░G░░T----░░G░░TGCT░░-----912
MYB14TaF  (1030) TTGAATCC░░G░░AGG░AG░░ACT░G░░G---░░GA░AATA░░AATTCATT
MYB92Gmax (922)  AAGATCAC░░T░CTT░CA░░----░TA░░A----CT░T░TGAT░GATCA░ATG
DcMYB3    (947)  AA-----AT░A░░ACT░CT░CTG░T░TGTTG░░T░░TGTA░AAAAAAAA
GHMYB10   (871)  CAGT----CCT░░CCTCCA░TTATT░░A---░░G░AATTG░░TGA---909
BnTT2-3   (939)  ----------------------------------------------------
GHMYB36   (817)  ----------------------------------------------------
```

FIGURE 7 cont.

```
                1151                                              1200
    LjTT2a (913) --------------------------------------------------
  MYB14TaF (1077) TTCCAATAAAATTAACTACTCTAGGTTTTTTTTTTTTTTTTTAATTTCA
 MYB92Gmax (966) TAAATATATCTGTAAATGATCTCTGAGTTATGAGATCTTTTTTGTCTTTA
    DcMYB3 (993) AAAAAAAA--1000------------------------------------
   GHMYB10 (910) --------------------------------------------------
    BnTT2-3 (939) --------------------------------------------------
   GHMYB36 (817) --------------------------------------------------

1201                                              1250
    LjTT2a (913) --------------------------------------------------
  MYB14TaF (1127) ATTTCATGTTAGGGTGGTTTAATAAATAAATATATTCTATGGTTTAATAT
 MYB92Gmax (1016) ATAAATATCGCCATCTAACTCAAAAAAAAAAAAA----1049
    DcMYB3 (1001) --------------------------------------------------
   GHMYB10 (910) --------------------------------------------------
    BnTT2-3 (939) --------------------------------------------------
   GHMYB36 (817) --------------------------------------------------

1251                                              1300
    LjTT2a (913) ---(SEQ ID NO:70)---------------------------------
  MYB14TaF (1177) TGCAAAAAAAAAAAAAAAAAAAAAAAAAAGTACTCTGCGTTGATACCACT
 MYB92Gmax (1050) ---(SEQ ID NO:72)---------------------------------
    DcMYB3 (1001) ---(SEQ ID NO:73)---------------------------------
   GHMYB10 (910) ---(SEQ ID NO:74)---------------------------------
    BnTT2-3 (939) ---(SEQ ID NO:75)---------------------------------
   GHMYB36 (817) ---(SEQ ID NO:76)---------------------------------

1301       1317
    LjTT2a (913) ---------------------
  MYB14TaF (1227) GCTTAAGGGCGAATTCC (SEQ ID NO:71)
   GHMYB36 (817) ---------------------
```

FIGURE 7 cont.

```
                    1                                                50
    At TT2    (1)  -M?RATTSVR??E??????TDHE??R?TT???ST?PNQ????
    BnTT2-1   (1)  MMR?RESSKVK?E??????WTDQE??K??MF????WST?PNQ????
      Zm P1   (1)  -M??R---A?????????KEDDTLAA??KA?G????E??PQ????
    MYB10Gh   (1)  -M?????????????T??LE??K?T?KV?L????N?????????
   MYB14FTa   (1)  -M?????????????T??QE????T?KL?????N??????????
   VvMYBPA1   (1)  -M??????V???RG???REDT??TKY?QAKG??HN?S??????L
     LjTT2a   (1)  -M??????????Q??????QE?EQ??R??HL?G?????PQS????
  MYB185Gmax  (1)  -M??????KV??RG?WTPREDA??TKY?QT?G??N?S???????L
  MYB11Malus  (1)  -M????P-C?SKD????T??ME????T??GN????????N????

51                                              100
    At TT2   (50)  ?C?KS??PLRWKN?L?P?GIKRGNI??S??L??????NIL????WSLIA?PLE
    BnTT2-1  (51)  ?C?KS??PLRWKN?L?P?GIKRGNI??S??L??????NIL????WSLIA?PLE
      Zm P1  (48)  ?G?KS??PLRW?N?L?PNIKRGNI?Y??L??????????W?LIA?PLE
    MYB10Gh  (48)  ?C?KS??PLRW?N?L?P?IKRGNI?P??L??????????????LIA?PLE
   MYB14FTa  (48)  ?C?KS??PLRW?N?L?P?IKRGNI??S??L??????NIL????WSLIA?PLE
   VvMYBPA1  (48)  ?G?KS??PLRW?N?L?P?IKRGNI?P??L??K?I??????????IA?PLE
     LjTT2a  (48)  ?G?KS??PLRW?N?L?P?IKRGNI??R??L??????????W?LIA?PLE
  MYB185Gmax (48)  ?G?KS??PLRW?N?L?P?IKRGNI?P??L??S?L??????W?LIA?PLE
  MYB11Malus (49)  ?G?KS??PLRW?N?L?P?IKRGNI?R??L?????????????????????

101                                              150
    At TT2  (100)  ??T????????????R???PKTQTK--------------QP?RI?H?
    BnTT2-1 (101)  ??T????????????R???PKSQTN--------------QQ?G?H?
      Zm P1  (98)  ?????????T?G??AGAAGAS-----------------RVVFAPD?
    MYB10Gh  (98)  ?????????????GS??SDRQKSP----------AAPSKKPEAAR?GTA
   MYB14FTa  (98)  ?????????????G??KDLNQQNTNNSSPTKLSAQPKNAKI?Q??IN
   VvMYBPA1  (98)  ?????????????GS??RSQGTDPNTH-------KKMTEPPEP?R?M?
     LjTT2a  (98)  ?????????????C??QDGVDVGDSKTPSSQEKNNHHDQKA?PQSV?
  MYB185Gmax (98)  ?????????????S??RNQGTDP----------KTHDKLTEAPE??KG
  MYB11Malus (99)  ?????????T?G??QVEGRSC----------SDGNRRPTQEKP?F?

151                                              200
    At TT2  (133)  TNN------E?NV????I?C?T?LFSDLSLQK-KS?T?P?PLKEQEM
    BnTT2-1 (134)  NNNN-----M?KV????I?P?A?TFQNQSS------IG?T?L?TVKENVI
      Zm P1 (131)  GSHA-----TPAA?GS?EM?GGQ?GAAPRADLGS----PG?AAV?WAPKAAR
    MYB10Gh (139)  GNGN-----T?GN?GSGS??T?HVV?TRATRCSKVFIN-PHHH?ONRHPKFSS
   MYB14FTa (148)  PKPM-----KPNS?????T?C??V?FINSLPNSP-MHDLQNKAEAETTT
   VvMYBPA1 (142)  RTRT-----N?GG?GSK??I?S?D??ENSNHKVHLPKP-VRVT?L?SMSRNNS
     LjTT2a (148)  PSVFSSSQPKNN??????S?C??V?LRDPLLCPPMQ?Q?DDFIAKLLE
  MYB185Gmax (139)  KKKNKQKNE?NK?GSE??LVYLPK?PIRVKALSSCIPRTD?TLT?NSNSATA
  MYB11Malus (140)  LSPKPSTNISCT?????S?C??V?LPHESQKFGYSTEQVVNAAPTLDQ
```

VI/VRTKAxR/KxSK (SEQ ID NO: 101) (New motif associated with MYB TFs that regulate CT pathways)

```
                   201                                              250
    At TT2  (177)  DQGGSS--------LMGDLEF?FDR?HSE?HFP?L--?DF?G?DCGN?TSI?S
    BnTT2-1 (177)  DHQAGSPS-----LLGDLKI?FDK?QSE?LFS?L--?DF?G?GCGN?MSL?S
      Zm P1 (174)  CTGGLFFHRDTPHAGETETPTPM?MAGGGGG?A-R?S?DCSSAASVSP?
    MYB10Gh (184)  TCSNHGDHREPKTMNELLLPIMSESENEGTT?H-?S?FTFD?N?G??C
   MYB14FTa (193)  KPSMLVDGVASDSMSNNEM?HGYGFLS?CDE?KE??A?L?ED?N?A?D?C
   VvMYBPA1 (187)  FESNTVSGGSGSSSGGNGESLPWPSFRDIRD?KV?GV?G?DF?IGD?QGQ
     LjTT2a (198)  EAEGEPLLSAVANDFTSGD?DGV?SFDPCGN?KE??T?L?LDLD?G?IC?
  MYB185Gmax (189)  STSEEK--------VQS-PEA?VKE?NMV?GVG?DADNG?IEIF?GEDH??
  MYB11Malus (190)  AVNNPM---------VGI?DPL?PMS?LDD?NNN?C?F?VD?K?D?NE?
```

FIGURE 8

```
                    251                                              300
   At TT2    (220)  SNE LG LVP-----AQGNL  N P  CHHRGD  W   FTC 259
  BnTT2-1    (222)  SDE LG YVSTDTSCLGNL  N P  CLQ----  C W FNC 260
    Zm P1    (223)  GSSQHDPCFSGDG-DGDWM DV ALASFLES-- D W CHI QLV-266
   MYB10Gh   (233)  SDL NS FCDVNELNYSNGFDSSPSP QPP DF  M  WT ASTHCC
   MYB14FTa  (243)  LSE LNSDFS-NACNFDYN  LSPC QTQ FS  L  WTQ NFADET
  VvMYBPA1   (237)  DLVASS PESQSKMPPTDNS D L  YLQ LE   TQVQLD AESLLI-287
    LjTT2a   (248)  PEF NS FSYVCDFSYNTH DLML  NTL QA DKYLGI TNL NNCFNE
 MYB185Gmax  (232)  NNTASY ECYSDVHTDDHGT E L  YLQ LN V KPI LD AQSLLV
 MYB11Malus  (230)  SDF NV FSVLYNNEGAGKAAAAAT DTSNKL HGPD  SSK  IIESEL
DExWRLxxT (SEQ ID NO: 102) (Motif of subgroup 5; Stracke et al., 2001)

301              323
   At TT2    (259)  -------------------------------(SEQ ID NO:77)
  BnTT2-1    (261)  -------------------------------(SEQ ID NO:78)
    Zm P1    (267)  -------------------------------(SEQ ID NO:79)
   MYB10Gh   (283)  HQSAASNLQSLPPFIENGIE----312--------(SEQ ID NO:80)
   MYB14FTa  (292)  NVSNNLHSFASFLESSEEVLGE---313------(SEQ ID NO:14)
  VvMYBPA1   (287)  ------------------------------- (SEQ ID NO:81)
    LjTT2a   (298)  EKDNGC---304----------------- (SEQ ID NO:82)
 MYB185Gmax  (282)  ------------------------------- (SEQ ID NO:83)
 MYB11Malus  (280)  DCWLVDN--286----------------- (SEQ ID NO:84)
```

FIGURE 8 cont.

```
                  1                                             50
MYB14FTa   (1)    MGRSPCCAKEGLNRGAWT   EDKILTEYIK HGEGKWRN PKRAGLKRCG
TaMYB14-2S (1)    MGRSPCCAKEGLNRGAWT   EDKILTEYIK HGEGKWRN PKRAGLKRCG
TrMYB14f   (1)    MGRSPCCAKEGLNRGAWTAH EDKILTEYIK HGEGKWRN PKRAGLKRCG
TrMYB14d   (1)    MGRSPCCAKEGLNRGAWTAH EDKILTEYIK HGEGKWRN PKRAGLKRCG
ToMYB14    (1)    MGRSPCCAKEGLNRGAWT   EDKILTEYIK HGEGKWRN PKRAGLKRCG
Taf11cDNA  (1)    MGRSPCCAKEGLNRGAWT   EDKILTEYIK HGEGKWRN PKRAGLKRCG
Consensus  (1)    MGRSPCCAKEGLNRGAWTTQ EDKILTEYIKLHGEGKWRNLPKRAGLKRCG 51                                            100
MYB14FTa   (51)   KSCRLRWLNYLRPDIKRGNISSDEEELIIRLHKLLGNRWSLIAGRLPGRT
TaMYB14-2S (51)   KSCRLRWLNYLRPDIKRGNISPDEEELIIRLHKLLGNRWSLIAGRLPGRT
TrMYB14f   (51)   KSCRLRWLNYLRPDIKRGNISSDEEELIIRLHKLLGNRWSLIAGRLPGRT
TrMYB14d   (51)   KSCRLRWLNYLRPDIKRGNISSDEEELIIRLHKLLGNRWSLIAGRLPGRT
ToMYB14    (51)   KSCRLRWLNYLRPDIKRGNISSDEEELIIRLHKLLGNRWSLIAGRLPGRT
Taf11cDNA  (51)   KSCRLRWLNYLRLDIKRGNISSDEEELIIRLHKLLGNRWSLIAGRLPGRT
Consensus  (51)   KSCRLRWLNYLRPDIKRGNISSDEEELIIRLHKLLGNRWSLIAGRLPGRT 101                                           150
MYB14FTa   (101)  DNEIKNYWNTNLGKKVKDLNQQNTNNSSPTKLSAQPKNAEIKQ   I
TaMYB14-2S (101)  DNEIKNYWNTNLGKKVKDLQQNTNTNSSPTKLSAQPKNAEIKQ   I
TrMYB14f   (101)  DNEIKNYWNTNLGKKVKDLQQNTNSSPTKPSAQPKNANIKQ QQ
TrMYB14d   (101)  DNEIKNYWNTNLGKKVKDLQQNTNSSPTKPSAQPKNANIKQ QQ
ToMYB14    (101)  DNEIKNYWNTNLGKKVKDLQQNTNKSSPTKLSAQPKNAEIKQ Q
Taf11cDNA  (101)  DNEIKNYWNTNLGKKVKDLQENTNSSPTKLSAQLKNAEIKQ
Consensus  (101)  DNEIKNYWNTNLGKKVKDLNQQNTNNSSPTKLSAQPKNAKIKQKQ INPK 151                                           200
MYB14FTa   (150)    PNSYVVRTKATKCSKVLFI  SL      HDLQNKAEAETK
TaMYB14-2S (147)  NP PNSYVVRTKATKCSKVLFI  S    P  DLQSKAEAETK ITKPSM
TrMYB14f   (151)    PNSYVVRTKATKCSKVLFI  S       HNLQNKAEAETK
TrMYB14d   (151)    PNSYVVRTKATKCSKVLFI  S       HNLQNKAEAETK
ToMYB14    (150)    PNSYVVRTKATKCSKVLFI  SL      HDLQNKAEAETK
Taf11cDNA  (150)    PNSYVVRTKATKCSKALFI   P      DLQNKAEAETK S  SM
Consensus  (151)  PMKPNSNVVRTKATKCSKVLFINSPPNSP MHDLQNKAEAETTTK 201                                           250
MYB14FTa   (194)  PLMLVDGVASDSMSNNEMEHGYGF SFCDEEKELSADLLEDFNIADDICL
TaMYB14-2S (197)  PSMLVDGVASDSMSNNEMECG    SFCDEEKELSADLLEDFNIADDICL
TrMYB14f   (192)  PLMLVNGVASDSMSNNEMERG    SFCDEEKELSADLLEDFNIADDICL
TrMYB14d   (192)  PLMLVNGVASDSMSNNEMERG    SFCDEEKELSADLLEDFNIADDICL
ToMYB14    (194)  PSMLVDGVASDSMSNNEMEHGYG  SFCDEEKELSADLLEDFNIADDICL
Taf11cDNA  (198)  PSMLVDGVASDSMSNNEMEHDGF  SFCDEEKELSADLLEDFNIADDICL
Consensus  (201)  PSMLVDGVASDSMSNNEMEHGNGFLSFCDEEKELSADLLEDFNIADDICL 251                                           300
MYB14FTa   (244)  SEFLNSDFSNAC   NDLLSPCSDQTQMFSDDEILKNWTQCNFADETN
TaMYB14-2S (247)  SEFLNFDFSNACDID NDLLSPCSDQTQMFSDDEILKNWTQCNFADETN
TrMYB14f   (242)  SEFLNSDFSNAC   DCNDLLSPCSDQTQMFSDDEILKNWTQCNFADETN
TrMYB14d   (242)  SEFLNSDFSNAC   DCNDLLSPCSDQTQMFSDDEILKNWTQCNFADETN
ToMYB14    (244)  SEFLNSDFSNAC   NDLLSPCSDQTQMFSDDEILKNWTQCNFADETN
Taf11cDNA  (248)  SEFMFDFSNAC    NDLLSPCSDQTQMFSDDEILKNSTQCNFADETNY
Consensus  (251)  SEFLNSDFSNACNFDYNDLLSPCSDQTQMFSDDEILKNWTQCNFADETNV
```

FIGURE 9

```
                         1                                               50
TRM4      (1)    --------------------------------------------------
TRM6      (1)    --------------------------------------------------
TRM3      (1)    --------------------------------------------------
TRM1      (1)    --------------------------------------------------
TRM5      (1)    --------------------------------------------------
TRM14     (1)    --------------------------------------------------
MYB14TaF  (1)    GAATTCGCCCTTAAGCAGTGGTATCAACGCAGAGTACGCGGGGGAAGTTA
TaM3      (1)    --------------------------------------------------
TaM4      (1)    --------------------------------------------------

51                                             100
TRM4      (1)    --------------------------------------------------
TRM6      (1)    --------------------------------------------------
TRM3      (1)    --------------------------------------------------
TRM1      (1)    --------------------------------------------------
TRM5      (1)    --------------------------------------------------
TRM14     (1)    --------------------------------------------------
MYB14TaF  (51)   TTTAATTTTATCTACATCAAACACTTCAAGAGGTTGGAATACAAGACAGA
TaM3      (1)    ------------------GAATTCGCCCTTAGGTTGGAATACAAGACAGA
TaM4      (1)    ------------------GAATTCGCCCTTAGGTTGGAATACAAGACAGA 101                                            150
TRM4      (1)    ---------GAATAACATCAATGGGAGAAGCCTTGTTGTGCAAAGGAA
TRM6      (1)    ---------GAATAACATCAATGGGAGAAGCCTTGTTGTGCAAAGGAA
TRM3      (1)    ---------GAATAACATCAATGGGAGAAGCCTTGTTGTGCAAAGGAA
TRM1      (1)    ---------GAATAACATCAATGGGAGAAGCCTTGTTGTGCAAAGGAA
TRM5      (1)    ---------GAATAACATCAATGGGAGAAGCCTTGTTGTGCAAAGGAA
TRM14     (1)    ---------GAATAACATCAATGGGAGAAGCCTTGTTGTGCAAAGGAA
MYB14TaF  (101)  CTAATTAAGAATAACATCA-ATGGGAGAAGCCTTGTTGTGCAAAGGAA
TaM3      (33)   CTAATTAAGAATAACATCA-ATGGGAGAAGCCTTGTTGTGCAAAGGAA
TaM4      (33)   CTAATTAAGAATAACATCA-ATGGGAGAAGCCTTGTTGTGCAAAGGAA 151                                            200
TRM4      (43)   GGCTTGAATAGAGGTGCTTGGACAACTCAAGAGGACAAAATCCTCACTGA
TRM6      (43)   GGCTTGAATAGAGGTGCTTGGACAACTCAAGAGGACAAAATCCTCACTGA
TRM3      (43)   GGCTTGAATAGAGGTGCTTGGACAACTCAAGAGGACAAAATCCTCACTGA
TRM1      (43)   GGCTTGAATAGAGGTGCTTGGACAACTCAAGAGGACAAAATCCTCACTGA
TRM5      (43)   GGCTTGAATAGAGGTGCTTGGACAACTCAAGAGGACAAAATCCTCACTGA
TRM14     (43)   GGCTTGAATAGAGGTGCTTGGACAACTCAAGAGGACAAAATCCTCACTGA
MYB14TaF  (150)  GGCTTGAATAGAGGTGCTTGGACAACTCAAGAGGACAAAATCCTCACTGA
TaM3      (82)   GGCTTGAATAGAGGTGCTTGGACAACTCAAGAGGACAAAATCCTCACTGA
TaM4      (82)   GGCTTGAATAGAGGTGCTTGGACAACTCAAGAGGACAAAATCCTCACTGA 201                                            250
TRM4      (93)   ATACATTAAGCTTCATGGTGAAGGAAAATGGACAAACCTTCAAAAAGAG
TRM6      (93)   ATACATTAAGCTTCATGGTGAAGGAAAATGGACAAACCTTCAAAAAGAG
TRM3      (93)   ATACATTAAGCTTCATGGTGAAGGAAAATGGACAAACCTTCAAAAAGAG
TRM1      (93)   ATACATTAAGCTTCATGGTGAAGGAAAATGGACAAACCTTCAAAAAGAG
TRM5      (93)   ATACATTAAGCTTCATGGTGAAGGAAAATGGACAAACCTTCAAAAAGAG
TRM14     (93)   ATACATTAAGCTTCATGGTGAAGGAAAATGGACAAACCTTCAAAAAGAG
MYB14TaF  (200)  ATACATTAAGCTTCATGGTGAAGGAAAATGGACAAACCTTCAAAAAGAG
TaM3      (132)  ATACATTAAGCTTCATGGTGAAGGAAAATGGACAAACCTTCAAAAAGAG
TaM4      (132)  ATACATTAAGCTTCATGGTGAAGGAAAATGGACAAACCTTCAAAAAGAG
```

FIGURE 10

```
             751                                                  800
TRM4    (594) AAAAAAXGTTAAGGATCTTXATCAACAAAACACCAACAAXTCTTCTCCTA
TRM6    (594) AAAAAAXGTTAAGGATCTTXATCAACAAAACACCAACAAXTCTTCTCCTA
TRM3    (593) AAAAAAXGTTAAGGATCTTXATCAACAAAACACCAACAAXTCTTCTCCTA
TRM1    (595) AAAAAAXGTTAAGGATCTTXATCAACAAAACACCAACAAXTCTTCTCCTA
TRM5    (597) AAAAAAXGTTAAGGATCTTXATCAACAAAACACCAACAAXTCTTCTCCTA
TRM14   (596) AAAAAAXGTTAAGGATCTTXATCAACAAAACACCAACAAXTCTTCTCCTA
MYB14TaF (458) AAAAAAGTTAAGGATCTTXATCAACAAAACACCAACAAXTCTTCTCCTA
TaM3    (675) AAAAAAGTTAAGGATCTTXATCAACAAAACACCAACAAGTCTTCTCCTA
TaM4    (672) AAAAAAGTTAAGGATCTTGATCAACAAAACACCAACAAXTCTTCTCCTA 801                                                  850
TRM4    (644) CTAAACXTCTGCTCAACCAAAAAATGCAXAXATCAAACAGAAACAX
TRM6    (644) CTAAACXTCTGCTCAACCAAAAAATGCAXAXATCAAACAGAAACAX
TRM3    (643) CTAAACXTCTGCTCAACCAAAAAATGCAXAXATCAAACAGAAACAX
TRM1    (645) CTAAACXTCTGCTCAACCAAAAAATGCAXAXATCAAACAGAAACAX
TRM5    (647) CTAAACXTCTGCTCAACCAAAAAATGCAXAXATCAAACAGAAACAX
TRM14   (646) CTAAACXTCTGCTCAACCAAAAAATGCAXAXATCAAACAGAAACAX
MYB14TaF (508) CTAAACTTCTGCTCAACCAAAAAATGCAXAGATCAAACAGAAACA----G
TaM3    (725) CTAAACTCXTGCTCAACCAAAAAATGXAXAGATCAAACAGAAACA----G
TaM4    (722) CTAAACTCXTGCTCAACCAAAAAATGXAGAGATCAAACAGAAACA----G 851                                                  900
TRM4    (694) ATCAATCCTAAGCCAAXXXXXXXXACTCXATGTTXTCCGTACAAAAGC
TRM6    (694) ATCAATCCTAAGCCAAXXXXXXXXACTCXATGTTXTCCGTACAAAAGC
TRM3    (693) ATCAATCCTAAGCCAAXXXXXXXXACTCXATGTTXTCCGTACAAAAGC
TRM1    (695) ATCAATCCTAAGCCAAXXXXXXXXACTCXATGTTXTCCGTACAAAAGC
TRM5    (697) ATCAATCCTAAGCCAAXXXXXXXXACTCXATGTTXTCCGTACAAAAGC
TRM14   (696) ATCAATCCTAAGCCAAXXXXXXXXACTCXATGTTXTCCGTACAAAAGC
MYB14TaF (555) ATCAATCCTAAGCCAAXXXXXXXXACTCAXATGTTXTCCGTACAAAAGC
TaM3    (772) ATCAATCCTAAGCCAAXXXXXXXXACTCAXATGTTXTCCGTACAAAAGC
TaM4    (769) ATCAATCCTAAGCCAA-----------ACTCATATGTXTCCGTACAAAAGC 901                                                  950
TRM4    (744) TACCAAXTGTTCTAAGGTATTGTTCATAAACTCAC----------CACCA-
TRM6    (744) TACCAAXTGTTCTAAGGTATTGTTCATAAACTCAC----------CACCA-
TRM3    (743) TACCAAXTGTTCTAAGGTATTGTTCATAAACTCAC----------CACCA-
TRM1    (745) TACCAAXTGTTCTAAGGTATTGTTCATAAACTCAC----------CACCA-
TRM5    (747) TACCAAXTGTTCTAAGGTATTGTTCATAAACTCAC----------CACCA-
TRM14   (746) TACCAATTGTTCTAAGGTATTGTTCATAAACTCAC----------CACCA-
MYB14TaF (605) TACCAAGTGTTCTAAGGTATTXTTCATAAACTCACTCCCCAACTXACCA-
TaM3    (822) TACCAAGTGTTCTAAGGTATTGTTCATAAACTCACTCCCCAACTXACCA-
TaM4    (810) TACCAAGTGTTCTAAGGTATTGTTCATAAACTCACCCCCCAACTXACCAC 951                                                 1000
TRM4    (784) --ATGCATXATTTGCAGAXCAAAGCTGAGGCAGAGACAAXGACAAX----
TRM6    (784) --ATGCATXATTTGCAGAXCAAAGCTGAGGCAGAGACAAXXACAAX----
TRM3    (783) --ATGCAXXATTTGCAGAXCAAAGCTGAGGCAGAGACAAXXACAAX----
TRM1    (785) --ATGCAXXATTTGCAGAXCAAAGCTGAGGCAGAGACAAXXACAAX----
TRM5    (787) --ATGCAXXATTTGCAGAXCAAAGCTGAGGCAGAGACAAXXACAAX----
TRM14   (786) --ATGCAXXATTTGCAGAXCAAAGCTGAGGCAGAGACAAXXACAAX----
MYB14TaF (654) --ATGCAXGATTTGCAGAXCAAAGCTGAGGCAGAGACAACXACAAX----
TaM3    (871) --ATGCAXGATTTGCAGAXCAAAGCTGAGGCAGAGACAACXACAAX----
TaM4    (860) CAAXCAXGATTGCAGAGCAAAGCTGAGGCAGAGACAXCXACAACAACA
```

```
              1251                                              1300
TRM4    (1067) TCCCTGATGATGAGATCCTAAGAATTGGACACAATGTAACTTTGCTGAT
TRM6    (1067) TCCCTGATGATGAGATCCTAAGAATTGGACACAATGTAACTTTGCTGAT
TRM3    (1066) TCCCTGATGATGAGATCCTAAGAATTGGACACAATGTAACTTTGCTGAT
TRM1    (1068) TCCCTGATGATGAGATCCTAAGAATTGGACACAATGTAACTTTGCTGAT
TRM5    (1070) TCCCTGATGATGAGATCCTAAGAATTGGACACAATGTAACTTTGCTGAT
TRM14   (1069) TCCCTGATGATGAGATCCTAAGAATTGGACACAATGTAACTTTGCTGAT
MYB14TaF (937) TCCCTGATGATGAGATCCTAAGAATTGGACACAATGTAACTTTGCTGAT
TaM3    (1154) TCCCTGATGATGAGATCCTAAGAATTGGACACAATGTAACTTTGCTGAT
TaM4    (1160) TCCCTGATGATGAGATCCTAAAGAATTGGACACAATGTAACTTTGCTGAT 1301                                              1350
TRM4    (1117) GAGACAAATGTGTCCAACAACCTTCATTCTTTGCTTCCTTCTGAATC
TRM6    (1117) GAGACAAATGTGTCCAACAACCTTCATTCTTTGCTTCCTTCTGAATC
TRM3    (1116) GAGACAAATGTGTCCAACAACCTTCATTCTTTGCTTCCTTCTGAATC
TRM1    (1118) GAGACAAATGTGTCCAACAACCTTCATTCTTTGCTTCCTTCTGAATC
TRM5    (1120) GAGACAAATGTGTCCAACAACCTTCATTCTTTGCTTCCTTCTGAATC
TRM14   (1119) GAGACAAATGTGTCCAACAACCTTCATTCTTTGCTTCCTTCTGAATC
MYB14TaF (987) GAGACAAATGTGTCCAACAACCTTCATTCTTTGCTTCCTTCTTGAATC
TaM3    (1204) GAGACAAATGTGTCCAACAACCTTCATTCTTTGCTTCCTTTCTTGAATC
TaM4    (1210) GAGACAAATGTGTCCAACAACCTTCAGTCTCTGCTTCCTTCTTGAATC 1351                                              1400
TRM4    (1167) CAGTGAGGAAGTACTAGGAGAATGAA------AATTC-------------
TRM6    (1167) CAGTGAGGAAGTACTAGGAGAATGAA------AATTC-------------
TRM3    (1166) CAGTGAGGAAGTACTAGGAGAATGAA------AATTC-------------
TRM1    (1168) CAGTGAGGAAGTACTAGGAGAATGAA------AATTCT------------
TRM5    (1170) CAGTGAGGAAGTACTAGGAGAATGAA------AATTC-------------
TRM14   (1169) CAGTGAGGAAGTACTAGGAGAATGAA------AATTC-------------
MYB14TaF (1037) CAGTGAGGAAGTACTAGGAGAATGATAATAAAATCATTTTCCAATAAA
TaM3    (1254) CAGTGAGGAAGTACTAGGAGAATGAA------AATTC-------------
TaM4    (1260) CAGTGAGGAAGTACTAGGAGAATGAA------AATTC-------------

1401                                              1450
TRM4    (1204) --------------------------------------------------
TRM6    (1204) --------------------------------------------------
TRM3    (1203) --------------------------------------------------
TRM1    (1206) --------------------------------------------------
TRM5    (1207) --------------------------------------------------
TRM14   (1206) --------------------------------------------------
MYB14TaF (1087) ATTAACTACTCTAGGTTTTTTTTTTTTTTTTAATTTCAATTTCATGTT
TaM3    (1291) --------------------------------------------------
TaM4    (1297) --------------------------------------------------

1451                                              1500
TRM4    (1204) --------------------------------------------------
TRM6    (1204) --------------------------------------------------
TRM3    (1203) --------------------------------------------------
TRM1    (1206) --------------------------------------------------
TRM5    (1207) --------------------------------------------------
TRM14   (1206) --------------------------------------------------
MYB14TaF (1137) AGGGTGGTTTAATAAATAAATATATTCTATGGTTTAATATTGCAAAAAA
TaM3    (1291) --------------------------------------------------
TaM4    (1297) --------------------------------------------------
```

FIGURE 10 cont.

```
              1501                                              1550
    TRM4 (1204) --------------------------------------------------
    TRM6 (1204) --------------------------------------------------
    TRM3 (1203) --------------------------------------------------
    TRM1 (1206) --------------------------------------------------
    TRM5 (1207) --------------------------------------------------
   TRM14 (1206) --------------------------------------------------
MYB14TaF (1187) AAAAAAAAAAAAAAAAAAAAAGTACTCTGCGTTGATACCACTGCTTAAGGGC
    TaM3 (1291) --------------------------------------------------
    TaM4 (1297) --------------------------------------------------

1551
    TRM4 (1204) -------------(SEQ ID NO:11)
    TRM6 (1204) -------------(SEQ ID NO:89)
    TRM3 (1203) -------------(SEQ ID NO:10)
    TRM1 (1206) -------------(SEQ ID NO:9)
    TRM5 (1207) -------------(SEQ ID NO:12)
   TRM14 (1206) -------------(SEQ ID NO:90)
MYB14TaF (1237) GAATTCC------(SEQ ID NO:1)
    TaM3 (1291) -------------(SEQ ID NO:2)
    TaM4 (1297) -------------(SEQ ID NO:3)
```

FIGURE 10 cont.

```
              1                                                50
MYB14TaF  (1) GAATTCGCCCTTAAGCAGTGGTATCAACGCAGAGTACGCGGGGGAAGTTA
   TaM3  (1) --------------------------------------------------
   TaM4  (1) --------------------------------------------------
    To1  (1) --------------------------------------------------
    To6  (1) --------------------------------------------------

51                                               100
MYB14TaF (51) TTTAATTTTATCTACATCA  CA TT AAG  CTT  GAA  AGA  AG
   TaM3  (1) -----------------------G  TT GC CTT            
   TaM4  (1) -----------------------G  TT GC CTT            
    To1  (1) --------------------------------------------------
    To6  (1) --------------------------------------------------

101                                              150
MYB14TaF (101)                                   -ATGGGGAGAAGCCCTTGTTGTGCAAAGGAA
   TaM3 (33)                                     -ATGGGGAGAAGCCCTTGTTGTGCAAAGGAA
   TaM4 (33)                                     -ATGGGGAGAAGCCCTTGTTGTGCAAAGGAA
    To1  (1) ----------GAATTCGCCCTTATGGGGAGAAGCCCTTGTTGTGCAAAGGAA
    To6  (1) ----------GAATTCGCCCTTATGGGGAGAAGCCCTTGTTGTGCAAAGGAA 151                                              200
MYB14TaF (150)
   TaM3 (82)
   TaM4 (82)
    To1 (43)
    To6 (43)

201                                              250
MYB14TaF (200) ATACATTAAGCTCCATGGTGAAGGAAAATGGAGAAACCTTCAAAAAGAG
   TaM3 (132) ATACATTAAGCTCCATGGTGAAGGAAAATGGAGAAACCTTCAAAAAGAG
   TaM4 (132) ATACATTAAGCTCCATGGTGAAGGAAAATGGAGAAACCTTCAAAAAGAG
    To1 (93) ATACATTAAGCTCCATGGTGAAGGAAAATGGAGAAACCTTCAAAAAGAG
    To6 (93) ATACATTAAGCTCCATGGTGAAGGAAAATGGAGAAACCTTCAAAAAGAG 251                                              300
MYB14TaF (250) 
   TaM3 (182)
   TaM4 (182)
    To1 (143)
    To6 (143)

301                                              350
MYB14TaF (253) --------------------------------------------------
   TaM3 (228)    ACTTTT  T G-CTTATAAATTTTCTTGCA   T   A
   TaM4 (227)    ACTTTT  T G-CTTATAAATTTTCTTGTA   T   A T  TT
    To1 (192) -------  A TT------------           C   A
    To6 (192) -------  A TT------------           C   A 351                                              400
MYB14TaF (253) --------------------------------------------------
   TaM3 (277)   GT AAA    AAT AC  C  AG  ATTA TA    T    TGCAAA
   TaM4 (276)   G  AAA    AAT AC  C AG  ATTA TA TA        GGCAAA
    To1 (218)   T AAA      A   A   A  ATT  TA  CA A       ------
    To6 (218)   T AAA      A   A   A  ATT  TA  CA A       ------
```

FIGURE 11

```
                401                                              450
MYB14TaF  (253) ---------------------AITTAAAAAGATG#GGAAAAAGTTGTAGACTT
    TaM3  (327) TATGTGTATGCCA#G##ATTAAAAAGATGC#GGAAAAAGTTGTAGACTT
    TaM4  (326) TATGTTTATGCCA#G##ATTAAAAAGATC#GGAAAAAGTTGTAGACTT
     To1  (262) -------------#C##ATTAAAAAGATG#CGAAAAAGTTGTAGACTT
     To6  (262) -------------#C##ATTAAAAAGATG#CGAAAAAGTTGTAGACTT 451                                              500
MYB14TaF  (285) AGATGCTTGAATTA#C##AGAC#AGATATTAAG##AGGTAATATATC#C
    TaM3  (377) AGATGCTTGAATTATC##AGACCAGATATTAAG##AGGTAATATATC#C
    TaM4  (376) AGATGCTTGAATTATCT#AGACCAGATATTAAG##AGGTAATATATC#C
     To1  (299) AGATGCTTGAATTATCTTAGACCAGATATTAAGAGAGGTAATATATCG#
     To6  (299) AGATGCTTGAATTATCTTAGACCAGATATTAAGAGAGGTAATATATCG#

501                                              550
MYB14TaF  (335) #ATGAAGAAGAACT#ATTAT#C#ACTTCACAAACTACTT#GGAAAC#---
    TaM3  (427) #ATGAAGAAGAACTTAT#AT##GACTTCACAAACTACT#GGAAA##
    TaM4  (426) #ATGAAGAAGAACT#ATTAT#CGACTTCACAAACTACT#GGAAA##
     To1  (349) C#ATGAAGAAGAACTTATT#AT#TGACTTCACAAACTACTTGGAAACC#
     To6  (349) C#ATGAAGAAGAACTTATT#AT#TGA#TTCACAAACTACTTGGAAACC#

551                                              600
MYB14TaF  (383) ------------------------------------------------
    TaM3  (477) ##A#A##C################T###A##TATCTATAATT###T
    TaM4  (476) ###-#CCTA###########T###G##TGTCTATAATT###T
     To1  (399) ##A-##T##########C##A##-----------------
     To6  (399) ###A##T#A#A####C##A##-----------------

601                                              650
MYB14TaF  (383) ------------------------------------------------
    TaM3  (527) TTTTTTGACAATTAGTACTACTAATTTAATT####A##G##A##T
    TaM4  (525) TTTTTTGACCATTAGTACTACTAATTTAATT##CA##G##A##T
     To1  (436) -----------------------------####A##A##-
     To6  (436) -----------------------------####A##A##-

651                                              700
MYB14TaF  (383) ----------------------ATGGTCT#AATAGCGGAAGACTTCC
    TaM3  (577) ##TT#G####AA#######ATGGTCT#AATAGCGGAAGACTTCC
    TaM4  (575) #T-#GT####A########ATGGTCT#AATAGCGGAAGACTTCC
     To1  (454) #GA#T##T##GA#######ATGGTCT#AATAGCGGAAGACTTCC
     To6  (454) #GA#T##T##GA#######ATGGTCT#AATAGCGGAAGACTTCC 701                                              750
MYB14TaF  (410) A#G##CGAACAGACAATCAAATAAA##A#TACTGGAACAC#AATTTAGGAA
    TaM3  (627) A#GACCGAACAGACAATCAAATAAA##A#TACTGGAACAC#AATTTAGGAA
    TaM4  (624) A#G##CAACAGACAATCAAATAAA##A#TACTGGAACAC#AATTTAGGAA
     To1  (504) A#G##CGAACAGACAATCAAATAAAAA#TTACTGGAACACGAATTTAGGAA
     To6  (504) A#G##CGAACAGACAATCAAATAAAAA#TTACTGGAACACGAATTTAGGAA 751                                              800
MYB14TaF  (460) A#AAAGCTTAAGTATCTT##ATCAACAAAACACCAACAA#TCTTCTCCTAC#
    TaM3  (677) AAAAAGCTTAAGTATCTT##ATCAACAAAACACCAACAAGTCTTCTCCTAC#
    TaM4  (674) AAAAAGCTTAAGTATCTT#GATCAACAAAACACCAACAA#TCTTCTCCTAC#
     To1  (554) AAAAAGCTTAAGTATCTTT#ATCAACAAAACACCAACAA#TCTTCTCCTAC#
     To6  (554) AAAAAGCTTAAGTATCTTT#ATCAACAAAACACCAACAA#TCTTCTCCTAC#
```

```
              1201                                              1250
MYB14TaF (886)
    TaM3 (1103)
    TaM4 (1109)
     To1 (977)
     To6 (977)

1251                                              1300
MYB14TaF (936)
    TaM3 (1153)
    TaM4 (1159)
     To1 (1027)
     To6 (1027)

1301                                              1350
MYB14TaF (986)
    TaM3 (1203)
    TaM4 (1209)
     To1 (1077)
     To6 (1077)

1351                                              1400
MYB14TaF (1036)                                       ATTTCCAATAA
    TaM3 (1253)                                       AATTC--------
    TaM4 (1259)                                       AATTC--------
     To1 (1127)                                       AATTC--------
     To6 (1127)                                       AATTC--------

1401                                              1450
MYB14TaF (1086) AATTAACTACTCTAGGTTTTTTTTTTTTTTTTTAATTTCAATTTCATGT
    TaM3 (1291) ------------------------------------------------
    TaM4 (1297) ------------------------------------------------
     To1 (1165) ------------------------------------------------
     To6 (1165) ------------------------------------------------

1451
MYB14TaF (1136) TAGGGTGGTTTAATAAATAAATATATTCTATGGTTTAATATTGCAAAAAA
    TaM3 (1291) --------------------------------------------------
    TaM4 (1297) --------------------------------------------------
     To1 (1165) --------------------------------------------------
     To6 (1165) --------------------------------------------------

1501                                              1550
MYB14TaF (1186) AAAAAAAAAAAAAAAAAAAAAGTACTCTGCGTTGATACCACTGCTTAAGGG
    TaM3 (1291) --------------------------------------------------
    TaM4 (1297) --------------------------------------------------
     To1 (1165) --------------------------------------------------
     To6 (1165) --------------------------------------------------

1551
MYB14TaF (1236) CGAATTCC  (SEQ ID NO:1)
    TaM3 (1291) --------  (SEQ ID NO:2)
    TaM4 (1297) --------  (SEQ ID NO:3)
     To1 (1165) --------  (SEQ ID NO:91)
     To6 (1165) --------  (SEQ ID NO:92)
```

FIGURE 11 cont.

```
                       1                                                  50
MYB14TaFF     (1)   GAATTCGCCCCTTAAGCAGTGGTATCAACGCAGAGTACGCGGGGGAAGTTA
      TaM3    (1)   --------------------------------------------------
     Taf11    (1)   --------------------------------------------------
   Taf2 r#2   (1)   --------------------------------------------------
      Taf3    (1)   --------------------------------------------------
      Taf7    (1)   --------------------------------------------------
      Taf4    (1)   --------------------------------------------------
     Taf10    (1)   --------------------------------------------------

51                                                100
MYB14TaFF    (51)   TTTAATTTTATCTACATCAAACACTTCAAGAGGTTGGAATACAAGACAGA
      TaM3    (1)   ------------------GAATTCGCCCTTAGGTTGGAATACAAGACAGA
     Taf11    (1)   --------------------------------------------------
   Taf2 r#2   (1)   --------------------------------------------------
      Taf3    (1)   --------------------------------------------------
      Taf7    (1)   --------------------------------------------------
      Taf4    (1)   --------------------------------------------------
     Taf10    (1)   --------------------------------------------------

101                                               150
MYB14TaFF   (101)   CTAATTAAGAATAACATCA-ATGGGGACAAGCCCTTGTTGTGCAAGGAA
      TaM3   (33)   CTAATTAAGAATAACATCA-ATGGGGACAAGCCCTTGTTGTGCAAGGAA
     Taf11    (1)   ---------GAAT........ATGGGGACAAGCCCTTGTTGTGCAAGGAA
   Taf2 r#2   (1)   --------GGAAT........ATGGGGACAAGCCCTTGTTGTGCAAGGAA
      Taf3    (1)   ---------GAAT........ATGGGGACAAGCCCTTGTTGTGCAAGGAA
      Taf7    (1)   ---------GAAT........ATGGGGACAAGCCCTTGTTGTGCAAGGAA
      Taf4    (1)   ---------GAAT........ATGGGGACAAGCCCTTGTTGTGCAAGGAA
     Taf10    (1)   ---------GAAT........ATGGGGACAAGCCCTTGTTGTGCAAGGAA 151                                               200
MYB14TaFF   (150)   GCCTTGAATAGAGGTGCCTGGACAACTCAAGAAGACAAAATCCTCACTGA
      TaM3   (82)   GCCTTGAATAGAGGTGCCTGGACAACTCAAGAAGACAAAATCCTCACTGA
     Taf11   (43)   GCCTTGAATAGAGGTGCCTGGACAACTCAAGAAGACAAAATCCTCACTGA
   Taf2 r#2  (44)   GCCTTGAATAGAGGTGCCTGGACAACTCAAGAAGACAAAATCCTCACTGA
      Taf3   (43)   GCCTTGAATAGAGGTGCCTGGACAACTCAAGAAGACAAAATCCTCACTGA
      Taf7   (43)   GCCTTGAATAGAGGTGCCTGGACAACTCAAGAAGACAAAATCCTCACTGA
      Taf4   (43)   GCCTTGAATAGAGGTGCCTGGACAACTCAAGAAGACAAAATCCTCACTGA
     Taf10   (43)   GCCTTGAATAGAGGTGCCTGGACAACTCAAGAAGACAAAATCCTCACTGA 201                                               250
MYB14TaFF   (200)   ATACATTAAGCTCCATGGTGAAGGAAAATGGAGAAACCTTCCAAAAAGAG
      TaM3  (132)   ATACATTAAGCTCCATGGTGAAGGAAAATGGAGAAACCTTCCAAAAAGAG
     Taf11   (93)   ATACATTAAGCTCCATGGTGAAGGAAAATGGAGAAACCTTCCAAAAAGAG
   Taf2 r#2  (94)   ATACATTAAGCTCCATGGTGAAGGAAAATGGAGAAACCTTCCAAAAAGAG
      Taf3   (93)   ATACATTAAGCTCCATGGTGAAGGAAAATGGAGAAACCTTCCAAAAAGAG
      Taf7   (93)   ATACATTAAGCTCCATGGTGAAGGAAAATGGAGAAACCTTCCAAAAAGAG
      Taf4   (93)   ATACATTAAGCTCCATGGTGAAGGAAAATGGAGAAACCTTCCAAAAAGAG
     Taf10   (93)   ATACATTAAGCTCCATGGTGAAGGAAAATGGAGAAACCTTCCAAAAAGAG 251                                               300
MYB14TaFF   (250)   GAG-----------------------------------------------
```

```
       Taf7  (1189)  ................----------------------................
       Taf4  (1189)  ................----------------------................
      Taf10  (1189)  ................----------------------................

1351                                              1400
MYB14TaFF  (1049)  ....................... ATTTTCCAATAAAATTAACTACTCT
      TaM3  (1266)  ....................---------------------------
     Taf11  (1215)  ...................T............................
  Taf2 r#2  (1216)  ...................-----------------------------
      Taf3  (1215)  ...................-----------------------------
      Taf7  (1215)  ...................-----------------------------
      Taf4  (1215)  ...................-----------------------------
     Taf10  (1215)  ...................-----------------------------

1401                                              1450
MYB14TaFF  (1099)  AGGTTTTTTTTTTTTTTTTTAATTTCAATTCATGTTAGGGTGGTTTAA
      TaM3  (1291)  ------------------------------------------------
     Taf11  (1241)  ------------------------------------------------
  Taf2 r#2  (1241)  ------------------------------------------------
      Taf3  (1240)  ------------------------------------------------
      Taf7  (1240)  ------------------------------------------------
      Taf4  (1240)  ------------------------------------------------
     Taf10  (1240)  ------------------------------------------------

1451                                              1500
MYB14TaFF  (1149)  TAAATAAATATATTCTATGGTTTAATATTGCAAAAAAAAAAAAAAAAAA
      TaM3  (1291)  ------------------------------------------------
     Taf11  (1241)  ------------------------------------------------
  Taf2 r#2  (1241)  ------------------------------------------------
      Taf3  (1240)  ------------------------------------------------
      Taf7  (1240)  ------------------------------------------------
      Taf4  (1240)  ------------------------------------------------
     Taf10  (1240)  ------------------------------------------------

1501                                1545
MYB14TaFF  (1199)  AAAAAAAGTACTCTGCGTTGATACCACTGCTTAAGGGCGAATTCC   (SEQ NO:1)
      TaM3  (1291)  ---------------------------------------------  (SEQ NO:2)
     Taf11  (1241)  ---------------------------------------------  (SEQ NO:93)
  Taf2 r#2  (1241)  ---------------------------------------------  (SEQ NO:94)
      Taf3  (1240)  ---------------------------------------------  (SEQ NO:95)
      Taf7  (1240)  ---------------------------------------------  (SEQ NO:96)
      Taf4  (1240)  ---------------------------------------------  (SEQ NO:97)
     Taf10  (1240)  ---------------------------------------------  (SEQ NO:98)
```

FIGURE 12 cont.

```
                    1                                              50
TaMYB14-1    (1)  MGRSPCCAKEGLNRGAWT QEDKILTEYIKLHGEGKWRNLPKRAGLKRCG
TaMYB14-2    (1)  MGRSPCCAKEGLNRGAWT QEDKILTEYIKLHGEGKWRNLPKRAGLKRCG
TafMYB14-1   (1)  MGRSPCCAKEGLNRGAWT QEDKILTEYIKLHGEGKWRNLPKRAGLKRCG
TafMYB14-2   (1)  MGRSPCCAKEGLNRGAWT QEDKILTEYIKLHGEGKWRNLPKRAGLKRCG
ToMYB14-1    (1)  MGRSPCCAKEGLNRGAWT QEDKILTEYIKLHGEGKWRNLPKRAGLKRCG
ToMYB14-2    (1)  MGRSPCCAKEGLNRGAWTAHEDKILTEYIKLHGEGKWRNLPKRAGLKRCG
TrMYB14-1    (1)  MGRSPCCAKEGLNRGAWTAHEDKILTEYIKLHGEGKWRNLPKRAGLKRCG
TrMYB14-2    (1)  MGRSPCCAKEGLNRGAWTAHEDKILTEYIKLHGEGKWRNLPKRAGLKRCG
TrMYB14-3    (1)  MGRSPCCAKEGLNRGAWTAHEDKILTEYIKLHGEGKWRNLPKRAGLKRCG
TrMYB14-4    (1)  MGRSPCCAKEGLNRGAWTAHEDKILTEYIKLHGEGKWRNLPKRAGLKRCG
Consensus    (1)  MGRSPCCAKEGLNRGAWTTQEDKILTEYIKLHGEGKWRNLPKRAGLKRCG 51                                            100
TaMYB14-1   (51)  KSCRLRWLNYLRPDIKRGNISSDEEELIIRLHKLLGNRWSLIAGRLPGRT
TaMYB14-2   (51)  KSCRLRWLNYLRPDIKRGNISPDEEELIRLHKLLGNRWSLIAGRLPGRT
TafMYB14-1  (51)  KSCRLRWLNYLRLDIKRGNISSDEEELIIRLHKLLGNRWSLIAGRLPGRT
TafMYB14-2  (51)  KSCRLRWLNYLRPDIKRGNISSDEEELIIRLHKLLGNRWSLIAGRLPGRT
ToMYB14-1   (51)  KSCRLRWLNYLRPDIKRGNISSDEEELIIRLHKLLGNRWSLIAGRLPGRT
ToMYB14-2   (51)  KSCRLRWLNYLRPDIKRGNISSDEEELIIRLHKLLGNRWSLIAGRLPGRT
TrMYB14-1   (51)  KSCRLRWLNYLRPDIKRGNISSDEEELIIRLHKLLGNRWSLIAGRLPGRT
TrMYB14-2   (51)  KSCRLRWLNYLRPDIKRGNISSDEEELIIRLHKLLGNRWSLIAGRLPGRT
TrMYB14-3   (51)  KSCRLRWLNYLRPDIKRGNISSDEEELIIRLHKLLGNRWSLIAGRLPGRT
TrMYB14-4   (51)  KSCRLRWLNYLRPDIKRGNISSDEEELIIRLHKLLGNRWSLIAGRLPGRT
Consensus   (51)  KSCRLRWLNYLRPDIKRGNISSDEEELIIRLHKLLGNRWSLIAGRLPGRT 101                                            150
TaMYB14-1  (101)  DNEIKNYWNTNLGKKVKDLQQNTNSSPTKLSAQKNAKKQKQI--NP
TaMYB14-2  (101)  DNEIKNYWNTNLGKKVKDLQQNTNSSPTKLSAQKNAPKQKQI--NP
TafMYB14-1 (101)  DNEIKNYWNTNLGKKVKDLQENTNSSPTKLSAQLKNAKKQKQI--NP
TafMYB14-2 (101)  DNEIKNYWNTNLGKKVKDLQENTNSSPTKLSAQLKNAKKQKQI--NP
```

FIGURE 34

```
ToMYB14-1   (101) DNEIKNYWNTNLGKKVKDLQQNTNKSSPTKLSAQPKNAKIKQKQI--NP
ToMYB14-2   (101) DNEIKNYWNTNLGKKVKDLQQNTNKSSPTKPSAQPKNAKIKQKQNNP
TrMYB14-1   (101) DNEIKNYWNTNLGKKVKDLQQNTNKSSPTKPSAQPKNANIKQKQ--NP
TrMYB14-2   (101) DNEIKNYWNTNLGKKVKDLQQNTNKSSPTKPSAQPKNANIKQKQ--NP
TrMYB14-3   (101) DNEIKNYWNTNLGKKVKDLQQNTNKSSPTKPSAQPKNANIKQKQ--NP
TrMYB14-4   (101) DNEIKNYWNTNLGKKVKDLQQNTNKSSPTKPSAQPKNANIKQKQ--NP
Consensus   (101) DNEIKNYWNTNLGKKVKDLNQQNTNNSSPTKPSAQPKNAKIKQKQQI NP 151                                              200
TaMYB14-1   (149) K---PNSYVRTKATKCSKVLFINSLPK--MHDLQNKAEAETKT-----
TaMYB14-2   (149) K---PNSYVVRTKATKCSKVLFINSPPMHDLQSKAEAETKTTTKPS
TafMYB14-1  (149) KPPNSYVVRTKATKCSKALFINSPPMHDLQNKAEAETKT---KSS
TafMYB14-2  (149) KPPNSYVVRTKATKCSKALFINSPPMHDLQNKAEAETKT---KSS
ToMYB14-1   (149) KPPNSYVVRTKATKCSKVLFINSLPK--MHDLQNKAEAETKT-----
ToMYB14-2   (151) KPPNSYVVRTKATKCSKVLFINSPP----MHLQNKAEAETKT-----
TrMYB14-1   (150) KPPNSYVVRTKATKCSKVLFINSPP----MHLQNKAEAETKT-----
TrMYB14-2   (150) KPPNSYVVRTKATKCSKVLFINSPP----MHLQNKAEAETKT-----
TrMYB14-3   (150) KPPNSYVVRTKATKCSKVLFINSPP----MHLQNKAEAETKT-----
TrMYB14-4   (150) KPPNSYVVRTKATKCSKVLFINSPP----MHLQNKAEAETKT-----
Consensus   (151) KPMKPNS              VLFINSPPNSP MHNLQNKAEAETTT 201                                              250
TaMYB14-1   (193) SMLVDGVASDSMSNNEMEHGYGFLSFCDEEKELSADLLDDFNIADDIC
TaMYB14-2   (196) MSMLVDGVASDSMSNNEMECGNGFLSFCDEEKELSADLLDDFNIADDIC
TafMYB14-1  (197) MSMLVDGVASDSMSNNEMEYGDGFLSFCDEEKELSADLLDDFNIADDIC
TafMYB14-2  (197) MSMLVDGVASDSMSNNEMEYGDGFLSFCDEEKELSADLLDDFNIADDIC
ToMYB14-1   (193) SMLVDGVASDSMSNNEMEHGYGFLSFCDEEKELSADLLDDFNIADDIC
ToMYB14-2   (192) TSMLVDGVASDSMSNNEMERGNGFLSFRDEEKELSADLLDDFNIADDIC
TrMYB14-1   (191) LMLVNGVASDSMSNNEMERGNGFLSFCDEEKELSADLLDDFNIADDIC
TrMYB14-2   (191) LMLVNGVASDSMSNNEMERGNGFLSFCDEEKELSADLLDDFNIADDIC
TrMYB14-3   (191) LMLVNGVASDSMSNNEMERGNGFLSFCDEEKELSADLLDDFNIADDIC
TrMYB14-4   (191) LMLVNGVASDSMSNNEMERGNGFLSFCDEEKELSADLLDDFNIADDIC
Consensus   (201) KPSMLVNGVASDSMSNNEMERGNGFLSFCDEEKELSADLLDDFNIADDIC
```

FIGURE 34 cont.

```
                251                                             300
TaMYB14-1  (243) ....................................................
TaMYB14-2  (246) ....................................................
TafMYB14-1 (247) ....................................................
TafMYB14-2 (247) ....................................................
ToMYB14-1  (243) ....................................................
ToMYB14-2  (242) ....................................................
TrMYB14-1  (241) ....................................................
TrMYB14-2  (241) ....................................................
TrMYB14-3  (241) ....................................................
TrMYB14-4  (241) ....................................................
Consensus  (251) LSEFLNSDFSNACNFDYNDLLSPCSDQTQMFS          WTQCNFADETN 301       321
TaMYB14-1  (293) ......................     (SEQ ID NO: 14)
TaMYB14-2  (296) .....Q..S.............     (SEQ ID NO: 46)
TafMYB14-1 (297) YVS.NQ--------........     (SEQ ID NO: 47)
TafMYB14-2 (297) ----------------------     (SEQ ID NO: 48)
ToMYB14-1  (293) ......................     (SEQ ID NO: 49)
ToMYB14-2  (292) ..........---300------     (SEQ ID NO: 99)
TrMYB14-1  (291) .....N................     (SEQ ID NO: 51)
TrMYB14-2  (291) .....N................     (SEQ ID NO: 52)
TrMYB14-3  (291) ......................     (SEQ ID NO: 53)
TrMYB14-4  (291) ......................     (SEQ ID NO: 54)
Consensus  (301) VSNNLHSFASFLESSEEVLGE  311   (SEQ ID NO: 100)
```

FIGURE 34 cont.

|  | TaMYB14-1 | TaMYB14-2 | TsfMYB14-1 | TsfMYB14-2 | ToMYB14-1 | ToMYB14-2 | ToMYB14-3 | TrMYB14-1 | TrMYB14-2 | TrMYB14-3 | TrMYB14-4 |
|---|---|---|---|---|---|---|---|---|---|---|---|
| TaMYB14-1 |  |  |  |  |  |  |  |  |  |  |  |
| TaMYB14-2 | 95 |  |  |  |  |  |  |  |  |  |  |
| TsfMYB14-1 | 92 | 92 |  |  |  |  |  |  |  |  |  |
| TsfMYB14-2 | 94 | 93 | 99 |  |  |  |  |  |  |  |  |
| ToMYB14-1 | 93 | 94 | 92 | 94 |  |  |  |  |  |  |  |
| ToMYB14-2 | 95 | 92 | 89 | 92 | 95 |  |  |  |  |  |  |
| ToMYB14-3 | 95 | 93 | 90 | 92 | 94 | 98 |  |  |  |  |  |
| TrMYB14-1 | 95 | 92 | 89 | 91 | 94 | 98 | 100 |  |  |  |  |
| TrMYB14-2 | 95 | 93 | 90 | 92 | 95 | 99 | 100 | 99 |  |  |  |
| TrMYB14-3 | 95 | 93 | 90 | 92 | 95 | 99 | 100 | 99 |  |  |  |
| TrMYB14-4 | 95 | 93 | 90 | 92 | 95 | 99 | 100 | 99 | 100 |  |  |

FIGURE 35

SEQUENCE LISTING

<160> NUMBER OF SEQ ID NOS: 102

<210> SEQ ID NO 1
<211> LENGTH: 1243
<212> TYPE: DNA
<213> ORGANISM: Trifolium arvense

<400> SEQUENCE: 1

```
gaattcgccc ttaagcagtg gtatcaacgc agagtacgcg ggggaagtta tttaatttta      60
tctacatcaa acacttcaag aggttggaat acaagacaga ctaattaaga ataacatcaa     120
tggggagaag cccttgttgt gcaaaggaag gcttgaatag aggtgcttgg acaactcaag     180
aagacaaaat cctcactgaa tacattaagc tccatggtga aggaaaatgg agaaaccttc     240 caaaagagc agatttaaaa agatgtggaa aaagttgtag acttagatgg ttgaattatc      300
taagaccaga tattaagcga ggtaatatat ccccggatga agaagaactt attatccgac     360
ttcacaaact actcggaaac agatggtctc taatagccgg aagacttcca gggcgaacag     420
acaatgaaat aaagaactac tggaacacaa atttaggaaa aaaggttaag gatcttaatc     480
aacaaaacac caacaattct tctcctacta aactttctgc tcaaccaaaa aatgcaaaga     540
tcaaacagaa acagatcaat cctaagccaa tgaagccaaa ctcaaatgtt gtccgtacaa     600
aagctaccaa gtgttctaag gtattgttca taaactcact ccccaactca ccaatgcatg     660
```

```
atttgcagaa caaagctgag gcagagacaa caacaaagcc atcaatgctg gttgatggtg    720
tggctagtga ttcaatgagt aacaacgaaa tggaacacgg ttatggattt ttgtcatttt    780
gcgatgaaga gaaagaacta tccgcagatt tgctagaaga ttttaacatc gcggatgata    840
tttgcttatc tgaacttttg aactctgatt tctcaaatgc gtgcaatttc gattacaatg    900
atctattgtc accttgttcg gaccaaactc aaatgttctc tgatgatgag attctcaaga    960
attggacaca atgtaacttt gctgatgaga caaatgtgtc caacaacctt cattcttttg   1020
cttcctttct tgaatccagt gaggaagtac taggagaatg ataataaaaa ttcatttcc    1080 aataaaatta actactctag gtttttttt tttttttta atttcaattt catgttaggg    1140
tggtttaata aataaatata ttctatggtt taatattgca aaaaaaaaaa aaaaaaaaa    1200 aaaaagtact ctgcgttgat accactgctt aagggcgaat tcc                     1243

<210> SEQ ID NO 2
<211> LENGTH: 1290
<212> TYPE: DNA
<213> ORGANISM: Trifolium arvense

<400> SEQUENCE: 2
gaattcgccc ttaggttgga atacaagaca gactaattaa gaataacatc aatggggaga     60
agcccttgtt gtgcaaagga aggcttgaat agaggtgctt ggacaactca agaagacaaa    120
atcctcactg aatacattaa gctccatggt gaaggaaaat ggagaaacct tccaaaaaga    180
gcaggttcat tcattctagt atcttgcaat tatagatcaa tcactttcat acttttgttt    240
gcttataaat tttcttgcat ttttcttca attttccatg tgaaatgcaa attactagta     300
cattattatg gatatgtttt tgcaaatatg tgtatgccat gcaggtttaa aaagatgcgg    360
aaaaagttgt agacttagat ggttgaatta tctaagacca gatattaagc gaggtaatat    420
atcctcggat gaagaagaac ttatcatcag acttcacaaa ctactcggaa acaggtaaaa    480
gtaccgacat aatcactaac ttattaacat ttatctataa tttgttttt ttgacaatta    540 gtactactaa tttaatttta taatgtgtgc taatttgctt tgcctttaat ttgtggtaga    600
tggtctctaa tagccggaag acttccagga cgaacagaca atgaaataaa gaactactgg    660
aacacaaatt taggaaaaaa ggttaaggat cttaatcaac aaaacaccaa caattcttct    720
cctactaaac tctctgctca accaaaaaat gcaaagatca acagaaaca gatcaatcct    780 aagccaatga agccaaactc aaatgttgtc cgtacaaaag ctaccaagtg ttctaaggta    840
ttgttcataa actcactccc caactcacca atgcatgatt tgcagaacaa agctgaggca    900
gagacaacaa caaagccatc aatgctggtt gatggtgtgg ctagtgattc aatgagtaac    960
aacgaaatgg aacacggtta tggattttg tcatttgcg atgaagagaa agaactatcc   1020
gcagatttgc tagaagattt taacatcgcg gatgatattt gcttatctga acttttgaac   1080
tctgatttct caaatgcgtg caatttcgat tacaatgatc tattgtcacc ttgttcggac   1140
caaactcaaa tgttctctga tgatgagatt ctcaagaatt ggacacaatg taactttgct   1200
gatgagacaa atgtgtccaa caaccttcat tcttttgctt cctttcttga atccagtgag   1260
gaagtactag gagaatgaaa gggcgaattc                                    1290

<210> SEQ ID NO 3
<211> LENGTH: 1296
<212> TYPE: DNA
<213> ORGANISM: Trifolium arvense
```

<400> SEQUENCE: 3

```
gaattcgccc ttaggttgga atacaagaca gactaattaa gaataacatc aatggggaga      60
agcccttgtt gtgcaaagga aggcttgaat agaggtgctt ggacaactca agaagacaaa     120
atcctcactg aatacattaa gctccatggt gaaggaaaat ggagaaacct tccaaaaaga     180
gcaggttcat tcattctgta tcttacaatt atagattaac cactttcata cttttgtttg     240
cttataaatt ttcttgtatt ttttcttcca ttttcatga gaaatgcaaa ttactagtac      300
attattatgg acatgttttg gcaaatatgt ttatgccatg cagatttaaa aagatgtgga     360
aaagttgta gacttagatg gttgaattat ctaagaccag atattaagcg aggtaatata      420
tccccggatg aagaagaact tattatccga cttcacaaac tactcggaaa caggtaaagt     480
cctaacataa tcactaactt attaacgttt gtctataatt tgttttttt gaccattagt      540
actactaatt taattttaca atgtgtgcta atttgcttgt ctttaatttg tggtagatgg     600
tctctaatag ccggaagact tccagggcga acagacaatg aaataaagaa ctactggaac     660
acaaatttag gaaaaaaggt taaggatctt gatcaacaaa acaccaacaa ttcttctcct     720
actaaactct ctgctcaacc aaaaaatgca gagatcaaac agaaacagat caatcctaag     780
ccaaactcat atgttgtccg tacaaaagct accaagtgtt ctaaggtatt gttcataaac     840
tcacccccca actcaccacc aatgcatgat tgcagagca aagctgaggc agagacaaca      900
acaacaacaa agccatcaat gccatcaatg ctggttgatg gtgtggctag tgattcaatg     960
agtaacaacg aaatggaatg cggtaatgga ttttttgtcat tttgcgatga agagaaagaa    1020
ctatccgcag atttgctaga agattttaac atcgcggatg atatttgctt atctgaattt    1080
ctaaacttcg atttctcaaa tgcgtgcgat atcgattaca atgatctatt gtcgccttgt    1140
tcggaccaaa ctcaaatgtt ccctgatgat gagattctaa agaattggac acaatgtaac    1200
tttgctgatg agacaaatgt gtccaacaac cttcagtctt ctgcttcctt tcttgaatcc    1260
agtgaggaag tactaggaga atgaaagggc gaattc                              1296
```

<210> SEQ ID NO 4
<211> LENGTH: 1239
<212> TYPE: DNA
<213> ORGANISM: Trifolium affine

<400> SEQUENCE: 4

```
gaattcgccc ttatggggag aagcccttgt tgtgcgaagg aaggcttgaa tagaggtgct      60
tggacaactc aagaagacaa aatcctcact gaatacatta agctccatgg tgaaggaaaa     120
tggagaaacc ttccaaaaag agcaggttca ttcattctgt atcttacaat tatagattaa     180
ccactttcat acttttgttt gcttataaat tttcttgtat ttttcttcc atttttcatg      240
agaaatgcaa attactagta cattattatg gacatgtttt tgcaaatatg tttatgccat     300
gcaggtttaa aaagatgtgg aaaagttgt gacttagatg gttgaatta tctaagacta       360
gatattaagc gaggtaatat atcctcggat gaagaagaac ttatcatccg acttcacaaa     420
ttactcggaa acaggtaaag tcctaacata atcactaact tattaacgtt tgtctataac     480
ttgttttttt gacaattagt actactaatt taattttata atgtgtgcta atttgcttgt     540
ctttaatttg tggtagatgg tctctaatag ccggaagact tccaggacga acagacaatg     600
aaataaagaa ctactggaac acaaatttag gaaaaaaggt taaggatctt aatcaagaaa     660
acaccaacaa ttcttctcct actaaacttt ctgctcaact aaaaaatgca agatcaaac      720
agaaacagat caatcctaag ccaatggagc caaactcaaa tgttgtccgt acaaaagcta     780
```

```
ccaagtgttc taaggcattg ttcataaact cacccccaa ctcaccacca atgcatgatt      840
tgcagaacaa agctgaggca gagacaacaa caaagtcatc aatgccatca atgctggttg      900
atggcgtggc tagtgattca atgagtaaca cgaaatgga atacggtgat ggatttgttt      960 catttgcga tgacgataaa gaactatccg cagatttgct agaagatttt aacatctcgg     1020
atgatatttg cttatccgaa tttctaaact tcgatttctc aaatgcgtgc aatttcgatt     1080
acaacgatct attgtcgcct tgttcggacc aaacacaaat gttctctgat gatgagattc     1140
tcaagaattc gacaccatgt aactttgctg ctgagacaaa ttatgtgtcc aacaaccaat     1200
ccagtgagga agtactagga gaatgaaagg gcgaattct                            1239
```

<210> SEQ ID NO 5
<211> LENGTH: 933
<212> TYPE: DNA
<213> ORGANISM: Trifolium affine

<400> SEQUENCE: 5

```
atggggagaa gcccttgttg tgcgaaggaa ggcttgaata gaggtgcttg acaactcaa       60 gaagacaaaa tcctcactga atacattaag ctccatggtg aaggaaaatg agaaacctt      120 ccaaaaagag caggtttaaa agatgtgga aaaagttgta gacttagatg gttgaattat      180
ctaagactag atattaagcg aggtaatata tcctcggatg aagaagaact tatcatccga      240
cttcacaaat tactcggaaa cagatggtct ctaatagccg aagacttcc aggacgaaca      300 gacaatgaaa taagaactca ctggaacaca aatttaggaa aaaggttaa ggatcttaat      360 caagaaaaca ccaacaattc ttctcctact aaactttctg ctcaactaaa aaatgcaaag      420
atcaaacaga aacagatcaa tcctaagcca atggagccaa actcaaatgt tgtccgtaca      480
aaagctacca agtgttctaa ggcattgttc ataaactcac ccccaactc accaccaatg      540 catgatttgc agaacaaagc tgaggcagag acaacaacaa agtcatcaat gccatcaatg      600
ctggttgatg gcgtggctag tgattcaatg agtaacaacg aaatggaata cggtgatgga      660
tttgtttcat tttgcgatga cgataaagaa ctatccgcag atttgctaga agattttaac      720
atctcggatg atatttgctt atccgaattt ctaaacttcg atttctcaaa tgcgtgcaat      780
ttcgattaca cgatctatt gtcgccttgt tcggaccaaa cacaaatgtt ctctgatgat      840
gagattctca gaattcgac accatgtaac tttgctgctg agacaaatta tgtgtccaac      900
aaccaatcca gtgaggaagt actaggagaa tga                                  933
```

<210> SEQ ID NO 6
<211> LENGTH: 1238
<212> TYPE: DNA
<213> ORGANISM: Trifolium affine

<400> SEQUENCE: 6

```
gaattcgccc ttatggggag aagcccttgt tgtgcaaagg aaggcttgaa tagaggtgct       60
tggacaactc aagaagacaa aatcctcact gaatacatta agctccatgg tgaaggaaaa      120
tggagaaacc ttccaaaaag agcaggttca ttcattctgt atcttacaat tatagattaa      180
ccactttcat acttttgttt tcttataaat tttcttgtat tttttcttcc attttttcatg      240 agaaatgcaa attactagta cattattatg gacatgtttt tgcaaatatg tttatgccat      300
gcaggtttaa aaagatgtgg aaaaagttgt agacttagat ggttgaatta tctaagacca      360
gatattaagc gaggtaatat atcctcggat gaagaagaac ttatcatccg acttcacaaa      420
```

```
ctactcggaa acaggtaaag tcataacata atcattaatt tattaacggt tatctataat      480
ttgttttttt gacaattatc actacaaatt taattttata atgtgcgcta atttgcttgt      540
ctttaatttg tggtagatgg tctctaatag ccggaagact tccagggcga acagacaatg      600
aaataaagaa ctactggaac acaaatttag gaaaaaggt taaggatctt aatcaagaaa       660
acaccaacaa ttcttctcct actaaacttt ctgctcaact aaaaaatgca aagatcaaac      720
agaaacagat caatcctaag ccaatggagc caaactcaaa tgttgtccgt acaaaagcta      780
ccaagtgttc taaggcattg ttcataaact cacccccccaa ctcaccacca atgcatgatt    840
tgcagaacaa agctgaggca gagacaacaa caaagtcatc aatgccatca atgctggttg     900
atggcgtggc tagtgattca atgagtaaca acgaaatgga atacggtgat ggatttgttt     960
cattttgcga tgacgataaa gaactatccg cagatttgct agaagatttt aacatctcgg    1020
atgatatttg cttatccgaa tttctaaact tcgatttctc aaatgcgtgc aatttcgatt    1080
acaacgatct attgtcgcct tgttcggacc aaacacaaat gttctctggt gatgagattc    1140
tcaagaattc gacacaatgt aactttgctg ctgacacaaa ttatgtgtcc aacaaccaat    1200
ccagtgagga agtactagga gaatgaaagg gcgaattc                            1238
```

<210> SEQ ID NO 7
<211> LENGTH: 1252
<212> TYPE: DNA
<213> ORGANISM: Trifolium occidentale

<400> SEQUENCE: 7

```
gaattcgccc ttatggggag aagcccttgt tgtgcaaagg aaggcttgaa tagaggtgct       60
tggacaactc aagaagacaa atcctcact gaatacatta agctccatgg tgaaggaaaa      120
tggagaaacc ttccaaaaag agcaggttca ttcattctag tatcttgcaa ttatagatca      180
atcactttca tactttgtt tgcttataaa ttttcttgca tttttcttc aattttccat        240
gtgaaatgca aattactagt acattattat ggatatgttt ttgcaaatat gtgtatgcca      300
tgcgaggttt aaaaagatgc ggaaaaagtt gtagacttag atggttgaat tatctaagac      360
cagatattaa gcgaggtaat atatcctcgg atgaagaaga acttatcatc agacttcaca      420
aactactcgg aaacaggtaa aagtaccgac ataatcacta acttattaac atttatctat      480
aatttgttt tttgacaat tagtactact aatttaattt tataatgtgt gctaatttgc        540
tttgccttta atttgtggta gatggtctct aatagccgga agacttccag gacgaacaga      600
caatgaaata aagaactact ggaacacaaa tttaggaaaa aaggttaagg atcttaatca     660
acaaaacacc aacaagtctt ctcctactaa actctctgct caaccaaaaa atgcaaagat      720
caaacagaaa cagatcaatc ctaagccaat gaagccaaac tcaaatgttg tccgtacaag      780
agctaccaag tgttctaagg tattgttcat aaactcactc cccaactcac caatgcatga     840
tttgcagaac aaagctgagg cagagacaac aacaaagcca tcaatgctgg ttgatggtgt     900
ggctagtgat tcaatgagta acaacgaaat ggaacacggt tatggatttt tgtcattttg     960
cgatgaagag aaagaactat ccgcagattt gctagaagat tttaacatcg cggatgatat    1020
ttgcttatct gaacttttga actctgattt ctcaaatgcg tgcaatttcg attacaatga    1080
tctattgtcm ccttgttcgg accaaactca atgttctct gatgatgaga ttctcaagaa     1140
ttggacacaa tgtaactttg ctgatgagac aaatgtgtcc aacaaccttc attcttttgc    1200
ttcctttctt gaatccagtg aggaagtact aggagaatga aagggcgaat tc            1252
```

<210> SEQ ID NO 8
<211> LENGTH: 1164
<212> TYPE: DNA
<213> ORGANISM: Trifolium occidentale

<400> SEQUENCE: 8

```
gaattcgccc ttatggggag aagcccttgt tgtgcaaagg aaggttttga tagaggtgct      60
tggacagctc atgaagacaa aatcctcact gaatacatta agctccatgg tgaaggaaaa     120
tggagaaacc ttccaaaaag agcaggttca ttcattctgt atcttactat ttatagatca     180
ataatcactt tcatgtattt ttttttcctt catttccat tagaaatgca aattaatagt      240
acattattat ggacatgttt ttccaggttt aaaaagatgt ggaaaagtt gtagacttag      300
atggttgaat tatcttagac cagatattaa gagaggtaat atatcgtccg atgaagaaga     360
acttatcatt agacttcaca aactacttgg aaaccggtaa agtatcgaca taatcactaa     420
cttactaaca tttgtttata atgtgtacta attgcgattc ctttgatttg tggtagatgg     480
tctctaatag ccggaagact tccagggcga acagacaatg aaataaaaaa ttactggaac     540
acgaatttag gaaaaaggt taaggatctt aatcaacaaa acaccaacaa ttcttctcct      600
actaaaccttt ctgctcaacc aaaaaatgca agatcaaac agaacaaca gatcaataat     660
cctaagccaa tgaagccaaa ctcgaatgtt gtccgtacaa agctaccaa atgttctaag     720
gtattgttca taaactcacc accaatgcat aatttgcaga acaaagctga ggcagagaca     780
aaaacaaaga catcaatgtt ggttaatggt gtagctagtg attcaatgag taacaacgaa     840
atggaacgag gtaatggatt tttgtcattt cgcgatgaag agaaagaact atccgctgat     900
ttgctagatg attttaacat cgcggatgac atttgcttat ccgaatttct aaactccgat     960
ttctcaaatg cgtgcaattt cgattacaat gatctattgt caccttgttc ggatcaaact    1020
caaatgttct ctgatgatga gattctcaag aattggacac aatgtaactt tgctgatgag    1080
acaaatgtgt ccaacaacct tcattctttt gcttcctttc tcgaatccag tgaggaagta    1140
ctaggagaat gaaagggcga attc                                          1164
```

<210> SEQ ID NO 9
<211> LENGTH: 1205
<212> TYPE: DNA
<213> ORGANISM: Trifolium repens

<400> SEQUENCE: 9

```
gaattcgccc ttatggggag aagcccttgt tgtgcaaaag aaggcttgaa tagaggtgct      60
tggacagctc atgaagacaa aatcctcact gaatacatta agctccatgg tgaaggaaaa     120
tggagaaacc ttccaaaaag agcaggttca ttcattctgt atcttactat tatagatcaa     180
taatcacttt cacacttttt tttttactta taaattttca tgtatttttt cttccatttt     240
ccattagaaa tgcaaattaa tagtacatta ttatggacat gttttttcaa aaatgtgtat     300
tccatgcagg tttaaaaaga tgtggaaaaa gttgtagact aaggtggttg aattatctta     360
gaccggatat taagagaggt aatatatcgt cggatgaaga agaacttatc attagacttc     420
acaaactact cggaaaccgg taaagtatcg acataatcac tgacttacta acatttgttt     480
ataatgtgtg ctaattgctc ttcctttgat ttgtggtaga tggtctctaa tagccggaag     540
acttccaggg cgaacagaca atgaaataaa gaactactgg aacacaaatt taggaaaaaa     600
agttaaggat cttaatcaac aaaacaccaa caattcttct cctactaaac cttctgctca     660
accaaaaaat gcaaatatca aacagaaaca acagatcaat cctaagccaa tgaagccaaa     720
```

```
ctcgaatgtt gtccgtacaa aagctaccaa atgttctaag gtattgttca taaactcacc    780
accaatgcat aatttgcaga acaaagctga ggcagagaca aaaacaaagc cattaatgct    840
ggttaatggt gtagctagtg attcaatgag taacaacgaa atggaacgcg gtaatggatt    900
tttgtcattt tgcgacgaag agaaagaact atccgcagat tgctagatga tttttaacat    960
cgcggatgat atttgcttat ctgaatttct aaactccgat ttctcaaatg cgtgcaattt   1020
cgattacaat gatctattgt cgccttgttc ggatcaaact caatgttct ctgatgatga    1080 gattctcaag aattggacac aatgtaactt tgctgatgag acaaatgtgt ccaacaacct   1140
taattctttt gcttcttttc tcgaatccag tgaggaagta ctaggagaat gaaagggcga   1200
attct                                                              1205
```

<210> SEQ ID NO 10
<211> LENGTH: 1202
<212> TYPE: DNA
<213> ORGANISM: Trifolium repens

<400> SEQUENCE: 10

```
gaattcgccc ttatggggag aagcccttgt tgtgcaaaag aaggcttgaa tagaggtgct     60
tggacagctc atgaagacaa atcctcact gaatacatta agctccatgg tgaaggaaaa    120
tggagaaacc ttccaaaaag agcaggttca ttcattctgt atcttactat tatagatcaa    180
taatcacttt cacactttt tttacttata aattttcatg tattttttct tccattttcc    240
attagaaatg caaattaata gtacattatt atggacatgt ttttcaaaa atgtgtattc    300 catgcaggtt taaaaagatg tggaaaaagt tgtagactaa ggtggttgaa ttatcttaga    360
ccggatatta agagaggtaa tatatcgtcg gatgaagaag aacttatcat tagacttcac    420
aaactactcg gaaccggta aagtatcgac ataatcacta acttactaac atttgtttat    480
aatgtgtgct aattgctctt cctttgattt gtggtagatg gtctctaata gccggaagac    540
ttccagggcg aacagacaat gaaataaaga actactggaa cacaaattta ggaaaaaaag    600
ttaaggatct taatcaacaa acaccaaca attcttctcc tactaaaacct tctgctcaac    660 caaaaaatgc aaatatcaaa cagaaacaac agatcaatcc taagccaatg aagccaaact    720
cgaatgttgt ccgtacaaaa gctaccaaat gttctaaggt attgttcata aactcaccac    780
caatgcataa tttgcagaac aaagctgagg cagagacaaa acaaagcca ttaatgctgg     840 ttaatggtgt agctagtgat tcaatgagta acaacgaaat ggaacgcggt aatggatttt    900
tgtcattttg cgacgaagag aaagaactat ccgcagattt gctagatgat tttaacatcg    960
cggatgatat ttgcttacct gaatttctaa actccgattt ctcaaatgcg tgcaatttcg   1020
attacaatga tctattgtcg ccttgttcgg atcaaactca atgttctct gatgatgaga    1080 ttctcaagaa ttggacacaa tgtaactttg ctgatgagac aaatgtgtcc aacaaccta    1140 attcttttgc ttcttttctc gaatccagtg aggaagtact aggagaatga aagggcgaat   1200
tc                                                                 1202
```

<210> SEQ ID NO 11
<211> LENGTH: 1203
<212> TYPE: DNA
<213> ORGANISM: Trifolium repens

<400> SEQUENCE: 11

```
gaattcgccc ttatggggag aagcccttgt tgtgcaaaag aaggcttgaa tagaggtgct     60
tggacagctc atgaagacaa atcctcact gaatacatta agctccatgg tgaaggaaaa    120
```

```
tggagaaacc ttccaaaaag agcaggttca ttcattctgt atcttactat tatagatcaa    180
tagtcacttt cacactttt tttttacttat aaattttcat gtattttttc ttccattttc    240
cattagaaat gcaaattaat agtacattat tatggacatg ttttttcaaa aatgtgtatt    300
ccatgcaggt ttaaaaagat gtggaaaaag ttgtagacta aggtggttga attatcttag    360
accggatatt aagagaggta atatatcgtc ggatgaagaa gaacttatca ttagacttca    420
caaactactc ggaaaccggt aaagtatcga cataatcact aacttactaa catttgttta    480
taatgtgtgc taattgctct tcctttgatt tgtggtagat ggtctctaat agccggaaga    540
cttccagggc gaacagacaa tgaaataaag aactactgga acacaaattt aggaaaaaaa    600
gttaaggatc ttaatcaaca aaacaccaac aattcttctc ctactaaacc ttctgctcaa    660
ccaaaaaatg caaatatcaa acagaaacaa cagatcaatc ctaagccaat gaagccaaac    720
tcgaatgttg tccgtacaaa agctaccaaa tgttctaagg tattgttcat aaactcacca    780
ccaatgcata atttgcagaa caaagctgag gcagagacaa agacaaagcc attaatgctg    840
gttaatggtg tagctagtga ttcaatgagt aacaacgaaa tggaacgcgg taatggattt    900
ttgtcatttt gcgacgaaga gaaagaacta tccgcagatt tgctagatga ttttaacatc    960
gcggatgata tttgcttatc tgaatttcta aactccgatt tctcaaatgc gtgcaatttc   1020
gattacaatg atctattgtc gccttgttcg gatcaaactc aaatgttctc tgatgatgag   1080
attctcaaga attggacaca atgtaacttt gctgatgaga caaatgtgtc caacaacctt   1140
cattcttttg cttcctttct cgaatccagt gaggaagtac taggagaatg aaagggcgaa   1200
ttc                                                                 1203
```

<210> SEQ ID NO 12
<211> LENGTH: 1206
<212> TYPE: DNA
<213> ORGANISM: Trifolium repens

<400> SEQUENCE: 12

```
gaattcgccc ttatggggag aagcccttgt tgtgcaaaag aaggcttgaa tagaggtgct     60
tggacagctc atgaggacaa aatcctcact gaatacatta agctccatgg tgaaggaaaa    120
tggagaaacc ttccaaaaag agcaggttca ttcattctgt atcttactat tatagatcaa    180
taatcacttt cactttttt ttttttact tataaatttt catgtatttt ttcttccatt    240
ttccattaga aatgcaaatt aatagtacat tattatggac atgttttttc aaaaatgtgt    300
attccatgca ggttaaaaa gatgtggaaa agttgtaga ctaaggtggt tgaattatct    360
tagaccggat attaagagag gtaatatatc gtcggatgaa gaagaactta tcattagact    420
tcacaaacta ctcggaaacc ggtaaagtat cgacataatc actaacttac taacatttgt    480
ttataatgtg tgctaattgc tcttcctttg atttgtggta gatggtctct aatagccgga    540
agacttccag gcgaacaga caatgaaata aagaactact ggaacacaaa tttaggaaaa    600
aaagttaagg atcttaatca acaaaacacc aacaattctt ctcctactaa accttctgct    660
caaccaaaaa atgcaaatat caaacagaaa caacagatca atcctaagcc aatgaagcca    720
aactcgaatg ttgtccgtac aaaagctacc aaatgttcta aggtattgtt cataaactca    780
ccaccaatgc ataatttgca gaacaaagct gaggcagaga caaaaacaaa gccattaatg    840
ctggttaatg gtgtagctag tgattcaatg agtaacaacg aaatggaacg cggtaatgga    900 ttttttgtcat tttgcgacga agagaaagaa ctatccgcag atttgctaga tgattttaac    960
```

```
atcgcggatg atatttgctt atctgaatt  ctaaactccg atttctcaaa tgcgtgcaat    1020
ttcgattaca atgatctatt gtcgccttgt tcggatcaaa ctcaaatgtt ctctgatgat    1080
gagattctca agaattggac acaatgtaac tttgctgatg agacaaatgt gtccaacaac    1140
cttaattctt tgcttctttt tctcgaatcc agtgaggaag tactaggaga atgaaagggc    1200
gaattc                                                               1206

<210> SEQ ID NO 13
<211> LENGTH: 1243
<212> TYPE: DNA
<213> ORGANISM: Trifolium arvense

<400> SEQUENCE: 13
gaattcgccc ttaagcagtg gtatcaacgc agagtacgcg ggggaagtta tttaatttta     60
tctacatcaa acacttcaag aggttggaat acaagacaga ctaattaaga ataacatcaa    120
tggggagaag cccttgttgt gcaaaggaag gcttgaatag aggtgcttgg acaactcaag    180
aagacaaaat cctcactgaa tacattaagc tccatggtga aggaaaatgg agaaaccttc    240 caaaagagc agatttaaaa agatgtggaa aagttgtag acttagatgg ttgaattatc    300
taagaccaga tattaagcga ggtaatatat ccccggatga agaagaactt attatccgac    360
ttcacaaact actcggaaac agatggtctc taatagccgg aagacttcca gggcgaacag    420
acaatgaaat aaagaactac tggaacacaa atttaggaaa aaggttaag gatcttaatc    480 aacaaaacac caacaattct tctcctacta aactttctgc tcaaccaaaa aatgcaaaga    540
tcaaacagaa acagatcaat cctaagccaa tgaagccaaa ctcaaatgtt gtccgtacaa    600
aagctaccaa gtgttctaag gtattgttca taaactcact ccccaactca ccaatgcatg    660
atttgcagaa caaagctgag gcagagacaa caacaaagcc atcaatgctg gttgatggtg    720
tggctagtga ttcaatgagt aacaacgaaa tggaacacgg ttatggattt ttgtcatttt    780
gcgatgaaga gaaagaacta tccgcagatt tgctagaaga ttttaacatc gcggatgata    840
tttgcttatc tgaactttg aactctgatt tctcaaatgc gtgcaatttc gattacaatg    900
atctattgtc accttgttcg gaccaaactc aaatgttctc tgatgatgag attctcaaga    960
attggacaca atgtaacttt gctgatgaga caaatgtgtc caacaacctt cattcttttg    1020
cttcctttct tgaatccagt gaggaagtac taggagaatg ataataaaaa ttcattttcc    1080
aataaaatta actactctag gtttttttt tttttttta atttcaattt catgttaggg    1140
tggtttaata aataaatata ttctatggtt taatattgca aaaaaaaaa aaaaaaaaa    1200 aaaagtact ctgcgttgat accactgctt aagggcgaat tcc                     1243

<210> SEQ ID NO 14
<211> LENGTH: 313
<212> TYPE: PRT
<213> ORGANISM: Trifolium arvense

<400> SEQUENCE: 14

Met Gly Arg Ser Pro Cys Cys Ala Lys Glu Gly Leu Asn Arg Gly Ala
1               5                   10                  15

Trp Thr Thr Gln Glu Asp Lys Ile Leu Thr Glu Tyr Ile Lys Leu His
            20                  25                  30

Gly Glu Gly Lys Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
    50                  55                  60
```

```
Ile Lys Arg Gly Asn Ile Ser Ser Asp Glu Glu Leu Ile Ile Arg
 65                  70                  75                  80

Leu His Lys Leu Leu Gly Asn Arg Trp Ser Leu Ile Ala Gly Arg Leu
                 85                  90                  95

Pro Gly Arg Thr Asp Asn Glu Ile Lys Asn Tyr Trp Asn Thr Asn Leu
            100                 105                 110

Gly Lys Lys Val Lys Asp Leu Asn Gln Gln Asn Thr Asn Asn Ser Ser
        115                 120                 125

Pro Thr Lys Leu Ser Ala Gln Pro Lys Asn Ala Lys Ile Lys Gln Lys
    130                 135                 140

Gln Ile Asn Pro Lys Pro Met Lys Pro Asn Ser Asn Val Val Arg Thr
145                 150                 155                 160

Lys Ala Thr Lys Cys Ser Lys Val Leu Phe Ile Asn Ser Leu Pro Asn
                165                 170                 175

Ser Pro Met His Asp Leu Gln Asn Lys Ala Glu Ala Glu Thr Thr Thr
            180                 185                 190

Lys Pro Ser Met Leu Val Asp Gly Val Ala Ser Asp Ser Met Ser Asn
        195                 200                 205

Asn Glu Met Glu His Gly Tyr Gly Phe Leu Ser Phe Cys Asp Glu Glu
    210                 215                 220

Lys Glu Leu Ser Ala Asp Leu Leu Gly Asp Phe Asn Ile Ala Asp Asp
225                 230                 235                 240

Ile Cys Leu Ser Glu Leu Leu Asn Ser Asp Phe Ser Asn Ala Cys Asn
                245                 250                 255

Phe Asp Tyr Asn Asp Leu Leu Ser Pro Cys Ser Asp Gln Thr Gln Met
            260                 265                 270

Phe Ser Asp Asp Glu Ile Leu Lys Asn Trp Thr Gln Cys Asn Phe Ala
        275                 280                 285

Asp Glu Thr Asn Val Ser Asn Asn Leu His Ser Phe Ala Ser Phe Leu
    290                 295                 300

Glu Ser Ser Glu Glu Val Leu Gly Glu
305                 310

<210> SEQ ID NO 15
<211> LENGTH: 7
<212> TYPE: PRT
<213> ORGANISM: Artificial
<220> FEATURE:
<223> OTHER INFORMATION: Motif

<400> SEQUENCE: 15

Asp Asp Glu Ile Leu Lys Asn
1               5

<210> SEQ ID NO 16
<211> LENGTH: 7
<212> TYPE: PRT
<213> ORGANISM: Artificial
<220> FEATURE:
<223> OTHER INFORMATION: Motif

<400> SEQUENCE: 16

Lys Pro Arg Pro Arg Ser Thr
1               5

<210> SEQ ID NO 17
<211> LENGTH: 12
<212> TYPE: PRT
```

```
<213> ORGANISM: Artificial
<220> FEATURE:
<223> OTHER INFORMATION: Motif
<220> FEATURE:
<221> NAME/KEY: MISC_FEATURE
<222> LOCATION: (1)..(1)
<223> OTHER INFORMATION: Xaa can be Asn, Tyr or His
<220> FEATURE:
<221> NAME/KEY: MISC_FEATURE
<222> LOCATION: (6)..(6)
<223> OTHER INFORMATION: Xaa can be Lys or Arg
<220> FEATURE:
<221> NAME/KEY: MISC_FEATURE
<222> LOCATION: (8)..(8)
<223> OTHER INFORMATION: Xaa can be Ile or Thr

<400> SEQUENCE: 17

Xaa Val Val Arg Thr Xaa Ala Xaa Lys Cys Ser Lys
1               5                   10

<210> SEQ ID NO 18
<211> LENGTH: 24
<212> TYPE: DNA
<213> ORGANISM: Artificial
<220> FEATURE:
<223> OTHER INFORMATION: Primer sequence

<400> SEQUENCE: 18
gacaatgaga taaagaatta cttg                                            24

<210> SEQ ID NO 19
<211> LENGTH: 21
<212> TYPE: DNA
<213> ORGANISM: Artificial
<220> FEATURE:
<223> OTHER INFORMATION: Primer sequence

<400> SEQUENCE: 19
aagagttgta gacttagmtg g                                               21

<210> SEQ ID NO 20
<211> LENGTH: 17
<212> TYPE: DNA
<213> ORGANISM: Artificial
<220> FEATURE:
<223> OTHER INFORMATION: Primer sequence

<400> SEQUENCE: 20
ytkggsaaca ggttgtc                                                    17

<210> SEQ ID NO 21
<211> LENGTH: 23
<212> TYPE: DNA
<213> ORGANISM: Artificial
<220> FEATURE:
<223> OTHER INFORMATION: Primer sequence

<400> SEQUENCE: 21
atggggagaa gcccttgttg tgc                                             23

<210> SEQ ID NO 22
<211> LENGTH: 26
<212> TYPE: DNA
<213> ORGANISM: Artificial
<220> FEATURE:
<223> OTHER INFORMATION: Primer sequence

<400> SEQUENCE: 22
```
tcattctcct agtacttcct cactgg                                              26

<210> SEQ ID NO 23
<211> LENGTH: 21
<212> TYPE: DNA
<213> ORGANISM: Artificial
<220> FEATURE:
<223> OTHER INFORMATION: Primer sequence

<400> SEQUENCE: 23 ctcttttgg aaggtttctc c                                                    21

<210> SEQ ID NO 24
<211> LENGTH: 23
<212> TYPE: DNA
<213> ORGANISM: Artificial
<220> FEATURE:
<223> OTHER INFORMATION: Primer sequence

<400> SEQUENCE: 24
ttctccattt ccttcacca tgg                                                  23

<210> SEQ ID NO 25
<211> LENGTH: 22
<212> TYPE: DNA
<213> ORGANISM: Artificial
<220> FEATURE:
<223> OTHER INFORMATION: Primer sequence

<400> SEQUENCE: 25
tccaagcacc tctattcaag cc                                                  22

<210> SEQ ID NO 26
<211> LENGTH: 31
<212> TYPE: DNA
<213> ORGANISM: Artificial
<220> FEATURE:
<223> OTHER INFORMATION: Primer sequence

<400> SEQUENCE: 26
ctcgagatgc aatgctggtt gatggtgtgg c                                        31

<210> SEQ ID NO 27
<211> LENGTH: 23
<212> TYPE: DNA
<213> ORGANISM: Artificial
<220> FEATURE:
<223> OTHER INFORMATION: Primer sequence

<400> SEQUENCE: 27
cattgcctgt agattctgta gcc                                                 23

<210> SEQ ID NO 28
<211> LENGTH: 22
<212> TYPE: DNA
<213> ORGANISM: Artificial
<220> FEATURE:
<223> OTHER INFORMATION: Primer sequence

<400> SEQUENCE: 28
tgaagattgt tggacacatt gg                                                  22

<210> SEQ ID NO 29
<211> LENGTH: 21
<212> TYPE: DNA
<213> ORGANISM: Artificial

```
<220> FEATURE:
<223> OTHER INFORMATION: Primer sequence

<400> SEQUENCE: 29
aggttggaat acaagacaga c                                              21

<210> SEQ ID NO 30
<211> LENGTH: 22
<212> TYPE: DNA
<213> ORGANISM: Artificial
<220> FEATURE:
<223> OTHER INFORMATION: Primer sequence

<400> SEQUENCE: 30
tctcctagta cttcctcact gg                                             22

<210> SEQ ID NO 31
<211> LENGTH: 23
<212> TYPE: DNA
<213> ORGANISM: Artificial
<220> FEATURE:
<223> OTHER INFORMATION: Primer sequence

<400> SEQUENCE: 31
ataatcatac taattaacat cac                                            23

<210> SEQ ID NO 32
<211> LENGTH: 20
<212> TYPE: DNA
<213> ORGANISM: Artificial
<220> FEATURE:
<223> OTHER INFORMATION: Primer sequence

<400> SEQUENCE: 32
tgatagatca tgtcattgtg                                                20

<210> SEQ ID NO 33
<211> LENGTH: 23
<212> TYPE: DNA
<213> ORGANISM: Artificial
<220> FEATURE:
<223> OTHER INFORMATION: Primer sequence

<400> SEQUENCE: 33
gccttccttt gcacaacaag ggc                                            23

<210> SEQ ID NO 34
<211> LENGTH: 21
<212> TYPE: DNA
<213> ORGANISM: Artificial
<220> FEATURE:
<223> OTHER INFORMATION: Primer sequence

<400> SEQUENCE: 34
gcacaacaag ggcttctccc c                                              21

<210> SEQ ID NO 35
<211> LENGTH: 23
<212> TYPE: DNA
<213> ORGANISM: Artificial
<220> FEATURE:
<223> OTHER INFORMATION: Primer sequence

<400> SEQUENCE: 35
atggggagaa gcccttgttg tgc                                            23
```

<210> SEQ ID NO 36
<211> LENGTH: 22
<212> TYPE: DNA
<213> ORGANISM: Artificial
<220> FEATURE:
<223> OTHER INFORMATION: Primer sequence

<400> SEQUENCE: 36
tctcctagta cttcctcact gg                                          22

<210> SEQ ID NO 37
<211> LENGTH: 28
<212> TYPE: DNA
<213> ORGANISM: Artificial
<220> FEATURE:
<223> OTHER INFORMATION: Primer sequence

<400> SEQUENCE: 37
ctcgagcaat gctggttgat ggtgtggc                                    28

<210> SEQ ID NO 38
<211> LENGTH: 27
<212> TYPE: DNA
<213> ORGANISM: Artificial
<220> FEATURE:
<223> OTHER INFORMATION: Primer sequence

<400> SEQUENCE: 38
tctagaggac acatttgtct catcagc                                     27

<210> SEQ ID NO 39
<211> LENGTH: 27
<212> TYPE: DNA
<213> ORGANISM: Artificial
<220> FEATURE:
<223> OTHER INFORMATION: Primer sequence

<400> SEQUENCE: 39
tctagattga gtttggtccg aacaagg                                     27

<210> SEQ ID NO 40
<211> LENGTH: 27
<212> TYPE: DNA
<213> ORGANISM: Artificial
<220> FEATURE:
<223> OTHER INFORMATION: Primer sequence

<400> SEQUENCE: 40
tctagaaatc ttctagcaaa tctgcgg                                     27

<210> SEQ ID NO 41
<211> LENGTH: 16
<212> TYPE: DNA
<213> ORGANISM: Artificial
<220> FEATURE:
<223> OTHER INFORMATION: Primer sequence

<400> SEQUENCE: 41
gtaaaacgac ggccag                                                 16

<210> SEQ ID NO 42
<211> LENGTH: 17
<212> TYPE: DNA
<213> ORGANISM: Artificial
<220> FEATURE:
<223> OTHER INFORMATION: Primer sequence

<400> SEQUENCE: 42
caggaaacag ctatgac                                                      17

<210> SEQ ID NO 43
<211> LENGTH: 30
<212> TYPE: DNA
<213> ORGANISM: Artificial
<220> FEATURE:
<223> OTHER INFORMATION: Primer sequence

<400> SEQUENCE: 43
aagcagtggt atcaacgcag agtacgcggg                                        30

<210> SEQ ID NO 44
<211> LENGTH: 28
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (28)..(28)
<223> OTHER INFORMATION: n is a, c, g, or t

<400> SEQUENCE: 44
aagcagtggt atcaacgcag agtactvn                                          28

<210> SEQ ID NO 45
<211> LENGTH: 23
<212> TYPE: DNA
<213> ORGANISM: Artificial
<220> FEATURE:
<223> OTHER INFORMATION: Primer sequence

<400> SEQUENCE: 45
aagcagtggt atcaacgcag agt                                               23

<210> SEQ ID NO 46
<211> LENGTH: 316
<212> TYPE: PRT
<213> ORGANISM: Trifolium arvense

<400> SEQUENCE: 46

Met Gly Arg Ser Pro Cys Cys Ala Lys Glu Gly Leu Asn Arg Gly Ala
1               5                   10                  15

Trp Thr Thr Gln Glu Asp Lys Ile Leu Thr Glu Tyr Ile Lys Leu His
            20                  25                  30

Gly Glu Gly Lys Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser Pro Asp Glu Glu Leu Ile Ile Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Asn Leu
            100                 105                 110

Gly Lys Lys Val Lys Asp Leu Asp Gln Gln Asn Thr Asn Asn Ser Ser
        115                 120                 125

Pro Thr Lys Leu Ser Ala Gln Pro Lys Asn Ala Glu Ile Lys Gln Lys
    130                 135                 140

```
Gln Ile Asn Pro Lys Pro Asn Ser Tyr Val Val Arg Thr Lys Ala Thr
145                 150                 155                 160

Lys Cys Ser Lys Val Leu Phe Ile Asn Ser Pro Asn Ser Pro Pro
            165                 170                 175

Met His Asp Leu Gln Ser Lys Ala Glu Ala Glu Thr Thr Thr Thr
            180                 185                 190

Lys Pro Ser Met Pro Ser Met Leu Val Asp Gly Val Ala Ser Asp Ser
            195                 200                 205

Met Ser Asn Asn Glu Met Glu Cys Gly Asn Gly Phe Leu Ser Phe Cys
210                 215                 220

Asp Glu Glu Lys Glu Leu Ser Ala Asp Leu Leu Glu Asp Phe Asn Ile
225                 230                 235                 240

Ala Asp Asp Ile Cys Leu Ser Glu Phe Leu Asn Phe Asp Phe Ser Asn
                245                 250                 255

Ala Cys Asp Ile Asp Tyr Asn Asp Leu Leu Ser Pro Cys Ser Asp Gln
                260                 265                 270

Thr Gln Met Phe Pro Asp Asp Glu Ile Leu Lys Asn Trp Thr Gln Cys
            275                 280                 285

Asn Phe Ala Asp Glu Thr Asn Val Ser Asn Asn Leu Gln Ser Ser Ala
            290                 295                 300

Ser Phe Leu Glu Ser Ser Glu Glu Val Leu Gly Glu
305                 310                 315

<210> SEQ ID NO 47
<211> LENGTH: 310
<212> TYPE: PRT
<213> ORGANISM: Trifolium affine

<400> SEQUENCE: 47

Met Gly Arg Ser Pro Cys Cys Ala Lys Glu Gly Leu Asn Arg Gly Ala
1               5                   10                  15

Trp Thr Thr Gln Glu Asp Lys Ile Leu Thr Glu Tyr Ile Lys Leu His
                20                  25                  30

Gly Glu Gly Lys Trp Arg Asn Leu Pro Lys Arg Ala Gly Leu Lys Arg
            35                  40                  45

Cys Gly Lys Ser Cys Arg Leu Arg Trp Leu Asn Tyr Leu Arg Leu Asp
50                  55                  60

Ile Lys Arg Gly Asn Ile Ser Ser Asp Glu Glu Leu Ile Ile Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Asn Leu
            100                 105                 110

Gly Lys Lys Val Lys Asp Leu Asn Gln Glu Asn Thr Asn Asn Ser Ser
            115                 120                 125

Pro Thr Lys Leu Ser Ala Gln Leu Lys Asn Ala Lys Ile Lys Gln Lys
        130                 135                 140

Gln Ile Asn Pro Lys Pro Met Glu Pro Asn Ser Asn Val Val Arg Thr
145                 150                 155                 160

Lys Ala Thr Lys Cys Ser Lys Ala Leu Phe Ile Asn Ser Pro Pro Asn
                165                 170                 175

Ser Pro Pro Met His Asp Leu Gln Asn Lys Ala Glu Ala Glu Thr Thr
            180                 185                 190

Thr Lys Ser Ser Met Pro Ser Met Leu Val Asp Gly Val Ala Ser Asp
```

```
            195                 200                 205
Ser Met Ser Asn Asn Glu Met Glu Tyr Gly Asp Gly Phe Val Ser Phe
210                 215                 220

Cys Asp Asp Lys Glu Leu Ser Ala Asp Leu Leu Glu Asp Phe Asn
225                 230                 235                 240

Ile Ser Asp Asp Ile Cys Leu Ser Glu Phe Leu Asn Phe Asp Phe Ser
                    245                 250                 255

Asn Ala Cys Asn Phe Asp Tyr Asn Asp Leu Leu Ser Pro Cys Ser Asp
                260                 265                 270

Gln Thr Gln Met Phe Ser Asp Asp Glu Ile Leu Lys Asn Ser Thr Pro
                275                 280                 285

Cys Asn Phe Ala Ala Glu Thr Asn Tyr Val Ser Asn Asn Gln Ser Ser
290                 295                 300

Glu Glu Val Leu Gly Glu
305                 310

<210> SEQ ID NO 48
<211> LENGTH: 296
<212> TYPE: PRT
<213> ORGANISM: Trifolium affine

<400> SEQUENCE: 48

Met Gly Arg Ser Pro Cys Cys Ala Lys Glu Gly Leu Asn Arg Gly Ala
1               5                   10                  15

Trp Thr Thr Gln Glu Asp Lys Ile Leu Thr Glu Tyr Ile Lys Leu His
                20                  25                  30

Gly Glu Gly Lys Trp Arg Asn Leu Pro Lys Arg Ala Gly Leu Lys Arg
            35                  40                  45

Cys Gly Lys Ser Cys Arg Leu Arg Trp Leu Asn Tyr Leu Arg Pro Asp
50                  55                  60

Ile Lys Arg Gly Asn Ile Ser Ser Asp Glu Glu Leu Ile Ile Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Asn Leu
            100                 105                 110

Gly Lys Lys Val Lys Asp Leu Asn Gln Glu Asn Thr Asn Asn Ser Ser
        115                 120                 125

Pro Thr Lys Leu Ser Ala Gln Leu Lys Asn Ala Lys Ile Lys Gln Lys
130                 135                 140

Gln Ile Asn Pro Lys Pro Met Glu Pro Asn Ser Asn Val Val Arg Thr
145                 150                 155                 160

Lys Ala Thr Lys Cys Ser Lys Ala Leu Phe Ile Asn Ser Pro Pro Asn
                165                 170                 175

Ser Pro Pro Met His Asp Leu Gln Asn Lys Ala Glu Ala Glu Thr Thr
            180                 185                 190

Thr Lys Ser Ser Met Pro Ser Met Leu Val Asp Gly Val Ala Ser Asp
        195                 200                 205

Ser Met Ser Asn Asn Glu Met Glu Tyr Gly Asp Gly Phe Val Ser Phe
210                 215                 220

Cys Asp Asp Lys Glu Leu Ser Ala Asp Leu Leu Glu Asp Phe Asn
225                 230                 235                 240

Ile Ser Asp Asp Ile Cys Leu Ser Glu Phe Leu Asn Phe Asp Phe Ser
                    245                 250                 255
```

```
Asn Ala Cys Asn Phe Asp Tyr Asn Asp Leu Leu Ser Pro Cys Ser Asp
            260                 265                 270

Gln Thr Gln Met Phe Ser Asp Asp Glu Ile Leu Lys Asn Ser Thr Gln
        275                 280                 285

Cys Asn Phe Ala Ala Glu Thr Asn
    290                 295

<210> SEQ ID NO 49
<211> LENGTH: 313
<212> TYPE: PRT
<213> ORGANISM: Trifolium occidentale

<400> SEQUENCE: 49

Met Gly Arg Ser Pro Cys Cys Ala Lys Glu Gly Leu Asn Arg Gly Ala
1               5                   10                  15

Trp Thr Thr Gln Glu Asp Lys Ile Leu Thr Glu Tyr Ile Lys Leu His
            20                  25                  30

Gly Glu Gly Lys Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser Ser Asp Glu Glu Leu Ile Ile Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Asn Leu
            100                 105                 110

Gly Lys Lys Val Lys Asp Leu Asn Gln Gln Asn Thr Asn Lys Ser Ser
        115                 120                 125

Pro Thr Lys Leu Ser Ala Gln Pro Lys Asn Ala Lys Ile Lys Gln Lys
    130                 135                 140

Gln Ile Asn Pro Lys Pro Met Lys Pro Asn Ser Asn Val Val Arg Thr
145                 150                 155                 160

Arg Ala Thr Lys Cys Ser Lys Val Leu Phe Ile Asn Ser Leu Pro Asn
                165                 170                 175

Ser Pro Met His Asp Leu Gln Asn Lys Ala Glu Ala Glu Thr Thr Thr
            180                 185                 190

Lys Pro Ser Met Leu Val Asp Gly Val Ala Ser Asp Ser Met Ser Asn
        195                 200                 205

Asn Glu Met Glu His Gly Tyr Gly Phe Leu Ser Phe Cys Asp Glu Glu
    210                 215                 220

Lys Glu Leu Ser Ala Asp Leu Leu Glu Asp Phe Asn Ile Ala Asp Asp
225                 230                 235                 240

Ile Cys Leu Ser Glu Leu Leu Asn Ser Asp Phe Ser Asn Ala Cys Asn
                245                 250                 255

Phe Asp Tyr Asn Asp Leu Leu Ser Pro Cys Ser Asp Gln Thr Gln Met
            260                 265                 270

Phe Ser Asp Asp Glu Ile Leu Lys Asn Trp Thr Gln Cys Asn Phe Ala
        275                 280                 285

Asp Glu Thr Asn Val Ser Asn Asn Leu His Ser Phe Ala Ser Phe Leu
    290                 295                 300

Glu Ser Ser Glu Glu Val Leu Gly Glu
305                 310

<210> SEQ ID NO 50
```

-continued

```
<211> LENGTH: 312
<212> TYPE: PRT
<213> ORGANISM: Trifolium occidentale

<400> SEQUENCE: 50

Met Gly Arg Ser Pro Cys Cys Ala Lys Glu Gly Leu Asn Arg Gly Ala
1               5                   10                  15

Trp Thr Ala His Glu Asp Lys Ile Leu Thr Glu Tyr Ile Lys Leu His
            20                  25                  30

Gly Glu Gly Lys Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
50                  55                  60

Ile Lys Arg Gly Asn Ile Ser Ser Asp Glu Glu Leu Ile Ile Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Asn Leu
            100                 105                 110

Gly Lys Lys Val Lys Asp Leu Asn Gln Gln Asn Thr Asn Asn Ser Ser
        115                 120                 125

Pro Thr Lys Pro Ser Ala Gln Pro Lys Asn Ala Lys Ile Lys Gln Lys
    130                 135                 140

Gln Gln Ile Asn Asn Pro Lys Pro Met Lys Pro Asn Ser Asn Val Val
145                 150                 155                 160

Arg Thr Lys Ala Thr Lys Cys Ser Lys Val Leu Phe Ile Asn Ser Pro
                165                 170                 175

Pro Met His Asn Leu Gln Asn Lys Ala Glu Ala Glu Thr Lys Thr Lys
            180                 185                 190

Thr Ser Met Leu Val Asn Gly Val Ala Ser Asp Ser Met Ser Asn Asn
        195                 200                 205

Glu Met Glu Arg Gly Asn Gly Phe Leu Ser Phe Arg Asp Glu Glu Lys
    210                 215                 220

Glu Leu Ser Ala Asp Leu Leu Asp Asp Phe Asn Ile Ala Asp Asp Ile
225                 230                 235                 240

Cys Leu Ser Glu Phe Leu Asn Ser Asp Phe Ser Asn Ala Cys Asn Phe
                245                 250                 255

Asp Tyr Asn Asp Leu Leu Ser Pro Cys Ser Asp Gln Thr Gln Met Phe
            260                 265                 270

Ser Asp Asp Glu Ile Leu Lys Asn Trp Thr Gln Cys Asn Phe Ala Asp
        275                 280                 285

Glu Thr Asn Val Ser Asn Asn Leu His Ser Phe Ala Ser Phe Leu Glu
    290                 295                 300

Ser Ser Glu Glu Val Leu Gly Glu
305                 310

<210> SEQ ID NO 51
<211> LENGTH: 311
<212> TYPE: PRT
<213> ORGANISM: Trifolium repens

<400> SEQUENCE: 51

Met Gly Arg Ser Pro Cys Cys Ala Lys Glu Gly Leu Asn Arg Gly Ala
1               5                   10                  15

Trp Thr Ala His Glu Asp Lys Ile Leu Thr Glu Tyr Ile Lys Leu His
            20                  25                  30
```

```
Gly Glu Gly Lys Trp Arg Asn Leu Pro Lys Arg Ala Gly Leu Lys Arg
            35                  40                  45

Cys Gly Lys Ser Cys Arg Leu Arg Trp Leu Asn Tyr Leu Arg Pro Asp
         50                  55                  60

Ile Lys Arg Gly Asn Ile Ser Ser Asp Glu Glu Leu Ile Ile Arg
 65                  70                  75                  80

Leu His Lys Leu Leu Gly Asn Arg Trp Ser Leu Ile Ala Gly Arg Leu
                     85                  90                  95

Pro Gly Arg Thr Asp Asn Glu Ile Lys Asn Tyr Trp Asn Thr Asn Leu
                100                 105                 110

Gly Lys Lys Val Lys Asp Leu Asn Gln Gln Asn Thr Asn Ser Ser
             115                 120                 125

Pro Thr Lys Pro Ser Ala Gln Pro Lys Asn Ala Asn Ile Lys Gln Lys
         130                 135                 140

Gln Gln Ile Asn Pro Lys Pro Met Lys Pro Asn Ser Asn Val Val Arg
145                 150                 155                 160

Thr Lys Ala Thr Lys Cys Ser Lys Val Leu Phe Ile Asn Ser Pro Pro
                165                 170                 175

Met His Asn Leu Gln Asn Lys Ala Glu Ala Glu Thr Lys Thr Lys Pro
             180                 185                 190

Leu Met Leu Val Asn Gly Val Ala Ser Asp Ser Met Ser Asn Asn Glu
         195                 200                 205

Met Glu Arg Gly Asn Gly Phe Leu Ser Phe Cys Asp Glu Lys Glu
210                 215                 220

Leu Ser Ala Asp Leu Leu Asp Asp Phe Asn Ile Ala Asp Ile Cys
225                 230                 235                 240

Leu Ser Glu Phe Leu Asn Ser Asp Phe Ser Asn Ala Cys Asn Phe Asp
                245                 250                 255

Tyr Asn Asp Leu Leu Ser Pro Cys Ser Asp Gln Thr Gln Met Phe Ser
             260                 265                 270

Asp Asp Glu Ile Leu Lys Asn Trp Thr Gln Cys Asn Phe Ala Asp Glu
         275                 280                 285

Thr Asn Val Ser Asn Asn Leu Asn Ser Phe Ala Ser Phe Leu Glu Ser
     290                 295                 300

Ser Glu Glu Val Leu Gly Glu
305                 310

<210> SEQ ID NO 52
<211> LENGTH: 311
<212> TYPE: PRT
<213> ORGANISM: Trifolium repens

<400> SEQUENCE: 52

Met Gly Arg Ser Pro Cys Cys Ala Lys Glu Gly Leu Asn Arg Gly Ala
 1               5                  10                  15

Trp Thr Ala His Glu Asp Lys Ile Leu Thr Glu Tyr Ile Lys Leu His
             20                  25                  30

Gly Glu Gly Lys Trp Arg Asn Leu Pro Lys Arg Ala Gly Leu Lys Arg
            35                  40                  45

Cys Gly Lys Ser Cys Arg Leu Arg Trp Leu Asn Tyr Leu Arg Pro Asp
         50                  55                  60

Ile Lys Arg Gly Asn Ile Ser Ser Asp Glu Glu Leu Ile Ile Arg
 65                  70                  75                  80

Leu His Lys Leu Leu Gly Asn Arg Trp Ser Leu Ile Ala Gly Arg Leu
```

85                  90                  95
Pro Gly Arg Thr Asp Asn Glu Ile Lys Asn Tyr Trp Asn Thr Asn Leu
            100                 105                 110

Gly Lys Lys Val Lys Asp Leu Asn Gln Gln Asn Thr Asn Asn Ser Ser
        115                 120                 125

Pro Thr Lys Pro Ser Ala Gln Pro Lys Asn Ala Asn Ile Lys Gln Lys
    130                 135                 140

Gln Gln Ile Asn Pro Lys Pro Met Lys Pro Asn Ser Asn Val Val Arg
145                 150                 155                 160

Thr Lys Ala Thr Lys Cys Ser Lys Val Leu Phe Ile Asn Ser Pro Pro
                165                 170                 175

Met His Asn Leu Gln Asn Lys Ala Glu Ala Glu Thr Lys Thr Lys Pro
            180                 185                 190

Leu Met Leu Val Asn Gly Val Ala Ser Asp Ser Met Ser Asn Asn Glu
        195                 200                 205

Met Glu Arg Gly Asn Gly Phe Leu Ser Phe Cys Asp Glu Lys Glu
    210                 215                 220

Leu Ser Ala Asp Leu Leu Asp Asp Phe Asn Ile Ala Asp Asp Ile Cys
225                 230                 235                 240

Leu Pro Glu Phe Leu Asn Ser Asp Phe Ser Asn Ala Cys Asn Phe Asp
                245                 250                 255

Tyr Asn Asp Leu Leu Ser Pro Cys Ser Asp Gln Thr Gln Met Phe Ser
            260                 265                 270

Asp Asp Glu Ile Leu Lys Asn Trp Thr Gln Cys Asn Phe Ala Asp Glu
        275                 280                 285

Thr Asn Val Ser Asn Asn Leu Asn Ser Phe Ala Ser Phe Leu Glu Ser
    290                 295                 300

Ser Glu Glu Val Leu Gly Glu
305                 310

<210> SEQ ID NO 53
<211> LENGTH: 311
<212> TYPE: PRT
<213> ORGANISM: Trifolium repens

<400> SEQUENCE: 53

Met Gly Arg Ser Pro Cys Cys Ala Lys Glu Gly Leu Asn Arg Gly Ala
1               5                   10                  15

Trp Thr Ala His Glu Asp Lys Ile Leu Thr Glu Tyr Ile Lys Leu His
            20                  25                  30

Gly Glu Gly Lys Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser Ser Asp Glu Glu Leu Ile Ile Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Asn Leu
            100                 105                 110

Gly Lys Lys Val Lys Asp Leu Asn Gln Gln Asn Thr Asn Asn Ser Ser
        115                 120                 125

Pro Thr Lys Pro Ser Ala Gln Pro Lys Asn Ala Asn Ile Lys Gln Lys
    130                 135                 140

```
Gln Gln Ile Asn Pro Lys Pro Met Lys Pro Asn Ser Asn Val Val Arg
145                 150                 155                 160

Thr Lys Ala Thr Lys Cys Ser Lys Val Leu Phe Ile Asn Ser Pro Pro
            165                 170                 175

Met His Asn Leu Gln Asn Lys Ala Glu Ala Glu Thr Lys Thr Lys Pro
        180                 185                 190

Leu Met Leu Val Asn Gly Val Ala Ser Asp Ser Met Ser Asn Asn Glu
    195                 200                 205

Met Glu Arg Gly Asn Gly Phe Leu Ser Phe Cys Asp Glu Glu Lys Glu
210                 215                 220

Leu Ser Ala Asp Leu Leu Asp Asp Phe Asn Ile Ala Asp Asp Ile Cys
225                 230                 235                 240

Leu Ser Glu Phe Leu Asn Ser Asp Phe Ser Asn Ala Cys Asn Phe Asp
            245                 250                 255

Tyr Asn Asp Leu Leu Ser Pro Cys Ser Asp Gln Thr Gln Met Phe Ser
        260                 265                 270

Asp Asp Glu Ile Leu Lys Asn Trp Thr Gln Cys Asn Phe Ala Asp Glu
    275                 280                 285

Thr Asn Val Ser Asn Asn Leu His Ser Phe Ala Ser Phe Leu Glu Ser
290                 295                 300

Ser Glu Glu Val Leu Gly Glu
305                 310

<210> SEQ ID NO 54
<211> LENGTH: 311
<212> TYPE: PRT
<213> ORGANISM: Trifolium repens

<400> SEQUENCE: 54

Met Gly Arg Ser Pro Cys Cys Ala Lys Glu Gly Leu Asn Arg Gly Ala
1               5                   10                  15

Trp Thr Ala His Glu Asp Lys Ile Leu Thr Glu Tyr Ile Lys Leu His
            20                  25                  30

Gly Glu Gly Lys Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser Ser Asp Glu Glu Leu Ile Ile Arg
65                  70                  75                  80

Leu His Lys Leu Leu Gly Asn Arg Trp Ser Leu Ile Ala Gly Arg Leu
            85                  90                  95

Pro Gly Arg Thr Asp Asn Glu Ile Lys Asn Tyr Trp Asn Thr Asn Leu
        100                 105                 110

Gly Lys Lys Val Lys Asp Leu Asn Gln Gln Asn Thr Asn Asn Ser Ser
    115                 120                 125

Pro Thr Lys Pro Ser Ala Gln Pro Lys Asn Ala Asn Ile Lys Gln Lys
130                 135                 140

Gln Gln Ile Asn Pro Lys Pro Met Lys Pro Asn Ser Asn Val Val Arg
145                 150                 155                 160

Thr Lys Ala Thr Lys Cys Ser Lys Val Leu Phe Ile Asn Ser Pro Pro
            165                 170                 175

Met His Asn Leu Gln Asn Lys Ala Glu Ala Glu Thr Lys Thr Lys Pro
        180                 185                 190

Leu Met Leu Val Asn Gly Val Ala Ser Asp Ser Met Ser Asn Asn Glu
    195                 200                 205
```

```
Met Glu Arg Gly Asn Gly Phe Leu Ser Phe Cys Asp Glu Lys Glu
    210                 215                 220
Leu Ser Ala Asp Leu Leu Asp Asp Phe Asn Ile Ala Asp Ile Cys
225                 230                 235                 240
Leu Ser Glu Phe Leu Asn Ser Asp Phe Ser Asn Ala Cys Asn Phe Asp
                245                 250                 255
Tyr Asn Asp Leu Leu Ser Pro Cys Ser Asp Gln Thr Gln Met Phe Ser
            260                 265                 270
Asp Asp Glu Ile Leu Lys Asn Trp Thr Gln Cys Asn Phe Ala Asp Glu
        275                 280                 285
Thr Asn Val Ser Asn Asn Leu His Ser Phe Ala Ser Phe Leu Glu Ser
    290                 295                 300
Ser Glu Glu Val Leu Gly Glu
305                 310
```

<210> SEQ ID NO 55
<211> LENGTH: 942
<212> TYPE: DNA
<213> ORGANISM: Trifolium arvense

<400> SEQUENCE: 55

```
atggggagaa gcccttgttg tgcaaaggaa ggcttgaata gaggtgcttg gacaactcaa      60
gaagacaaaa tcctcactga atacattaag ctccatggtg aaggaaaatg gagaaacctt     120
ccaaaaagag caggtttaaa aagatgcgga aaaagttgta gacttagatg gttgaattat     180
ctaagaccag atattaagcg aggtaatata tcctcggatg aagaagaact tatcatcaga     240
cttcacaaac tactcggaaa cagatggtct ctaatagccg gaagacttcc aggacgaaca     300
gacaatgaaa taagaactac tggaacacaa aatttaggaa aaaaggttaa ggatcttaat     360
caacaaaaca ccaacaattc ttctcctact aaactctctg ctcaaccaaa aaatgcaaag     420
atcaaacaga aacagatcaa tcctaagcca atgaagccaa actcaaatgt tgtccgtaca     480
aaagctacca agtgttctaa ggtattgttc ataaactcac tccccaactc accaatgcat     540
gatttgcaga acaaagctga ggcagagaca acaacaaagc catcaatgct ggttgatggt     600
gtggctagtg attcaatgag taacaacgaa atggaacacg ttatggatt tttgtcattt      660
tgcgatgaag agaaagaact atccgcagat ttgctagaag attttaacat cgcggatgat     720
atttgcttat ctgaactttt gaactctgat ttctcaaatg cgtgcaattt cgattacaat     780
gatctattgt cacccttgttc ggaccaaact caaatgttct ctgatgatga gattctcaag     840
aattggacac aatgtaactt tgctgatgag acaaatgtgt ccaacaacct tcattctttt     900
gcttcctttc ttgaatccag tgaggaagta ctaggagaat ga                        942
```

<210> SEQ ID NO 56
<211> LENGTH: 933
<212> TYPE: DNA
<213> ORGANISM: Trifolium arvense

<400> SEQUENCE: 56

```
atggggagaa gcccttgttg tgcaaaggaa ggcttgaata gaggtgcttg gacaactcaa      60
gaagacaaaa tcctcactga atacattaag ctccatggtg aaggaaaatg gagaaacctt     120
ccaaaaagag caggtttaaa aagatgtgga aaaagttgta gacttagatg gttgaattat     180
ctaagaccag atattaagcg aggtaatata tcctcggatg aagaagaact tatcatccga     240
cttcacaaac tactcggaaa cagatggtct ctaatagccg gaagacttcc agggcgaaca     300
```

```
gacaatgaaa taaagaacta ctggaacaca aatttaggaa aaaaggttaa ggatcttaat      360
caagaaaaca ccaacaattc ttctcctact aaactttctg ctcaactaaa aaatgcaaag      420
atcaaacaga aacagatcaa tcctaagcca atggagccaa actcaaatgt tgtccgtaca      480
aaagctacca agtgttctaa ggcattgttc ataaactcac cccccaactc accaccaatg      540
catgatttgc agaacaaagc tgaggcagag acaacaacaa agtcatcaat gccatcaatg      600
ctggttgatg gcgtggctag tgattcaatg agtaacaacg aaatggaata cggtgatgga      660
tttgtttcat tttgcgatga cgataaagaa ctatccgcag atttgctaga agattttaac      720
atctcggatg atatttgctt atccgaattt ctaaacttcg atttctcaaa tgcgtgcaat      780
ttcgattaca acgatctatt gtcgccttgt tcggaccaaa cacaaatgtt ctctggtgat      840
gagattctca agaattcgac acaatgtaac tttgctgctg agacaaatta tgtgtccaac      900
aaccaatcca gtgaggaagt actaggagaa tga                                    933
```

```
<210> SEQ ID NO 57
<211> LENGTH: 933
<212> TYPE: DNA
<213> ORGANISM: Trifolium affine

<400> SEQUENCE: 57
atggggagaa gcccttgttg tgcgaaggaa ggcttgaata gaggtgcttg gacaactcaa       60
gaagacaaaa tcctcactga atacattaag ctccatggtg aaggaaaatg gagaaacctt      120
ccaaaaagag caggttttaaa aagatgtgga aaaagttgta gacttagatg gttgaattat     180
ctaagactag atattaagcg aggtaatata tcctcggatg aagaagaact tatcatccga      240
cttcacaaat tactcggaaa cagatggtct ctaatagccg gaagacttcc aggacgaaca      300
gacaatgaaa taaagaacta ctggaacaca aatttaggaa aaaaggttaa ggatcttaat      360
caagaaaaca ccaacaattc ttctcctact aaactttctg ctcaactaaa aaatgcaaag      420
atcaaacaga aacagatcaa tcctaagcca atggagccaa actcaaatgt tgtccgtaca      480
aaagctacca agtgttctaa ggcattgttc ataaactcac cccccaactc accaccaatg      540
catgatttgc agaacaaagc tgaggcagag acaacaacaa agtcatcaat gccatcaatg      600
ctggttgatg gcgtggctag tgattcaatg agtaacaacg aaatggaata cggtgatgga      660
tttgtttcat tttgcgatga cgataaagaa ctatccgcag atttgctaga agattttaac      720
atctcggatg atatttgctt atccgaattt ctaaacttcg atttctcaaa tgcgtgcaat      780
ttcgattaca acgatctatt gtcgccttgt tcggaccaaa cacaaatgtt ctctgatgat      840
gagattctca agaattcgac accatgtaac tttgctgctg agacaaatta tgtgtccaac      900
aaccaatcca gtgaggaagt actaggagaa tga                                    933
```

```
<210> SEQ ID NO 58
<211> LENGTH: 891
<212> TYPE: DNA
<213> ORGANISM: Trifolium affine

<400> SEQUENCE: 58
atggggagaa gcccttgttg tgcaaaggaa ggcttgaata gaggtgcttg gacaactcaa       60
gaagacaaaa tcctcactga atacattaag ctccatggtg aaggaaaatg gagaaacctt      120
ccaaaaagag caggttttaaa aagatgtgga aaaagttgta gacttagatg gttgaattat     180
ctaagaccag atattaagcg aggtaatata tcctcggatg aagaagaact tatcatccga      240
```

```
cttcacaaac tactcggaaa cagatggtct ctaatagccg aagacttcc agggcgaaca      300 gacaatgaaa taaagaacta ctggaacaca aatttaggaa aaaaggttaa ggatcttaat      360
caagaaaaca ccaacaattc ttctcctact aaactttctg ctcaactaaa aaatgcaaag      420
atcaaacaga aacagatcaa tcctaagcca atggagccaa actcaaatgt tgtccgtaca      480
aaagctacca agtgttctaa ggcattgttc ataaactcac cccccaactc accaccaatg      540
catgatttgc agaacaaagc tgaggcagag acaacaacaa agtcatcaat gccatcaatg      600
ctggttgatg gcgtggctag tgattcaatg agtaacaacg aaatggaata cggtgatgga      660
tttgtttcat tttgcgatga cgataaagaa ctatccgcag atttgctaga agattttaac      720
atctcggatg atatttgctt atccgaattt ctaaacttcg atttctcaaa tgcgtgcaat      780
ttcgattaca acgatctatt gtcgccttgt tcggaccaaa cacaaatgtt ctctgatgat      840
gagattctca agaattcgac acaatgtaac tttgctgctg agacaaatta a              891
```

<210> SEQ ID NO 59
<211> LENGTH: 942
<212> TYPE: DNA
<213> ORGANISM: Trifolium occidentale

<400> SEQUENCE: 59

```
atggggagaa gcccttgttg tgcaaaggaa ggcttgaata gaggtgcttg gacaactcaa       60
gaagacaaaa tcctcactga atacattaag ctccatggtg aaggaaaatg gagaaacctt      120
ccaaaaagag caggttttaaa aagatgcgga aaaagttgta gacttagatg gttgaattat      180
ctaagaccag atattaagcg aggtaatata tcctcggatg aagaagaact tatcatcaga      240
cttcacaaac tactcggaaa cagatggtct ctaatagccg aagacttcc aggacgaaca      300 gacaatgaaa taaagaacta ctggaacaca aatttaggaa aaaaggttaa ggatcttaat      360
caacaaaaca ccaacaagtc ttctcctact aaactctctg ctcaaccaaa aaatgcaaag      420
atcaaacaga aacagatcaa tcctaagcca atgaagccaa actcaaatgt tgtccgtaca      480
agagctacca agtgttctaa ggtattgttc ataaactcac tccccaactc accaatgcat      540
gatttgcaga caaagctga ggcagagaca acaacaaagc catcaatgct ggttgatggt       600
gtggctagtg attcaatgag taacaacgaa atggaacacg ttatggatt tttgtcattt      660 tgcgatgaag agaagaact atccgcagat ttgctagaag attttaacat cgcggatgat      720
atttgcttat ctgaactttt gaactctgat ttctcaaatg cgtgcaattt cgattacaat      780
gatctattgt cmccttgttc ggaccaaact caaatgttct ctgatgatga gattctcaag      840
aattggacac aatgtaactt tgctgatgag acaaatgtgt ccaacaacct tcattctttt      900
gcttcctttc ttgaatccag tgaggaagta ctaggagaat ga                          942
```

<210> SEQ ID NO 60
<211> LENGTH: 939
<212> TYPE: DNA
<213> ORGANISM: Trifolium occidentale

<400> SEQUENCE: 60

```
atggggagaa gcccttgttg tgcaaaggaa ggtttgaata gaggtgcttg gacagctcat       60
gaagacaaaa tcctcactga atacattaag ctccatggtg aaggaaaatg gagaaacctt      120
ccaaaaagag caggttttaaa aagatgtgga aaaagttgta gacttagatg gttgaattat      180
cttagaccag atattaagag aggtaatata tcgtccgatg aagaagaact tatcattaga      240
cttcacaaac tacttggaaa ccgatggtct ctaatagccg aagacttcc agggcgaaca      300
```

```
gacaatgaaa taaaaaatta ctggaacacg aatttaggaa aaaaggttaa ggatcttaat      360
caacaaaaca ccaacaattc ttctcctact aaaccttctg ctcaaccaaa aaatgcaaag      420
atcaaacaga acaacagat  caataatcct aagccaatga agccaaactc gaatgttgtc      480
cgtacaaaag ctaccaaatg ttctaaggta ttgttcataa actcaccacc aatgcataat      540
ttgcagaaca agctgaggc  agagacaaaa acaagacat  caatgttggt taatggtgta      600
gctagtgatt caatgagtaa caacgaaatg aacgaggta  atggatttttt gtcatttcgc     660 gatgaagaga aagaactatc cgctgatttg ctagatgatt ttaacatcgc ggatgacatt      720
tgcttatccg aatttctaaa ctccgatttc tcaaatgcgt gcaatttcga ttacaatgat      780
ctattgtcac cttgttcgga tcaaactcaa atgttctctg atgatgagat tctcaagaat      840
tggacacaat gtaactttgc tgatgagaca aatgtgtcca acaaccttca ttcttttgct      900
tcctttctcg aatccagtga ggaagtacta ggagaatga                             939
```

```
<210> SEQ ID NO 61
<211> LENGTH: 936
<212> TYPE: DNA
<213> ORGANISM: Trifolium repens

<400> SEQUENCE: 61
atggggagaa gcccttgttg tgcaaaagaa ggcttgaata gaggtgcttg gacagctcat       60
gaagacaaaa tcctcactga atacattaag ctccatggtg aaggaaaatg gagaaacctt      120
ccaaaaagag caggtttaaa aagatgtgga aaaagttgta gactaaggtg gttgaattat      180
cttagaccgg atattaagag aggtaatata tcgtcggatg aagaagaact tatcattaga      240
cttcacaaac tactcggaaa ccgatggtct ctaatagccg gaagacttcc agggcgaaca      300
gacaatgaaa taaagaacta ctggaacaca aatttaggaa aaaaagttaa ggatcttaat      360
caacaaaaca ccaacaattc ttctcctact aaaccttctg ctcaaccaaa aaatgcaaat      420
atcaaacaga acaacagat  caatcctaag ccaatgaagc caaactcgaa tgttgtccgt      480
acaaaagcta ccaaatgttc taaggtattg ttcataaact caccaccaat gcataatttg      540
cagaacaaag ctgaggcaga gacaaaaaca aagccattaa tgctggttaa tggtgtagct      600
agtgattcaa tgagtaacaa cgaaatggaa cgcggtaatg gatttttgtc attttgcgac      660
gaagagaaag aactatccgc agatttgcta gatgatttta acatcgcgga tgatatttgc      720
ttatctgaat ttctaaactc cgatttctca aatgcgtgca atttcgatta caatgatcta      780
ttgtcgcctt gttcggatca aactcaaatg ttctctgatg atgagattct caagaattgg      840
acacaatgta actttgctga tgagacaaat gtgtccaaca accttaattc ttttgcttct      900
tttctcgaat ccagtgagga agtactagga gaatga                               936
```

```
<210> SEQ ID NO 62
<211> LENGTH: 936
<212> TYPE: DNA
<213> ORGANISM: Trifolium repens

<400> SEQUENCE: 62
atggggagaa gcccttgttg tgcaaaagaa ggcttgaata gaggtgcttg gacagctcat       60
gaagacaaaa tcctcactga atacattaag ctccatggtg aaggaaaatg gagaaacctt      120
ccaaaaagag caggtttaaa aagatgtgga aaaagttgta gactaaggtg gttgaattat      180
cttagaccgg atattaagag aggtaatata tcgtcggatg aagaagaact tatcattaga      240
```

| | |
|---|---|
| cttcacaaac tactcggaaa ccgatggtct ctaatagccg aagacttcc agggcgaaca | 300 |
| gacaatgaaa taaagaacta ctggaacaca aatttaggaa aaaaagttaa ggatcttaat | 360 |
| caacaaaaca ccaacaattc ttctcctact aaaccttctg ctcaaccaaa aaatgcaaat | 420 |
| atcaaacaga acaacagat caatcctaag ccaatgaagc caaactcgaa tgttgtccgt | 480 |
| acaaaagcta ccaaatgttc taaggtattg ttcataaact caccaccaat gcataatttg | 540 |
| cagaacaaag ctgaggcaga gacaaaaaca aagccattaa tgctggttaa tggtgtagct | 600 |
| agtgattcaa tgagtaacaa cgaaatggaa cgcggtaatg gattttttgtc attttgcgac | 660 |
| gaagagaaag aactatccgc agatttgcta gatgatttta acatcgcgga tgatatttgc | 720 |
| ttacctgaat ttctaaactc cgatttctca aatgcgtgca atttcgatta caatgatcta | 780 |
| ttgtcgcctt gttcggatca aactcaaatg ttctctgatg atgagattct caagaattgg | 840 |
| acacaatgta actttgctga tgagacaaat gtgtccaaca accttaattc ttttgcttct | 900 |
| tttctcgaat ccagtgagga agtactagga gaatga | 936 |

<210> SEQ ID NO 63
<211> LENGTH: 936
<212> TYPE: DNA
<213> ORGANISM: Trifolium repens

<400> SEQUENCE: 63

| | |
|---|---|
| atggggagaa gcccttgttg tgcaaaagaa ggcttgaata gaggtgcttg gacagctcat | 60 |
| gaagacaaaa tcctcactga atacattaag ctccatggtg aaggaaaatg gagaaaccttt | 120 |
| ccaaaaagag caggtttaaa aagatgtgga aaaagttgta gactaaggtg gttgaattat | 180 |
| cttagaccgg atattaagag aggtaatata tcgtcggatg aagaagaact tatcattaga | 240 |
| cttcacaaac tactcggaaa ccgatggtct ctaatagccg aagacttcc agggcgaaca | 300 |
| gacaatgaaa taaagaacta ctggaacaca aatttaggaa aaaaagttaa ggatcttaat | 360 |
| caacaaaaca ccaacaattc ttctcctact aaaccttctg ctcaaccaaa aaatgcaaat | 420 |
| atcaaacaga acaacagat caatcctaag ccaatgaagc caaactcgaa tgttgtccgt | 480 |
| acaaaagcta ccaaatgttc taaggtattg ttcataaact caccaccaat gcataatttg | 540 |
| cagaacaaag ctgaggcaga gacaaagaca aagccattaa tgctggttaa tggtgtagct | 600 |
| agtgattcaa tgagtaacaa cgaaatggaa cgcggtaatg gattttttgtc attttgcgac | 660 |
| gaagagaaag aactatccgc agatttgcta gatgatttta acatcgcgga tgatatttgc | 720 |
| ttatctgaat ttctaaactc cgatttctca aatgcgtgca atttcgatta caatgatcta | 780 |
| ttgtcgcctt gttcggatca aactcaaatg ttctctgatg atgagattct caagaattgg | 840 |
| acacaatgta actttgctga tgagacaaat gtgtccaaca accttcattc ttttgcttcc | 900 |
| tttctcgaat ccagtgagga agtactagga gaatga | 936 |

<210> SEQ ID NO 64
<211> LENGTH: 936
<212> TYPE: DNA
<213> ORGANISM: Trifolium repens

<400> SEQUENCE: 64

| | |
|---|---|
| atggggagaa gcccttgttg tgcaaaagaa ggcttgaata gaggtgcttg gacagctcat | 60 |
| gaagacaaaa tcctcactga atacattaag ctccatggtg aaggaaaatg gagaaaccttt | 120 |
| ccaaaaagag caggtttaaa aagatgtgga aaaagttgta gactaaggtg gttgaattat | 180 |
| cttagaccgg atattaagag aggtaatata tcgtcggatg aagaagaact tatcattaga | 240 |

-continued

```
cttcacaaac tactcggaaa ccgatggtct ctaatagccg gaagacttcc agggcgaaca      300
gacaatgaaa taaagaacta ctggaacaca aatttaggaa aaaaagttaa ggatcttaat      360
caacaaaaca ccaacaattc ttctcctact aaaccttctg ctcaaccaaa aaatgcaaat      420
atcaaacaga aacaacagat caatcctaag ccaatgaagc caaactcgaa tgttgtccgt      480
acaaaagcta ccaaatgttc taaggtattg ttcataaact caccaccaat gcataatttg      540
cagaacaaag ctgaggcaga gacaaagaca aagccattaa tgctggttaa tggtgtagct      600
agtgattcaa tgagtaacaa cgaaatggaa cgcggtaatg gattttttgtc attttgcgac      660 gaagagaaag aactatccgc agatttgcta gatgatttta acatcgcgga tgatatttgc      720
ttatctgaat ttctaaactc cgatttctca aatgcgtgca atttcgatta caatgatcta      780
ttgtcgcctt gttcggatca aactcaaatg ttctctgatg atgagattct caagaattgg      840
acacaatgta actttgctga tgagacaaat gtgtccaaca accttcattc ttttgcttcc      900
tttctcgaat ccagtgagga agtactagga gaatga                               936
```

<210> SEQ ID NO 65
<211> LENGTH: 299
<212> TYPE: DNA
<213> ORGANISM: Trifolium arvense

<400> SEQUENCE: 65

```
caatgctggt tgatggtgtg gctagtgatt caatgagtaa caacgaaatg gaacacggtt       60 atggatttttt gtcattttgc gatgaagaga aagaactatc cgcagatttg ctagaagatt     120
ttaacatcgc ggatgatatt tgcttatctg aacttttgaa ctctgatttc tcaaatgcgt     180
gcaatttcga ttacaatgat ctattgtcac cttgttcgga ccaaactcaa atgttctctg     240
atgatgagat tctcaagaat tggacacaat gtaactttgc tgatgagaca aatgtgtcc     299
```

<210> SEQ ID NO 66
<211> LENGTH: 28
<212> TYPE: DNA
<213> ORGANISM: Artificial
<220> FEATURE:
<223> OTHER INFORMATION: Primer sequence

<400> SEQUENCE: 66

```
tctagacaat gctggttgat ggtgtggc                                          28
```

<210> SEQ ID NO 67
<211> LENGTH: 27
<212> TYPE: DNA
<213> ORGANISM: Artificial
<220> FEATURE:
<223> OTHER INFORMATION: Primer sequence

<400> SEQUENCE: 67

```
tctagaggac acatttgtct catcagc                                           27
```

<210> SEQ ID NO 68
<211> LENGTH: 28
<212> TYPE: DNA
<213> ORGANISM: Artificial
<220> FEATURE:
<223> OTHER INFORMATION: Primer sequence

<400> SEQUENCE: 68

```
ctcgagcaat gctggttgat ggtgtggc                                          28
```

<210> SEQ ID NO 69
<211> LENGTH: 27
<212> TYPE: DNA
<213> ORGANISM: Artificial
<220> FEATURE:
<223> OTHER INFORMATION: Primer sequence

<400> SEQUENCE: 69
ctcgagggac acatttgtct catcagc        27

<210> SEQ ID NO 70
<211> LENGTH: 912
<212> TYPE: DNA
<213> ORGANISM: Lotus japonicus

<400> SEQUENCE: 70
atgggaagaa gcccttgttg ttcaaagcag ggtttgaacc gaggtgcctg gacagcacag    60
gaagaccaaa tcctccgaga ctatgttcat ctccatggcc aaggaaaatg gaggaacctt   120
cctcaaagtg caggtttgaa acgttgtggc aaaagctgta gacttagatg gttgaattat   180
ctaagaccag atatcaaaag aggcaatata tccagagatg aagaagagct tatcatccga   240
cttcacaagc tcctaggaaa cagatggtct ctaatagctg aaggcttcc aggaagaaca   300 gacaatgaga taaagaacta ctggaacacc aatctatgta aaagagttca agatggtgtt   360
gatgttggtg actccaaaac cccatcttca caagaaaaga caatcacca tgatcagaaa   420 gcaaagcctc aatctgttac tccctcagta ttctcctcat cacagcctaa aaacaataat   480
gtgattcgta caaaggcatc gaagtgctcc aaggtgctgc tccgggatcc tcttctccct   540
tgcccgccaa tgcaaacgca gagcgacgat ttcatcgcaa aattattaga agaagcagaa   600
ggagagccat tgctttctgc tgtggccaat gattttacta gtggcgacga agacggggtt   660 cttttcatttg atccttgtgg aaatgagaag gaactctcca cggatttgct cttggatttg   720
gacattggtg aaatttgctt gcctgaattt atcaactcag attttcata tgtgtgtgac   780 ttcagctaca acactcatga ggatctaatg ctttttttccg agaacacact tgtccaggca   840
cagaagtacc tcggtgatga aacaaatttg gtaaataatt gttttaatga ggagaaggat   900
aatggttgct aa                                                      912

<210> SEQ ID NO 71
<211> LENGTH: 1143
<212> TYPE: DNA
<213> ORGANISM: Trifolium affine

<400> SEQUENCE: 71
ctaattaaga ataacatcaa tggggagaag cccttgttgt gcaaaggaag gcttgaatag    60
aggtgcttgg acaactcaag aagacaaaat cctcactgaa tacattaagc tccatggtga   120
aggaaaatgg agaaaccttc caaaagagc agatttaaaa agatgtggaa aaagttgtag   180
acttagatgg ttgaattatc taagaccaga tattaagcga ggtaatatat ccccggatga   240
agaagaactt attatccgac ttcacaaact actcggaaac agatggtctc taatagccgg   300
aagacttcca gggcgaacag acaatgaaat aaagaactac tggaacacaa atttaggaaa   360
aaaggttaag gatcttaatc aacaaaacac caacaattct tctcctacta aactttctgc   420
tcaaccaaaa aatgcaaaga tcaaacagaa acagatcaat cctaagccaa tgaagccaaa   480
ctcaaatgtt gtccgtacaa aagctaccaa gtgttctaag gtattgttca taactcact   540 cccccaactca ccaatgcatg atttgcagaa caaagctgag gcagagacaa caacaaagcc   600

| | |
|---|---:|
| atcaatgctg gttgatggtg tggctagtga ttcaatgagt aacaacgaaa tggaacacgg | 660 |
| ttatggattt ttgtcatttt gcgatgaaga gaaagaacta tccgcagatt tgctagaaga | 720 |
| ttttaacatc gcggatgata tttgcttatc tgaacttttg aactctgatt tctcaaatgc | 780 |
| gtgcaatttc gattacaatg atctattgtc accttgttcg gaccaaactc aaatgttctc | 840 |
| tgatgatgag attctcaaga attggacaca atgtaacttt gctgatgaga caaatgtgtc | 900 |
| caacaacctt cattcttttg cttcctttct tgaatccagt gaggaagtac taggagaatg | 960 |
| ataataaaaa ttcatttttcc aataaaatta actactctag gttttttttt tttttttta | 1020 |
| atttcaattt catgttaggg tggtttaata aataaatata ttctatggtt taatattgca | 1080 |
| aaaaaaaaaa aaaaaaaaaa aaaaagtact ctgcgttgat accactgctt aagggcgaat | 1140 |
| tcc | 1143 |

<210> SEQ ID NO 72
<211> LENGTH: 1049
<212> TYPE: DNA
<213> ORGANISM: Glycine max

<400> SEQUENCE: 72

| | |
|---|---:|
| gcaaaaaatg ggaagggctc cttgttgttc caaagtgggg ttgcacaaag gtccatggac | 60 |
| tcctaaagaa gatgcattgc ttaccaagta tatccaagct catggagaag gccaatggaa | 120 |
| atcactaccc aaaaaagcag ggcttcttag atgtggaaaa agttgtagat tgagatggat | 180 |
| gaactatctg agaccagaca taagagagg gaacatagca ccagaagaag atgatcttat | 240 |
| aatcagaatg cattcacttt tgggaaacag atggtccctc atagcaggaa ggttaccagg | 300 |
| gagaacagac aatgaaataa agaactactg gaacacccat ctaagcaaaa agctgaaaat | 360 |
| tcaaggaaca gaagacacag acacacacaa aatgttagag aatcctcaag aagaggctgc | 420 |
| aagtgatggt ggcaacaaca acaaaaagaa gaagaagaag aagaacggtg caaaaagaa | 480 |
| caagcagaag aacaaaggca agaaaatga tgagccgcca agacacaag tttacctacc | 540 |
| aaaaccaatt agagtgaagg caatgtattt acaaagaacg gatagtaaca ccttcacctt | 600 |
| tgattccaat tcagctagtg gatcaacaag ccaagagaag gaggaaagcc ccgtgacaaa | 660 |
| agaatcaaac gtggttagtg aagttggtaa tgtgggagaa gaaagtgatg gttttggctt | 720 |
| cttcagtgag gaccatgact tagtcaacgt ctcagatatt gaatgccact cttattttcc | 780 |
| cacagatcat ggcaacctac agcaattgta tgaagaatat ttccagctct tgaacatgga | 840 |
| ccatggccaa ttcgaactga attcatttgc agaatcttta ttagattaaa agaatatcaa | 900 |
| caaagatttg ttcagttcat gaagatcaca ttgcttacat ataaactttg ttgatagatc | 960 |
| atatgtaaat atatctgtaa atgatctctg agttatgaga tcttttttgt ctttaataaa | 1020 |
| tatcgccatc taactcaaaa aaaaaaaa | 1049 |

<210> SEQ ID NO 73
<211> LENGTH: 1000
<212> TYPE: DNA
<213> ORGANISM: Daucus carota

<400> SEQUENCE: 73

| | |
|---|---:|
| gaagaatggg aaggagccct tgttgctcaa aagttgggct gaacaaagga gcctggacca | 60 |
| ctgctgagga caaaattctc actgatttca ttcatcttca tggtgaaggt ggatggagaa | 120 |
| accttcccaa aagagcaggt ttgaagagat gcggaaagag ttgcaggctg agatggttga | 180 |

```
attatttgag accggatatc aagagaggca acatttctga tgatgaagaa gacctcatca    240
ttcgtcttca caagcttctc ggtaataggt ggtctttaat agctggaagg ctccctggcc    300
gaacagacaa tgaaatcaag aactactgga acacgacatt gaggaaaaag gctcatgata    360
atcacacttc atctgcagct gctccaaaga ccccgactaa acaatgcaac aacaagaaga    420
cgaagaaaca caagaagaag cgcgagaaat ctgagccaat taaaccggaa atcaaggcca    480
atgcatccga tgttagggcc aaggccgctc tggacgaggc tgatcatcaa ctcataacta    540
gtactagtac catggagcca ttggttcaac aagcattaca aaataagact actgatcaat    600
cttcggatct ggtccctggc gttgactcca gcgacatgtg cttaacggat tttcttaatt    660
atgatttctc aggtttgtta acactgata ttaatcacca ggattacgac atggagagcg    720
cgtcgccttg ttcgtcgtcg gagaagccta atgcagat actggaggag ttctggaatg    780
cagaggaacc atgtctggtt ctaactcta atctttattt tacctcatta tcagagtgtt    840
tagtgggtga ttggttggcc taatatgtga aaactgggaa gtgtacattt tactgttgtt    900
catttttactt aacttcccgg aaataaagat gcatgtatca tagttcaaat aatgactact    960
tctgatgtgt tgaattgttg taaaaaaaaa aaaaaaaaaa                          1000

<210> SEQ ID NO 74
<211> LENGTH: 909
<212> TYPE: DNA
<213> ORGANISM: Gossypium hirsutum

<400> SEQUENCE: 74
atgggaagga gtccttgttg ttctaaggaa ggccttaaca gaggagcttg gactgctctt     60
gaagacaaaa ttcttaaaga ttatatcaaa gtacacggtg aaggtcgttg gagaaatctc    120
cccaaaagag ctggtcttaa agatgtgggg aaaagttgta ggcttcggtg gttgaattat    180
ttgagacctg atattaaaag aggtaacata tcacctgacg aggaagagct tatcatcaaa    240
ctccacaaac tcttgggaaa cagatggtct ttgatagctg ggaggcttcc aggacgaaca    300
gacaatgaaa taagaattta ctggaacacc aacttaagta aaagagtttc cgatcgtcaa    360
aagtcacccg ccgctccttc gaaaaaaccc gaggcggctc gacgaggaac tgctggtaat    420
ggcaatacca atggtaatgg tagtggtagt tcctcgacac acgtggtgcg gacaagggcg    480
acaaggtgct ccaaggtttt cataaaccct catcaccaca cacaaaacag cacccaaag    540
ccttcctcaa cttgttcaaa tcatggggat caccgggaac ctaaaacaat gaatgagttg    600
ttattaccga taatgtcaga atccgagaat gaagggacga ccgatcatat atcatcggat    660
tttacatttg acttcaacat gggagagttt tgtttatcgg atcttttgaa ttccgatttc    720
tgcgatgtaa acgagcttaa ttacagcaat ggttttgatt cgtcaccctc accggatcag    780
cctcctatgg atttctccga cgaaatgcta aaagagtgga cggccgccgc ctccactcac    840
tgctgtcacc aaagtgcggc ttccaatctc cagtccttgc ctccatttat tgaaaatgga    900
attgaatga                                                            909

<210> SEQ ID NO 75
<211> LENGTH: 938
<212> TYPE: DNA
<213> ORGANISM: Brassica napus

<400> SEQUENCE: 75
aatctattct caacacaacg ctaaagacaa gtctaccaac cacacaacaa caagagagat     60
gatgagaaag agagaaagta gtaaggtgaa gaaagaggag ttaaacagag gggcttggac    120
```

```
cgatcaagaa gacaagatcc ttaaagacta tatcatgttc cacggcgaag gaaaatggag      180
cacactccca aaccaagctg gtctcaagag gtgtggcaaa agctgcagac ttcggtggaa      240
gaactacttg agaccaggca taaagcgcgg aaacatctca tctgatgaag aagaacttat      300
aatccgcctc cataatctcc ttggaaacag atggtcgttg atagctggga ggcttccagg      360
gcgaacagac aatgaaataa agaaccactg aactcaaac ctccgcaaaa gacttccaaa       420
atctcaaacc aaccaacaga aaagtcgaaa acattccaac aacaacaaca tgaataaagt      480
atgtgttata cgtccaaagg cgattaggat cccaaaggct ctgacatttc agaatcagag      540
tagtattggt agtaccagtc ttcttactgt gaaggaaaac gtgattgatc atcaagctgg      600
ttctccttcg ttgttgggag atcttaaaat cgattttgat aaaattcagt ctgagtatct      660
cttctctgat ttaatgggct tgatggtttt ggggttgtgga aacgtaatgt ctcttgtttc     720
atctgacgag gtgctaggag attatgtttc ggctgatgct tcttgtctgg gtaatcttga     780
tcttaataga cctttcactt cttgtcttca agaagattgt ctctgggact ttaattgtta     840
gaccctatcg taaatcttca tatattacgt ctacctctgt acgaacaaaa gtatatattt     900
atattctgtt tgaacgcttc taattacaag taatatct                             938
```

<210> SEQ ID NO 76
<211> LENGTH: 816
<212> TYPE: DNA
<213> ORGANISM: Gossypium hirsutum

<400> SEQUENCE: 76

```
atgggaagaa gtccatgttg ctccaaggaa ggactcaaca aaggagcttg gactgcttta       60
gaagataaaa tacttgcatc atatattcat gttcatggtg aaggcaaatg gagaaacctc      120
cccaagagag ctggttttgaa gagatgtggc aaaagttgca gacttagatg gctgaattat      180
cttagaccag atattaaaag aggcaacatc tctcatgatg aagaagaact cattataaga      240
ctccataatc ttcttggcaa cagatggtct ttaatagctg gaaggctacc cgggcgaaca      300
gacaatgaaa tcaagaacta ctggaacact actttaggta agagagctaa agctcaagca      360
tccattgatg ctaaaacgat accaaccgag tctaggctca atgaaccctc gaaaagttca      420
actaaaatcg aagtgattcg aactaaagct attaggtgta gcagcaaggt gatggtccca      480
ttacaaccac ctgcaactca tcaacatggt caacatcact gtacaaataa taatgaagaa      540
atgggtggtg gtattgcaac aattgaagct cacaatggaa ttcaaatgct cgagtcattg      600
tacagtgatg gcggctcaaa tttgttgagc ttcgagatca atgaactgtt gaaatcacac      660
gatggtggag aatttgagga gaatcctatg cagcagcact ttccgttggg tgaggcaatg      720
cttaaggatt ggtctacatg tcattgtctt gatgacaatg gtgccactga tttggaatca      780
ttggcctttt tgcttgacac tgatgaatgg ccatga                               816
```

<210> SEQ ID NO 77
<211> LENGTH: 258
<212> TYPE: PRT
<213> ORGANISM: Arabidopsis thaliana

<400> SEQUENCE: 77

Met Gly Lys Arg Ala Thr Thr Ser Val Arg Arg Glu Glu Leu Asn Arg
1               5                   10                  15

Gly Ala Trp Thr Asp His Glu Asp Lys Ile Leu Arg Asp Tyr Ile Thr
            20                  25                  30

```
Thr His Gly Glu Gly Lys Trp Ser Thr Leu Pro Asn Gln Ala Gly Leu
             35                  40                  45

Lys Arg Cys Gly Lys Ser Cys Arg Leu Arg Trp Lys Asn Tyr Leu Arg
 50                  55                  60

Pro Gly Ile Lys Arg Gly Asn Ile Ser Ser Asp Glu Glu Leu Ile
 65                  70                  75                  80

Ile Arg Leu His Asn Leu Leu Gly Asn Arg Trp Ser Leu Ile Ala Gly
                 85                  90                  95

Arg Leu Pro Gly Arg Thr Asp Asn Glu Ile Lys Asn His Trp Asn Ser
                100                 105                 110

Asn Leu Arg Lys Arg Leu Pro Lys Thr Gln Thr Lys Gln Pro Lys Arg
                115                 120                 125

Ile Lys His Ser Thr Asn Asn Glu Asn Asn Val Cys Val Ile Arg Thr
            130                 135                 140

Lys Ala Ile Arg Cys Ser Lys Thr Leu Leu Phe Ser Asp Leu Ser Leu
145                 150                 155                 160

Gln Lys Lys Ser Ser Thr Ser Pro Leu Pro Lys Glu Gln Glu Met
                165                 170                 175

Asp Gln Gly Gly Ser Ser Leu Met Gly Asp Leu Glu Phe Asp Phe Asp
                180                 185                 190

Arg Ile His Ser Glu Phe His Phe Pro Asp Leu Met Asp Phe Asp Gly
                195                 200                 205

Leu Asp Cys Gly Asn Val Thr Ser Leu Val Ser Ser Asn Glu Ile Leu
                210                 215                 220

Gly Glu Leu Val Pro Ala Gln Gly Asn Leu Asp Leu Asn Arg Pro Phe
225                 230                 235                 240

Thr Ser Cys His His Arg Gly Asp Asp Glu Asp Trp Leu Arg Asp Phe
                    245                 250                 255

Thr Cys

<210> SEQ ID NO 78
<211> LENGTH: 260
<212> TYPE: PRT
<213> ORGANISM: Brassica napus

<400> SEQUENCE: 78

Met Met Arg Lys Arg Glu Ser Ser Lys Val Lys Lys Glu Glu Leu Asn
 1               5                  10                  15

Arg Gly Ala Trp Thr Asp Gln Glu Asp Lys Ile Leu Lys Asp Tyr Ile
                 20                  25                  30

Met Phe His Gly Glu Gly Lys Trp Ser Thr Leu Pro Asn Gln Ala Gly
             35                  40                  45

Leu Lys Arg Cys Gly Lys Ser Cys Arg Leu Arg Trp Lys Asn Tyr Leu
 50                  55                  60

Arg Pro Gly Ile Lys Arg Gly Asn Ile Ser Ser Asp Glu Glu Leu
 65                  70                  75                  80

Ile Ile Arg Leu His Asn Leu Leu Gly Asn Arg Trp Ser Leu Ile Ala
                 85                  90                  95

Gly Arg Leu Pro Gly Arg Thr Asp Asn Glu Ile Lys Asn His Trp Asn
                100                 105                 110

Ser Asn Leu Arg Lys Arg Leu Pro Lys Ser Gln Thr Asn Gln Gln Lys
                115                 120                 125

Ser Arg Lys His Ser Asn Asn Asn Met Asn Lys Val Cys Val Ile
            130                 135                 140
```

```
Arg Pro Lys Ala Ile Arg Phe Pro Lys Ala Leu Thr Phe Gln Asn Gln
145                 150                 155                 160

Ser Ser Ile Gly Ser Thr Ser Leu Leu Thr Val Lys Glu Asn Val Ile
            165                 170                 175

Asp His Gln Ala Gly Ser Pro Ser Leu Leu Gly Asp Leu Lys Ile Asp
            180                 185                 190

Phe Asp Lys Ile Gln Ser Glu Tyr Leu Phe Ser Asp Leu Met Asp Phe
            195                 200                 205

Asp Gly Leu Gly Cys Gly Asn Val Met Ser Leu Val Ser Ser Asp Glu
            210                 215                 220

Val Leu Gly Asp Tyr Val Ser Thr Asp Thr Ser Cys Leu Gly Asn Leu
225                 230                 235                 240

Asp Leu Asn Arg Pro Phe Thr Ser Cys Leu Gln Glu Asp Cys Leu Trp
            245                 250                 255

Asp Phe Asn Cys
            260

<210> SEQ ID NO 79
<211> LENGTH: 266
<212> TYPE: PRT
<213> ORGANISM: Zea mays

<400> SEQUENCE: 79

Met Gly Arg Arg Ala Cys Cys Ala Lys Glu Gly Val Lys Arg Gly Ala
1               5                   10                  15

Trp Thr Ala Lys Glu Asp Asp Thr Leu Ala Ala Tyr Val Lys Ala His
            20                  25                  30

Gly Glu Gly Lys Trp Arg Glu Val Pro Gln Lys Ala Gly Leu Arg Arg
            35                  40                  45

Cys Gly Lys Ser Cys Arg Leu Arg Trp Leu Asn Tyr Leu Arg Pro Asn
50                  55                  60

Ile Lys Arg Gly Asn Ile Ser Tyr Asp Glu Glu Asp Leu Ile Val Arg
65                  70                  75                  80

Leu His Lys Leu Leu Gly Asn Arg Trp Ser Leu Ile Ala Gly Arg Leu
            85                  90                  95

Pro Gly Arg Thr Asp Asn Glu Ile Lys Asn Tyr Trp Asn Ser Thr Leu
            100                 105                 110

Gly Arg Arg Ala Gly Ala Gly Ala Ser Arg Val Val Phe Ala Pro
            115                 120                 125

Asp Thr Gly Ser His Ala Thr Pro Ala Ala Ser Gly Ser Arg Glu Met
            130                 135                 140

Thr Gly Gly Gln Lys Gly Ala Ala Pro Arg Ala Asp Leu Gly Ser Pro
145                 150                 155                 160

Gly Ser Ala Ala Val Val Trp Ala Pro Lys Ala Ala Arg Cys Thr Gly
            165                 170                 175

Gly Leu Phe Phe His Arg Asp Thr Pro His Ala Gly Glu Thr Glu Thr
            180                 185                 190

Pro Thr Pro Met Met Met Ala Gly Gly Gly Gly Glu Ala Arg Ser
            195                 200                 205

Ser Asp Asp Cys Ser Ser Ala Ala Ser Val Ser Pro Leu Val Gly Ser
            210                 215                 220

Ser Gln His Asp Pro Cys Phe Ser Gly Asp Gly Asp Gly Asp Trp Met
225                 230                 235                 240

Asp Asp Val Arg Ala Leu Ala Ser Phe Leu Glu Ser Asp Glu Glu Trp
            245                 250                 255
```

```
Leu Arg Cys His Thr Ala Glu Gln Leu Val
            260                 265

<210> SEQ ID NO 80
<211> LENGTH: 302
<212> TYPE: PRT
<213> ORGANISM: Gossypium hirsutum

<400> SEQUENCE: 80

Met Gly Arg Ser Pro Cys Cys Ser Lys Glu Gly Leu Asn Arg Gly Ala
1               5                   10                  15

Trp Thr Ala Leu Glu Asp Lys Ile Leu Lys Asp Tyr Ile Lys Val His
            20                  25                  30

Gly Glu Gly Arg Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser Pro Asp Glu Glu Leu Ile Ile Lys
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Asn Leu
            100                 105                 110

Ser Lys Arg Val Ser Asp Arg Gln Lys Ser Pro Ala Ala Pro Ser Lys
        115                 120                 125

Lys Pro Glu Ala Ala Arg Arg Gly Thr Ala Gly Asn Gly Asn Thr Asn
    130                 135                 140

Gly Asn Gly Ser Gly Ser Ser Ser Thr His Val Val Arg Thr Arg Ala
145                 150                 155                 160

Thr Arg Cys Ser Lys Val Phe Ile Asn Pro His His Thr Gln Asn
                165                 170                 175

Arg His Pro Lys Pro Ser Ser Thr Cys Ser Asn His Gly Asp His Arg
            180                 185                 190

Glu Pro Lys Thr Met Asn Glu Leu Leu Leu Pro Ile Met Ser Glu Ser
        195                 200                 205

Glu Asn Glu Gly Thr Thr Asp His Ile Ser Ser Asp Phe Thr Phe Asp
    210                 215                 220

Phe Asn Met Gly Glu Phe Cys Leu Ser Asp Leu Leu Asn Ser Asp Phe
225                 230                 235                 240

Cys Asp Val Asn Glu Leu Asn Tyr Ser Asn Gly Phe Asp Ser Ser Pro
                245                 250                 255

Ser Pro Asp Gln Pro Pro Met Asp Phe Ser Asp Glu Met Leu Lys Glu
            260                 265                 270

Trp Thr Ala Ala Ala Ser Thr His Cys Cys His Gln Ser Ala Ala Ser
        275                 280                 285

Asn Leu Gln Ser Leu Pro Pro Phe Ile Glu Asn Gly Ile Glu
    290                 295                 300

<210> SEQ ID NO 81
<211> LENGTH: 286
<212> TYPE: PRT
<213> ORGANISM: Vitis vinifera

<400> SEQUENCE: 81

Met Gly Arg Ala Pro Cys Cys Ser Lys Val Gly Leu His Arg Gly Ser
1               5                   10                  15
```

Trp Thr Ala Arg Glu Asp Thr Leu Leu Thr Lys Tyr Ile Gln Ala Lys
            20                  25                  30

Gly Glu Gly His Trp Arg Ser Leu Pro Lys Lys Ala Gly Leu Leu His
        35                  40                  45

Cys Gly Lys Ser Cys Arg Leu Arg Trp Met Asn Tyr Leu Arg Pro Asp
    50                  55                  60

Ile Lys Arg Gly Asn Ile Thr Pro Asp Lys Asp Asp Leu Ile Ile Arg
65                  70                  75                  80

Leu Lys Ser Leu Leu Gly Asn Arg Trp Ser Leu Ile Ala Gly Arg Leu
                85                  90                  95

Pro Gly Arg Thr Asp Asn Ser Ile Lys Asn Tyr Trp Asn Thr His Leu
            100                 105                 110

Ser Lys Lys Leu Arg Ser Gln Gly Thr Asp Pro Asn Thr His Lys Lys
        115                 120                 125

Met Thr Glu Pro Pro Glu Pro Lys Arg Arg Lys Asn Thr Arg Thr Arg
130                 135                 140

Thr Asn Asn Gly Gly Gly Ser Lys Arg Val Lys Ile Ser Lys Asp Glu
145                 150                 155                 160

Glu Asn Ser Asn His Lys Val His Leu Pro Lys Pro Val Arg Val Thr
                165                 170                 175

Ser Leu Ile Ser Met Ser Arg Asn Asn Ser Phe Glu Ser Asn Thr Val
            180                 185                 190

Ser Gly Gly Ser Gly Ser Ser Gly Gly Asn Gly Glu Ser Leu Pro
        195                 200                 205

Trp Pro Ser Phe Arg Asp Ile Arg Asp Asp Lys Val Ile Gly Val Asp
            210                 215                 220

Gly Val Asp Phe Phe Ile Gly Asp Asp Gln Gly Gln Asp Leu Val Ala
225                 230                 235                 240

Ser Ser Asp Pro Glu Ser Gln Ser Lys Met Pro Pro Thr Asp Asn Ser
                245                 250                 255

Leu Asp Lys Leu Tyr Glu Glu Tyr Leu Gln Leu Leu Glu Arg Glu Asp
            260                 265                 270

Thr Gln Val Gln Leu Asp Ser Phe Ala Glu Ser Leu Leu Ile
        275                 280                 285

<210> SEQ ID NO 82
<211> LENGTH: 303
<212> TYPE: PRT
<213> ORGANISM: Lotus japonicus

<400> SEQUENCE: 82

Met Gly Arg Ser Pro Cys Cys Ser Lys Gln Gly Leu Asn Arg Gly Ala
1               5                   10                  15

Trp Thr Ala Gln Glu Asp Gln Ile Leu Arg Asp Tyr Val His Leu His
            20                  25                  30

Gly Gln Gly Lys Trp Arg Asn Leu Pro Gln Ser Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser Arg Asp Glu Glu Glu Leu Ile Ile Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Asn Leu

```
            100                 105                 110
Cys Lys Arg Val Gln Asp Gly Val Asp Val Gly Asp Ser Lys Thr Pro
        115                 120                 125

Ser Ser Gln Glu Lys Asn Asn His His Asp Gln Lys Ala Lys Pro Gln
130                 135                 140

Ser Val Thr Pro Ser Val Phe Ser Ser Gln Pro Lys Asn Asn Asn
145                 150                 155                 160

Val Ile Arg Thr Lys Ala Ser Lys Cys Ser Lys Val Leu Leu Arg Asp
                165                 170                 175

Pro Leu Leu Pro Cys Pro Pro Met Gln Thr Gln Ser Asp Asp Phe Ile
            180                 185                 190

Ala Lys Leu Leu Glu Glu Ala Glu Gly Glu Pro Leu Leu Ser Ala Val
        195                 200                 205

Ala Asn Asp Phe Thr Ser Gly Asp Glu Asp Gly Val Leu Ser Phe Asp
        210                 215                 220

Pro Cys Gly Asn Glu Lys Glu Leu Ser Thr Asp Leu Leu Leu Asp Leu
225                 230                 235                 240

Asp Ile Gly Glu Ile Cys Leu Pro Glu Phe Ile Asn Ser Asp Phe Ser
                245                 250                 255

Tyr Val Cys Asp Phe Ser Tyr Asn Thr His Glu Asp Leu Met Leu Phe
            260                 265                 270

Ser Glu Asn Thr Leu Val Gln Ala Gln Lys Tyr Leu Gly Asp Glu Thr
        275                 280                 285

Asn Leu Val Asn Asn Cys Phe Asn Glu Glu Lys Asp Asn Gly Cys
        290                 295                 300

<210> SEQ ID NO 83
<211> LENGTH: 281
<212> TYPE: PRT
<213> ORGANISM: Glycine max

<400> SEQUENCE: 83

Met Gly Arg Ala Pro Cys Cys Ser Lys Val Gly Leu His Arg Gly Pro
1               5                   10                  15

Trp Thr Pro Arg Glu Asp Ala Leu Leu Thr Lys Tyr Ile Gln Thr His
                20                  25                  30

Gly Glu Gly Gln Trp Arg Ser Leu Pro Lys Arg Ala Gly Leu Leu Arg
            35                  40                  45

Cys Gly Lys Ser Cys Arg Leu Arg Trp Met Asn Tyr Leu Arg Pro Asp
        50                  55                  60

Ile Lys Arg Gly Asn Ile Thr Pro Glu Glu Asp Asp Leu Ile Val Arg
65                  70                  75                  80

Met His Ser Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr His Leu
            100                 105                 110

Ser Lys Lys Leu Arg Asn Gln Gly Thr Asp Pro Lys Thr His Asp Lys
        115                 120                 125

Leu Thr Glu Ala Pro Glu Lys Lys Gly Lys Lys Asn Lys Gln
130                 135                 140

Lys Asn Glu Asn Asn Lys Gly Ser Glu Lys Thr Leu Val Tyr Leu Pro
145                 150                 155                 160

Lys Pro Ile Arg Val Lys Ala Leu Ser Ser Cys Ile Pro Arg Thr Asp
                165                 170                 175
```

-continued

```
Ser Thr Leu Thr Leu Asn Ser Asn Ser Ala Thr Ala Ser Thr Ser Glu
            180                 185                 190

Glu Lys Val Gln Ser Pro Glu Ala Glu Val Lys Glu Val Asn Met Val
            195                 200                 205

Trp Gly Val Gly Asp Ala Asp Asn Gly Gly Ile Glu Ile Phe Phe
    210                 215                 220

Gly Glu Asp His Asp Leu Val Asn Asn Thr Ala Ser Tyr Glu Glu Cys
225                 230                 235                 240

Tyr Ser Asp Val His Thr Asp Asp His Gly Thr Leu Glu Lys Leu Tyr
                245                 250                 255

Glu Glu Tyr Leu Gln Leu Leu Asn Val Glu Glu Lys Pro Asp Glu Leu
            260                 265                 270

Asp Ser Phe Ala Gln Ser Leu Leu Val
            275                 280

<210> SEQ ID NO 84
<211> LENGTH: 286
<212> TYPE: PRT
<213> ORGANISM: Malus domestica

<400> SEQUENCE: 84

Met Gly Arg Ser Pro Cys Cys Ser Lys Asp Glu Gly Leu Asn Arg Gly
1               5                   10                  15

Ala Trp Thr Ala Met Glu Asp Lys Val Leu Thr Glu Tyr Ile Gly Asn
            20                  25                  30

His Gly Glu Gly Lys Trp Arg Asn Leu Pro Lys Arg Ala Gly Leu Lys
        35                  40                  45

Arg Cys Gly Lys Ser Cys Arg Leu Arg Trp Leu Asn Tyr Leu Arg Pro
    50                  55                  60

Asp Ile Lys Arg Gly Asn Ile Thr Arg Asp Glu Glu Leu Ile Ile
65                  70                  75                  80

Arg Leu His Lys Leu Leu Gly Asn Arg Trp Ser Leu Ile Ala Gly Arg
                85                  90                  95

Leu Pro Gly Arg Thr Asp Asn Glu Ile Lys Asn Tyr Trp Asn Thr Thr
            100                 105                 110

Ile Gly Lys Arg Ile Gln Val Glu Gly Arg Ser Cys Ser Asp Gly Asn
        115                 120                 125

Arg Arg Pro Thr Gln Glu Lys Pro Lys Pro Thr Leu Ser Pro Lys Pro
    130                 135                 140

Ser Thr Asn Ile Ser Cys Thr Lys Val Val Arg Thr Lys Ala Ser Arg
145                 150                 155                 160

Cys Thr Lys Val Val Leu Pro His Glu Ser Gln Lys Phe Gly Tyr Ser
                165                 170                 175

Thr Glu Gln Val Val Asn Ala Ala Pro Thr Leu Asp Gln Ala Val Asn
            180                 185                 190

Asn Pro Met Val Gly Ile Asp Asp Pro Leu Leu Pro Met Ser Phe Leu
        195                 200                 205

Asp Asp Glu Asn Asn Ser Cys Glu Phe Leu Val Asp Phe Lys Met
    210                 215                 220

Asp Glu Asn Phe Leu Ser Asp Phe Leu Asn Val Asp Phe Ser Val Leu
225                 230                 235                 240

Tyr Asn Asn Glu Gly Ala Gly Lys Ala Ala Ala Ala Thr Thr Glu
                245                 250                 255

Asp Thr Ser Asn Lys Leu His Gly Pro Asp Leu Arg Ser Ser Lys Ala
            260                 265                 270
```

```
Pro Ile Ile Glu Ser Glu Leu Asp Cys Trp Leu Val Asp Asn
        275                 280                 285
```

<210> SEQ ID NO 85
<211> LENGTH: 316
<212> TYPE: PRT
<213> ORGANISM: Trifolium arvense

<400> SEQUENCE: 85

```
Met Gly Arg Ser Pro Cys Cys Ala Lys Glu Gly Leu Asn Arg Gly Ala
1               5                   10                  15

Trp Thr Thr Gln Glu Asp Lys Ile Leu Thr Glu Tyr Ile Lys Leu His
            20                  25                  30

Gly Glu Gly Lys Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser Pro Asp Glu Glu Leu Ile Ile Arg
65                  70                  75                  80

Leu His Lys Leu Leu Gly Asn Arg Trp Ser Leu Ile Ala Gly Arg Leu
            85                  90                  95

Pro Gly Arg Thr Asp Asn Glu Ile Lys Asn Tyr Trp Asn Thr Asn Leu
        100                 105                 110

Gly Lys Lys Val Lys Asp Leu Asp Gln Gln Asn Thr Asn Asn Ser Ser
    115                 120                 125

Pro Thr Lys Leu Ser Ala Gln Pro Lys Asn Ala Glu Ile Lys Gln Lys
130                 135                 140

Gln Ile Asn Pro Lys Pro Asn Ser Tyr Val Val Arg Thr Lys Ala Thr
145                 150                 155                 160

Lys Cys Ser Lys Val Leu Phe Ile Asn Ser Pro Asn Ser Pro Pro
            165                 170                 175

Met His Asp Leu Gln Ser Lys Ala Glu Ala Glu Thr Thr Thr Thr Thr
        180                 185                 190

Lys Pro Ser Met Pro Ser Met Leu Val Asp Gly Val Ala Ser Asp Ser
    195                 200                 205

Met Ser Asn Asn Glu Met Glu Cys Gly Asn Gly Phe Leu Ser Phe Cys
210                 215                 220

Asp Glu Glu Lys Glu Leu Ser Ala Asp Leu Leu Glu Asp Phe Asn Ile
225                 230                 235                 240

Ala Asp Asp Ile Cys Leu Ser Glu Phe Leu Asn Phe Asp Phe Ser Asn
            245                 250                 255

Ala Cys Asp Ile Asp Tyr Asn Asp Leu Leu Ser Pro Cys Ser Asp Gln
        260                 265                 270

Thr Gln Met Phe Pro Asp Asp Glu Ile Leu Lys Asn Trp Thr Gln Cys
    275                 280                 285

Asn Phe Ala Asp Glu Thr Asn Val Ser Asn Asn Leu Gln Ser Ser Ala
290                 295                 300

Ser Phe Leu Glu Ser Ser Glu Glu Val Leu Gly Glu
305                 310                 315
```

<210> SEQ ID NO 86
<211> LENGTH: 311
<212> TYPE: PRT
<213> ORGANISM: Trifolium repens

<400> SEQUENCE: 86

```
Met Gly Arg Ser Pro Cys Cys Ala Lys Glu Gly Leu Asn Arg Gly Ala
1               5                   10                  15

Trp Thr Ala His Glu Asp Lys Ile Leu Thr Glu Tyr Ile Lys Leu His
            20                  25                  30

Gly Glu Gly Lys Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
    50                  55                  60

Ile Lys Arg Gly Asn Ile Ser Ser Asp Glu Glu Leu Ile Ile Arg
65                  70                  75                  80

Leu His Lys Leu Leu Gly Asn Arg Trp Ser Leu Ile Ala Gly Arg Leu
                85                  90                  95

Pro Gly Arg Thr Asp Asn Glu Ile Lys Asn Tyr Trp Asn Thr Asn Leu
            100                 105                 110

Gly Lys Lys Val Lys Asp Leu Asn Gln Gln Asn Thr Asn Asn Ser Ser
        115                 120                 125

Pro Thr Lys Pro Ser Ala Gln Pro Lys Asn Ala Asn Ile Lys Gln Lys
    130                 135                 140

Gln Gln Ile Asn Pro Lys Pro Met Lys Pro Asn Ser Asn Val Val Arg
145                 150                 155                 160

Thr Lys Ala Thr Lys Cys Ser Lys Val Leu Phe Ile Asn Ser Pro Pro
                165                 170                 175

Met His Asn Leu Gln Asn Lys Ala Glu Ala Glu Thr Lys Thr Lys Pro
            180                 185                 190

Leu Met Leu Val Asn Gly Val Ala Ser Asp Ser Met Ser Asn Asn Glu
        195                 200                 205

Met Glu Arg Gly Asn Gly Phe Leu Ser Phe Cys Asp Glu Glu Lys Glu
    210                 215                 220

Leu Ser Ala Asp Leu Leu Asp Asp Phe Asn Ile Ala Asp Asp Ile Cys
225                 230                 235                 240

Leu Ser Glu Phe Leu Asn Ser Asp Phe Ser Asn Ala Cys Asn Phe Asp
                245                 250                 255

Cys Asn Asp Leu Leu Ser Pro Cys Ser Asp Gln Thr Gln Met Phe Ser
            260                 265                 270

Asp Asp Glu Ile Leu Lys Asn Trp Thr Gln Cys Asn Phe Ala Asp Glu
        275                 280                 285

Thr Asn Val Ser Asn Asn Leu Asn Ser Phe Ala Ser Phe Leu Glu Ser
    290                 295                 300

Ser Glu Glu Val Leu Gly Glu
305                 310

<210> SEQ ID NO 87
<211> LENGTH: 313
<212> TYPE: PRT
<213> ORGANISM: Trifolium occidentale

<400> SEQUENCE: 87

Met Gly Arg Ser Pro Cys Cys Ala Lys Glu Gly Leu Asn Arg Gly Ala
1               5                   10                  15

Trp Thr Thr Gln Glu Asp Lys Ile Leu Thr Glu Tyr Ile Lys Leu His
            20                  25                  30

Gly Glu Gly Lys Trp Arg Asn Leu Pro Lys Arg Ala Gly Leu Lys Arg
        35                  40                  45

Cys Gly Lys Ser Cys Arg Leu Arg Trp Leu Asn Tyr Leu Arg Pro Asp
```

```
        50                  55                  60
Ile Lys Arg Gly Asn Ile Ser Ser Asp Glu Glu Leu Ile Ile Arg
 65                  70                  75                  80

Leu His Lys Leu Leu Gly Asn Arg Trp Ser Leu Ile Ala Gly Arg Leu
                 85                  90                  95

Pro Gly Arg Thr Asp Asn Glu Ile Lys Asn Tyr Trp Asn Thr Asn Leu
                100                 105                 110

Gly Lys Lys Val Lys Asp Leu Asn Gln Gln Asn Thr Asn Lys Ser Ser
                115                 120                 125

Pro Thr Lys Leu Ser Ala Gln Pro Lys Asn Ala Lys Ile Lys Gln Lys
                130                 135                 140

Gln Ile Asn Pro Lys Pro Met Lys Pro Asn Ser Asn Val Val Arg Thr
145                 150                 155                 160

Arg Ala Thr Lys Cys Ser Lys Val Leu Phe Ile Asn Ser Leu Pro Asn
                165                 170                 175

Ser Pro Met His Asp Leu Gln Asn Lys Ala Glu Ala Glu Thr Thr Thr
                180                 185                 190

Lys Pro Ser Met Leu Val Asp Gly Val Ala Ser Asp Ser Met Ser Asn
                195                 200                 205

Asn Glu Met Glu His Gly Tyr Gly Phe Leu Ser Phe Cys Asp Glu Glu
                210                 215                 220

Lys Glu Leu Ser Ala Asp Leu Leu Glu Asp Phe Asn Ile Ala Asp Asp
225                 230                 235                 240

Ile Cys Leu Ser Glu Leu Leu Asn Ser Asp Phe Ser Asn Ala Cys Asn
                245                 250                 255

Phe Asp Tyr Asn Asp Leu Leu Ser Pro Cys Ser Asp Gln Thr Gln Met
                260                 265                 270

Phe Ser Asp Asp Glu Ile Leu Lys Asn Trp Thr Gln Cys Asn Phe Ala
                275                 280                 285

Asp Glu Thr Asn Val Ser Asn Asn Leu His Ser Phe Ala Ser Phe Leu
                290                 295                 300

Glu Ser Ser Glu Glu Val Leu Gly Glu
305                 310

<210> SEQ ID NO 88
<211> LENGTH: 314
<212> TYPE: PRT
<213> ORGANISM: Artificial sequence
<220> FEATURE:
<223> OTHER INFORMATION: Consensus sequence of MYB14 protein sequences

<400> SEQUENCE: 88

Met Gly Arg Ser Pro Cys Cys Ala Lys Glu Gly Leu Asn Arg Gly Ala
  1               5                  10                  15

Trp Thr Thr Gln Glu Asp Lys Ile Leu Thr Glu Tyr Ile Lys Leu His
                 20                  25                  30

Gly Glu Gly Lys Trp Arg Asn Leu Pro Lys Arg Ala Gly Leu Lys Arg
                 35                  40                  45

Cys Gly Lys Ser Cys Arg Leu Arg Trp Leu Asn Tyr Leu Arg Pro Asp
                 50                  55                  60

Ile Lys Arg Gly Asn Ile Ser Ser Asp Glu Glu Leu Ile Ile Arg
 65                  70                  75                  80

Leu His Lys Leu Leu Gly Asn Arg Trp Ser Leu Ile Ala Gly Arg Leu
                 85                  90                  95

Pro Gly Arg Thr Asp Asn Glu Ile Lys Asn Tyr Trp Asn Thr Asn Leu
```

```
                100                 105                 110
Gly Lys Lys Val Lys Asp Leu Asn Gln Gln Asn Thr Asn Asn Ser Ser
            115                 120                 125

Pro Thr Lys Leu Ser Ala Gln Pro Lys Asn Ala Lys Ile Lys Gln Lys
            130                 135                 140

Gln Ile Asn Pro Lys Pro Met Lys Pro Asn Ser Asn Val Val Arg Thr
145                 150                 155                 160

Lys Ala Thr Lys Cys Ser Lys Val Leu Phe Ile Asn Ser Pro Pro Asn
                165                 170                 175

Ser Pro Met His Asp Leu Gln Asn Lys Ala Glu Ala Glu Thr Thr Thr
            180                 185                 190

Lys Pro Ser Met Leu Val Asp Gly Val Ala Ser Asp Ser Met Ser Asn
            195                 200                 205

Asn Glu Met Glu His Gly Asn Gly Phe Leu Ser Phe Cys Asp Glu Glu
            210                 215                 220

Lys Glu Leu Ser Ala Asp Leu Leu Glu Asp Phe Asn Ile Ala Asp Asp
225                 230                 235                 240

Ile Cys Leu Ser Glu Phe Leu Asn Ser Asp Phe Ser Asn Ala Cys Asn
                245                 250                 255

Phe Asp Tyr Asn Asp Leu Leu Ser Pro Cys Ser Asp Gln Thr Gln Met
                260                 265                 270

Phe Ser Asp Asp Glu Ile Leu Lys Asn Trp Thr Gln Cys Asn Phe Ala
            275                 280                 285

Asp Glu Thr Asn Val Val Ser Asn Asn Leu His Ser Phe Ala Ser Phe
            290                 295                 300

Leu Glu Ser Ser Glu Glu Val Leu Gly Glu
305                 310

<210> SEQ ID NO 89
<211> LENGTH: 1203
<212> TYPE: DNA
<213> ORGANISM: Trifolium repens

<400> SEQUENCE: 89
gaattcgccc ttatggggag aagcccttgt tgtgcaaaag aaggcttgaa tagaggtgct      60
tggacagctc atgaagacaa atcctcact  gaatacatta agctccatgg tgaaggaaaa     120
tggagaaacc ttccaaaaag agcaggttca ttcattctgt atcttactat tatagatcaa     180
taatcacttt cacactttt  ttttacttat aaattttcat gtattttttc ttccattttc     240
cattagaaat gcaaattaat agtacattat tatggacatg ttttttcaaa aatgtgtatt     300
ccatgcaggt ttaaaagat  gtggaaaaag ttgtagacta aggtggttga attatcttag     360
accggatatt aagagaggta atatatcgtc ggatgaagaa gaacttatca ttagacttca     420
caaactactc ggaaaccggt aaagtatcga cataatcact aacttactaa catttgttta     480
taatgtgtgc taattgctct tcctttgatt tgtggtagat ggtctctaat agccggaaga     540 cttccaggc  gaacagacaa tgaaataaag aactactgga acacaaattt aggaaaaaaa     600
gttaaggatc ttaatcaaca aaacaccaac aattcttctc ctactaaacc ttctgctcaa     660
ccaaaaaatg caaatatcaa acagaaacaa cagatcaatc ctaagccaat gaagccaaac     720
tcgaatgttg tccgtacaaa agctaccaaa tgttctaagg tattgttcat aaactcacca     780
ccaatgcata atttgcagaa caaagctgag gcagagacaa aaacaaagcc attaatgctg     840
gttaatggtg tagctagtga ttcaatgagt aacaacgaaa tggaacgcgg taatggattt     900
```

```
ttgtcattttt gcgacgaaga gaaagaacta tccgcagatt tgctagatga tttaacatc    960
gcggatgata tttgcttatc tgaatttcta aactccgatt tctcaaatgc gtgcaatttc   1020
gattgcaatg atctattgtc gccttgttcg gatcaaactc aaatgttctc tgatgatgag   1080
attctcaaga attggacaca atgtaacttt gctgatgaga caaatgtgtc caacaacctt   1140
aattcttttg cttcttttct cgaatccagt gaggaagtac taggagaatg aaagggcgaa   1200
ttc                                                                 1203
```

<210> SEQ ID NO 90
<211> LENGTH: 1205
<212> TYPE: DNA
<213> ORGANISM: Trifolium repens

<400> SEQUENCE: 90

```
gaattcgccc ttatggggag aagcccttgt tgtgcaaaag aaggcttgaa tagaggtgct     60
tggacagctc atgaagacaa atcctcact gaatacatta agctccatgg tgaaggaaaa    120
tggagaaacc ttccaaaaag agcaggttca ttcattctgt atcttactat tatagatcaa   180
taatcacttt cacactttt tttttactt ataaatttc atgtattttt tcttccattt     240
tccattagaa atgcaaatta atagtacatt attatgaca tgttttttca aaaatgtgta     300
ttccatgcag gttaaaaag atgtggaaaa agttgtagac taaggtggtt gaattatctt     360
agaccggata ttaagagagg taatatatcg tcggatgaag aagaactat cattagactt     420
cacaaactac tcggaaaccg gtaaagtatc gacataatca ctaacttact aacatttgtt    480
tataatgtgt gctaattgct cttcctttga tttgtggtag atggtctcta atagccggaa    540
gacttccagg gcgaacagac aatgaaataa agaactactg gaacacaaat ttaggaaaaa    600
aagttaagga tcttaatcaa caaaacacca acaattcttc tcctactaaa ccttctgctc    660
aaccaaaaaa tgcaaatatc aaacagaaac aacagatcaa tcctaagcca atgaagccaa    720
actcgaatgt tgtccgtaca aaagctacca attgttctaa ggtattgttc ataaactcac    780
caccaatgca taatttgcag aacaaagctg aggcagagac aaaaacaaag ccattaatgc    840
tggttaatgg tgtagctagt gattcaatga gtaacaacga aatggaacgc ggtaatggat    900
ttttgtcatt ttgcgacgaa gagaaagaac tatccgcaga tttgctagat gattttaaca   960
tcgcggatga tatttgctta tctgaatttc taaactccga tttctcaaat gcgtgcaatt   1020
tcgattacaa tgatctattg tcgccttgtt cggatcaaac tcaaatgttc tctgatgatg   1080
agattctcaa gaattggaca caatgtaact tgctgatga gacaaatgtg tccaacaacc   1140
ttaattcttt tgcttctttt ctcgaatcca gtgaggaagt actaggagaa tgaaagggcg   1200
aattc                                                              1205
```

<210> SEQ ID NO 91
<211> LENGTH: 1164
<212> TYPE: DNA
<213> ORGANISM: Trifolium occidentale

<400> SEQUENCE: 91

```
gaattcgccc ttatggggag aagcccttgt tgtgcaaagg aaggttttgaa tagaggtgct    60
tggacagctc atgaagacaa atcctcact gaatacatta agctccatgg tgaaggaaaa    120
tggagaaacc ttccaaaaag agcaggttca ttcattctgt atcttactat ttatagatca   180
ataatcactt tcatgtattt ttttccttc cattttccat tagaaatgca attaatagt     240
acattattat ggacatgttt ttccaggttt aaaaagatgt ggaaaaagtt gtagacttag    300
```

```
atggttgaat tatcttagac cagatattaa gagaggtaat atatcgtccg atgaagaaga      360
acttatcatt agacttcaca aactacttgg aaaccggtaa agtatcgaca taatcactaa      420
cttactaaca tttgtttata atgtgtacta attgcgattc ctttgatttg tggtagatgg      480
tctctaatag ccggaagact tccagggcga acagacaatg aaataaaaaa ttactggaac      540
acgaatttag gaaaaaaggt taaggatctt tatcaacaaa acaccaacaa ttcttctcct      600
actaaacctt ctgctcaacc aaaaaatgca aagatcaaac agaaacaaca gatcaataat      660
cctaagccaa tgaagccaaa ctcgaatgtt gtccgtacaa aagctaccaa atgttctaag      720
gtattgttca taaactcacc accaatgcat aatttgcaga acaaagctga ggcagagaca      780
aaaacaaaga catcaatgtt ggttaatggt gtagctagtg attcaatgag taacaacgaa      840
atggaacgag gtaatggatt tttgtcattt cgcgatgaag agaaagaact atccgctgat      900
ttgctagatg attttaacat cgcggatgac atttgcttat ccgaatttct aaactccgat      960
ttctcaaatg cgtgcaattt cgattacaat gatctattgt caccttgttc ggatcaaact     1020
caaatgttct ctgatgatga gattctcaag aattggacac aatgtaactt tgctgatgag     1080
acaaatgtgt ccaacaacct tcattctttt gcttcctttc tcgaatccag tgaggaagta     1140
ctaggagaat gaaagggcga attc                                             1164

<210> SEQ ID NO 92
<211> LENGTH: 1164
<212> TYPE: DNA
<213> ORGANISM: Trifolium occidentale

<400> SEQUENCE: 92
gaattcgccc ttatggggag aagcccttgt tgtgcaaagg aaggtttgaa tagaggtgct       60
tggacagctc atgaagacaa aatcctcact gaatacatta agctccatgg tgaaggaaaa      120
tggagaaacc ttccaaaaag agcaggttca ttcattctgt atcttactat ttatagatca      180
ataatcactt tcatgtattt tttttccttc cattttccat tagaaatgca aattaatagt      240
acattattat ggacatgttt ttccaggttt aaaaagatgt ggaaaaagtt gtagacttag      300
atggttgaat tatcttagac cagatattaa gagaggtaat atatcgtccg atgaagaaga      360
acttatcatt agacttcaca aactacttgg aaaccggtaa agtatcgaca taatcactaa      420
cttactaaca tttgtttata atgtgtacta attgcgattc ctttgatttg tggtagatgg      480
tctctaatag ccggaagact tccagggcga acagacaatg aaataaaaaa ttactggaac      540
acgaatttag gaaaaaaggt taaggatctt aatcaacaaa acaccaacaa ttcttctcct      600
actaaacctt ctgctcaacc aaaaaatgca aagatcaaac agaaacaaca gatcaataat      660
cctaagccaa tgaagccaaa ctcgaatgtt gtccgtacaa aagctaccaa atgttctaag      720
gtattgttca taaactcacc accaatgcat aatttgcaga acaaagctga ggcagagaca      780
aaaacaaaga catcaatgtt ggttaatggt gtagctagtg attcaatgag taacaacgaa      840
atggaacggg gtaatggatt tttgtcattt cgcgatgaag agaaagaact atccgctgat      900
ttgctagatg attttaacat cgcggatgac atttgcttat ccgaatttct aaactccgat      960
ttctcaaatg cgtgcaattt cgattacaat gatctattgt caccttgttc ggatcaaact     1020
caaatgttct ctgatgatga gattctcaag aattggacac aatgtaactt tgctgatgag     1080
acaaatgtgt ccaacaacct tcattctttt gcttcctttc tcgaatccag tgaggaagta     1140
ctaggagaat gaaagggcga attc                                             1164
```

<210> SEQ ID NO 93
<211> LENGTH: 1240
<212> TYPE: DNA
<213> ORGANISM: Trifolium affine

<400> SEQUENCE: 93

```
gaattcgccc ttatggggag aagcccttgt tgtgcgaagg aaggcttgaa tagaggtgct      60
tggacaactc aagaagacaa aatcctcact gaatacatta agctccatgg tgaaggaaaa     120
tggagaaacc ttccaaaaag agcaggttca ttcattctgt atcttacaat tatagattaa     180
ccactttcat acttttgttt gcttataaat tttcttgtat tttttcttcc atttttcatg     240
agaaatgcaa attactagta cattattatg gacatgtttt tgcaaatatg tttatgccat     300
gcaggtttaa aaagatgtgg aaaaagttgt agacttagat ggttgaatta tctaagacta     360
gatattaagc gaggtaatat atcctcggat gaagaagaac ttatcatccg acttcacaaa     420
ttactcggaa acaggtaaag tcctaacata atcactaact tattaacgtt tgtctataac     480
ttgtttttt gacaattagt actactaatt taatttata atgtgtgcta atttgcttgt      540
ctttaatttg tggtagatgg tctctaatag ccggaagact tccaggacga acagacaatg     600
aaataaagaa ctactggaac acaaatttag gaaaaaggt taaggatctt aatcaagaaa      660
acaccaacaa ttcttctcct actaaacttt ctgctcaact aaaaaatgca agatcaaac      720
agaaacagat caatcctaag ccaatggagc caaactcaaa tgttgtccgt acaaaagcta     780
ccaagtgttc taaggcattg ttcataaact caccccccaa ctcaccacca atgcatgatt     840
tgcagaacaa agctgaggca gagacaacaa caaagtcatc aatgccatca atgctggttg     900
atggcgtggc tagtgattca atgagtaaca acgaaatgga atacggtgat ggatttgttt     960
cattttgcga tgacgataaa gaactatccg cagatttgct agaagatttt aacatctcgg    1020
atgatatttg cttatccgaa tttctaaact tcgatttctc aaatgcgtgc aatttcgatt    1080
acaacgatct attgtcgcct tgttcggacc aaacacaaat gttctctgat gatgagattc    1140
tcaagaattc gacaccatgt aactttgctg ctgagacaaa ttaatgtgtc caacaaccaa    1200
tccagtgagg aagtactagg agaatgaaag ggcgaattct                         1240
```

<210> SEQ ID NO 94
<211> LENGTH: 1240
<212> TYPE: DNA
<213> ORGANISM: Trifolium affine

<400> SEQUENCE: 94

```
ggaattcgcc cttatgggga gaagcccttg ttgtgcaaag gaaggcttga atagaggtgc      60
ttggacaact caagaagaca aatcctcac tgaatacatt aagctccatg gtgaaggaaa      120
atggagaaac cttccaaaaa gagcaggttc attcattctg tatcttacaa ttatagatta     180
accactttca acttttgtt ttcttataaa ttttcttgta tttttcttc cattttcat       240
gagaaatgca aattactagt acattattat ggacatgttt ttgcaaatat gtttatgcca     300
tgcaggttta aaaagatgtg gaaaaagttg tagacttaga tggttgaatt atctaagacc     360
agatattaag cgaggtaata tatcctcgga tgaagaagaa cttatcatcc gacttcacaa     420
actactcgga aacaggtaaa gtcataacat aatcattaat ttattaacgg ttatctataa     480
tttgtttttt tgacaattat tactacaaat ttaattttat aatgtgtgct aatttgcttg     540
tctttaattt gtggtagatg gtctctaata gccggaagac ttccagggcg aacagacaat     600
gaaataaaga actactggaa cacaaattta ggaaaaaagg ttaaggatct taatcaagaa     660
```

```
aacaccaaca attcttctcc tactaaactt tctgctcaac taaaaaatgc aaagatcaaa      720
caaaaacaga tcaatcctaa gccaatgaag ccaaactcaa atgttgtccg tacaaaagct      780
accaagtgtt ctaaggtatt gttcataaac tcaccccca  actcaccacc aatgcatgat      840
ttgcagaaca aagctgaggc agagacaaca acaaagccat caatgccatc aatgctggtt      900
gatggcgtgg ctagtgattc aatgagtaac aacgaaatgg gatacggtga tggatttgtt      960
tcattttgcg atgacgataa agaactatcc gcagatttgc tagaagattt taacatctcg     1020
gatgatattt gcttatccga atttctaaac ttcgatttct caaatgcgtg caatttcgat     1080
tacaacgatc tattgtcgcc ttgttcggac caaacacaaa tgttctctga tgatgagatt     1140
ctcaagaatt cgacacaatg taactttgct gctgagacaa attaatgtgt ccaacaacca     1200
atccagtgag gaagtactag gagaatgaaa gggcgaattc                            1240
```

<210> SEQ ID NO 95
<211> LENGTH: 1239
<212> TYPE: DNA
<213> ORGANISM: Trifolium affine

<400> SEQUENCE: 95

```
gaattcgccc ttatggggag aagcccttgt tgtgcaaagg aaggcttgaa tagaggtgct       60
tggacaactc aagaagacaa aatcctcact gaatacatta agctccatgg tgaaggaaaa      120
tggagaaacc ttccaaaaag agcaggttca ttcattctgt atcttacaat tatagattaa      180
ccactttcat acttttgttt tcttataaat tttcttgtat ttttttcttcc attttttcatg    240 agaaatgcaa attactagta cattattatg gacatgtttt tgcaaatatg tttatgccat      300
gcaggtttaa aaagatgtgg aaaaagttgt agacttagat ggttgaatta tctaagacca      360
gatattaagc gaggtaatat atcctcggat gaagaagaac ttatcatccg acttcacaaa      420
ctactcggaa acaggtaaag tcataacatg atcattaatt tattaacggt tatctataat      480
ttgttttttt gacaattatc actacaaatt taattttata atgtgcgcta atttgcttgt      540
ctttaatttg tggtagatgg tctctaatag ccggaagact tccagggcga acaaacaatg      600
aaataaagaa ctactggaac acaaatttag gaaaaaaggt taaggatctt aatcaagaaa      660
acaccaacaa ttcttctcct actaaacttt ctgctcaact aaaaaatgca aagatcaaac      720
agaaacagat caatcctaag ccaatggagc caaactcaaa tgttgtccgt acaaaagcta      780
ccaagtgttc taaggcattg ttcataaact cacccccaa  ctcaccacca atgcatgatt      840
tgcagaacaa agctgaggca gagacaacaa caaagtcatc aatgccatca atgctggttg      900
atggcgtggc tagtgattca gtgagtaaca acgaaatgga atacggtgat ggatttgttt      960
cattttgcga tgacgataaa gaactatccg cagatttgct agaagattt  aacatctcgg     1020 atgatatttg cttatccgaa tttctaaact tcgatttctc aaatgcgtgc aatttcgatt     1080
acaacgatct attgtcgcct tgttcggacc aaacacaaat gttctctgat gatgagattc     1140
tcaagaattc gacacaatgt aactttgctg ctgagacaaa ttaatgtgtc caacaaccaa     1200
tccagtgagg aagtactagg agaatgaaag ggcgaattc                             1239
```

<210> SEQ ID NO 96
<211> LENGTH: 1239
<212> TYPE: DNA
<213> ORGANISM: Trifolium affine

<400> SEQUENCE: 96

```
gaattcgccc ttatggggag aagcccttgt tgtgcaaagg aaggcttgaa tagaggtgct    60
tggacaactc aagaagacaa aatcctcact gaatacatta agctccatgg tgaaggaaaa   120
tggagaaacc ttccaaaaag agcaggttca ttcattctgt atcttacaat tatagattaa   180
ccactttcat acttttgttt tcttataaat tttcttgtat ttttcttcc  attttcatg    240 agaaatgcaa attactagta cattattatg gacatgtttt tgcaaatatg tttatgccat   300
gcaggtttaa aaagatgtgg aaaaagttgt agacttagat ggttgaatta tctaagacca   360
gatattaagc gaggtaatat atcctcggat gaagaagaac ttatcatccg acttcacaaa   420
ctactcggaa acaggtaaag tcataacata atcattaatt tattaacggt tatctataat   480 ttgtttttt  gacaattatc actacaaatt taatttttata atgtgcgcta atttgcttgt   540
ctttaatttg tggtagatgg tctctaatag ccggaagact tccagggcga acagacaatg   600
aaataaagaa ctactggaac acaaatttag gaaaaaaggt taaggatctt aatcaagaaa   660
acaccaacaa ttcttctcct actaaacttt ctgctcaact aaaaaatgca aagatcaaac   720
agaaacagat caatcctaag ccaatggagc caaactcaaa tgttgtccgt acaaaagcta   780
ccaagtgttc taaggcattg ttcataaact cacccccccaa ctcaccacca atgcatgatt   840
tgcagaacaa agctgaggca gagacaacaa caaagtcatc aatgccatca atgctggttg   900
atggcgtggc tagtgattca atgagtaaca acgaaatgga atacggtgat ggatttgttt   960
cattttgcga tgacgataaa gaactatccg cagatttgct agaagatttt aacatctcgg  1020
atgatatttg cttatccgaa tttctaaact tcgatttctc aaatgcgtgc aatttcgatt  1080
acaacgatct attgtcgcct tgttcggacc aaacacaaat gttctctgat gatgagattc  1140
tcaagaattc gacacaatgt aactttgctg ctgagacaaa ttaatgtgtc caacaaccaa  1200
tccagtgagg aagtactagg agaatgaaag ggcgaattc                         1239
```

<210> SEQ ID NO 97
<211> LENGTH: 1239
<212> TYPE: DNA
<213> ORGANISM: Trifolium affine

<400> SEQUENCE: 97

```
gaattcgccc ttatggggag aagcccttgt tgtgcaaagg aaggcttgaa tagaggtgct    60
tggacaactc aagaagacaa aatcctcact gaatacatta agctccatgg tgaaggaaaa   120
tggagaaacc ttccaaaaag agcaggttca ttcattctgt atcttacaat tatagattaa   180
ccactttcat acttttgttt tcttataaat tttcttgtat ttttcttcc  attttcatg    240 agaaatgcaa attactagta cattattatg gacatgtttt tgcaaatatg tttatgccat   300
gcaggtttaa aaagatgtgg aaaaagttgt agacttagat ggttgaatta tctaagacca   360
gatattaagc gaggtaatat atcctcggat gaagaagaac ttatcatccg acttcacaaa   420
ctactcggaa acaggtaaag tcataacata atcattaatt tattaacggt tatctataat   480 ttgtttttt  gacaattatc actacaaatt taatttttata atgtgcgcta atttgcttgt   540
ctttaatttg tggtagatgg tctctaatag ccggaagact tccagggcga acagacaatg   600
aaataaagaa ctactggaac acaaatttag gaaaaaaggt taaggatctt aatcaagaaa   660
acaccaacaa ttcttctcct actaaacttt ctgctcaact aaaaaatgca aagatcaaac   720
agaaacagat caatcctaag ccaatggagc caaactcaaa tgttgtccgt acaaaagcta   780
ccaagtgttc taaggcattg ttcataaact cacccccccaa ctcaccacca atgcatgatt   840
tgcagaacaa agctgaggca gagacaacaa caaagtcatc aatgccatca atgctggttg   900
```

```
atggcgtggc tagtgattca atgagtaaca acgaaatgga atacggtgat ggatttgttt      960
cattttgcga tgacgataaa gaactatccg cagatttgct agaagatttt aacatctcgg     1020
atgatatttg cttatccgaa tttctaaact tcgatttctc aaatgcgtgc aatttcgatt     1080
acaacgatct attgtcgcct tgttcggacc aaacacaaat gttctctgat gatgagattc     1140
tcaagaattc gacacaatgt aactttgctg ctgagacaaa ttaatgtgtc caacaaccaa     1200
tccagtgagg aagtactagg agaatgaaag ggcgaattc                            1239
```

<210> SEQ ID NO 98
<211> LENGTH: 1239
<212> TYPE: DNA
<213> ORGANISM: Trifolium affine

<400> SEQUENCE: 98

```
gaattcgccc ttatggggag aagcccttgt tgtgcaaagg aaggcttgaa tagaggtgct       60
tggacaactc aagaagacaa aatcctcact gaatacatta agctccatgg tgaaggaaaa      120
tggagaaacc ttccaaaaag agcaggttca ttcattctgt atcttacaat tatagattaa      180
ccactttcat acttttgttt tcttataaat tttcttgtat tttttcttcc attttttcatg     240 agaaatgcaa attactagta cattattatg gacatgtttt tgcaaatatg tttatgccat      300
gcaggtttaa aaagatgtgg aaaaagttgt agacttagat ggttgaatta tctaagacca      360
gatattaagc gaggtaatat atcctcggat gaagaagaac ttatcatccg acttcacaaa      420
ctactcggaa acaggtaaag tcataacata tcattaatt tattaacggt tatctataat       480 ttgtttttttt gacaattatc actacaaatt taattttata atgtgcgcta atttgcttgt    540
ctttaatttg tggtagatgg tctctaatag ccggaagact tccagggcga acagacaatg     600
aaataaagaa ctactggaac acaaatttag gaaaaaggt taaggatctt aatcaagaaa      660
acaccaacaa ttcttctcct actaaacttt ctgctcaact aaaaaatgca agatcaaac      720 agaaacagat caatcctaag ccaatggagc caaactcaaa tgttgtccgt acaaaagcta     780
ccaagtgttc taaggcattg ttcataaact caccccccaa ctcaccacca atgcatgatt     840
tgcagaacaa agctgaggca gagacaacaa caaagtcatc aatgccatca atgctggttg     900
atggcgtggc tagtgattca atgagtaaca acgaaatgga atacggtgat ggatttgttt      960
cattttgcga tgacgataaa gaactatccg cagatttgct agaagatttt aacatctcgg     1020
atgatatttg cttatccgaa tttctaaact tcgatttctc aaatgcgtgc aatttcgatt     1080
acaacgatct attgtcgcct tgttcggacc aaacacaaat gttctctggt gatgagattc     1140
tcaagaattc gacacaatgt aactttgctg ctgagacaaa ttaatgtgtc caacaaccaa     1200
tccagtgagg aagtactagg agaatgaaag ggcgaattc                            1239
```

<210> SEQ ID NO 99
<211> LENGTH: 300
<212> TYPE: PRT
<213> ORGANISM: Trifolium occidentale

<400> SEQUENCE: 99

Met Gly Arg Ser Pro Cys Cys Ala Lys Glu Gly Leu Asn Arg Gly Ala
1               5                   10                  15

Trp Thr Ala His Glu Asp Lys Ile Leu Thr Glu Tyr Ile Lys Leu His
            20                  25                  30

Gly Glu Gly Lys Trp Arg Asn Leu Pro Lys Arg Ala Gly Leu Lys Arg
        35                  40                  45

```
Cys Gly Lys Ser Cys Arg Leu Arg Trp Leu Asn Tyr Leu Arg Pro Asp
 50                  55                  60

Ile Lys Arg Gly Asn Ile Ser Asp Glu Glu Leu Ile Ile Arg
 65                  70                  75                  80

Leu His Lys Leu Leu Gly Asn Arg Trp Ser Leu Ile Ala Gly Arg Leu
                     85                  90                  95

Pro Gly Arg Thr Asp Asn Glu Ile Lys Asn Tyr Trp Asn Thr Asn Leu
                    100                 105                 110

Gly Lys Lys Val Lys Asp Leu Asn Gln Gln Asn Thr Asn Asn Ser Ser
                115                 120                 125

Pro Thr Lys Pro Ser Ala Gln Pro Lys Asn Ala Lys Ile Lys Gln Lys
130                 135                 140

Gln Gln Ile Asn Asn Pro Lys Pro Met Lys Pro Asn Ser Asn Val Val
145                 150                 155                 160

Arg Thr Lys Ala Thr Lys Cys Ser Lys Val Leu Phe Ile Asn Ser Pro
                165                 170                 175

Pro Met His Asn Leu Gln Asn Lys Ala Glu Ala Glu Thr Lys Thr Lys
                180                 185                 190

Thr Ser Met Leu Val Asn Gly Val Ala Ser Asp Ser Met Ser Asn Asn
195                 200                 205

Glu Met Glu Arg Gly Asn Gly Phe Leu Ser Phe Arg Asp Glu Glu Lys
210                 215                 220

Glu Leu Ser Ala Asp Leu Leu Asp Asp Phe Asn Ile Ala Asp Asp Ile
225                 230                 235                 240

Cys Leu Ser Glu Phe Leu Asn Ser Asp Phe Ser Asn Ala Cys Asn Phe
                245                 250                 255

Asp Tyr Asn Asp Leu Leu Ser Pro Cys Ser Gln Thr Gln Met Phe
                260                 265                 270

Ser Asp Asp Glu Ile Leu Lys Asn Trp Thr Gln Cys Asn Phe Ala Asp
                275                 280                 285

Glu Thr Asn Val Ser Asn Asn Leu His Ser Phe Ala
290                 295                 300

<210> SEQ ID NO 100
<211> LENGTH: 314
<212> TYPE: PRT
<213> ORGANISM: Artificial sequence
<220> FEATURE:
<223> OTHER INFORMATION: Consensus sequence of MYB14 protein sequences

<400> SEQUENCE: 100

Met Gly Arg Ser Pro Cys Cys Ala Lys Glu Gly Leu Asn Arg Gly Ala
 1               5                  10                  15

Trp Thr Thr Gln Glu Asp Lys Ile Leu Thr Glu Tyr Ile Lys Leu His
                 20                  25                  30

Gly Glu Gly Lys Trp Arg Asn Leu Pro Lys Arg Ala Gly Leu Lys Arg
             35                  40                  45

Cys Gly Lys Ser Cys Arg Leu Arg Trp Leu Asn Tyr Leu Arg Pro Asp
 50                  55                  60

Ile Lys Arg Gly Asn Ile Ser Asp Glu Glu Leu Ile Ile Arg
 65                  70                  75                  80

Leu His Lys Leu Leu Gly Asn Arg Trp Ser Leu Ile Ala Gly Arg Leu
                     85                  90                  95

Pro Gly Arg Thr Asp Asn Glu Ile Lys Asn Tyr Trp Asn Thr Asn Leu
                    100                 105                 110
```

```
Gly Lys Lys Val Lys Asp Leu Asn Gln Gln Asn Thr Asn Asn Ser Ser
            115                 120                 125

Pro Thr Lys Pro Ser Ala Gln Pro Lys Asn Ala Lys Ile Lys Gln Lys
    130                 135                 140

Gln Gln Ile Asn Pro Lys Pro Met Lys Pro Asn Ser Asn Val Val Arg
145                 150                 155                 160

Thr Lys Ala Thr Lys Cys Ser Lys Val Leu Phe Ile Asn Ser Pro Pro
                165                 170                 175

Asn Ser Pro Met His Asn Leu Gln Asn Lys Ala Glu Ala Glu Thr Thr
            180                 185                 190

Thr Lys Pro Ser Met Leu Val Asn Gly Val Ala Ser Asp Ser Met Ser
        195                 200                 205

Asn Asn Glu Met Glu Arg Gly Asn Gly Phe Leu Ser Phe Cys Asp Glu
    210                 215                 220

Glu Lys Glu Leu Ser Ala Asp Leu Leu Asp Asp Phe Asn Ile Ala Asp
225                 230                 235                 240

Asp Ile Cys Leu Ser Glu Phe Leu Asn Ser Asp Phe Ser Asn Ala Cys
                245                 250                 255

Asn Phe Asp Tyr Asn Asp Leu Leu Ser Pro Cys Ser Asp Gln Thr Gln
            260                 265                 270

Met Phe Ser Asp Asp Glu Ile Leu Lys Asn Trp Thr Gln Cys Asn Phe
        275                 280                 285

Ala Asp Glu Thr Asn Val Ser Asn Asn Leu His Ser Phe Ala Ser Phe
    290                 295                 300

Leu Glu Ser Ser Glu Glu Val Leu Gly Glu
305                 310

<210> SEQ ID NO 101
<211> LENGTH: 13
<212> TYPE: PRT
<213> ORGANISM: Artificial sequence
<220> FEATURE:
<223> OTHER INFORMATION: Motif associated with MYB TFs that regulate CT
      pathways
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 101

Val Ile Val Arg Thr Lys Ala Xaa Arg Lys Xaa Ser Lys
1               5                   10

<210> SEQ ID NO 102
<211> LENGTH: 9
<212> TYPE: PRT
<213> ORGANISM: Artificial sequence
<220> FEATURE:
<223> OTHER INFORMATION: Motif of subgroup 5 common to previously known
      CT MYB activators
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
```

```
<400> SEQUENCE: 102

Asp Glu Xaa Trp Arg Leu Xaa Xaa Thr
1               5
```

MYB14 SEQUENCES AND USES THEREOF FOR FLAVONOID BIOSYNTHESIS

CROSS-REFERENCE TO RELATED APPLICATIONS

This application is a National Stage Application filed under 35 U.S.C. §371 of PCT Application No. PCT/NZ2009/000099, filed on Jun. 5, 2008 and published in English on Dec. 10, 2009 as WO 2009/148336, which claims priority to U.S. Provisional Application 61/059,691, filed on Jun. 6, 2008, and New Zealand Application 568928, filed on Jun. 6, 2008, all of which are incorporated by reference in their entireties to the extent there is no inconsistency with the present disclosure.

TECHNICAL FIELD

The invention relates to a novel gene(s) involved in biosynthesis. In particular, the present invention relates to gene(s) encoding a regulatory factor controlling the expression of key genes involved in the production of flavonoids including condensed tannins in plants.

BACKGROUND ART

The Molecular Phenylpropanoid Pathway

The phenylpropanoid pathway (shown in FIG. 1) produces an array of secondary metabolites including flavones, anthocyanins, flavonoids, condensed tannins and isoflavonoids (Dixon et al., 1996; 2005). In particular, the condensed tannin (CT) biosynthetic pathway shares its early steps with the anthocyanin pathway before diverging to proanthocyanidin biosynthesis.

Anthocyanidins are precursors of flavan-3-ols (e.g. (−)-epicatechin), which are important building blocks for CTs. These cis-flavan-3-ols are formed from anthocyanidins by anthocyanidin reductase (ANR), which has been cloned from many species including *A. thaliana* and *M. truncatula* (Xie et al., 2003; 2004). In *A. thaliana* (−)-epicatechin is the exclusive CT monomer (Abrahams et al., 2002), but in many other species, including legumes, both (+)- and (−)-flavan-3-ols are polymerized to CTs. The biosynthesis of these alternate (+)-flavan-3-ols (catechins) is catalysed by leucoanthocyanidin reductase (LAR). This enzyme has been cloned and characterized from legumes including the CT-rich legume tree *Desmodium uncinatum* (Tanner et al., 2003), as well as from other species such as grapes and apples (Pfeiffer et al., 2006). The enzyme catalyses the reduction of leucopelargonidin, leucocyanidin, and leucodelphinidin to afzelechin, catechin, and gallocatechin, respectively. No homologues of LAR have been found in *A. thaliana*, consistent with the exclusive presence of (−)-epicatechin derived CT building blocks in this plant.

Whereas information on TF regulation of this pathway in *Arabidopsis* seeds is well defined, TFs that control leaf CT biosynthesis within the tribe of Trifolieae have yet to be identified. An important family of TF proteins, the MYB family, controls a diverse range of functions including the regulation of secondary metabolism such as the anthocyanin and CT pathways in plants. The expression of the MYB TF AtTT2 coordinately turns on or off the late structural genes in *Arabidopsis thaliana*, ultimately controlling the expression of the CT pathway.

An array of *Arabidopsis thaliana* transparent testa (TT) mutants (Winkel-Shirley, 2002; Debeaujon et al., 2001) and tannin deficient seed (TDS) mutants (Abrahams et al. 2002; 2003) have been made—all being deficient in CT accumulation in the seed coat. Molecular genetic studies of these mutants has allowed for the identification of a number of structural genes and transcription factors (TFs) that regulate the expression and tissue specificity of both anthocyanin and CT synthesis in *A. thaliana* (Walker et al., 1999; Nesi et al., 2000; 2002).

Although most of the structural genes within the CT pathway have been identified in a range of legumes, attempts to manipulate CT biosynthesis in leaves by engineering the expression of these individual genes has failed so far. The major reason for this is that not one (or a few) enzyme(s) are rate-limiting, but that activity of virtually all enzymes in a pathway has to be increased to achieve an overall increased flux into specific end-products such as condensed tannins.

Transcription factors (TFs) are regulatory proteins that act as repressors or activators of metabolic pathways. TFs can therefore be used as a powerful tool for the manipulation of entire metabolic pathways in plants. Many MYB TFs are important regulators of the phenylpropanoid pathway including both the anthocyanin and condensed tannin biosynthesis (Debaujon et al, 2003; Davies and Schwinn, 2003). For example, the *A. thaliana* TT2 (AtTT2) gene encodes an R2R3-MYB TF factor which is solely expressed in the seed coat during early stages of embryogenesis, when condensed tannin biosynthesis occurs (Nesi et al., 2001). TT2 has been shown to regulate the expression of the flavonoid late biosynthetic structural genes TT3 (DFR), TT18, TT12 (MATE protein) and ANR during the biosynthesis and storage of CTs. AtTT2 partially determines the stringent spatial and temporal expression of genes, in combination with two other TFs; namely TT8 (bHLH protein) and TTG1 (WD-40 repeat protein; Baudry et al., 2004).

Other MYB TFs in *Vitis vinifera*; grape (VvMYBPA1) Birdsfoot trefoil and *Brassica napus* (BnTT2) that are involved in the regulation of CT biosynthesis have also recently been reported (Wei et al., 2007; Bogs et al., 2007; Yoshida et al., 2008).

The AtTT2 gene has also been shown to share a degree of similarity to the rice (*Oryza sativa*) OsMYB3, the maize (*Zea mays*) ZmC1, AmMYBROSEA from *Antirrhinum majus* and PhMYBAN2 from *Petunia hybrida*, genes which have been shown to regulate anthocyanin biosynthesis (Stracke et al., 2001; Mehrtens et al., 2005).

Condensed Tannins

Condensed tannins (CTs) also called proanthocyanidins (PAs) are colourless polymers, one of several secondary plant metabolites. CTs are polymers of 2 to 50 (or more) flavonoid units (see compound (I) below) that are joined by carbon-carbon bonds which are not susceptible to being cleaved by hydrolysis. The base flavonoid structure is:

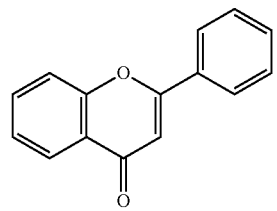

COMPOUND (I)

Condensed tannins are located in a range of plant parts, for example; the leaves, stem, flowers, roots, wood products, bark, buds. CTs are generally found in vacuoles or on the surface epidermis of the plant Condensed Tannins in Forage Plants Forage plants, such as forage legumes, are beneficial in pasture-based livestock systems because they improve both the intake and quality of the animal diet. Also, their value to the nitrogen (N) economy of pastures and to ruminant production are considerable (Caradus et al., 2000). However, while producing a cost-effective source of feed for grazing ruminants, pasture is often sub-optimal when it comes to meeting the nutritional requirements of both the rumen microflora and the animal itself. Thus the genetic potential of grazing ruminants for meat, wool or milk production is rarely achieved on a forage diet.

New Zealand pastures contain up to 20% white clover, while increasing the levels of white clover in pastures helps address this shortfall, it also exacerbates the incidence of bloat. White clover (*Trifolium repens*), red clover (*Trifolium pratense*) and lucerne (*Medicago sativa*) are well documented causes of bloat, due to the deficiency of plant polyphenolic compounds, such as CT, in these species. Therefore the development of forage cultivars producing higher levels of tannins in plant tissue would be a important development in the farming industry to reduce the incidence of bloat (Burggraaf et al., 2006).

In particular, condensed tannins, if present in sufficient amounts, not only helps eliminate bloat, but also strongly influences plant quality, palatability and nutritive value of forage legumes and can therefore help improve animal performance. The animal health and productivity benefits reported from increased levels of CTs include increased ovulation rates in sheep, increased liveweight gain, wool growth and milk production, changed milk composition and improved anthelmintic effects on gastrointestinal parasites (Rumbaugh, 1985; Marten et al., 1987; Niezen et al., 1993; 1995; Tanner et al., 1994; McKenna, 1994; Douglas et al., 1995; Waghorn et al., 1998; Aerts et al, 1999; McMahon et al., 2000; Molan et al., 2001; Sykes and Coop, 2001).

A higher level of condensed tannin also represents a viable solution to reducing greenhouse gases (methane, nitrous oxide) released into the environment by grazing ruminants (Kingston-Smith and Thomas, 2003). Ruminant livestock produce at least 88% of New Zealand's total methane emissions and are a major contributor of greenhouse gas emissions (Clark, 2001). The principle source of livestock methane is enteric fermentation in the digestive tract of ruminants. Methane production, which represents an energy loss to ruminants of around 3 to 9% of gross energy intake (Blaxter and Clapperton, 1965), can be reduced by as much as 5% by improving forage quality. Forage high in CT has been shown to reduce methane emission from grazing animals (Woodward, et al 2001; Puchala, et al., 2005). Increasing the CT content of pasture plants can therefore contribute directly to reduced levels of methane emission from livestock.

Therefore, the environmental and agronomical benefits that could be derived from triggering the accumulation of even a moderate amount of condensed tannins in forage plants including white clover are of considerable importance in the protection and nutrition of ruminants (Damiani et al., 1999).

Legumes

It is the inventors understanding that the regulation of CT foliar-specific pathway in *Trifolium* legumes, involving the interaction of regulatory transcription factors (TFs) with the pathway, remains unknown. Modification or manipulation of this pathway to influence the amount CT has been explored but, as the process is not straightforward, there has been little firm success in understanding this pathway.

The clover genus, *Trifolium*, for example, is one of the largest genera in the family Leguminosae (D Fabaceae), with ca. 255 species (Ellison et al., 2006). Only two *Trifolium* species; *T. affine* (also known as *Trifolium preslianum* Boiss. Is) and *T. arvense* (also known as hare-foot clover) are known to accumulate high levels of foliar CTs (Fay and Dale, 1993). Although significant levels of CTs are present in white clover flower heads (Jones et al., 1976), only trace amounts can be detected in leaf trichomes (Woodfield et al., 1998). Several approaches including gene pool screening and random mutagenesis have failed to provide white or red clover plants with increased levels of foliar CTs (Woodfield et al., 1998).

Genetic Manipulation of Condensed Tannins

The inventors in relation to US2006/012508 created a transgenic alfalfa plant using the TT2 MYB regulatory gene and managed to surprisingly produce CTs constitutively throughout the root tissues. However, importantly, the inventors were unable to achieve CT accumulation in the leaves of this forage legume. It has been previously reported no known circumstances exist that can induce proanthocyanidins (CTs) in alfalfa forage (Ray et al., 2003). The authors of this paper assessed amongst other things whether the LC myc-like regulatory gene (TF) from maize or the C1 myb regulatory gene (TF) from maize could stimulate the flavonoid pathway in alfalfa forage and seed coat. The authors of this paper found that only the LC gene, and not C1 could stimulate anthocyanin and proanthocyanidin biosynthesis in alfalfa forage, but stimulation only occurred in the presence of an unknown stress-responsive alfalfa factor.

Studies assessing condensed tannin production in *Lotus* plants using a maize bHLH regulatory gene (TF) found that transformation of this TF into *Lotus* plants resulted in CT's only a very small (1%) increase in levels of condensed tannins in leaves (Robbins et al., 2003).

Previous attempts to alter and enhance agriculturally important compounds in white clover involved altering anthocyanin biosynthesis-derived from the phenylpropanoid pathway. Despite attempts to activate this pathway using several heterologous myc and MYB TFs only one success has been reported, using the maize myc TF B-Peru (de Majnik et al., 2000). All other TFs investigated resulted in poor or no regenerants, implying a deleterious effect from their overexpression.

More recently, TT2 homologs derived from the high-CT legume, *Lotus japonicus*, have been reported (Yoshida et al., 2008). Bombardment of these genes into *A. thaliana* leaf cells has shown transient expression resulting in detectable expression of ANR and limited CT accumulation as detected by DMACA. However, these genes have not been transformed and analysed in any legume species.

The expression of the maize Lc gene resulted in the accumulation of PA-like compounds in alfalfa only if the plants were under abiotic stress (Ray et al., 2003). The co-expression of three transcription factors, TT2, PAP1 and Lc in *Arabidopsis* was required to overcome cell-type-specific expression of PAs, but this constitutive accumulation of PAs was accompanied by death of the plants (Sharma and Dixon, 2005).

Introduction of PAs into plants by combined expression of a MYB family transcription factor and anthocyanidin reductase for conversion of anthocyanidin into (epi)-flavan-3-ol has been attempted by Xie et al. (2006).

This attempt to increase the levels of proanthocyanidins (PAs) in the leaves of tobacco by co-expressing PAP1 (a MYB TF) and ANR were reported as having levels of PAs in tobacco that if translated to alfalfa may potentially provide bloat protection (Xie et al., 2006). Anthocyanin-containing leaves of transgenic *M. truncatula* constitutively expressing MtANR contained up to three times more PAs than those of wild-type plants at the same stage of development, and these compounds were of a specific subset of PA oligomers. Additionally, these levels of PA produced in *M. truncatula* fell well short of those necessary for an improved agronomic benefit. The authors state that it remained unclear which additional biosynthetic and non-biosynthetic genes will be needed for engineering of PAs in any specific plant tissue that does naturally accumulate the compounds.

Similar difficulties in expressing CTs or PAs in leaves were also encountered when the TT2 and/or BAN genes were transformed into alfalfa—refer US 2004/0093632 and US 2006/0123508.

Condensed Tannins Useful in Natural Health Products

The use of any flavonoid including proanthocyanidins to form food supplements, compositions or medicaments is also widely known. For example;

US patent application NO: 2003/0180406 describes a method using polyphenol compositions specifically derived from cocoa to improve cognitive function.

Patent publication WO 2005/044291 describes use of grape seed (*Vitus* genus) to prevent degenerative brain diseases including; stroke, cerebral concussion, Huntington's disease, CJD, Alzheimer's, Parkinsons, and senile dementia.

Patent publication WO 2005/067915 discloses a synergistic combination of flavonoids and hydroxystilbenes (synthetic or from green tea) combined with flavones, flavonoids, proanthocyanidins and anthocyanidins (synthetic or from bark extract) to reduce neuronal degeneration associated with disease states such as dementia, Alzheimer's, cerebrovascular disease, age-related cognitive impairment and depression.

U.S. Pat. No. 5,719,178 describes use of proanthocyanidin extract to treat ADHD.

PCT publication number 06/126895 describes a composition containing bark extract from the genus *Pinus* to improve, or prevent a decline in, human cognitive abilities or improve, or prevent symptoms of, neurological disorders in a human.

None of the above considers use of legumes as a raw material source of CT.

It would therefore be useful if there could be provided nucleic acid molecules and polypeptides useful in studying the metabolic pathways involved in flavonoids and/or condensed tannin biosynthesis.

It would also be useful if there could be provided nucleic acid molecules and polypeptides which are capable of altering levels of flavonoids and/or condensed tannins in plants or parts thereof.

In particular, it would be useful if there could be provided nucleic acid molecules which can be used to produce flavonoids and/or condensed tannins in plants or parts thereof de novo.

It is therefore one object of the invention to provide a method to increase CT levels in the leaves of forage legume species. The identification of the gene also provides a method to prevent CT accumulation in legume species which produce detrimental high levels of CT in leaves or seeds.

It would also be useful if there could be provided nucleic acid molecules which can be used alone or together with other nucleic acid molecules to produce plants, particularly forages and legumes, with enhanced levels of flavonoids and/or condensed tannins.

It is an object of the present invention to address the foregoing problems or at least to provide the public with a useful choice.

SUMMARY OF THE INVENTION

The present invention is concerned with the identification and uses of a novel MYB gene and associated polypeptide which has been termed by the inventors 'MYB14' which has been isolated by the applicants and shown to be involved in the production of flavonoid compounds including condensed tannins.

Throughout this specification the nucleic acid molecules and polypeptides of the present invention may be designated by the descriptor MYB14.

The present invention contemplates the use of MYB14 independently or together with other nucleic acid molecules to manipulate the flavonoid/condensed tannin biosynthetic pathway in plants.

Polynucleotides Encoding Polypeptides

In the one aspect the invention provides an isolated nucleic acid molecule encoding a MYB14 polypeptide as herein defined, or a functional variant or fragment thereof.

In one embodiment the MYB14 polypeptide comprises the sequence of SEQ ID NO: 15.

In one embodiment the MYB14 polypeptide comprises the sequence of SEQ ID NO: 17.

In one embodiment the MYB14 polypeptide comprises the sequence of SEQ ID NO: 15 and SEQ ID NO: 17, but lacks the sequence of SEQ ID NO: 16.

In a further embodiment the MYB14 polypeptide comprises a sequence with at least 70% identity to any one of SEQ ID NO: 14 and 46 to 54.

In a further embodiment the MYB14 polypeptide comprises a sequence with at least 70% identity to SEQ ID NO: 14.

In a further embodiment the MYB14 polypeptide comprises the sequence of any one of SEQ ID NO: 14 and 46 to 54.

In a further embodiment the MYB14 polypeptide comprises the sequence of SEQ ID NO: 14.

In a further embodiment the MYB14 polypeptide regulates the production of flavonoids in a plant.

In a further embodiment the flavonoids are condensed tannins.

In a further embodiment the MYB14 polypeptide regulates at least one gene in the flavonoid biosynthetic pathway in a plant.

In a further embodiment the MYB14 polypeptide regulates at least one gene in the condensed tannin biosynthetic pathway in a plant.

In a further embodiment the functional fragment has substantially the same activity as the MYB14 polypeptide.

In a further embodiment the functional fragment comprises an amino acid sequence with at least 70% identity to SEQ ID NO: 17.

In a further embodiment the functional fragment comprises the amino acid sequence of SEQ ID NO: 17.

In a further aspect invention provides a nucleic acid molecule encoding a polypeptide comprising an amino acid sequence substantially as shown in SEQ ID NO: 17.

In a further aspect invention provides a nucleic acid molecule encoding a polypeptide having an amino acid sequence substantially as shown in SEQ ID NO: 17.

In a further aspect invention provides a nucleic acid molecule encoding a polypeptide comprising an amino acid sequence substantially as shown in SEQ ID NO: 14.

In a further aspect invention provides a nucleic acid molecule encoding a polypeptide having an amino acid sequence substantially as shown in SEQ ID NO: 14.

In a further aspect invention provides an isolated nucleic acid molecule encoding a polypeptide comprising 3' amino acid sequence motif as set forth in SEQ ID NO: 17

Polynucleotides

In a further aspect invention provides an isolated nucleic acid molecule having a nucleotide sequence selected from the group consisting of:
 a) at least one of SEQ ID NO: 1 to 13 and 55 to 64, or a combination thereof;
 b) a complement of the sequence(s) in a);
 c) a functional fragment or variant of the sequence(s) in a) or b);
 d) a homolog or an ortholog of the sequence(s) in a), b), or c);
 e) an antisense sequence to a RNA sequence obtained from a sequence in a), b), c) or d).

In one embodiment the variant has at least 70% identity to the coding sequence of the specified sequence.

In a further embodiment the variant has at least 70% identity to the specified sequence.

In a further embodiment the fragment comprises the coding sequence of the specified sequence.

In a further aspect invention provides an isolated nucleic acid molecule having a nucleotide sequence selected from the group consisting of:
 a) SEQ ID NO: 1, 2 or 55;
 b) a complement of the sequence(s) in a);
 c) a functional fragment or variant of the sequence(s) in a) or b);
 d) a homolog or an ortholog of the sequence(s) in a), b), or c);
 e) an antisense sequence to a RNA sequence obtained from a sequence in a), b), c) or d).

In one embodiment the variant has at least 70% identity to the coding sequence of the specified sequence.

In a further embodiment the variant has at least 70% identity to the specified sequence.

In a further embodiment the fragment comprises the coding sequence of the specified sequence.

In a further embodiment isolated nucleic acid molecule comprises the sequence of SEQ ID NO: 2.

In a further embodiment isolated nucleic acid molecule comprises the sequence of SEQ ID NO: 1.

In a further embodiment isolated nucleic acid molecule comprises the sequence of SEQ ID NO:55.

Probes

In a further aspect the invention provides a probe capable of binding to a nucleic acid of the invention According to another aspect of the present invention there is a probe capable of binding to a 3' domain of the MYB14 nucleic acid molecule substantially as described above.

In one embodiment the probe is capable of binding to a nucleic acid molecule that encodes the amino acid sequence of SEQ ID NO: 17, or to a complement of the nucleic acid molecule.

In one embodiment the probe is capable of binding to the nucleic acid molecule, or complement thereof under stringent hybridisation conditions.

According to a further aspect of the present invention there is provided a probe to a 3' sequence encoding the motif as set forth in SEQ ID NO: 17.

Primers

In a further aspect the invention provides a primer capable of binding to a nucleic acid of the invention According to another aspect of the present invention there is a primer capable of binding to a 3' domain of the MYB14 nucleic acid molecule substantially as described above.

In one embodiment the probe is capable of binding to a nucleic acid molecule that encodes the amino acid sequence of SEQ ID NO: 15, or to a complement of the nucleic acid molecule.

In one embodiment the probe is capable of binding to the nucleic acid molecule, or complement thereof under PCR conditions.

According to a further aspect of the present invention there is provided a primer to a nucleic acid encoding a 3' sequence encoding the motif as set forth in SEQ ID NO: 17.

Polypeptides

In the one aspect the invention provides a MYB14 polypeptide as herein defined, or a functional fragment thereof.

In one embodiment the MYB14 polypeptide comprises the sequence of SEQ ID NO: 15 and SEQ ID NO: 17, but lacks the sequence of SEQ ID NO: 16.

In a further aspect the invention provides an isolated polypeptide having an amino acid sequence selected from the group consisting of:
 a) any one of SEQ ID NO: 14 and 46 to 54;
 b) a functional fragment or variant of the sequence listed in a).

In a further embodiment the variant comprises a sequence with at least 70% identity to any one of SEQ ID NO: 14 and 46 to 54.

In a further embodiment the variant comprises a sequence with at least 70% identity to SEQ ID NO: 14.

In a further embodiment the MYB14 polypeptide comprises the sequence of any one of SEQ ID NO: 14 and 46 to 54.

In a further embodiment the MYB14 polypeptide comprises the sequence of SEQ ID NO: 14.

In a further embodiment the MYB14 polypeptide regulates the production of flavonoids in a plant.

In a further embodiment the flavonoids are condensed tannins.

In a further embodiment the MYB14 polypeptide regulates at least one gene in the flavonoid biosynthetic pathway in a plant.

In a further embodiment the MYB14 polypeptide regulates the condensed tannin biosynthetic pathway in a plant.

In a further embodiment the MYB14 polypeptide regulates at least one gene in the condensed tannin biosynthetic pathway in a plant.

In a further embodiment the functional fragment has substantially the same activity as the MYB14 polypeptide.

According to another aspect of the present invention there is provided an isolated polypeptide having an amino acid sequence selected from the group consisting of:
 a) SEQ ID NO: 14;
 b) a functional fragment or variant of the sequence listed in a).

According to another aspect of the present invention there is provided an isolated polypeptide comprising a 3' amino acid sequence motif as set forth in SEQ ID NO: 17.

According to another aspect of the present invention there is provided an isolated polypeptide having a 3' amino acid sequence motif as set forth in SEQ ID NO: 17.

According to a further aspect of the present invention there is provided an isolated MYB14 polypeptide or a functional fragment thereof wherein said MYB14 polypeptide includes an amino acid sequence motif of subgroup 5 as shown in SEQ ID NO: 15 as well as an amino acid sequence 3' motif as shown in SEQ ID NO: 17 but which lacks an amino acid sequence motif of subgroup 6 as shown in SEQ ID NO: 16.

According to another aspect of the present invention there is provided an isolated polypeptide encoded by a nucleic acid molecule having a nucleotide sequence selected from those set forth in any one of SEQ ID NO:1 to 13 and 55 to 64.

According to another aspect of the present invention there is provided an isolated polypeptide encoded by a nucleic acid molecule having a nucleotide sequence as set forth in either SEQ ID NO: 1, 2 or 55.

In a further aspect the invention provides a nucleic acid molecule comprising a sequence encoding a polypeptide of the invention.

Constructs

According to a further aspect of the present invention there is provided a construct including a nucleotide sequence substantially as described above.

According to a further aspect of the present invention, there is provided a construct which includes:
- at least one promoter; and
- a nucleic acid molecule substantially as described above;
wherein the promoter is operably linked to the nucleic acid molecule to control the expression of the nucleic acid molecule.

Preferably, the construct may include one or more other nucleic acid molecules of interest and/or one or more further regulatory sequences, such as inter alia terminator sequences.

Most preferably, the nucleic acid molecule in the construct may have a nucleotide sequence selected from SEQ ID NO: 1, 2 or 55.

Host Cells

According to a further aspect of the present invention there is provided a host cell which has been altered from the wild type to include a nucleic acid molecule substantially as described above.

In one embodiment the nucleic acid is part of a genetic construct of the invention.

In one embodiment the host cell does not form part of a human being.

In a further embodiment the host cell is a plant cell.

Plant Cells and Plants

According to a further aspect of the present invention there is provided a plant or plant cell transformed with a construct substantially as described above.

According to a further aspect of the present invention there is provided a plant transformed with a construct substantially as described above.

According to a further aspect of the present invention there is provided a plant or part thereof which has been altered from the wild type to include a nucleic acid molecule substantially as described above.

According to a further aspect of the present invention, there is provided a plant cell, plant or part thereof which has been manipulated via altered expression of a MYB14 gene to have increased or decreased levels of flavonoids and/or condensed tannins than a corresponding wild-type plant or part thereof.

According to a further aspect of the present invention, there is provided a plant cell, plant cell which has been manipulated via altered expression of a MYB14 gene to have increased or decreased levels of flavonoids and/or condensed tannins than a corresponding wild-type plant cell.

According to a further aspect of the present invention, there is provided a leaf of a plant which via altered expression of a MYB14 gene to have increased levels of flavonoids and/or condensed tannins than a corresponding wild-type plant or part thereof.

According to a further aspect of the present invention, there is provided the progeny of a plant cell or a plant substantially as described above which via altered expression of a MYB14 gene has increased or decreased to levels of flavonoids and/or condensed tannins than a corresponding wild-type plant cell or plant.

According to a further aspect of the present invention there is provided the seed of a transgenic plant substantially as described above.

Compositions

According to a further aspect of the present invention, there is provided a composition which includes an ingredient which is, or is obtained from, a plant and/or part thereof, wherein said plant or part thereof has been manipulated via altered expression of a MYB14 gene to have increased or decreased levels of flavonoids and/or condensed tannins compared to those of a corresponding wild type plant or part thereof.

Methods Using Polynucleotides

According to a further aspect of the present invention there is provided the use of a nucleic acid molecule substantially as described above to alter a plant or plant cell.

According to a further aspect of the present invention there is provided a method for producing an altered plant or plant cell using a nucleic acid molecule substantially as described above.

In one embodiment the plant or plant cell is altered in the production of flavonoids, or an intermediate in the production of flavonoids.

In a further embodiment the flavonoids include at least one condensed tannin.

In a further embodiment the condensed tannin is selected from catechin, epicatechin, epigallocatechin and gallocatechin.

In a preferred embodiment the alteration is an increase.

In a further embodiment the plant or plant cell is altered in expression of at least one enzyme in a flavonoid biosynthetic pathway.

In one embodiment the flavonoid biosynthetic pathway is the condensed tannin biosynthetic pathway.

In a preferred embodiment the altered expression is increased expression.

In a further embodiment the enzyme is LAR or ANR.

In a further embodiment the plant is altered in the expression of both LAR and ANR.

The plant may be any plant, and the plant cell may be from any plant.

In one embodiment the plant is a forage crop plant.

In a further embodiment the plant is a legumionous plant.

In one embodiment the altered production or expression, described above, is in substantially all tissues of the plant.

In one embodiment the altered production or expression, described above, is in the foliar tissue of the plant.

In one embodiment the altered production or expression, described above, is in the vegetative portions of the plant.

In one embodiment the altered production or expression, described above, is in the epidermal tissues of the plant.

For the purposes of this specification, the epidermal tissue refers to the outer single-layered group of cells, including the leaf, stems, and roots and young tissues of a vascular plant.

In one embodiment the altered production flavonoids, described above, is in a tissue of the plant that is substantially devoid of the flavonoids.

In one embodiment the altered production condensed tannins described above is in a tissue of the plant that is substantially devoid of the condensed tannins.

Therefore, in some embodiments of the invention, the production of flavonoids or condensed tannins is de novo production.

In one embodiment the nucleic acid encodes a MYB14 protein as herein defined.

In a further embodiment the nucleic acid encodes a protein comprising an amino acid sequence as set forth in any one of SEQ ID NOs 1-13 and 55 to 64, or fragment or variant thereof.

In a further embodiment the nucleic acid comprises a sequence substantially as set forth in any one of SEQ ID NOs 1-13 and 55 to 64, or fragment or variant thereof.

In a further embodiment the nucleic acid comprises a sequence substantially as set forth in SEQ ID NOs 1, 2 or 55, or fragment or variant thereof.

In a further embodiment the nucleic acid is part of a construct substantially as described above.

In one embodiment the plant is altered by transforming the plant with the nucleic acid or construct.

In a further embodiment the plant is altered by manipulating the genome of a plant so as to express increase or decrease levels of the nucleic acid, or fragment or variant thereof, in the plant compared to that produced in a corresponding wild-type plant or plant thereof.

According to a further aspect of the present invention there is provided the use of a nucleic acid molecule or polypeptide of the present invention to identify other related flavonoid and/or condensed tannin regulatory genes/polypeptides.

According to a further aspect of the present invention there is provided the use of a nucleic acid molecule substantially as described above to alter a plant or plant cell wherein said plant is, or plant cell is from, a forage crop.

In one embodiment the plant is altered in production of condensed tannins.

In one embodiment the plant has increased production of condensed tannins.

Preferably, the forage crop may be a forage legume.

According to a further aspect of the present invention there is provided the use of a nucleic acid molecule substantially as described above to alter the levels of flavonoids or condensed tannins in leguminous plants or leguminous plant cells.

Preferably, the levels of condensed tannins are altered.

Preferably, the levels of condensed tannins are altered in foliar tissue.

According to a further aspect of the present invention there is provided the use of nucleic acid sequence information substantially as set forth in any one of SEQ ID NO: 1-13 and 55 to 64 to alter the flavonoid or condensed tannin biosynthetic pathway in planta.

According to a further aspect of the present invention there is provided the use of nucleic acid sequence information substantially as set forth in any one of SEQ ID NO:1, 2 and 55 to alter the flavonoid or condensed tannin biosynthetic pathway in planta.

According to a further aspect of the present invention there is provided use of a construct substantially as described above to transform a leguminous plant or plant cell to alter the levels of flavonoids and/or condensed tannins in the vegetative portions of the leguminous plant or plant cell.

According to a further aspect of the present invention, there is provided a method of altering flavonoids and/or condensed tannins production within a leguminous plant or part thereof, including the step of manipulating the genome of a plant so as to express increased or decreased levels a of leguminous MYB14 gene, or fragment or variant thereof, in the plant compared to that produced in a corresponding wild-type plant or plant thereof.

According to a further aspect of the present invention, there is provided a method of altering flavonoids and/or condensed tannins production within a leguminous plant or part thereof, including the step of manipulating the genome of a plant so as to express increased or decreased levels a of leguminous MYB14 gene, or fragment or variant thereof, in the plant compared to that produced in a corresponding wild-type plant or plant thereof.

According to a further aspect of the present invention, there is provided the use of a nucleic acid molecule to produce flavonoids or condensed tannins in planta in a leguminous plant or part thereof de novo.

According to a further aspect of the present invention, there is provided the use of a nucleic acid molecule substantially as described above to manipulate in a leguminous plant or part thereof the flavonoids and/or condensed tannin biosynthetic pathway in planta.

According to a further aspect of the present invention, there is provided the use of a construct substantially as described above, to manipulate the flavonoids and/or condensed tannin biosynthetic pathway in planta.

According to a further aspect of the present invention, there is provided the use of a MYB14 gene having a nucleic acid sequence substantially corresponding to a nucleic acid molecule of the present invention to manipulate the biosynthetic pathway in planta.

According to a further aspect of the present invention, there is provided the use of a nucleic acid molecule substantially as described above to produce a flavonoid and/or condensed tannin, enzyme, intermediate or other chemical compound associated with the flavonoid and/or condensed tannin biosynthetic pathway.

According to a further aspect of the present invention, there is provided a method of manipulating the flavonoid and/or condensed tannin biosynthetic pathway characterized by the step of altering a nucleic acid substantially as described above to produce a gene encoding a non-functional polypeptide.

According another aspect there is provided the use of an isolated nucleic acid molecule of the present invention in planta to manipulate the levels of LAR and/or ANR within a leguminous plant or plant cell.

According another aspect there is provided the use of an isolated nucleic acid molecule of the present invention in planta to manipulate the levels of catechin and/or epicatechin or other tannin monomer (epigallocatechin or gallocatechin) within a leguminous plant or plant cell.

According to a further aspect of the present invention there is provided the use of a nucleic acid molecule or polypeptide to identify other related flavonoid and/or condensed tannin regulatory genes/polypeptides.

In one embodiment, the whole of the plant tissue may be manipulated. In an alternative embodiment, the epidermal tissue of the plant may be manipulated. For the purposes of this specification, the epidermal tissue refers to the outer single-layered group of cells, the leaf, stems, and roots and young tissues of a vascular plant.

Most preferably, the levels of flavonoids and/or condensed tannins altered by the present invention are sufficient to provide a therapeutic or agronomic benefit to a subject consuming the plant with altered levels of flavonoids and/or condensed tannins.

Plants Produced via the Methods

In a further embodiment the invention provides a plant produced by a method of the invention. In a further embodiment the invention provides a part, seed, fruit, harvested material, propagule or progeny of a plant of any the invention.

In a further embodiment the part, seed, fruit, harvested material, propagule or progeny of the plant is genetically modified to comprise at least one nucleic acid molecule of the invention, or a construct of the invention.

Source of Nucleic Acids and Proteins of the Invention

The nucleic acids and proteins of the invention may derived from any plant, as described below, or may be synthetically or recombinantly produced.

Plants

The plant cells and plants of the invention, or those transformed or manipulated in methods and uses of the inventions, may be from any species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Preferably the plants are from dicotyledonous species.

Other preferred plants are forage plant species from a group comprising but not limited to the following genera: *Lolium, Festuca, Dactylis, Bromus, Thinopyrum, Trifolium, Medicago, Pheleum, Phalaris, Holcus, Lotus, Plantago* and *Cichorium*.

Other preferred plants are leguminous plants. The leguminous plant or part thereof may encompass any plant in the plant family Leguminosae or Fabaceae. For example, the plants may be selected from forage legumes including, alfalfa, clover; *leucaena*; grain legumes including, beans, lentils, lupins, peas, peanuts, soy bean; bloom legumes including lupin, pharmaceutical or industrial legumes; and fallow or green manure legume species.

A particularly preferred genus is *Trifolium*.

Preferred *Trifolium* species include *Trifolium repens; Trifolium arvense; Trifolium affine*; and *Trifolium occidentale*.

A particularly preferred *Trifolium* species is *Trifolium repens*.

Another preferred genus is *Medicago*.

Preferred *Medicago* species include *Medicago sativa* and *Medicago truncatula*.

A particularly preferred *Medicago* species is *Medicago sativa*, commonly known as alfalfa.

Another preferred genus is *Glycine*.

Preferred *Glycine* species include *Glycine max* and *Glycine wightii* (also known as *Neonotonia wightii*)

A particularly preferred Glycine species is *Glycine max*, commonly known as soy bean A particularly preferred *Glycine* species is *Glycine wightii*, commonly known as perennial soybean.

Another preferred genus is *Vigna*.

Preferred *Vigna* species include *Vigna unguiculata*

A particularly preferred *Vigna* species is *Vigna unguiculata* commonly known as cowpea.

Another preferred genus is *Mucana*.

Preferred *Mucana* species include *Mucana pruniens*

A particularly preferred *Mucana* species is *Mucana pruniens* commonly known as velvetbean.

Another preferred genus is *Arachis*

Preferred *Mucana* species include *Arachis glabrata*

A particularly preferred *Arachis* species is *Arachis glabrata* commonly known as perennial peanut.

Another preferred genus is *Pisum*

Preferred *Pisum* species include *Pisum sativum*

A particularly preferred *Pisum* species is *Pisum sativum* commonly known as pea.

Another preferred genus is *Lotus*

Preferred *Lotus* species include *Lotus corniculatus, Lotus pedunculatus, Lotus glabar, Lotus tenuis* and *Lotus uliginosus*.

A particularly preferred *Lotus* species is *Lotus corniculatus* commonly known as Birdsfoot Trefoil.

A particularly preferred *Lotus* species is *Lotus glabar* commonly known as Narrow-leaf Birdsfoot Trefoil A particularly preferred *Lotus* species is *Lotus pedunculatus* commonly known as Big trefoil.

A particularly preferred *Lotus* species is *Lotus tenuis* commonly known as Slender trefoil. Another preferred genus is *Brassica*.

Preferred *Brassica* species include *Brassica oleracea*

A particularly preferred *Brassica* species is *Brassica oleracea*, commonly known as forage kale and cabbage.

The term 'plant' as used herein refers to the plant in its entirety, and any part thereof, may include but is not limited to: selected portions of the plant during the plant life cycle, such as plant seeds, shoots, leaves, bark, pods, roots, flowers, fruit, stems and the like. A preferred 'part thereof' is leaves.

DETAILED DESCRIPTION OF THE INVENTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner. However, in preferred embodiments comprising can be replaced with consisting.

The term "MYB14 polypeptide" refers to an R2R3 class MYB transcription factor.

Preferably the MYB14 polypeptide comprises a sequence with at least 70% identity to any one of SEQ ID NO: 14 and 46 to 54.

Preferably the MYB14 polypeptide comprises the sequence motif of SEQ ID NO:15

Preferably the MYB14 polypeptide comprises the sequence motif of SEQ ID NO:17

More preferably the MYB14 polypeptide comprises the sequence of SEQ ID NO: 15 and SEQ ID NO: 17, but lacks the sequence of SEQ ID NO: 16.

Preferably MYB14 polypeptide comprises a sequence with at least 70% identity to SEQ ID NO: 14.

A "MYB14 gene" is a gene, by the standard definition of gene, that encodes a MYB14 polypeptide.

The term "MYB transcription factor" is a term well understood by those skilled in the art to refer to a class of transcription factors characterised by a structurally conserved DNA binding domain consisting of single or multiple imperfect repeats.

The term "R2R3 transcription factor" or "MYB transcription with an R2R3 DNA binding domain" is a term well understood by those skilled in the art to refer to MYB transcription factors of the two-repeat class.

The terms 'proanthocyanidins' and 'condensed tannins' may be used interchangeably throughout the specification The term "sequence motif" as used herein means a stretch of amino acids or nucleotides. Preferably the stretch of amino acids or nucleotides is contiguous.

The term "altered" with respect to a plant with "altered production" or "altered expression", means altered relative to the same plant, or plant of the same type, in the non-transformed state.

The term "altered" may mean increased or decreased. Preferably altered is increased Polynucleotides and Fragments The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

The term "polynucleotide" can be used interchangably with "nucleic acid molecule".

A "fragment" of a polynucleotide sequence provided herein is a subsequence of contiguous nucleotides that is preferably at least 15 nucleotides in length. The fragments of the invention preferably comprises at least 20 nucleotides, more preferably at least 30 nucleotides, more preferably at least 40 nucleotides, more preferably at least 50 nucleotides and most preferably at least 60 contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods.

Preferably fragments of polynucleotide sequences of the invention comprise at least 25, more preferably at least 50, more preferably at least 75, more preferably at least 100, more preferably at least 150, more preferably at least 200, more preferably at least 300, more preferably at least 400, more preferably at least 500, more preferably at least 600, more preferably at least 700, more preferably at least 800, more preferably at least 900, more preferably at least 1000 contiguous nucleotides of the specified polynucleotide.

The term "primer" refers to a short polynucleotide, usually having a free 3'OH group, that is hybridized to a template and used for priming polymerization of a polynucleotide to complementary to the template. Such a primer is preferably at least 5, more preferably at least 6, more preferably at least 7, more preferably at least 9, more preferably at least 10, more preferably at least 11, more preferably at least 12, more preferably at least 13, more preferably at least 14, more preferably at least 15, more preferably at least 16, more preferably at least 17, more preferably at least 18, more preferably at least 19, more preferably at least 20 nucleotides in length.

The term "probe" refers to a short polynucleotide that is used to detect a polynucleotide sequence, that is complementary to the probe, in a hybridization-based assay. The probe may consist of a "fragment" of a polynucleotide as defined herein. Preferably such a probe is at least 5, more preferably at least 10, more preferably at least 20, more preferably at least 30, more preferably at least 40, more preferably at least 50, more preferably at least 100, more preferably at least 200, more preferably at least 300, more preferably at least 400 and most preferably at least 500 nucleotides in length.

Polypeptides and Fragments

The term "polypeptide", as used herein, encompasses amino acid chains of any length but preferably at least 5 amino acids, including full-length proteins, in which amino acid residues are linked by covalent peptide bonds. The polypeptides may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "derived from" with respect to a polynucleotide or polypeptide sequence being derived from a particular genera or species, means that the sequence has the same sequence as a polynucleotide or polypeptide sequence found naturally in that genera or species. The sequence, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polynucleotides and polypeptides possess biological activities that are the same or similar to those of the inventive polynucleotides or polypeptides. The term "variant" with reference to polynucleotides and polypeptides encompasses all forms of polynucleotides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a specified polynucleotide sequence. Identity is found over a comparison window of at least 20 nucleotide positions, more preferably at least 50 nucleotide positions, more preferably at least 100 nucleotide positions, more preferably at least 200 nucleotide positions, more preferably at least 300 nucleotide positions, more preferably at least 400 nucleotide positions, more preferably at least 500 nucleotide positions, more preferably at least 600 nucleotide positions, more preferably at least 700 nucleotide positions, more preferably at least 800 nucleotide positions, more preferably at least 900 nucleotide positions, more preferably at least 1000 nucleotide positions and most preferably over the entire length of the specified polynucleotide sequence.

Polynucleotide sequence identity can be determined in the following manner. The subject polynucleotide sequence is compared to a candidate polynucleotide sequence using BLASTN (from the BLAST suite of programs, version 2.2.5 [Nov 2002]) in bl2seq (Tatiana A. Tatusova, Thomas L. Madden (1999), "Blast 2 sequences —a new tool for comparing protein and nucleotide sequences", FEMS Microbiol Lett. 174:247-250), which is publicly available from NCBI ncbi<dot>nih<dot>gov/blast). The default parameters of bl2seq are utilized except that filtering of low complexity parts should be turned off.

The identity of polynucleotide sequences may be examined using the following unix command line parameters:
bl2seq -i nucleotideseq1 -j nucleotideseq2 -F F -p blastn The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics Jun. 2000, vol 16, No 6. pp.276-277) which can be obtained from hgmp<dot>mrc<dot>ac<dot>uk/Software/EMBOSS/. The European Bioinformatics Institute server also provides the facility to perform EMBOSS-needle global alignments between two sequences on line at ebi<dot>ac<dot>uk/emboss/align/ebi.

Alternatively the GAP program, which computes an optimal global alignment of two sequences without penalizing terminal gaps, may be used to calculate sequence identity. GAP is described in the following paper: Huang, X. (1994) On Global Sequence Alignment. Computer Applications in the Biosciences 10, 227-235.

Sequence identity may also be calculated by aligning sequences to be compared using Vector NTI version 9.0, which uses a Clustal W algorithm (Thompson et al., 1994, Nucleic Acids Research 24, 4876-4882), then calculating the percentage sequence identity between the aligned sequences using Vector NTI version 9.0 (Sep. 2, 2003© 1994-2003 InforMax, licensed to Invitrogen).

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polynucleotides may be determined using the publicly available bl2seq program from the BLAST suite of programs (version 2.2.5 [Nov 2002]) from NCBI (ncbi<dot>nih<dot>gov/blast).

The similarity of polynucleotide sequences may be examined using the following unix command line parameters:
bl2seq -i nucleotideseq1 -j nucleotideseq2 -F F -p tblastx The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1 \times 10^{-10}$, more preferably less than $1 \times 10^{-20}$, more preferably less than $1 \times 10^{-30}$, more preferably less than $1 \times 10^{-40}$, more preferably less than $1 \times 10^{-60}$, more preferably less than $1 \times 10^{-60}$, more preferably less than $1 \times 10^{-70}$, more preferably less than $1 \times 10^{-80}$, more preferably less than $1 \times 10^{-90}$ and most preferably less than $1 \times 10^{-100}$ when compared with any one of the specifically identified sequences.

Alternatively, variant polynucleotides of the present invention hybridize to a specified polynucleotide sequence, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing). Tm for polynucleotide molecules greater than about 100 bases can be calculated by the formula Tm=81.5+0.41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides such as those in constructs of the invention encoding proteins to be expressed, also encompasses polynucleotides that differ from the specified sequences but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also contemplated. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [Nov 2002]) from NCBI (ncbi<dot>nih<dot>gov/blast) via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [Nov 2002]) in bl2seq, which is publicly available from NCBI (ncbi<dot>nih<dot>gov/blast). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at ebi<dot>ac<dot>uk/emboss/align/ebi) and GAP (Huang, X. (1994) On Global Sequence Alignment. Computer Applications in the Biosciences 10, 227-235.) as discussed above are also suitable global sequence alignment programs for calculating polypeptide sequence identity.

Sequence identity may also be calculated by aligning sequences to be compared using Vector NTI version 9.0, which uses a Clustal W algorithm (Thompson et al., 1994, Nucleic Acids Research 24, 4876-4882), then calculating the percentage sequence identity between the aligned polypeptide sequences using Vector NTI version 9.0 (Sep. 2, 2003 ©1994-2003 InforMax, licensed to Invitrogen).

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [Nov 2002]) from NCBI (ncbi<dot>nih<dot>gov/blast). The similarity of polypeptide sequences may be examined using the following unix command line parameters:

bl2seq -i peptideseq1 -j peptideseq2 -F F -p blastp

Variant polypeptide sequences preferably exhibit an E value of less than $1^-\times10^{-6}$ more preferably less than $1\times10^{-9}$, more preferably less than $1\times10^{-12}$, more preferably less than $1\times10^{15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably $1\times10^{-100}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain a promoter polynucleotide including the necessary elements that permit transcribing the insert polynucleotide molecule, and, optionally, translating the transcript into a polypeptide. The insert polynucleotide molecule may be derived from the host cell, or may be derived from a different cell or organism and/or may be a synthetic or recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as *E. coli*.

The term "expression construct" refers to a genetic construct that includes the necessary elements that permit transcribing the insert polynucleotide molecule, and, optionally, translating the transcript into a polypeptide.

An expression construct typically comprises in a 5' to 3' direction:
  a) a promoter functional in the host cell into which the construct will be transformed,
  b) the polynucleotide to be expressed, and
  c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

The term "operably-linked" means that the sequenced to be expressed is placed under the control of regulatory elements that include promoters, tissue-specific regulatory elements, temporal regulatory elements, enhancers, repressors and terminators.

The term "noncoding region" includes to untranslated sequences that are upstream of the translational start site and downstream of the translational stop site. These sequences are also referred to respectively as the 5' UTR and the 3' UTR. These sequences may include elements required for transcription initiation and termination and for regulation of translation efficiency. The term "noncoding" also includes intronic sequences within genomic clones.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to a polynucleotide sequence capable of regulating or driving the expression of a polynucleotide sequence to which the promoter is operably linked in a cell, or cell free transcription system. Promoters may comprise cis-initiator elements which specify the transcription initiation site and conserved boxes such as the TATA box, and motifs that are bound by transcription factors.

Methods for Isolating or Producing Polynucleotides

The polynucleotide molecules of the invention can be isolated by using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser, incorporated herein by reference. The polynucleotides of the invention can be amplified using primers, as defined herein, derived from the polynucleotide sequences of the invention.

Further methods for isolating polynucleotides of the invention, or useful in the methods of the invention, include use of all or portions, of the polynucleotides set forth herein as hybridization probes. The technique of hybridizing labeled polynucleotide probes to polynucleotides immobilized on solid supports such as nitrocellulose filters or nylon membranes, can be used to screen the genomic. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence and/or the whole gene/ and/or the promoter. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a polynucleotide. The fragment is then circularized by intramolecular ligation and used as a PCR template. Divergent primers are designed from the known region. Promoter and flanking sequences may also be isolated by PCR genome walking using a GenomeWalker™ kit (Clontech, Mountain View, Calif.), following the manufacturers instructions. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

Methods for Identifying Variants

Physical Methods

Variant polynucleotides may be identified using PCR-based methods (Mullis et al., Eds. 1994 The Polymerase Chain Reaction, Birkhauser).

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Computer-Based Methods

Polynucleotide and polypeptide variants may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [Nov 2002]) including BLASTN, BLASTP, BLASTX, tBLASTN and tBLASTX, which are publicly available from (ncbi<dot>nih<dot>gov/blast) or from the National Center for Biotechnology Information (NCBI), National Library of Medicine, Building 38A, Room 8N805, Bethesda, MD 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, www-igbmc<dot>u-strasbg<dot>fr/BioInfo/ClustalW/Top<dot>html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351). Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Function of Variants

The function of the polynucleotides/polypeptides of the invnetion can be tested using methods provided herein. In particular, see Example 7.

Methods for Producing Constructs and Vectors

The genetic constructs of the present invention comprise one or more polynucleotide sequences of the invention and/or polynucleotides encoding polypeptides disclosed, and may be useful for transforming, for example, bacterial, fungal, insect, mammalian or particularly plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Constructs and Vectors

The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides. Such methods may involve the culture of host cells in an appropriate medium in conditions suitable for or conducive to expression of a polypeptide of the invention.

The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide. Plants comprising such cells also form an aspect of the invention.

Methods for transforming plant cells, plants and portions thereof with polynucleotides are described in Draper et al., 1988, Plant Genetic Transformation and Gene Expression. A Laboratory Manual, Blackwell Sci. Pub. Oxford, p. 365; Potrykus and Spangenburg, 1995, Gene Transfer to Plants. Springer-Verlag, Berlin; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9,: 821); cassaya (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); perennial ryegrass (Bajaj et al., 2006, Plant Cell Rep. 25, 651); grasses (U.S. Pat. Nos. 5,187,073, 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792, 935); soybean (U.S. Pat. Nos. 5,416,011; 5,569,834; 5,824, 877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); brassica (U.S. Pat. Nos. 5,188,958; 5,463,174 and 5,750,871); and cereals (U.S. Pat. No. 6,074,877); pear (Matsuda et al., 2005, Plant Cell Rep. 24(1):45-51); Prunus (Ramesh et al., 2006, Plant Cell Rep. 25(8):821-8; Song and Sink 2005, Plant Cell Rep. 2006; 25(2):117-23; Gonzalez Padilla et al., 2003, Plant Cell Rep. 22(1):38-45); strawberry (Oosumi et al., 2006, Planta.; 223(6):1219-30; Folta et al., 2006, Planta. 2006 Apr. 14; PMID: 16614818), rose (Li et al., 2003, Planta. 218(2): 226-32), Rubus (Graham et al., 1995, Methods Mol. Biol. 1995; 44:129-33). Clover (Voisey et al., 1994, Plant Cell Reports 13: 309-314, and Medicago (Bingham, 1991, Crop Science 31: 1098). Transformation of other species is also contemplated by the invention. Suitable methods and protocols for transformation of other species are available in the scientific literature.

Methods for Genetic Manipulation of Plants

A number of strategies for genetically manipulating plants are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. Strategies may also be designed to increase expression of a polynucleotide/polypeptide in response to external stimuli, such as environmental stimuli. Environmental stimuli may include environmental stresses such as mechanical (such as herbivore activity), dehydration, salinity and temperature stresses. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed or to reduce expression of a polynucleotide/polypeptide in response to an external stimuli. Such strategies are known as gene silencing strategies.

Genetic constructs for expression of genes in transgenic plants typically include promoters, such as promoter polynucleotides of the invention, for driving the expression of one or more cloned polynucleotide, terminators and selectable marker sequences to detect presence of the genetic construct in the transformed plant.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zin gene terminator, the *Oryza sativa* ADP-glucose pyrophosphorylase terminator and the *Solanum tuberosum* PI-II terminator.

Selectable markers commonly used in plant transformation include the neomycin phosphotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide may include an antisense copy of a polynucleotide. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

| 5'GATCTA 3' | 3'CTAGAT 5' |
| (coding strand) | (antisense strand) |
| 3'CUAGAU 5' | 5'GAUCUCG 3' |
| mRNA | antisense RNA |

Genetic constructs designed for gene silencing may also include an inverted repeat. An 'inverted repeat' is a sequence that is repeated where the second half of the repeat is in the complementary strand, e.g.,

```
5'-GATCTA........TAGATC-3'
3'-CTAGAT........ATCTAG-5'
```

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polynucleotides useful for effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a sequence operably-linked to promoter of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

Plants

The term "plant" is intended to include a whole plant or any part of a plant, propagules and progeny of a plant.

The term 'progeny' as used herein refers to any cell, plant or part thereof which has been obtained or derived from a cell or transgenic plant of the present invention. Thus, the term progeny includes but is not limited to seeds, plants obtained from seeds, plants or parts thereof, or derived from plant tissue culture, or cloning, techniques.

The term 'propagule' means any part of a plant that may be used in reproduction or propagation, either sexual or asexual, including seeds and cuttings.

A "transgenic" or "transformed" plant refers to a plant which contains new genetic material as a result of genetic manipulation or transformation. The new genetic material may be derived from a plant of the same species as the resulting transgenic of transformed plant or from a different species. A transformed plant includes a plant which is either stably or transiently transformed with new genetic material.

The plants of the invention may be grown and either self-ed or crossed with a different plant strain and the resulting hybrids, with the desired phenotypic characteristics, may be identified. Two or more generations may be grown. Plants resulting from such standard breeding approaches also form part of the present invention.

BRIEF DESCRIPTION OF DRAWINGS

Further aspects of the present invention will become apparent from the following description which is given by way of example only and with reference to the accompanying drawings in which:

FIG. 2(A) illustrates the cDNA sequence representing the full length cDNA sequence of TaMYB14, cloned from mature *T. arvense* leaf tissue.

FIG. 2(B) illustrates the amino acid translation of TaMYB14.

FIG. 7 shows the alignment of the full-length cDNA sequences of *Trifolium* MYB14, top BLASTN hits and AtTT2 with similarities highlighted in light grey.

FIG. 8 shows the alignment of the translated open reading frames of *Trifolium arvense* TaMYB14, top BLASTP hits and AtTT2 with similarities highlighted in light grey and motifs boxed.

FIG. 11 shows the alignment of the full-length genomic DNA sequences of *Trifolium occidentale* ToMYB14 alleles (To1, To6) aligned with *Trifolium arvense* TaMYB14 alleles (TaM3, TaM4), with differences in exons (light grey) and introns (dark grey) highlighted.

B: B1 Ladder, B2-B11 transformed *T. arvense*, B12 M14pHANNIBAL positive plasmid control. Primers were 35S (promoter) and PHMYBR (to 3' end of gene) amplifying a 393 bp fragment.

Figure 27:
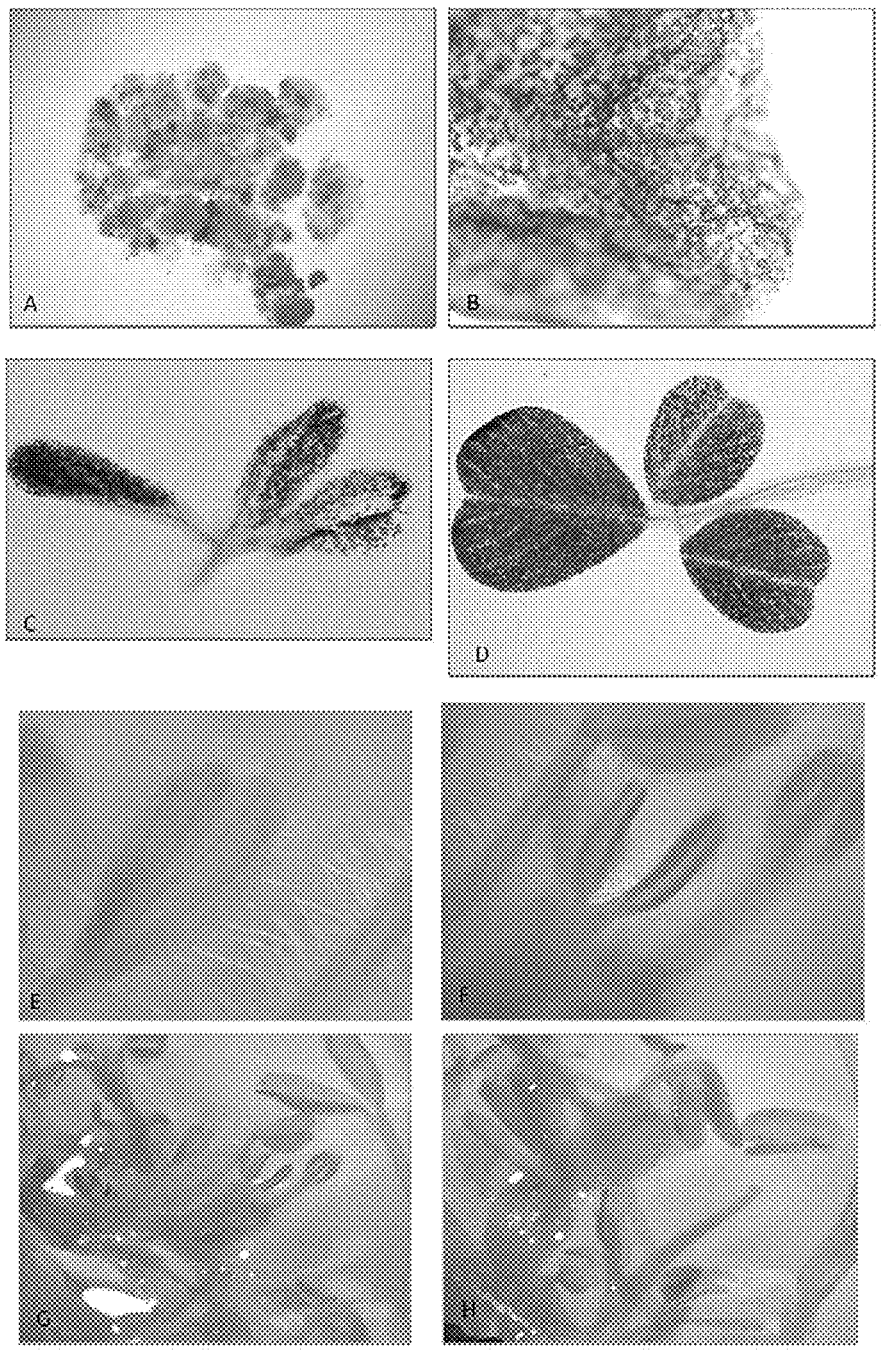
Figure 27A:
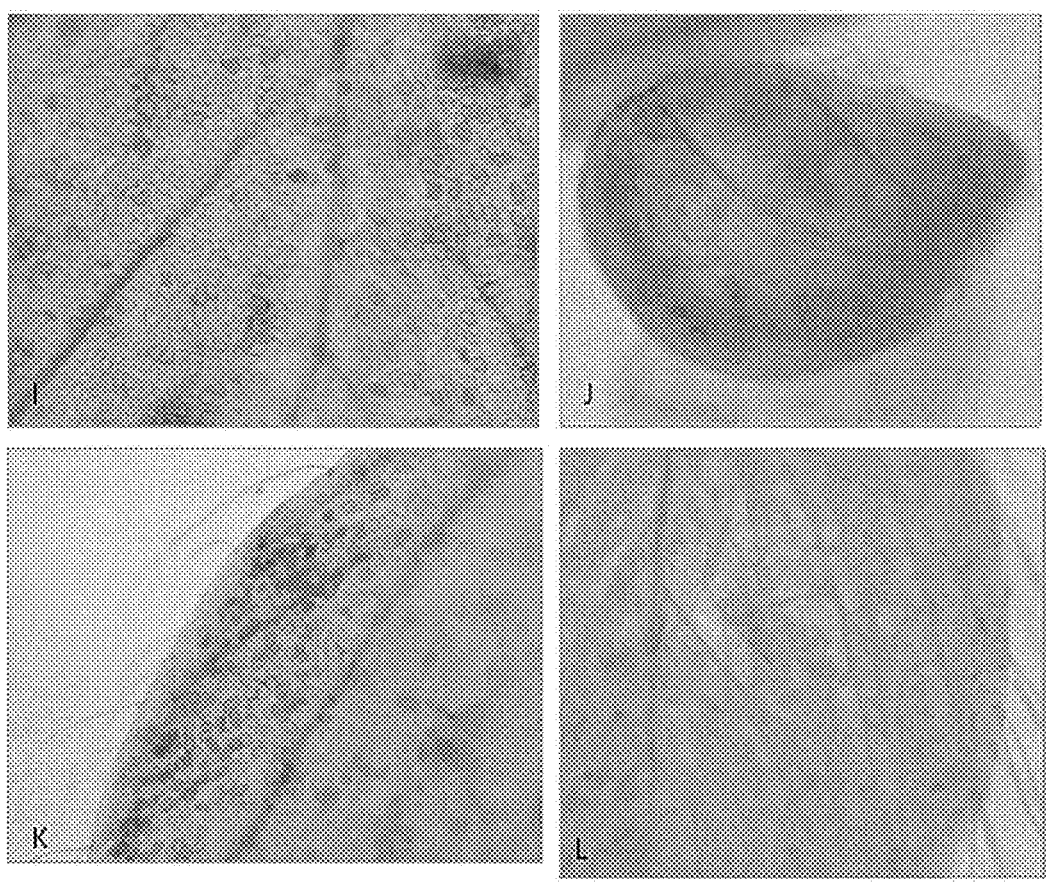

FIG. 27 shows the results of DMACA screening of wild type *T. arvense* callus (A) and plantlets (B to D) regenerated on tissue culture media. No DMACA staining occurs in callus and DMACA screening of transgenic (E to L) *T. arvense* plantlets regenerated on tissue culture media. Staining is greatly diminished compared to wild type plants.

Figure 28:
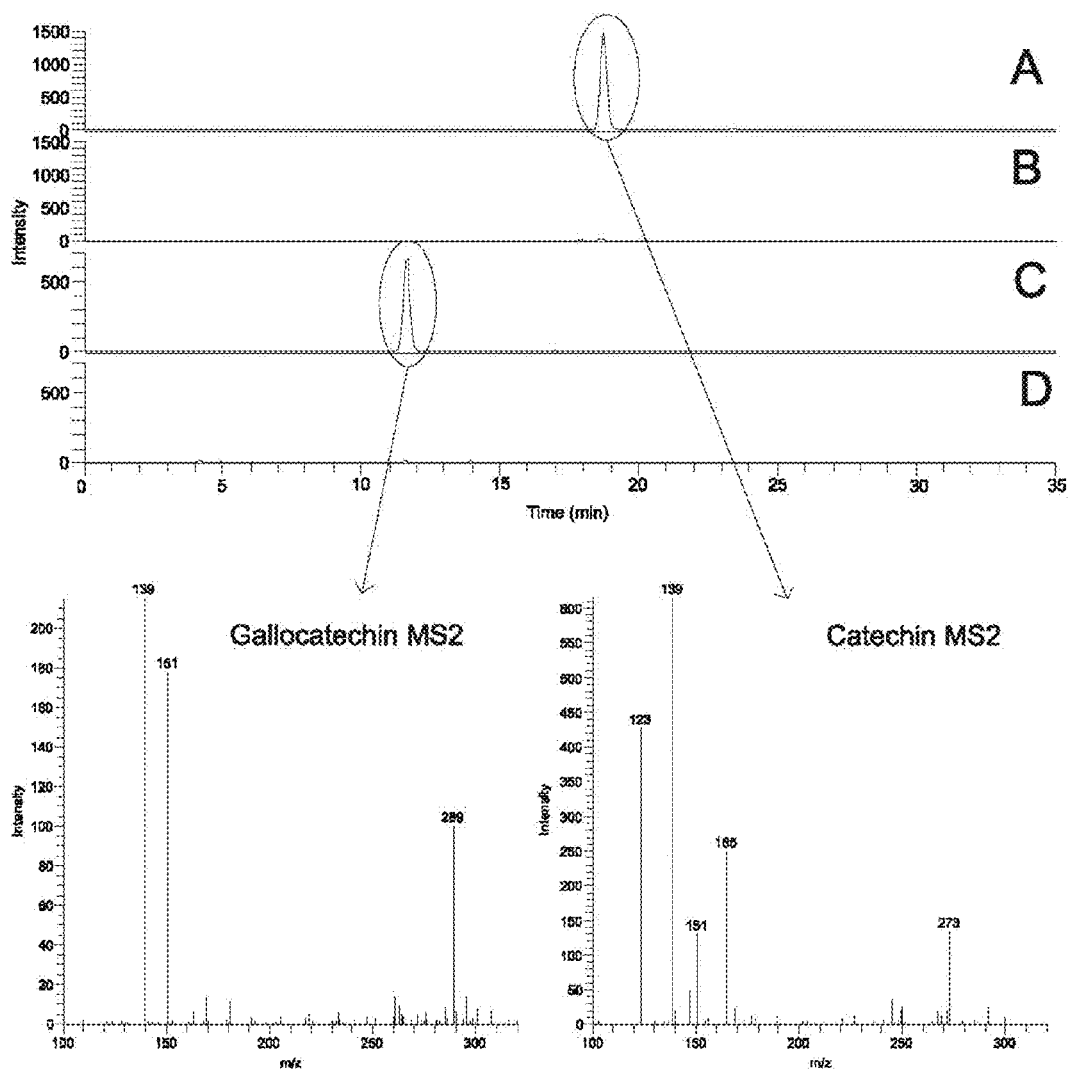

FIG. 28 shows the four monomer SRM chromatograms for *T. arvense* control and knockout plants: Trace A is a sum of the product ions 123, 139 and 165 m/z of the SRM of 291.3 m/z (PC; catechin and epicatechin) for a control plant. B is a sum of the product ions 123, 139 and 165 m/z of the SRM of 291.3 m/z (PC; catechin and epicatechin) for a knockout plant. C is a sum of the product ions 139 and 151 m/z of the SRM of 307.3 m/z (PD; gallocatechin and epigallocatechin) for a control plant. D is a sum of the product ions 139 and 151 m/z of the SRM of 307.3 m/z (PD; gallocatechin and epigallocatechin) for a knockout plant. The MS2 spectra are provided from the control plant as evidence of catechin and gallocatechin in the control plant. The chromatogram scales for traces A, B, C and D have been fixed to show the disappearance of catechin and gallocatechin in the knockout plant.

Figure 29:
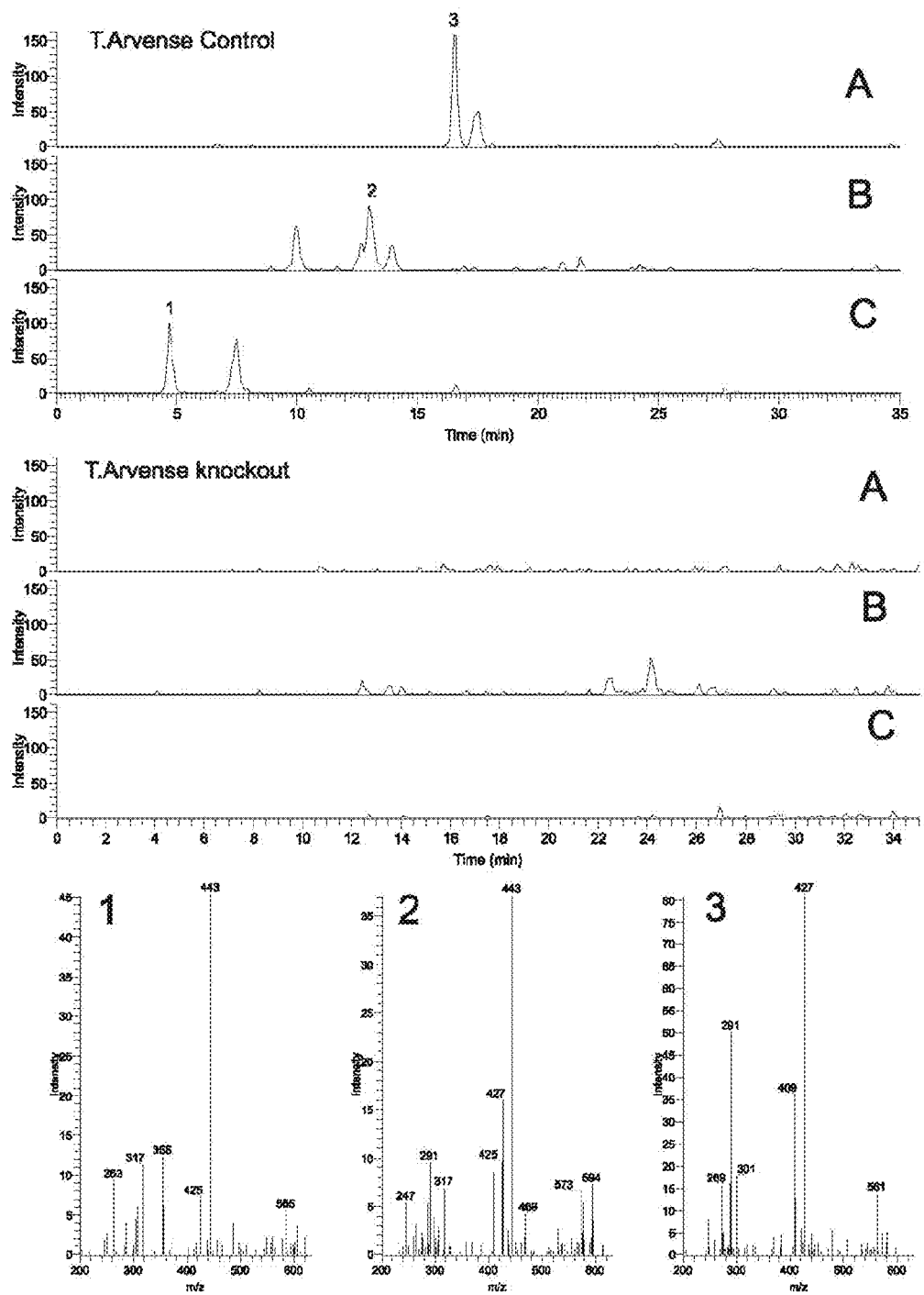

FIG. 29 shows the dimer SRM chromatograms for the control and knockout *T. arvense* plants. Trace A is a sum of the product ions 291 and 427 m/z of the SRM of 579.3 m/z (PC:PC dimer). Trace B is a sum of the product ions 307, 427 and 443 m/z of the SRM of 595.3 m/z (PC:PD dimer). Trace C is a sum of the product ions 307 and 443 m/z of the SRM of 611.3 m/z (PD:PD dimer). The chromatogram scales are fixed to show the disappearance of dimers in the knockout plant. The MS2 spectra are provided from the control plant as evidence of all three types of dimers in the control.

Figure 30:
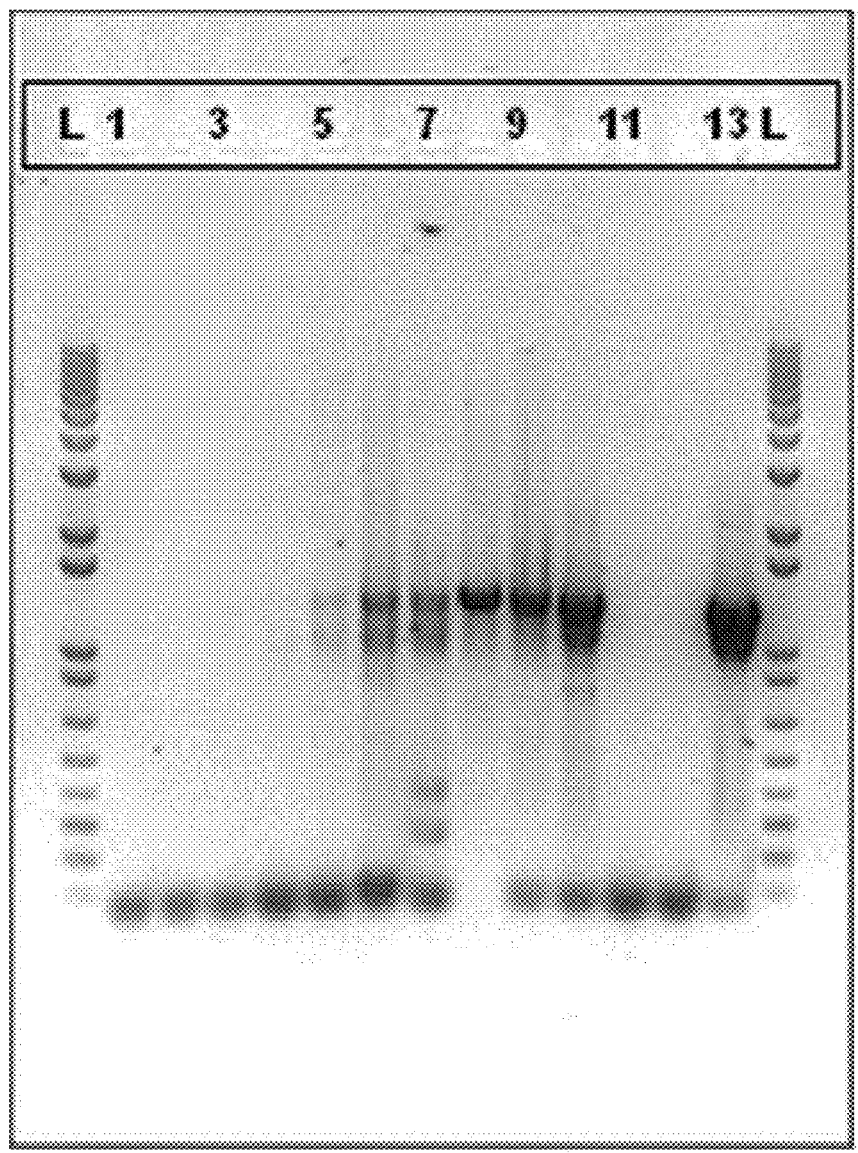

FIG. 30 shows the PCR analysis for the presence of pTaMyb14A from genomic DNA (SEQ ID NO:2) isolated from putatively transformed alfalfa. Lanes L; ladder; 1-3, non-transformed, 4-10 transformed, 11 wild type, 12 water control, 13 plasmid control. Primers were 35S and PMY8R (to 3' end of gene).

Figure 31:
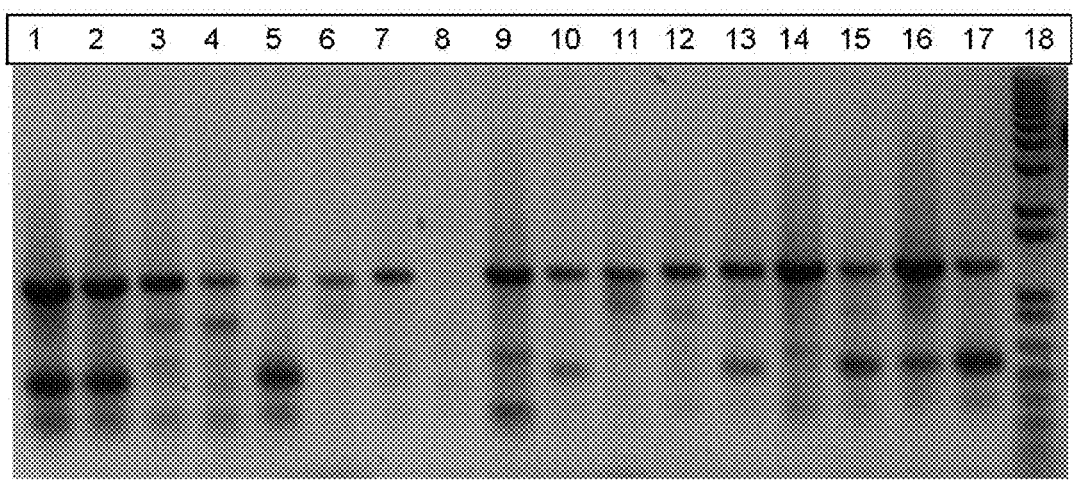

FIG. 31 shows the PCR analysis for the presence of M14ApHZBAR from genomic DNA isolated from putatively transformed *brassica* plantlets. Lane 8, *brassica* control; Lane 18 Ladder; Lane 1-7 and 9-17 transformed *brassica*. Primers were 35S (promoter) and PMYBR (to 3' end of gene) amplifying a 1,244 bp fragment.

Figure 32:
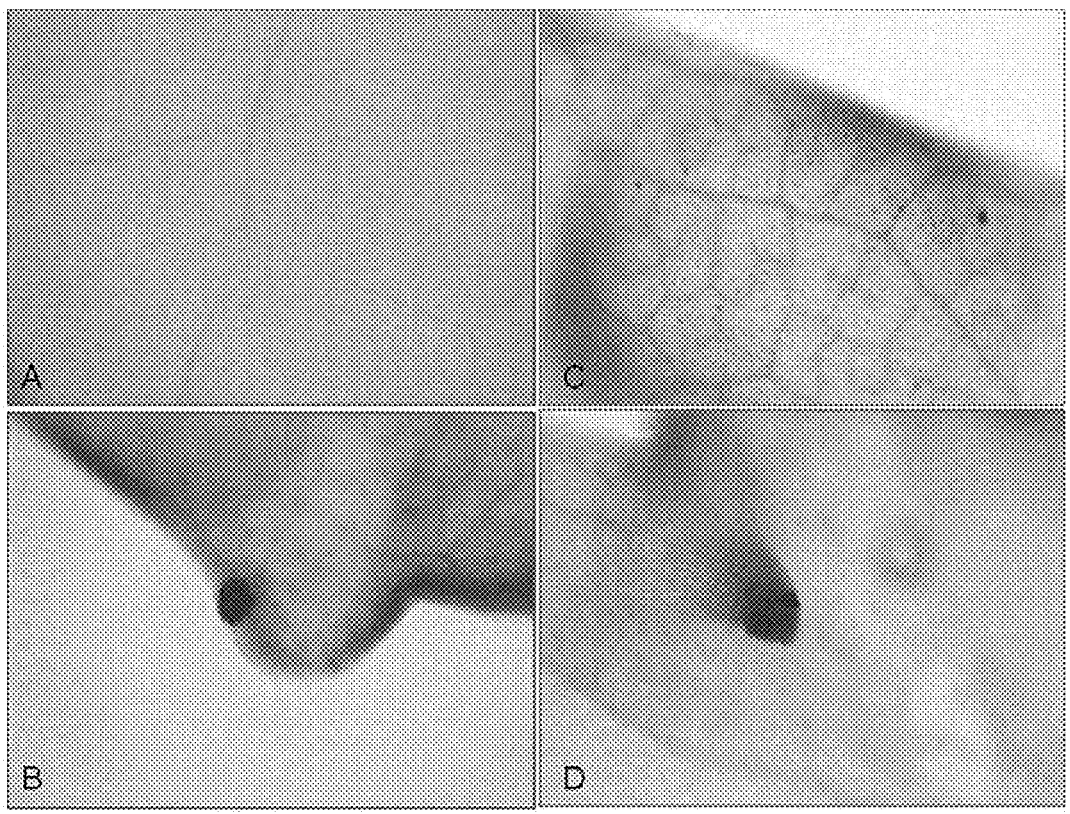

FIG. 32 shows the results of DMACA screening of wild type *brassica* (*Brassica oleracea*) (A) and transgenic (B to D) leaves, transformed with M14ApHZBARP construct.

Figure 33:
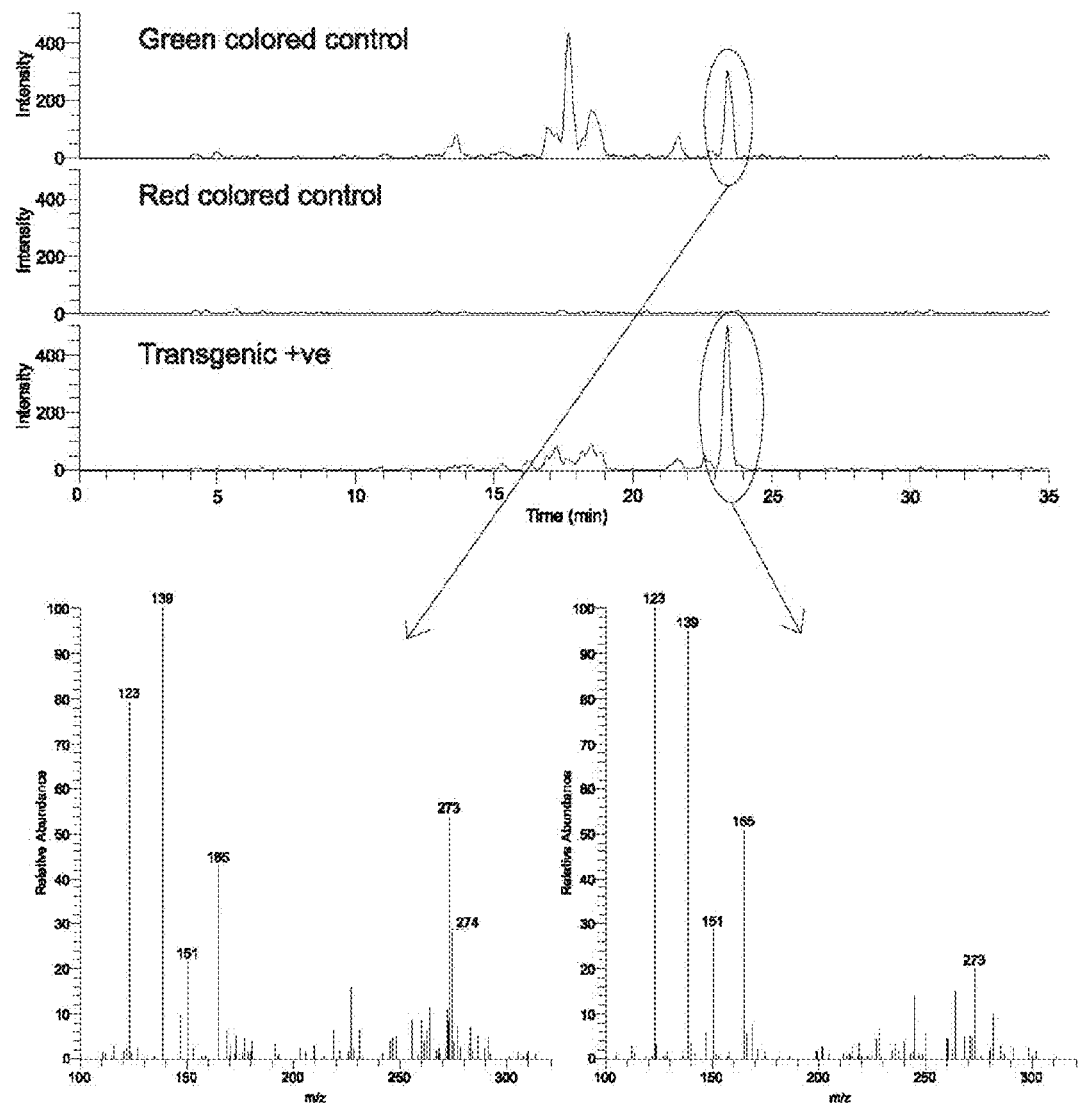

FIG. 33 shows the SRM chromatograms of the product ions 123, 139 and 165 m/z of the SRM of 291.3 m/z (catechin (C) and epicatechin (EC)) in two controls and a transgenic *brassica* expressing MYB14. The MS2 spectra of the epicatechin detected in the green control and the transgenic +ve sample are provided as evidence of identification of these metabolites. No epicatechin was detected in the red control sample.

FIG. 34 shows an alignment of all the *Trifolium* MYB14 protein sequences identified by the applicant.

FIG. 35 shows the percent identity between the sequences aligned in FIG. 34.

| BRIEF DESCRIPTION OF SEQUENCE LISTING | | |
|---|---|---|
| SEQ ID NO: | Description | Corresponding sequence |
| 1 | Polynucleotide, *Trifolium arvense*, TaMYB14-1 cDNA | Sequence of Ta MYB14 cDNA of expressed gene |
| 2 | Polynucleotide, *Trifolium arvense*, TaMYB14-1 gDNA | Sequence genomic of Ta MYB14 1 from allele 1 from *Trifolium arvense*. |
| 3 | Polynucleotide, *Trifolium arvense*, TaMYB14-2 gDNA | Sequence genomic of Ta MYB14 2 from allele 2 from *Trifolium arvense*. |
| 4 | Polynucleotide, *Trifolium affine*, TafMYB14-1 gDNA | Sequence genomic of Taf MYB14 1 from allele 1 from *Trifolium affine*. |
| 5 | Polynucleotide, *Trifolium affine*, TafMYB14-1 cDNA | Sequence of Taf MYB14 cDNA of expressed gene |
| 6 | Polynucleotide, *Trifolium affine*, TafMYB14-2 gDNA | Sequence genomic of Taf MYB14 2 from allele 2 from *Trifolium affine*. |
| 7 | Polynucleotide, *Trifolium occidentale*, ToMYB14-1 gDNA | Sequence genomic of ToMYB14 1 from allele 1 from *Trifolium occidentale*. |
| 8 | Polynucleotide, *Trifolium occidentale*, ToMYB14-2 gDNA | Sequence genomic of ToMYB14 2 from allele 2 from *Trifolium occidentale*. |
| 9 | Polynucleotide, *Trifolium repens*, TrMYB14-1 gDNA | Sequence genomic of TrMYB14 1 from allele 1 from *Trifolium repens*. |
| 10 | Polynucleotide, *Trifolium repens*, TrMYB14-2 gDNA | Sequence genomic of TrMYB14 2 from allele 2 from *Trifolium repens*. |
| 11 | Polynucleotide, *Trifolium repens*, TrMYB14-3 gDNA | Sequence genomic of TrMYB14 3 from allele 3 from *Trifolium repens*. |
| 12 | Polynucleotide, *Trifolium repens*, TrMYB14-4 gDNA | Sequence genomic of TrMYB14 4 from allele 4 from *Trifolium repens*. |
| 13 | Polynucleotide, *Trifolium arvense*, TaMYB14-1 cDNA | cDNA sequence representing the full length cDNA sequence of TaMYB14 |
| 14 | Polypeptide, *Trifolium arvense*, TaMYB14-1 | amino acid translation of TaMYB14 |
| 15 | Polypeptide, artificial, consensus | motif similar to Motif of subgroup 5 (Stracke et al., 2001) common to known CT MYB activators |
| 16 | Polypeptide, artificial, consensus | motif common to known anthocyanin MYB activators (Motif of subgroup 6, Stracke et al., 2001) |
| 17 | Polypeptide, artificial, consensus | novel MYB motif of MYB14 TFs |
| 18 | Polynucleotide, artificial, primer | MYB domain hunt - MYBFX |
| 19 | Polynucleotide, artificial, primer | MYB domain hunt - MYBFY |
| 20 | Polynucleotide, artificial, primer | MYB domain hunt - MYBFZ |

-continued

Figure 7:
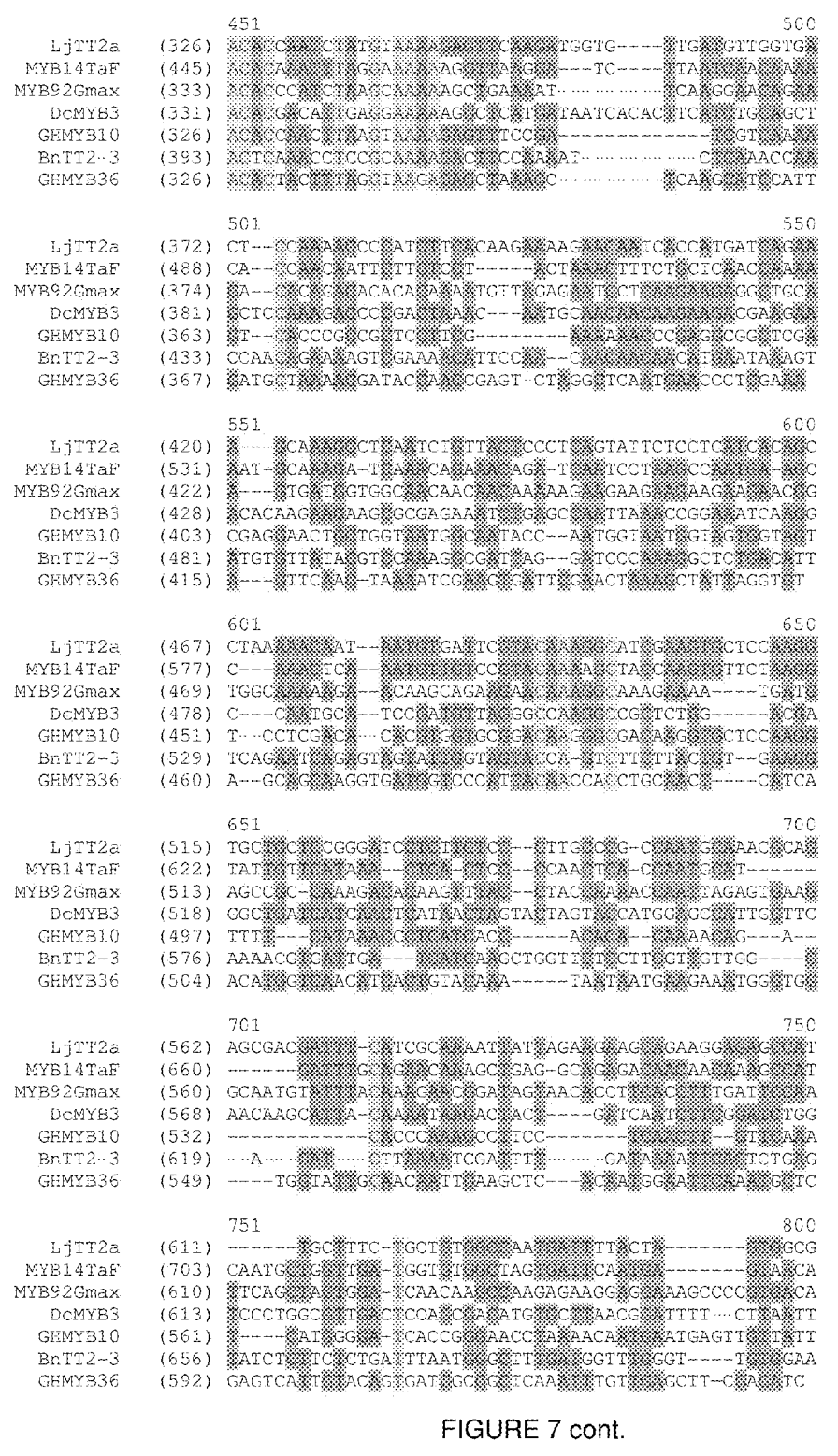
Figure 9:
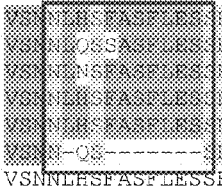
FIG. 9 shows the alignment of the full-length protein sequences of TaMYB14 (expressed TaMYB14FTa and silent TaMYB14-2S), ToMYB14 allele, and TrMYB14 alleles with differences highlighted in dark grey/white regions and deletion/insertion areas highlight in boxes.

| SEQ ID NO: | Description | Corresponding sequence |
|---|---|---|
| | BRIEF DESCRIPTION OF SEQUENCE LISTING | |
| 21 | Polynucleotide, artificial, primer | Isolation of full length - M14ATG |
| 22 | Polynucleotide, artificial, primer | Isolation of full length - M14TGA |
| 23 | Polynucleotide, artificial, primer | Gene walking - M14TSP1 |
| 24 | Polynucleotide, artificial, primer | Gene walking - M14TSP2 |
| 25 | Polynucleotide, artificial, primer | Gene walking - M14TSP3 |
| 26 | Polynucleotide, artificial, primer | Cloning into vector - M14FATG |
| 27 | Polynucleotide, artificial, primer | Lotus corniculatus - MYBLF |
| 28 | Polynucleotide, artificial, primer | Lotus corniculatus - MYBLR |
| 29 | Polynucleotide, artificial, primer | 5' UTR end of MYB14 - MYB148N |
| 30 | Polynucleotide, artificial, primer | 3' UTR end of MYB14 - MYB14RR |
| 31 | Polynucleotide, artificial, primer | Primer for intron 1-15 |
| 32 | Polynucleotide, artificial, primer | Primer for intron 1-13 |
| 33 | Polynucleotide, artificial, primer | Gene walking - TSP4 |
| 34 | Polynucleotide, artificial, primer | Gene walking - TSP5 |
| 35 | Polynucleotide, artificial, primer | 5' start site Forward - MYB148F |
| 36 | Polynucleotide, artificial, primer | 5' start site Reverse - MYB14RR |
| 37 | Polynucleotide, artificial, primer | Expression analysis/ Silencing vector - MYB14F |
| 38 | Polynucleotide, artificial, primer | Expression analysis/ Silencing vector - MYB14R |
| 39 | Polynucleotide, artificial, primer | Gene walking - MYB14R2 |
| 40 | Polynucleotide, artificial, primer | Gene walking - MYB14R3 |
| 41 | Polynucleotide, artificial, primer | Sequencing - M13 Forward |
| 42 | Polynucleotide, artificial, primer | Sequencing - M13 Reverse |
| 43 | Polynucleotide, artificial, primer | cDNA production - BD SMART II ™ A Oligonucleotide |
| 44 | Polynucleotide, artificial, primer | cDNA production - 3' BD SMART ™ CDS Primer II A |
| 45 | Polynucleotide, artificial, primer | Amplification of mRNA - 5' PCR Primer II A |
| 46 | Polypeptide, *Trifolium arvense*, TaMYB14-2 | |
| 47 | Polypeptide, *Trifolium affine*, TafMYB14-1 | |
| 48 | Polypeptide, *Trifolium affine*, TafMYB14-2 | |
| 49 | Polypeptide, *Trifolium occidentale*, ToMYB14-1 | |
| 50 | Polynucleotide, *Trifolium occidentale*, ToMYB14-2 | |
| 51 | Polypeptide, *Trifolium repens*, TrMYB14-1 | |
| 52 | Polypeptide, *Trifolium repens*, TrMYB14-2 | |
| 53 | Polypeptide, *Trifolium repens*, TrMYB14-3 | |
| 54 | Polypeptide, *Trifolium repens*, TrMYB14-4 | |
| 55 | Polynucleotide, *Trifolium arvense*, TaMYB14-1 cDNA/ORF | |
| 56 | Polynucleotide, *Trifolium arvense*, TaMYB14-2 cDNA/ORF | |
| 57 | Polynucleotide, *Trifolium affine*, TafMYB14-1 cDNA/ORF | |
| 58 | Polynucleotide, *Trifolium affine*, TafMYB14-2 cDNA/ORF | |
| 59 | Polynucleotide, *Trifolium occidentale*, ToMYB14-1 cDNA/ORF | |
| 60 | Polynucleotide, *Trifolium occidentale*, ToMYB14-2 cDNA/ORF | |
| 61 | Polynucleotide, *Trifolium repens*, TrMYB14-1 cDNA/ORF | |
| 62 | Polynucleotide, *Trifolium repens*, TrMYB14-2 cDNA/ORF | |
| 63 | Polynucleotide, *Trifolium repens*, TrMYB14-3 cDNA/ORF | |
| 64 | Polynucleotide, *Trifolium repens*, TrMYB14-4 cDNA/ORF | |
| 65 | Polynucleotide, *Trifolium arvense*, silencing sequence | |
| 66 | Polynucleotide, artifical, primer, MYB F1 | |
| 67 | Polynucleotide, artifical, primer, MYB R | |
| 68 | Polynucleotide, artifical, primer, MYB F | |
| 69 | Polynucleotide, artifical, primer, MYB R1 | |
| 70 | Polynucleotide, *Lotus japonicus* | LjTT2a from FIG. 7 |
| 71 | Polynucleotide, *Trifolium affine* | MYB14 Taf from FIG. 7 |
| 72 | Polynucleotide, *Glycine max* | MYB92Gmax from FIG. 7 |
| 73 | Polynucleotide, *Daucus carota* | MYB3 from FIG. 7 |
| 74 | Polynucleotide, *Gossypium hirsutum* | GHMYB10 from FIG. 7 |
| 75 | Polynucleotide, *Brassica napus* | BnTT2-3 from FIG. 7 |
| 76 | Polynucleotide, *Gossypium hirsutum* | GHMYB36 from FIG. 7 |
| 77 | Polypeptide, *Arabidopsis thaliana* | AtTT2 from FIG. 8 |
| 78 | Polypeptide, *Brassica napus* | BnTT2-1 from FIG. 8 |
| 79 | Polypeptide, *Zea mays* | ZMP1 from FIG. 8 |
| 80 | Polypeptide, *Gossypium hirsutum* | GHMYB10 from FIG. 8 |
| 81 | Polypeptide, *Vitis vinifera* | VvMYBPA1 from FIG. 8 |
| 82 | Polypeptide, *Lotus japonicus* | LjTT2a from FIG. 8 |
| 83 | Polypeptide, *Glycine max* | MYB185Gmax from FIG. 8 |
| 84 | Polypeptide, *Malus domestica* | MYB11 Malus from FIG. 8 |
| 85 | Polypeptide, *Trifolium arvense* | TaMYB14-25 from FIG. 9 |
| 86 | Polypeptide, *Trifolium repens* | TrMYB14f from FIG. 9 |
| 87 | Polypeptide, *Trifolium occidentale* | ToMYB14 from FIG. 9 |

Figure 10:
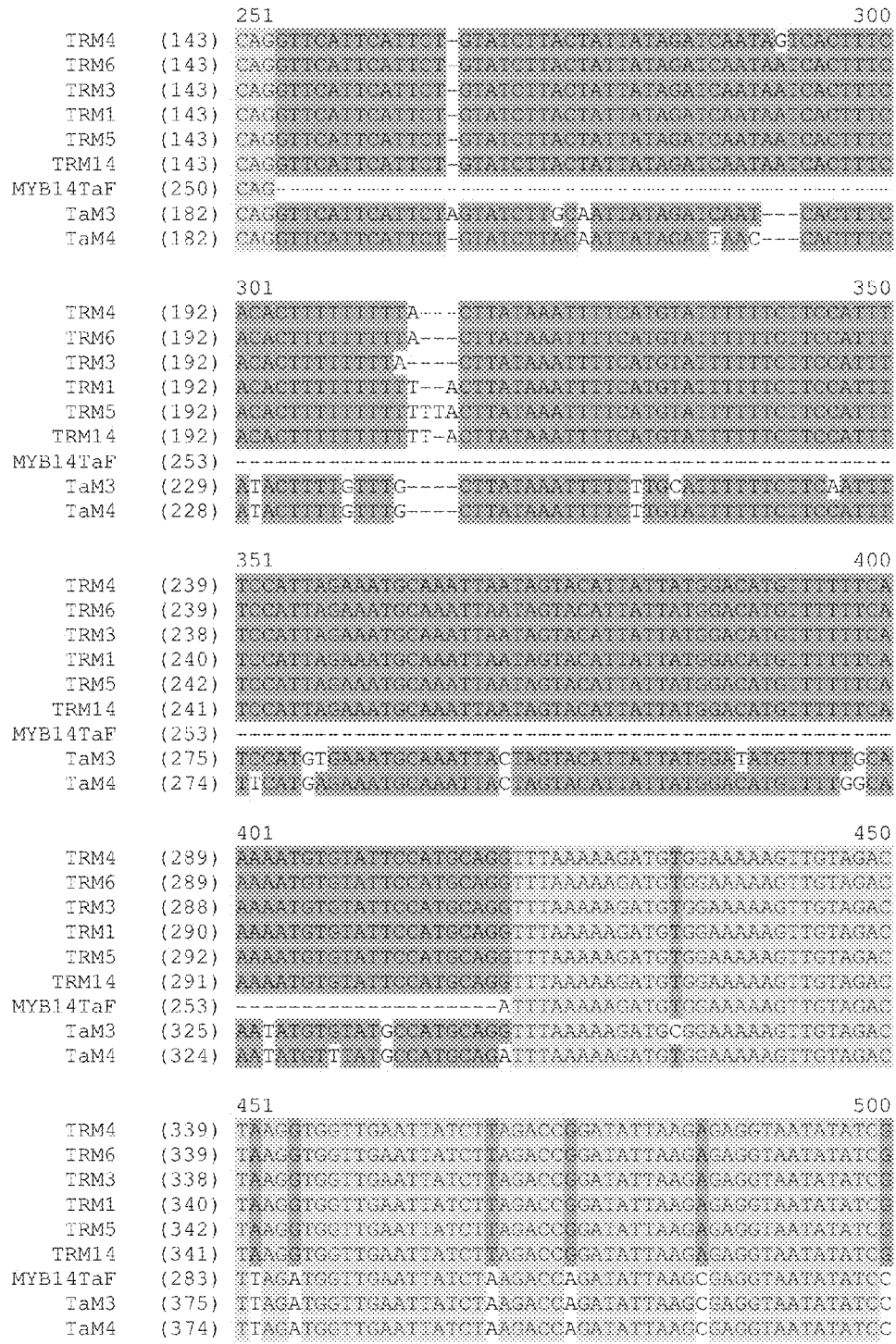
FIG. 10 shows the alignment of the full-length genomic DNA sequences of *Trifolium repens* TrMYB14 allelles (TRM*) aligned with *Trifolium arvense* TaMYB14 alleles (TaM3, TaM4), with differences in exons (light grey) and introns (dark grey) highlighted.
Figure 10:
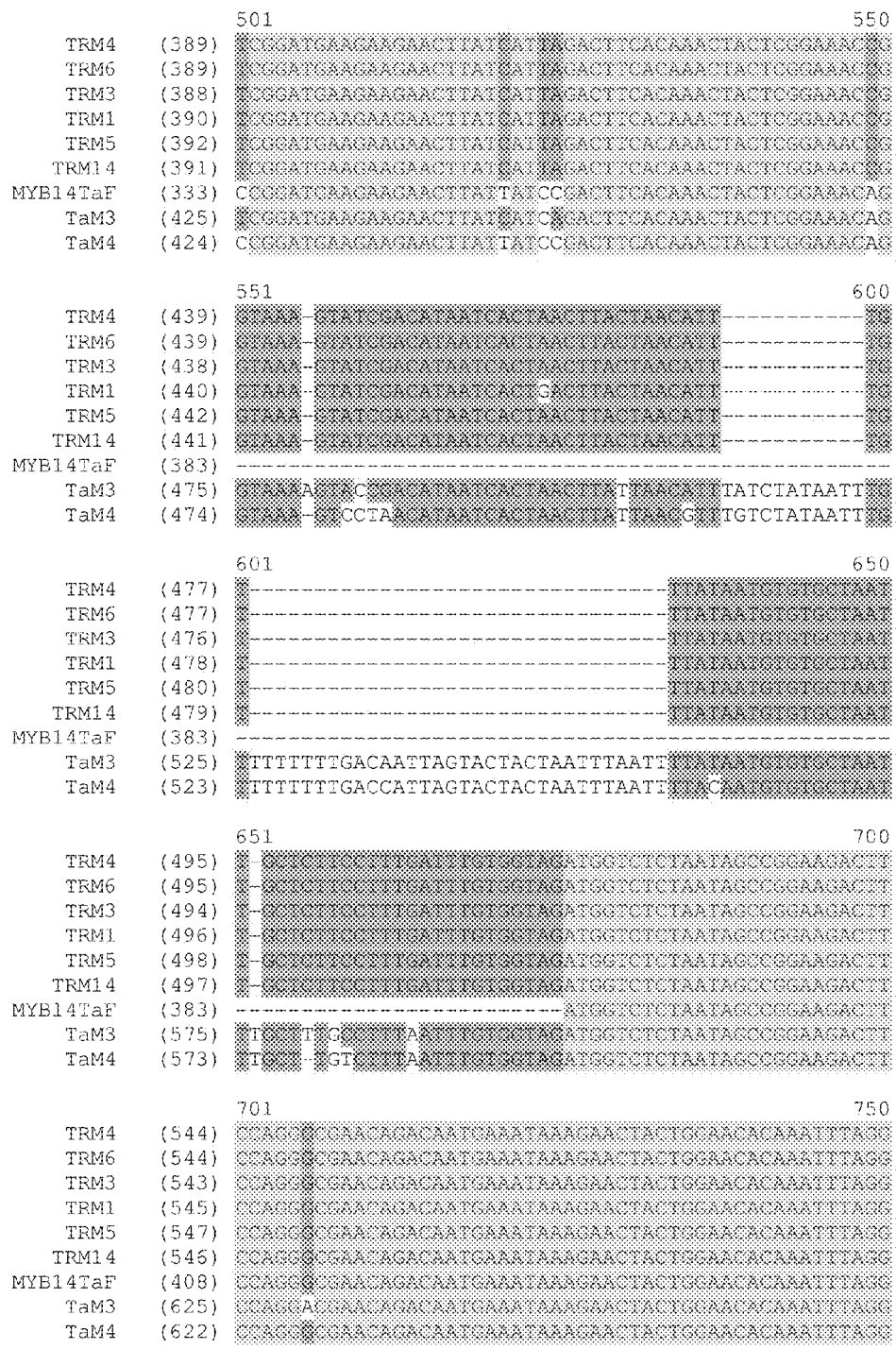
Figure 11:
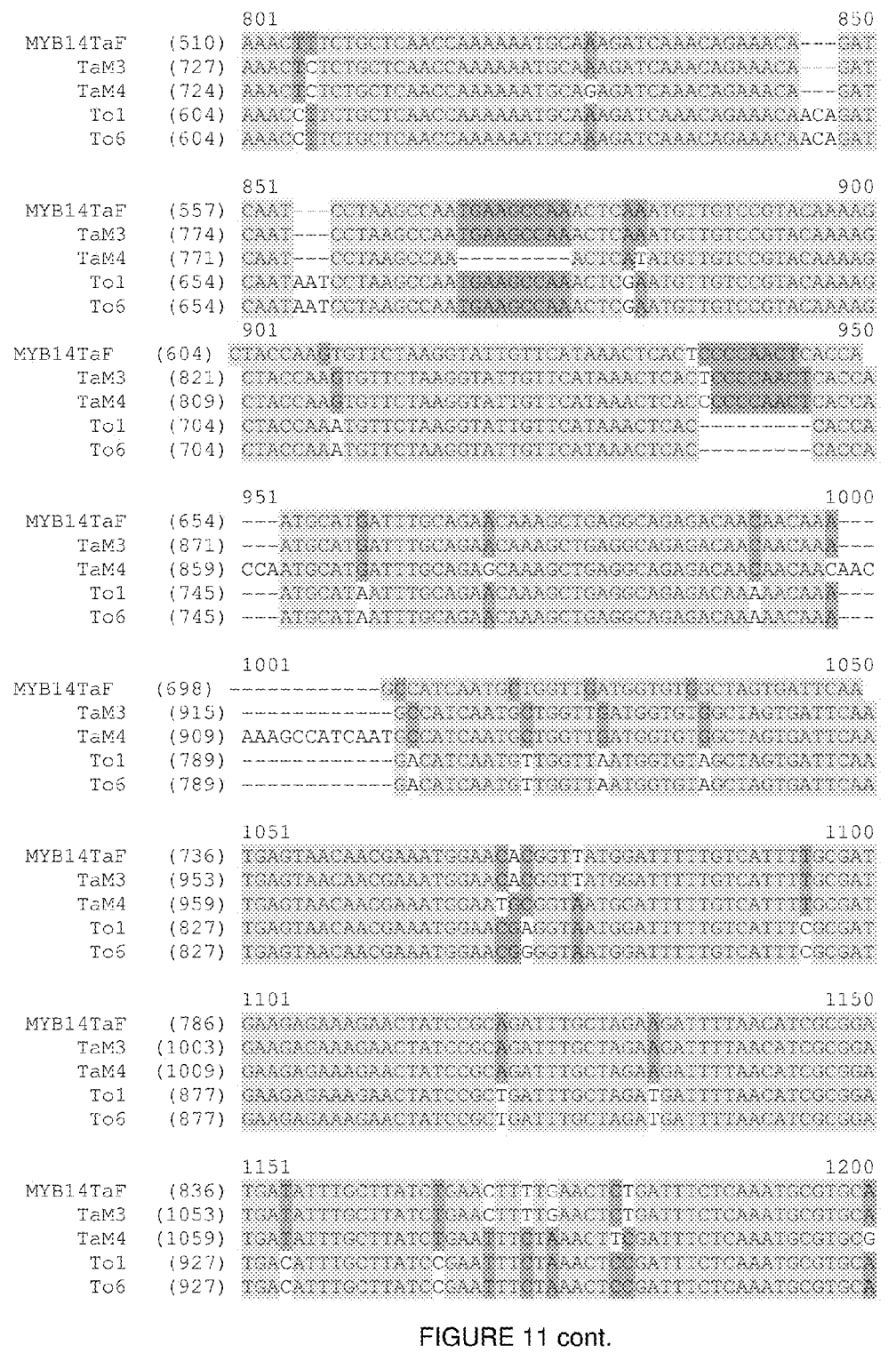
Figure 12:
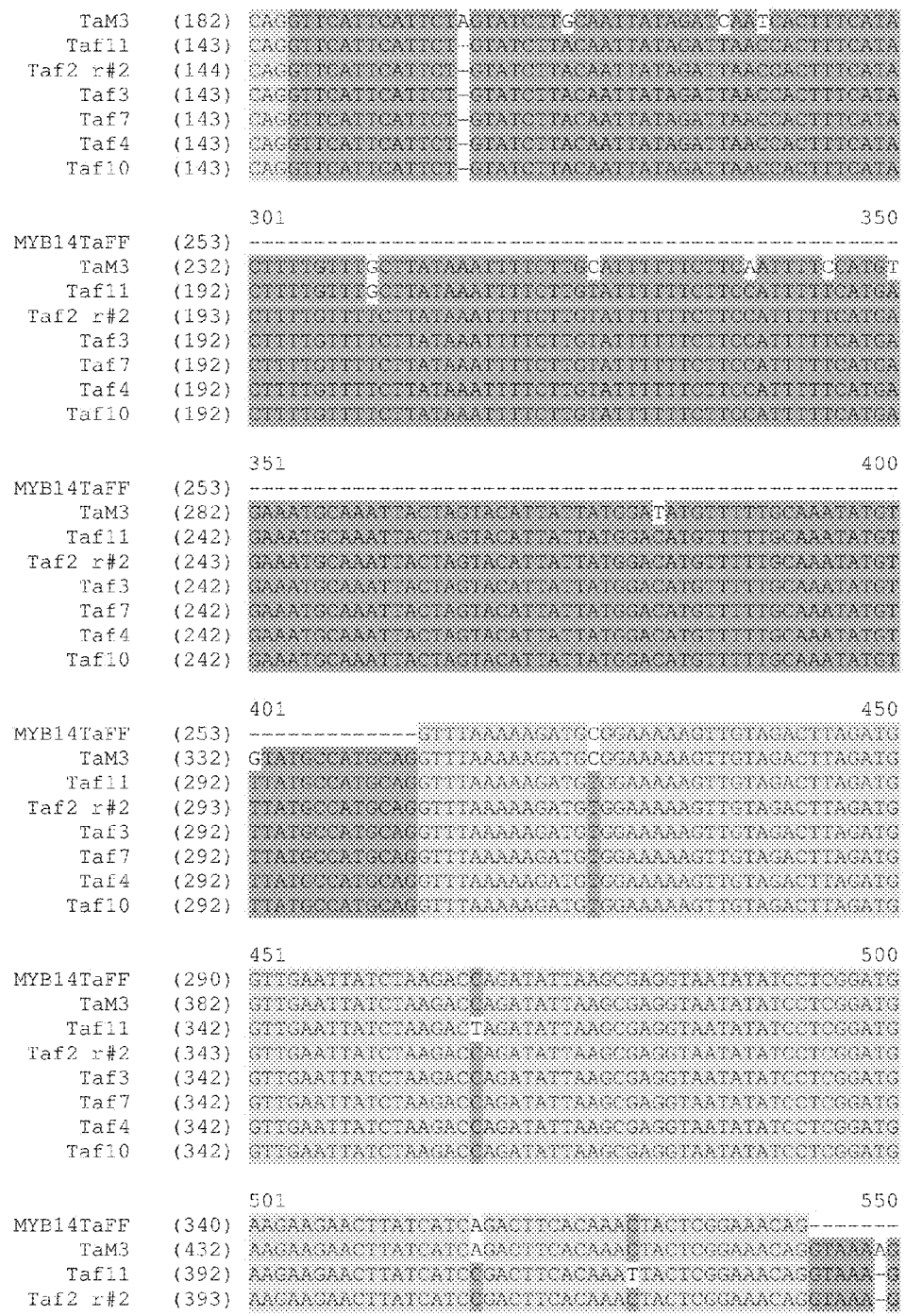
FIG. 12 shows the alignment of the full-length genomic DNA sequences of *Trifolium arvense* TaMYB14 allelles (Ta*) and *Trifolium affine* TafMYB14 allelles (Taf*) with exons (light grey) and introns (dark grey) showing differences.

| SEQ ID NO: | Description | Corresponding sequence |
|---|---|---|
| 88 | Polypeptide, Artificial | Consensus sequence from FIG. 9 |
| 89 | Polynucleotide, Trifolium repens | TRM6 from FIG. 10 |
| 90 | Polynucleotide, Trifolium repens | TRM14 from FIG. 10 |
| 91 | Polynucleotide, Trifolium occidentale | To1 from FIG. 11 |
| 92 | Polynucleotide, Trifolium occidentale | To6 from FIG. 11 |
| 93 | Polynucleotide, Trifolium affine | Taf11 from FIG. 12 |
| 94 | Polynucleotide, Trifolium affine | Taf2 r#2 from FIG. 12 |
| 95 | Polynucleotide, Trifolium affine | Taf3 from FIG. 12 |
| 96 | Polynucleotide, Trifolium affine | Taf7 from FIG. 12 |
| 97 | Polynucleotide, Trifolium affine | Taf4 from FIG. 12 |
| 98 | Polynucleotide, Trifolium affine | Taf10 from FIG. 12 |
| 99 | Polypeptide, Trifolium occidentale | ToMYB14-2 from FIG. 12 |
| 100 | Polypeptide, Artificial | Consensus sequence from FIG. 34 |
| 101 | Polypeptide, Artificial | Motif associated with MYB TFs that regulate CT pathways |
| 102 | Polypeptide, Artificial | Motif of subgroup 5 common to previously known CT MYB activators |

The invention will now be illustrated with reference to the following non-limiting examples.

EXAMPLE 1

Identification of the MYB14 Genes/Nucleic Acids/Proteins of the Invention, and Analysis of Expression Profiles Introduction Using primers designed to the MYB domain of legume species, the applicant has amplified sequences encoding novel MYB transcription factors (TFs) by PCR of cDNA and genomic DNA (gDNA) isolated from a range of *Trifolium* species. These species differ in their capacity to accumulate CTs in mature leaf tissue. Because white clover does not express CT genes in leaf tissue the applicants used an alternative strategy that allowed isolation of the expressed MYB TF from closely related *Trifolium* species (*T. arvense*; *T. affine*) which do accumulate CTs in all cells of foliar tissue throughout the life of the leaf. This was achieved by investigating the differential expression patterns of MYB TFs in various *Trifolium* leaf types; namely (a) within white clover (*T. repens*) leaf tissue, where CT gene expression is restricted to the leaf trichomes during meristematic development prior to leaf emergence; (b) within the closely related species (*T. arvense*), where CT gene expression is found within most cells of the leaf during its entire life span (except the trichome hairs); (c) with white clover mature leaf tissue where CT biosynthesis has already ceased. Such specific temporal and spatial expression requires the differential regulation by different MYB TFs specific to the CT branch pathway. Comparison of the MYB TFs from each leaf type eliminated common MYB factors that have functions other than in CT biosynthesis. Analysis of the remaining isolated MYB TFs allowed identification of those that are unique to CT accumulating tissues.

Sequencing of PCR products resulted in the identification of a previously unidentified MYB TFs from a number of *Trifolium* species. Full-length sequencing of these MYB genes revealed a highly dissimilar protein code when compared to the published AtTT2 sequence (NP_198405), including the presence of several deletions and insertions of bases in the genes from the different *Trifolium* species (FIGS. 7 and 8). Translation of the cDNA sequence revealed that the protein encoded by this MYB TF also has substantial number of amino acid deletions, insertions, and exchanges (FIG. 9). The applicants have designated this gene TaMYB14. Analysis of full-length gDNA sequences from 2 different *Trifolium* species revealed the presence of three exons and two introns of varying sizes in all TaMYB14 isoforms/alleles (FIGS. 10-12).

Seeds from a number of accessions representing various genotypes from four *Trifolium* species, respectively, were grown in a glasshouse and the presence or absence of CTs was determined in leaves using DMACA staining. Primers specific for TaMYB14 were designed and transcript levels in various tissues were determined by PCR. Expression of TaMYB14 was correlated with CT accumulation in leaf tissues. Its expression was undetectable in CT free tissues. TaMyb14 was very highly expressed in tissues actively accumulating CTs and coincided with the detectable expression of the two enzymes specifically involved in CT biosynthesis; namely ANR and LAR.

Transformation and over-expression of TaMYB14 in white clover (see Example 2) resulted in increased levels of CTs in tissues usually devoid of CTs. This shows that expression of TaMYB14 is critical for the accumulation of CTs. Overexpression of TaMYB14 in *T. repens* by means of transgenesis will therefore allow accumulation of significant levels of CTs in foliar tissues of various plant species, thereby providing the means to improve pasture quality for livestock.

Materials and Methods

Plant Material and Analysis of Condensed Tannin Levels

Seeds from several cultivars of four legume species differing in their levels of foliar CT were grown in glasshouses. *Trifolium repens* (Huia); *T. arvense* (AZ2925; AZ4755; AZ1353); *T. affine* (AZ925), and *T. occidentale* (AZ4270). Plant material of various ages and types were harvested and the material immediately frozen in liquid nitrogen and subsequently ground and used for isolation of DNA or RNA DMACA Staining of Plant Material.

CTs were histochemically analysed using the acidified DMACA (4-dimethylamino-cinnamaldehyde) method essentially as described by Li et al. (1996). This method uses the DMACA (p-dimethylaminocinnamaldehyde) reagent as a rapid histochemical stain that allows specific screening of plant material for very low CT accumulation. The DMACA-HCl protocol is highly specific for proanthocyanidins. This method was preferentially used over the vanillin test as anthocyanins seriously interfere with the vanillin assay. Tissues of various ages were sampled and tested.

Selection Methods of MYB R2R3 Candidates

Two methods were used to identify legume sequences containing a MYB R2R3 DNA-binding domain: hidden Markov models (HMMs) and profiles. Both methods depend on first creating a "model" of the domain from known MYB R2R3 DNA-binding domain protein sequences, which is then used as the basis of the search. The HMM and profile models were created using known plant MYB R2R3 domains as indicated in Table 1 below. These were taken from FIG. 2 in Miyake et. al. (2003) and FIG. 4C in Nesi et. al. (2001; the human MYB sequence in this figure was excluded). The species distribution of the sequences used in constructing the model as follows:

TABLE 1

Plant MYB R2R3 domains taken from Miyake et. al. (2003) and Nesi et. al. (2001)

| Source | Species | Domain count |
|---|---|---|
| Miyake et. al. (2003) | Lotus japonicus | 3 |
| | Glycine max | 1 |
| Nesi et. al. (2001) | Arabidopsis thaliana | 10 |
| | Zea mays | 3 |
| | Hordeum vulgare subsp. vulgare | 2 |
| | Oryza sativa | 1 |
| | Petunia x hybrida | 1 |
| | Picea mariana | 1 |

The legume sequence sets searched are listed in Table 2 below. Prior to searching, all EST and EST contig sets were translated in six frames to generate protein sequences suitable for the HMM/profile analyses. The *M. truncatula* protein sequences were used as-is (these are FGENESH gene predictions obtained from TIGR).

The HMMER program hmmbuild was used to create an HMM from the model DNA-binding domains, and this was searched against the legume sequence sets using the HMMER program hmmsearch (E-value cut-off=0.01). The EMBOSS program prophecy was used to create a profile from the same domains, and this was also searched against the legume sequences using the EMBOSS program profit (score cut-off=50). The numbers of hits identified by each method in each set of sequences are listed in Table 2 below:

TABLE 2

Legume sequence sets searched

| Sequence set | Total number of sequences | Number of hits - Profile method | Number of hits - HMM method | Number of hits passed to phylogenetic analysis |
|---|---|---|---|---|
| White clover EST contigs (CS35) | 17,758 | 18 | 24 | 17 |
| White clover PG NR | 159,017 | 0 | 9 | 3 |
| Red clover EST contigs | 38,099 | 1 | 2 | 0 |
| Lotus EST contigs | 28,460 | 5 | 9 | 4 |
| Soybean EST contigs | 63,676 | 15 | 40 | 15 |
| *Medicago truncatula* predicted proteins | 41,315 | 60 | 80 | 69 |
| *Medicago sativa* glandular trichome ESTs | 5,647 | 1 | 2 | 1 |
| Total | 353,972 | 100 | 166 | 109 |

The HMM method appeared to be more sensitive than the profile method, identifying all profile hits as well as many additional hits. For this reason the HMM method was selected as the method of choice—the HMM hit proteins were used to generate the alignments and were passed to the phylogenetic analysis. The profile hits are still quite useful: the profile method is more stringent and therefore there is a higher likelihood that the profile candidates represent true hits.

Generation of Alignments

DNA-binding domain sequences were extracted from the 166 legume MYB R2R3 candidates identified above. The protein domains were aligned using the HMMER alignment program hmmalign, which aligns the domains using information in the original HMM model. Nucleotide alignments were generated by overlaying the corresponding nucleotide sequences onto the protein alignments, thereby preserving the structure of the alignments at the protein level. This was done to obtain a more accurate alignment that better represents the domain structure.

Phylogenetic Analysis

A phylogenetic analysis was performed on plant MYB R2R3 DNA-binding domains, to see whether the resulting tree nodes could be used to identify MYB R2R3 subtypes, related to TT2 transcription factors. 109 Full length DNA-binding domains were extracted from the 166 legume MYB R2R3 candidates identified in this study, and these were combined with the known MYB R2R3 genes from Nesi et. al. (2001) and Miyake et. al. (2003), giving 130 DNA-binding domains in total. A protein alignment of these 130 domains was generated using hmmalign, and corresponding nucleotide domain sequences were aligned based on this. The nucleotide alignment was submitted to a maximum likelihood analysis to generate a phylogenetic tree based on 100 bootstrap replicates, using the programs fastDNAml and the Phylip program consensus to generate the consensus tree. This information was used to design three primers to legume MYBR2R3 domain.

Isolation of DNA and RNA, and cDNA Synthesis

Genomic DNA was isolated from fresh or frozen plant tissues (100 mg) using DNeasy® Plant Mini kit (Qiagen) following the manufacturer's instructions. DNA preparations were treated with RNAse H (Sigma) to remove RNA from the samples. Total RNA was isolated from fresh or frozen tissues using RNeasy® Plant Mini kit (Qiagen). Isolated total RNA (100 µg) was treated with RNAse free DNAse I to remove DNA from the samples during the isolation, following the manufacturer's instructions. Concentration and purity of DNA and RNA samples was assessed by determining the ratio of absorbance at 260 and 280 nm using a NanoDrop ND-100 spectrophotometer. Total RNA (1 µg) was reverse-transcribed into cDNA using SMART™ cDNA Synthesis Kit (Clontech) using the SMART™ CDS primer IIA and SMART II™ A oligonucleotides following manufacturer's instructions.

Polymerase Chain Reaction (PCR) and TOPO Cloning of PCR Products

Standard PCR reactions were carried out in a Thermal Cycler (Applied Biosystems), a quantity of approximately 5 ng DNA or 1 µl cDNA was used as template. The thermal cycle conditions were as follows: Initial reaction at 94° C. for 30 sec, 35 cycles at 94° C. for 30 sec, 50-64° C. for 30 sec (depending on the Tm of the primers), and at 72° C. for 1-2 min (1 min/kb), respectively, and a final reaction at 72° C. for 10 min.

PCR products were separated by agarose gel electrophoresis and visualised by ethidium bromide staining. Bands of interest were cut out and DNA subsequently extracted from the gel slice using the QIAquick Gel Extraction Kit (Qiagen) following the manufacturer's instructions. Extracted PCR products were cloned into TOPO 2.1 vectors (Invitrogen) and transformed into OneShot® *Escherichia. coli* cells by chemical transformation following the manufacturer's instructions. Bacteria were subsequently plated onto pre-warmed Luria-Bertani (LB; Invitrogen) agar plates (1% tryptone, 0.5% yeast extract, 1.0% NaCl, and 1.5% agar) containing 50 µg ml$^{-1}$ kanamycin and 40 µl of 40 mg ml$^{-1}$ X-gal (5-bromo-4-chloro-3-indolyl-X-D-galactopyranoside; Invitrogen) and incubated at 37° C. overnight. Positive colonies were selected using white-blue selection in combination with antibiotic selection. Colonies were picked and inoculated into 6 ml LB broth (1% tryptone, 0.5% yeast extract, 1.0% NaCl) containing 50 µg ml$^{-1}$ kanamycin and incubated at 37° C. in a shaking incubator at 200 rpm.

Bacterial cultures were extracted and purified from LB broth culture using the Qiagen Prep Plasmid Miniprep Kit (Qiagen) following the manufacturer's instructions.

DNA Sequencing

Isolated plasmid DNA was sequenced using the dideoxynucleotide chain termination method (Sanger et al., 1977), using Big-Dye (Version 3.1) chemistry (Applied Biosystems). Either M13 forward and reverse primers or specific gene primers were used. The products were separated on an ABI Prism 3100 Genetic Analyser (Applied Biosystems) and sequence data were compared with sequence information published in GenBank (NCBI) using AlignX (Invitrogen).

Results

Identification and Sequencing of TaMYB14

Total RNA and genomic DNA (gDNA) were isolated from developing and mature *T. arvense* leaf tissue and total RNA was reverse transcribed into cDNA. Initially, primers were designed to the generic MYB region of the coding sequence and PCR performed. PCR products were separated on agarose gels and visualised by ethidium bromide staining. Bands ranging in size were cut out, DNA extracted, purified, cloned into TOPO vectors, and transformed into *E. coli* cells. Two hundred transformants from the cloning event were randomly chosen, plasmid DNA isolated and subsequently sequenced. Additional primers were designed to sequence the N-terminal regions where required (Table 4).

An array of partial MYBs were identified by sequencing of the isolated cDNA; >50% were unknowns, yielding no substantial hit to known MYB proteins. The remaining were identified as orthologues for MYBs expressed during abiotic stress, response to water deprivation, light stimulus, salt stress, ethylene stimulus, auxin stimulus, abscisic acid stimulus, gibberellic acid stimulus, salicylic acid stimulus, jasmonic acid stimulus, cadmium, light, stomatal movement and control, regulation, mixta-like (epidermal cell growth), down-regulation of caffeic acid O-methyl-transferase, and meristem control.

Two partial MYB cDNAs coded for a protein that fell within the correct MYB clades (NO8 and NO9) whose members include those known to activate anthocyanin or CT biosynthesis. Primers were designed to the 3' end of the gene to isolate the remaining 5' end and hence the entire cDNA clone. The full-length TaMYB14 contains a 942 bp coding region coding for a 314 amino acid protein. In comparison, AtTT2 codes for a 258 amino acid protein.

Blast Results for TaMYB14

The cDNA sequence of TaMYB14 from *T. arvense* genotype AZ2925 was blasted against the public databases. BlastN returned the following top 5 hits:

AB300033.1 "*Lotus japonicus* LjTT2-1 mRNA for R2R3-MYB transcription factor", (e-value 3e-69)

AB300035.1 *Lotus japonicus* LjTT2-3 mRNA for R2R3-MYB transcription factor", (e-value 4e-62)

AB300034.1 *Lotus japonicus* LjTT2-2 mRNA for R2R3-MYB transcription factor", (e-value 4e-59)

AF336284.1 *Gossypium hirsutum* GhMYB36 mRNA, (e-value 1e-40)

AB298506.1 *Daucus carota* DcMYB3-1 mRNA for transcription factor, (e-value 7e-39)

While BlastX of the translated sequence of TaMYB14 from *T. arvense* genotype AZ2925 returned the following 5 top hits:

BAG12893.1 "*Lotus japonicus* R2R3-MYB transcription factor LjTT2-1", (e-value 2e-81)

AAK19615.1AF336282_1 "*Gossypium hirsutum* GhMYB10", (e-value 3e-76);

BAG12895.1 "*Lotus japonicus* R2R3-MYB transcription factor LjTT2-3", (e-value 8e-74);

BAG12894.1 "*Lotus japonicus* R2R3-MYB transcription factor LjTT2-2", (e-value 2e-72);

AAZ20431.1 "MYB11" [*Malus×domestica*], (e-value 2e-66)

Alignment of TaMYB14 cDNA to AtTT2 and other BLAST hits are shown in FIG. 7 with highest similarities shown in yellow. Translation of the open reading frame also showed substantial differences in the amino acid composition, sharing 52% homology to *A. thaliana* TT2 (FIG. 8). Moreover TaMYB14 shares the motifs common to known CT MYB activators (N09).

Alignment of TaMYB14 cDNA to AtTT2 and other BLAST hits are shown in FIG. 7. with similarities highlighted in yellow and blue. Translation of the open reading frame (FIG. 8) also showed substantial differences in the amino acid composition, sharing 52% homology to *A. thaliana* TT2, primarily within the MYB domain region.

TaMYB14 includes a motif similar to the motif of subgroup 5 (DExWRLxxT (SEQ ID NO:102)) according to Stracke et al., 2001, that is common to previously known CT MYB activators.

TaMYB14 lacks the motif of subgroup 6 (KPRPR[S/T, shown in SEQ ID NO:16) according to Stracke et al., 2001, that is common to previously known anthocyanin MYB activators.

Moreover this alignment has identified a novel MYB motif (VI/VRTKAxR/KxSK (SEQ ID NO:101)). This new motif (highlighted in FIG. 8) appears associated with a number of novel MYB14 TFs that regulate CT pathways TaMYB14 Transcript Levels CT accumulation occurred in the species *T. arvense* and *T. affine*, where they were detectable throughout the entire leaf lamina in the abaxial and adaxial epidermal layer, and the petiole; except for the petiolule region. CTs are only detectable in *T. repens* and *T. occidentale* in the leaf trichomes on the abaxial epidermal surface. Transcript analysis using primers specific to TaMYB14 revealed that this gene was expressed only in tissues actively accumulating CTs. TaMYB14 was expressed in *T. arvense* mature and immature leaf tissue, but not in callus (which does not synthesise CTs). Primers designed to TaMYB14 also amplified a MYB14 in *T. repens*, which was expressed in meristem leaf and early meristematic trichomes, where CTs are actively accumulating, but were not detected in mature or emergent leaf tissue, stolons, internodes, roots, and petioles. MYB14 was also not detected in mature *T. occidentale* tissues where CTs are only present in leaf trichomes. Results of the analysis are shown in Table 3 below:

TABLE 3

The expression of MYB14 also coincides with expression of anthocyanidin reductase (ANR; BAN) and LAR, two key enzymes specific to CT biosynthesis in legumes.

| Species | Library | Result | Expect | Pathway |
|---|---|---|---|---|
| T. repens Huia | Mature Leaf | − | − | CT? |
| T. repens Huia | young leaf | − | − | |
| T. repens Huia | meristem leaf | + | + | |
| T. repens Huia | early trichome | + | + | |
| T. repens Huia | stolon nodes and internodes | − | − | |
| T. repens Huia | Roots | − | − | |
| T. repens Huia | floral | − + | + | |
| T. repens Huia | petioles | − | − | |
| T. occidentale | mature plant | − | − | |
| T. repens Isabelle | Mature leaf | − | − | Anthocyanin |
| T. arvense | callus | − | − | CT-ve |
| T. arvense | mature leaf | + | + | CT |
| T. arvense | immature leaf | + | + | |

Figure 1:
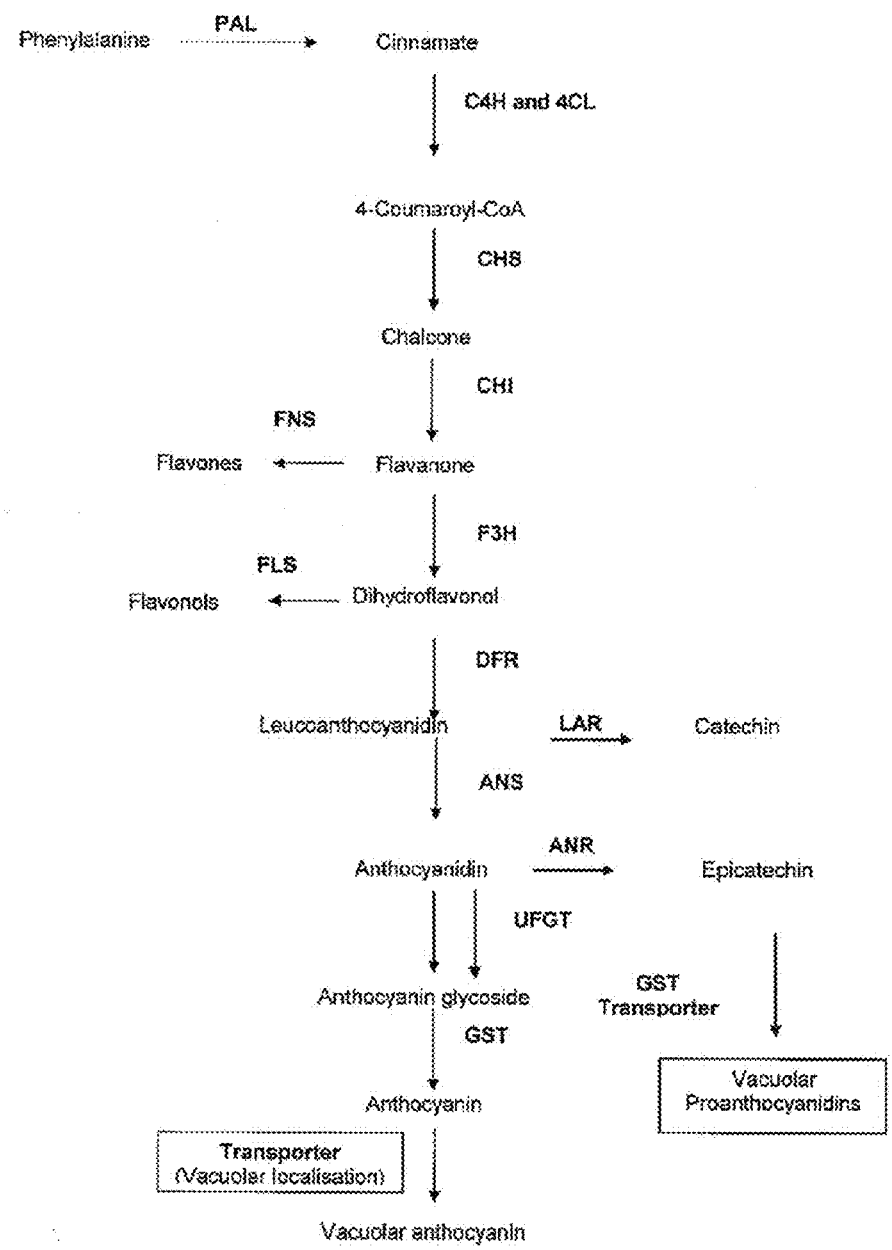
FIG. 1 shows the general condensed tannin pathway.
Figure 3:
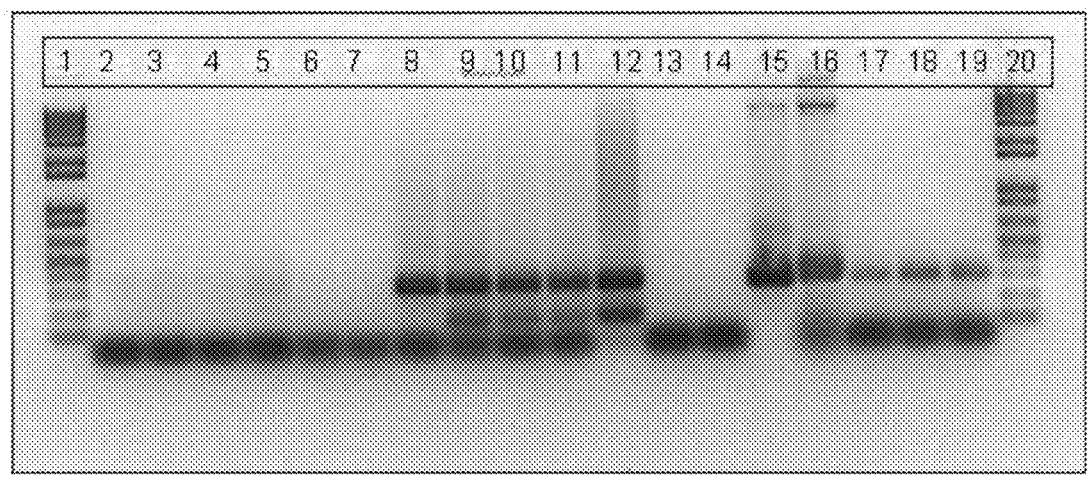
FIG. 3 shows the transcript levels of TaMYB14 in varying tissues from *Trifolium* species and cultivars grown in identical glasshouse conditions. Lane 1, (ladder); Lane 2, *T. repens* mature leaf cDNA library (Cultivar Huia); Lane 3, *T. repens* mature root cDNA library (Cultivar Huia); Lane 4, *T. repens* mature stolon cDNA library (Cultivar Huia); Lane 5, *T. repens* mature floral cDNA library (Cultivar DC111); Lane 6, *T. repens* emerging leaf cDNA (Cultivar Hula); Lane 7, *T. repens* mature leaf cDNA (High anthocyanin Cultivar Isabelle); Lane 8, *T. arvense* immature leaf cDNA (Cultivar AZ2925); Lane 9, *T. arvense* mature leaf cDNA (Cultivar AZ2925); Lane 10, *T. repens* meristem floral cDNA (Cultivar Huia); Lane 11, *T. repens* meristem leaf cDNA (Cultivar Huia); Lane 12, *T. repens* meristem trichome only cDNA (Cultivar Huia); Lane 13, *T. occidentale* mature plant (leaf, root and stolon cDNA library (Cultivar Hula); Lane 14, *T. repens* mature nodal cDNA library (Cultivar Huia); Lane 15, cloned *T. arvense* MYB14cDNA clone in TOPO, Lane 16, cloned *T. arvense* MYB14 genomic clone in TOPO, lane 17, *T. occidentale* genomic DNA; lane 17, *T. repens* genomic DNA; lane 17, *T. arvense* genomic DNA; Lane 20, (ladder).
Figure 4:
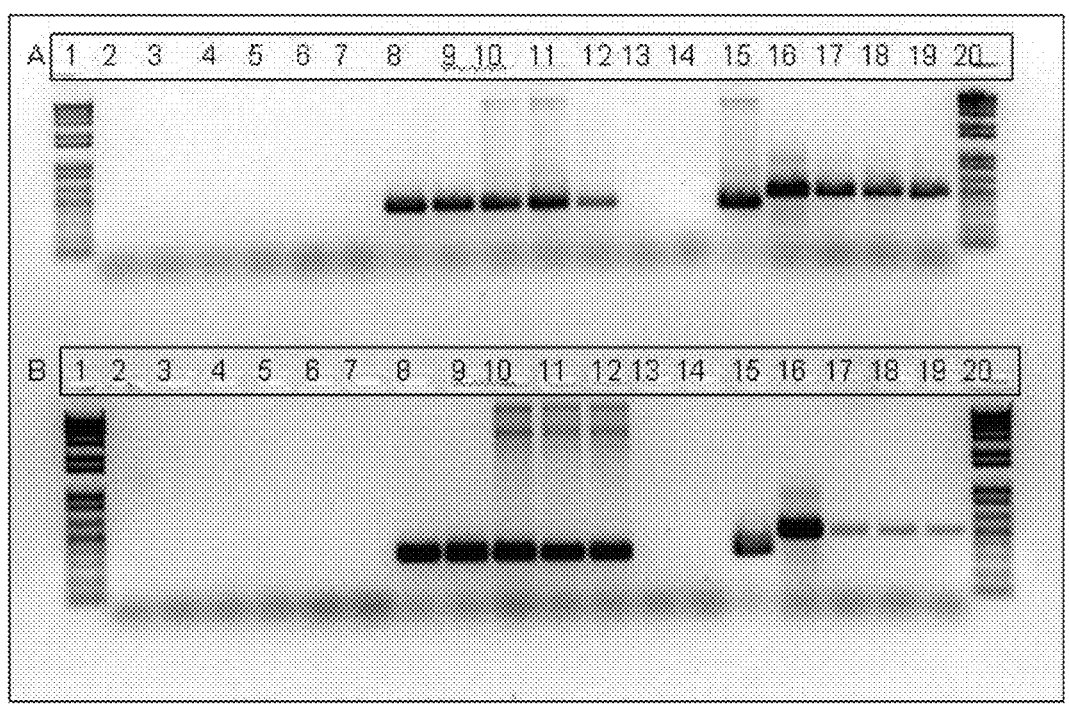
FIG. 4 shows the transcript levels of BANYULS (A) and LAR (B) in varying tissues from *Trifolium* species and cultivars grown in identical glasshouse conditions. Lane 1, (ladder); Lane 2, *T. repens* mature leaf cDNA library (Cultivar Hula); Lane 3, *T. repens* mature root cDNA library (Cultivar Hula); Lane 4, *T. repens* mature stolon cDNA library (Cultivar Huia); Lane 5, *T. repens* mature floral cDNA library (Cultivar DC111); Lane 6, *T. repens* emerging leaf cDNA (Cultivar Hula); Lane 7, *T. repens* mature leaf cDNA (High anthocyanin Cultivar Isabelle); Lane 8, *T. arvense* immature leaf cDNA (Cultivar AZ2925); Lane 9, *T. arvense* mature leaf cDNA (Cultivar AZ2925); Lane 10, *T. repens* meristem floral cDNA (Cultivar Huia); Lane 11, *T. repens* meristem leaf cDNA (Cultivar Huia); Lane 12, *T. repens* meristem trichome only cDNA (Cultivar Huia); Lane 13, *T. occidentale* mature plant (leaf, root and stolon cDNA library (Cultivar Huia); Lane 14, *T. repens* mature nodal cDNA library (Cultivar Hula); Lane 15, cloned *T. arvense* cDNA BAN or LAR clone in TOPO, Lane 16, cloned *T. arvense* BAN or LAR genomic clone in TOPO, lane 17, *T. occidentale* genomic DNA; lane 17, *T. repens* genomic DNA; lane 17, *T. arvense* genomic DNA; Lane 20, (ladder).

FIGS. 3 and 4 also showed the comparison of transcript levels in various tissues in the Trifolium species; FIG. 3 shows transcript levels of TaMYB14 in varying tissues from Trifolium species and cultivars grown in identical glasshouse conditions; Lane 1, (ladder); Lane 2, T. repens mature leaf cDNA library (Cultivar Huia); Lane 3, T. repens mature root cDNA library (Cultivar Huia); Lane 4, T. repens mature stolon cDNA library (Cultivar Huia); Lane 5, T. repens mature floral cDNA library (Cultivar DC111); Lane 6, T. repens emerging leaf cDNA (Cultivar Huia); Lane 7, T. repens mature leaf cDNA (High anthocyanin Cultivar Isabelle); Lane 8, T. arvense immature leaf cDNA (Cultivar AZ2925); Lane 9, T. arvense mature leaf cDNA (Cultivar AZ2925); Lane 10, T. repens meristem floral cDNA (Cultivar Huia); Lane 11, T. repens meristem leaf cDNA (Cultivar Huia); Lane 12, T. repens meristem trichome only cDNA (Cultivar Huia); Lane 13, T. occidentale mature plant (leaf, root and stolon cDNA library (Cultivar Huia); Lane 14, T. repens mature nodal cDNA library (Cultivar Huia); Lane 15, cloned T. arvense MYB14cDNA clone in TOPO, Lane 16, cloned T. arvense MYB14 genomic clone in TOPO, lane 17, T. occidentale genomic DNA; lane 17, T. repens genomic DNA; lane 17, T. arvense genomic DNA; Lane 20, (ladder).

While FIG. 4 shows transcript levels of BANYULS(A) and LAR (B) in varying tissues from Trifolium species and cultivars grown in identical glasshouse conditions. Lane 1, (ladder); Lane 2, T. repens mature leaf cDNA library (Cultivar Huia); Lane 3, T. repens mature root cDNA library (Cultivar Huia); Lane 4, T. repens mature stolon cDNA library (Cultivar Huia); Lane 5, T. repens mature floral cDNA library (Cultivar DC111); Lane 6, T. repens emerging leaf cDNA (Cultivar Huia); Lane 7, T. repens mature leaf cDNA (High anthocyanin Cultivar Isabelle); Lane 8, T. arvense immature leaf cDNA (Cultivar AZ2925); Lane 9, T. arvense mature leaf cDNA (Cultivar AZ2925); Lane 10, T. repens meristem floral cDNA (Cultivar Huia); Lane 11, T. repens meristem leaf cDNA (Cultivar Huia); Lane 12, T. repens meristem trichome only cDNA (Cultivar Huia); Lane 13, T. occidentale mature plant(leaf, root and stolon cDNA library (Cultivar Huia); Lane 14, T. repens mature nodal cDNA library (Cultivar Huia); Lane 15, cloned T. arvense cDNA BAN or LAR clone in TOPO, Lane 16, cloned T. arvense BAN or LAR genomic clone in TOPO, lane 17, T. occidentale genomic DNA; lane 17, T. repens genomic DNA; lane 17, T. arvense genomic DNA; Lane 20, (ladder).

Identification and Sequencing of MYB14 from gDNA of T. arvense, T. affine, T. occidentale and T. repens Using primers designed to the start and stop region of TaMYB14 (see Table 4) the inventors amplified homologues of TaMYB14 by PCR of cDNA and gDNA isolated from a range of several Trifolium species; namely T. arvense, T. affine, T. repens and T. occidentale. Isolation of the genomic DNA sequence and full-length sequencing of the cloned PCR products showed T. arvense has two isoforms or alleles of this gene, one of which corresponds to the expressed cDNA sequence, the other corresponding to a previously unidentified isoform/allelic variant of TaMYB14.

Alignment of these isoform or allelic variant revealed the presence of several deletions and insertions of bases compared to the cDNA sequence of TaMYB14 (see FIG. 10). Translation of the putative cDNA sequence revealed that the protein encoded by this isoform or allelic variant also has amino acid deletions, insertions, and exchanges (see FIG. 9). The inventors designated the allelic variant as TaMYB14-2.

The corresponding full-length gDNA sequences for this gene were also isolated from three other Trifolium species; T. affine, T. repens and T. occidentale. All MYB14 alleles had three exons and two introns of varying sizes (see FIGS. 10-12). T. affine and T. occidentale both have one allele, while T. repens has two alleles. The translated sequences of MYB14 from the various species were 95% homologous to TaMYB14 with changes in amino acid composition. The majority of amino acid differences are located in the 3' unique region downstream of the MYB domain.

TABLE 4

Primer sequences for PCR, cloning and sequencing of MYB14 from various Trifolium species (T. arvense; T. repens; T. affine; T. occidentale).

| Primer usage | Code | Primer sequence | SEQ ID NO: |
|---|---|---|---|
| MYB domain hunt | MYBFX | GACAATGAGATAAAGAAT TACTTG | 18 |
| MYB domain hunt | MYBFY | AAGAGTTGTAGACTTAGM TGG | 19 |
| MYB domain hunt | MYBFZ | YTKGGSAACAGGTTGTC | 20 |
| Isolation of full length | M14ATG | ATGGGGAGAAGCCCTTGT TGTGC | 21 |
| Isolation of full length | M14TGA | TCATTCTCCTAGTACTTCC TCACTGG | 22 |
| Gene walking | M14TSP1 | CTCTTTTTGGAAGGTTTC TCC | 23 |
| Gene walking | M14TSP2 | TTCTCCATTTTCCTTCACC ATGG | 24 |
| Gene walking | M14TSP3 | TCCAAGCACCTCTATTCA AGCC | 25 |
| Cloning into vector | M14FATG | CTCGAGATGCAATGCTGG TTGATGGTGTGGC | 26 |
| Lotus corniculatus | MYBLF | CATTGCCTGTAGATTCTG TAGCC | 27 |
| Lotus corniculatus | MYBLR | TGAAGATTGTTGGACACA TTGG | 28 |

TABLE 4-continued

Primer sequences for PCR, cloning and sequencing of MYB14 from various Trifolium species (T. arvense; T. repens; T. affine; T. occidentale).

| Primer usage | Code | Primer sequence | SEQ ID NO: |
|---|---|---|---|
| 5' UTR end of MYB14 | MYB148N | AGGTTGGAATACAAGACAGAC | 29 |
| 3' UTR end of MYB14 | MYB14RR | TCTCCTAGTACTTCCTCACTGG | 30 |
| Primer for intron 1 | I5 | ATAATCATACTAATTAACATCAC | 31 |
| Primer for intron 1 | I3 | TGATAGATCATGTCATTGTG | 32 |
| Gene walking | TSP4 | GCCTTCCTTTGCACAACAAGGGC | 33 |
| Gene walking | TSP5 | GCACAACAAGGGCTTCTCCCC | 34 |
| 5'start site Forward | MYB148F | ATGGGAGAAGCCCTTGTTGTGC | 35 |
| 5'start site Reverse | MYB14RR | TCTCCTAGTACTTCCTCACTGG | 36 |
| Expression analysis/ Silencing vector | MYB14F | CTCGAGCAATGCTGGTTGATGGTGTGGC | 37 |
| Expression analysis/ Silencing vector | MYB14R | TCTAGAGGACACATTTGTCTCATCAGC | 38 |
| Gene walking | MYB14R2 | TCTAGATTGAGTTTGGTCCGAACAAGG | 39 |
| Gene walking | MYB14R3 | TCTAGAAATCTTCTAGCAAATCTGCGG | 40 |
| Sequencing | M13 Forward | GTAAAACGACGGCCAG | 41 |
|  | M13 Reverse | CAGGAAACAGCTATGAC | 42 |
| cDNA production | BD SMART II™ A Oligonucleotide | AAGCAGTGGTATCAACGCAGAGTACGCGGG | 43 |
| cDNA production | 3' BD SMART™ CDS Primer II A | AAGCAGTGGTATCAACGCAGAGTACT(30)V N-3' | 44 |
| Amplification of mRNA | 5' PCR Primer II A | AAGCAGTGGTATCAACGCAGAGT | 45 |

In summary the applicants have identified and isolated ten novel MYB14 proteins/genes, as summarised in Table 5 below, which also shows the SEQ ID NO: associated with each sequence in the sequence listing:

TABLE 5

Summary of MYB14 sequences of the invention.

| Species, and sequence reference | SEQ ID NO: | | | |
|---|---|---|---|---|
| | Full-length cDNA | gDNA | Protein | ORF |
| Trifolium arvense, TaMYB14-1 | 1, 13 | 2 | 14 | 55 |
| Trifolium arvense, TaMYB14-2 | — | 3 | 46 | 56 |
| Trifolium affine, TafMYB14-1 | 5 | 4 | 47 | 57 |
| Trifolium affine, TafMYB14-2 | — | 6 | 48 | 58 |
| Trifolium occidentale, ToMYB14-1 | — | 7 | 49 | 59 |
| Trifolium occidentale, ToMYB14-2 | — | 8 | 50 | 60 |
| Trifolium repens, TrMYB14-1 | — | 9 | 51 | 61 |
| Trifolium repens, TrMYB14-2 | — | 10 | 52 | 62 |
| Trifolium repens, TrMYB14-3 | — | 11 | 53 | 63 |
| Trifolium repens, TrMYB14-4 | — | 12 | 54 | 64 |

An alignment of all of these MYB14 sequences is shown in FIG. 34. The applicants identified two sequence motifs common to all of the MYB14 protein sequences.

The first motif is DDEILKN (SEQ ID NO:15)

The second motif is $X_1$VVRTX$_2$AX$_3$KCSK (SEQ ID NO:17), where $X_1$=N, Y or H, $X_2$=K or R, and $X_3$=T or I.

The presence of either or both of these mofits appears to be diagnostic for MYB14 proteins, particulary when associated with a lack of motif of SEQ ID NO:16.

FIG. 35 shows the percent identity between each of the MYB14 proteins aligned in FIG. 34.

The applicants have also shown that spatial and temporal expression pattern of TaMYB14 is consistently correlated with production of CT in plants in vivo.

EXAMPLE 2

Use of the MYB14 Nucleic Acid Sequence of the Invention to Produce Condensed Tannins in White Clover (Trifolium repens)

Materials and Methods

Genetic Constructs Used in the Transformation Protocol

Figure 6:
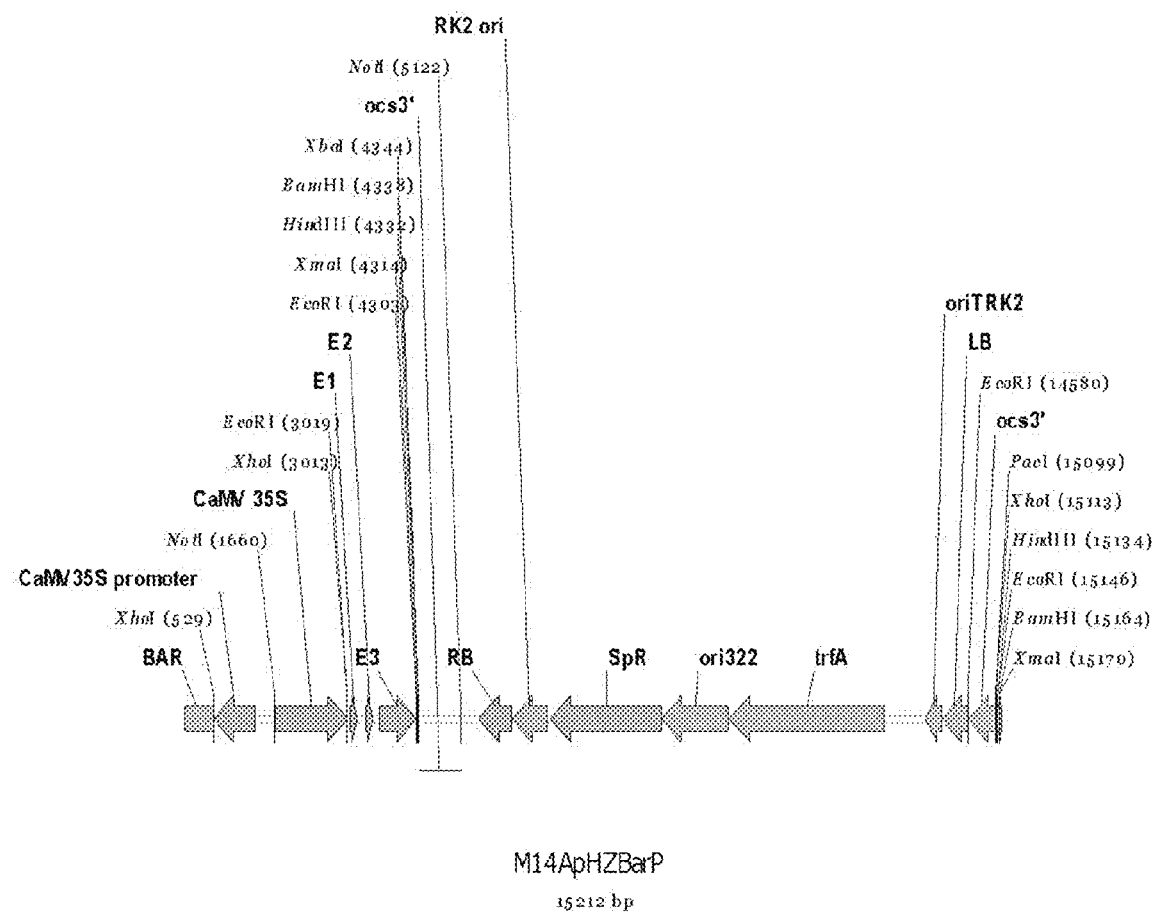
FIG. 6 shows the plasmid vector M14ApHZBarP, used for plant transformation. E1, E2 and E3 indicate the 3 exons of the genomic allele TaMYB14-1.

The plant transformation vector, pHZBar is derived from pART27 (Gleave 1992). The pnos-nptII-nos3' selection cassette has been replaced by the CaMV35S-BAR-OCS3' selection cassette with the bar gene (which confers resistance to the herbicide ammonium glufosinate) expressed from the CaMV 35S promoter. Cloning of expression cassettes into this binary vector is facilitated by a unique NotI restriction site and selection of recombinants by blue/white screening for β-galactosidase. White clover was transformed using M14ApHZBarP which contains the expressed allele from Trifolium arvense. Over-expression cassettes for M14ApHZBarP were firstly cloned in pART7. The construct were then shuttled to pHZBar as a NotI fragment. T-DNAs of the genetic constructs, showing orientation of cloned genes, are represented graphically in FIG. 6.

Genetic constructs in pHZBar were transferred into Agrobacterium tumefaciens strain GV3101 as plasmid DNA using freeze-thaw transformation method (Ditta et al 1980). The structure of the constructs maintained in Agrobacterium was confirmed by restriction digest of plasmid DNA's prepared from bacterial culture. Agrobacterium cultures were prepared in glycerol and transferred to −80° C. for long term storage. Genetic constructs maintained in Agrobacterium strain GV3101 are inoculated into 25 mL of MGL broth containing spectinomycin at a concentration of 100 mg/L. Cultures are grown overnight (16 hours) on a rotary shaker (200 rpm) at 28° C. Bacterial cultures are harvested by centrifugation (3000×g, 10 minutes). The supernatant is removed and the cells resuspended in a 5 mL solution of 10 mM MgSO$_4$.

Transformation of Cotyledonary Explants.

Clover was transformed using a modified method of Voisey et al. (1994). Seeds are weighed to provide approximately 400-500 cotyledons (ie. 200-250 seeds) for dissection (0.06 μm=100 seeds). In a centrifuge tube, seeds are rinsed with 70% ethanol for 1 minute. Seeds are surface sterilised in bleach (5% available chlorine) by shaking on a circular mixer for 15 minutes followed by four washes in sterile water. Seeds are imbibed overnight at 4° C. Cotyledons are dissected from seeds using a dissecting microscope. Initially, the seed coat and endosperm are removed. Cotyledons are separated from the radical with the scalpel by placing the blade between the cotyledons and slicing through the remaining stalk. Cotyledonary explants are harvested onto a sterile filter disk on CR7 media.

For transformation, a 3 ul aliquot of *Agrobacterium* suspension is dispensed on to each dissected cotyledon. Plates are sealed and cultured at 25° C. under a 16 hour photoperiod. Following a 72 hour period of co-cultivation, transformed cotyledons are transferred to plates containing CR7 medium supplemented with ammonium glufosinate (2.5 mg/L) and timentin (300 mg/L) and returned to the culture room. Following the regeneration of shoots, explants are transferred to CR5 medium supplemented with ammonium glufosinate (2.5 mg/L) and timentin (300 mg/L). Regenerating shoots are subcultured three weekly to fresh CR5 media containing selection. As root formation occurs, plantlets are transferred into tubs containing CR0 medium containing ammonium glufosinate selection. Large clumps of regenerants are divided to individual plantlets at this stage. Whole, rooted plants growing under selection are then potted into sterile peat plugs.

LCMSMS Methodology for HPLC Analysis

To extract flavonoids for HPLC analysis, leaf tissue (0.5 g fresh weight) was frozen in liquid N$_2$, ground to a fine powder and extracted with acetic acid:methanol (80:20 v/v) for 30 mins at 4° C. The plant debris was pelleted in a microcentrifuge at 13K rpm for 10 mins. The supernatant was removed and placed at −20° C. for 30 mins. An aliquot was used for HPLC analysis. An aliquot was analysed by HPLC using both UV-PDA and MS/MS detection on a Thermo LTQ Ion Trap Mass Spectrometer System. The extracts were resolved on a Phenomonex Luna C18 reversed phase column by gradient elution with water and acetonitrile with 0.1% formic acid as the mobile phase system. Detection of the anthocyanins were by UV absorption at 550 nm, and the other metabolites were estimated by either MS1 or MS2 detection by the mass spectrometer.

The instrument used was a linear ion trap mass spectrometer (Thermo LTQ) coupled to a Thermo Finnigan Surveyor HPLC system (both San Jose, Calif., USA) equipped with a Thermo photo diode array (PDA) detector. Thermo Finnigan Xcalibur software (version 2.0) was used for data acquisition and processing.

A 5 μL aliquot of sample was injected onto a 150×2.1 mm Luna C18(2) column (Phenomenex, Torrance, Calif.) held at a constant 25° C. The HPLC solvents used were: solvent A=0.1% formic acid in H$_2$O; solvent B=0.1% formic acid in Acetonitrile. The flow rate was 200 μL min$^{-1}$ and the solvent gradient used is shown in Table 6 below. PDA data was collected across the range of 220 nm-600 nm for the entire chromatogram.

TABLE 6

HPLC gradient

| Time (min) | Solvent A % | Solvent B % |
| --- | --- | --- |
| 0 | 95 | 5 |
| 6 | 95 | 5 |
| 11 | 90 | 10 |
| 26 | 83 | 17 |
| 31 | 77 | 23 |
| 41 | 70 | 30 |
| 45 | 50 | 50 |
| 52 | 50 | 50 |
| 52 | 3 | 97 |
| 59 | 3 | 97 |
| 62 | 95 | 5 |
| 70 | 95 | 5 |

The mass spectrometer was set for electrospray ionisation in positive mode. The spray voltage was 4.5 kV and the capillary temperature 275° C., and flow rates of sheath gas, auxiliary gas, and sweep gas were set (in arbitrary units/min) to 20, 10, and 5, respectively. The first 4 and last 11 minutes of flow from the HPLC were diverted to waste. The MS was programmed to scan from 150-2000 m/z (MS$^1$ scan), then perform data dependant MS$^3$ on the most intense MS$^1$ ion. The isolation windows for the data dependant MS$^3$ method was 2 mu (nominal mass units) and fragmentation (35% CE (relative collision energy)) of the most intense ion from the MS$^1$ spectrum was followed by the isolation (2 mu) and fragmentation (35% CE) of the most intense ion from the MS$^2$ spectrum. The mass spectrometer then sequentially performed selected reaction monitoring (SRM) on the masses in Table 7 below, with isolation windows for each SRM of 2.5 mu and fragmentation CE of 35%. These masses listed cover the different combinations of procyanidin (catechin and/or epicatechin) and prodelphinidin (gallocatechin or epigallocatechin) masses up to trimer.

TABLE 7

SRM masses for monomers, dimers and trimers:

| SRM mass (m/z) | MS2 scan range (m/z) | Target compound |
| --- | --- | --- |
| 291.3 | 80-700 | PC monomers |
| 307.3 | 80-700 | PD monomers |
| 579.3 | 155-2000 | PC:PC dimers |
| 595.3 | 160-2000 | PC:PD dimers |
| 611.3 | 165-2000 | PD:PD dimers |
| 867.3 | 235-2000 | PC:PC:PC trimers |
| 883.3 | 240-2000 | PC:PC:PD trimers |
| 899.3 | 245-2000 | PC:PD:PD trimers |
| 915.3 | 250-2000 | PD:PD:PD trimers |

Results

DMACA Analysis of White Clover with MYB14 from gDNA of *T. arvense*

Figure 5:
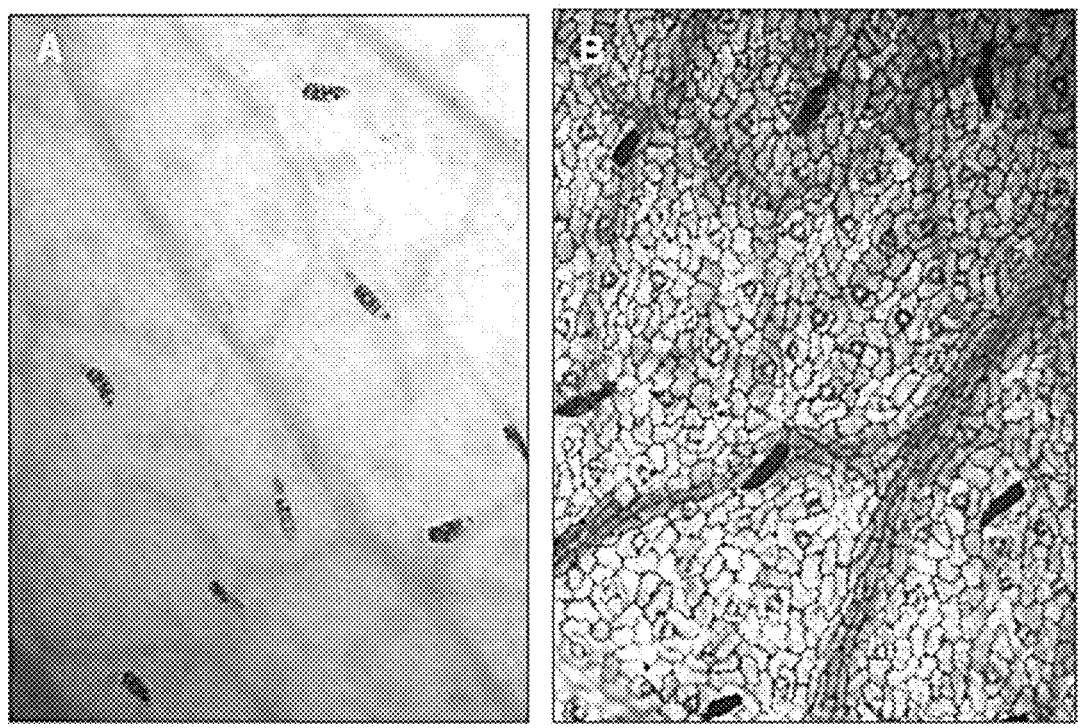
FIG. 5 shows the results of DMACA staining of transformed white clover mature leaf tissue. DMACA staining (light/dark grey colour) of mature white clover leaf tissue identifying Condensed Tannins in (A) Wild Type and (B) transformed with TaMYB14 gene.

White clover cotyledons were transformed with the *T. arvense* allele corresponding to the expressed cDNA sequence, under the control of the CaMV 35S promoter, and regenerated as described in the methods. Leaves from all regenerated plantlets were screened for CT production with DMACA staining, as described in Example 1. A number of these transformed plants were positive for CT production, resulting in blue staining when stained with DMACA. Such staining occurred in most epidermal cells of leaf tissues, including the six middle cells of leaf trichomes. In comparison, non-transformed wild type white clover plants were negative for CT, apart from the trichomes on the abaxial leaf side (FIG. 5). CTs were also present within some root and petiolar cells of some plants. This indicates that constitutive expression of TaMYB14 alters the temporal and spatial patterning of CT accumulation in white clover plants.

Molecular Analysis, DMACA Screen and Biochemistry of Transgenic White Clover

White Clover Molecular Analysis

Figure 14:
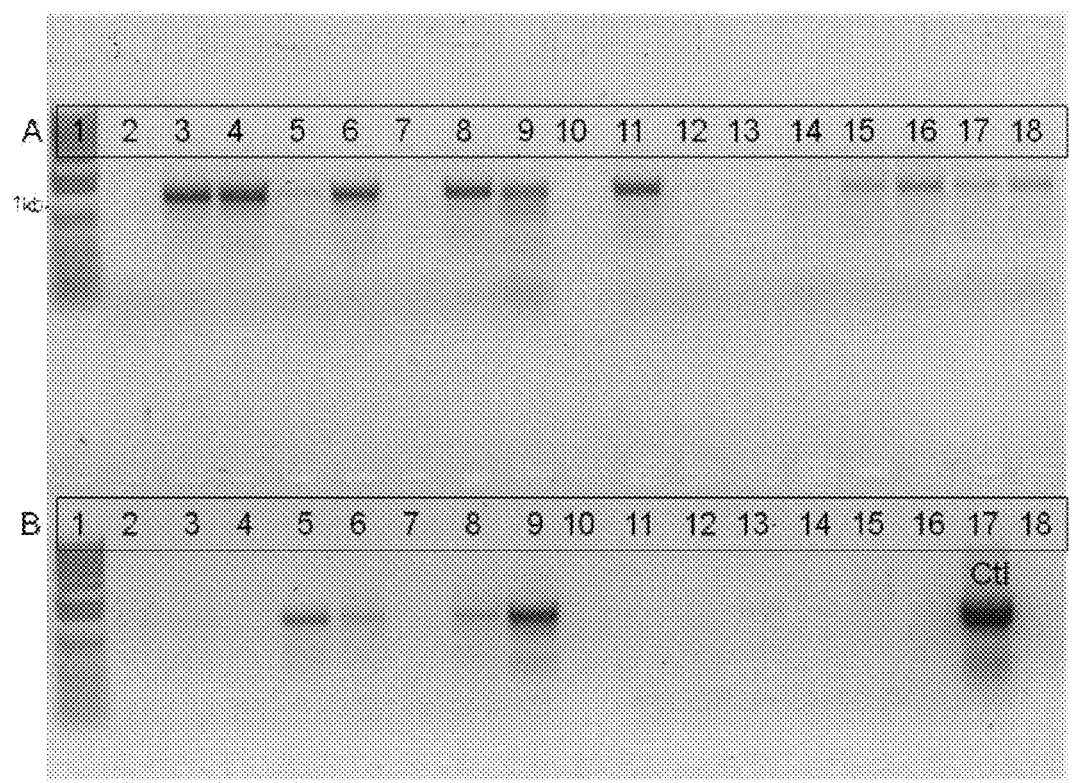
FIG. 14 shows the PCR reaction for the presence of M14ApHZBAR from genomic DNA isolated from putatively transformed white clover. Lanes; A1, B1 Ladder; A2-18 and B2-B15 transformed clovers, B16 non-transformed white clover, B17 plasmid control, B18 water control. Primers were 35S (promoter) and PMYBR (to 3' end of gene) amplifying a 1,244 bp fragment.

DNA extracted from transgenic white clover plants was tested for integration of the M14ApHZBAR vector. PCR reactions were performed using primer sets designed to amplify a product including a portion of the 35S promoter and the majority of the TaMYB14 gene. Results of this analysis indicated integration of the binary vector containing the TaMyb14A gene (SEQ ID NO:2) into the white clover genome (FIG. 14)

White Clover DMACA Analysis

Figure 15:
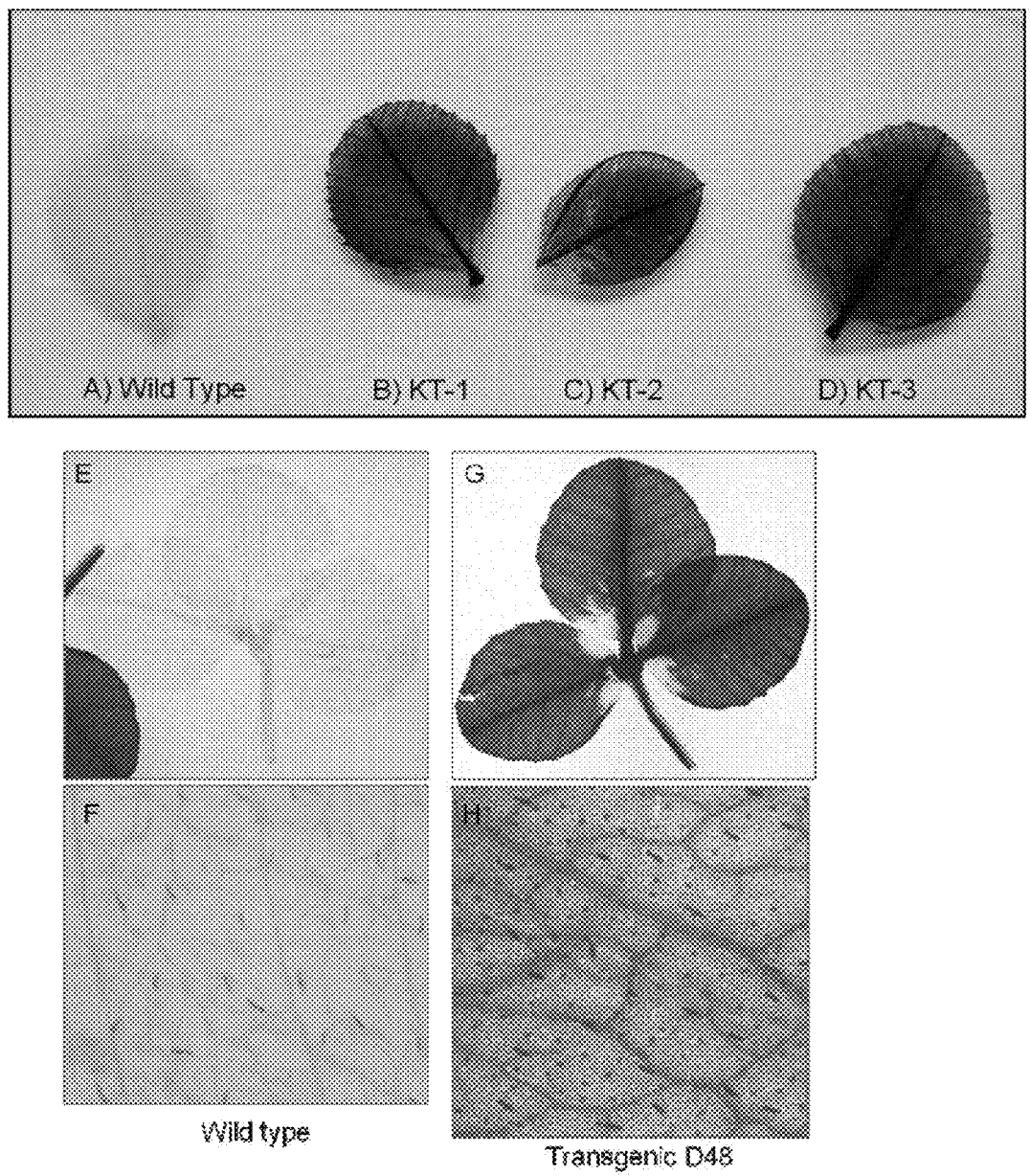
FIGS. 15 A-H show the results of DMACA screening of wild type (A, E, F) and transgenic (B to D, G and H) *T. repens* leaves, transformed with TaMYB14 construct.

The results achieved from DMACA staining of white clover leaf tissues are shown (FIG. 15). The CT specific stain, DMACA, has heavily stained the leaf blade and petiole of the transgenic clover leaves (B, C, D, G, H), compared to wild type white clover leaf (A, E, F).

Figure 16:
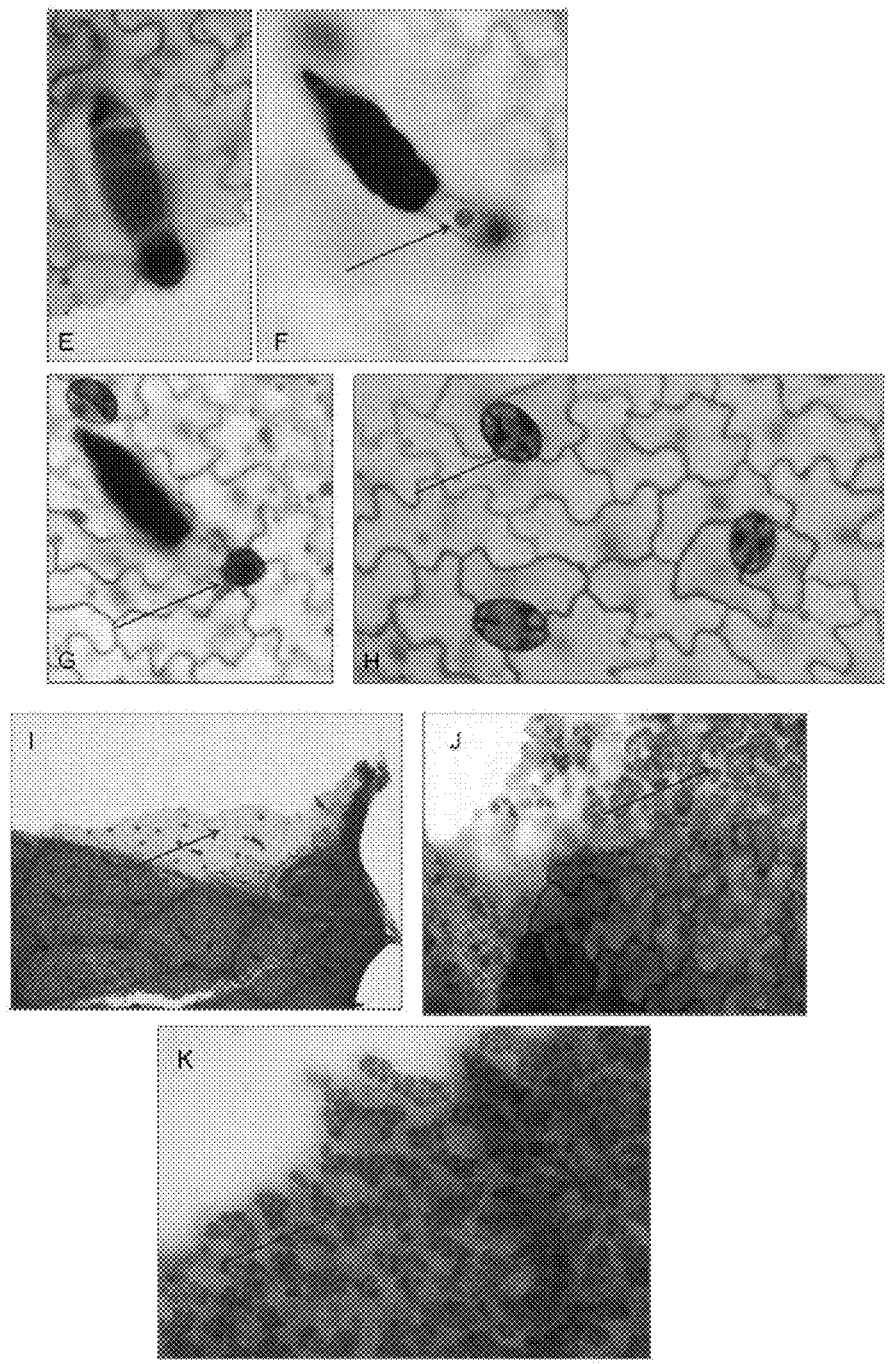
FIG. 16 shows oil microscopy of trichomes (E-G), epidermal cells (H) and mesophyll cell (I-K) of DMACA stained transgenic leaflets expressing the TaMyb14A gene (SEQ ID NO:2).

In addition (FIG. 16), the trichome tier cells and apical cells were much more strongly stained (F, G) than normally seen in wild type leaves (E). The guard cells of the stomata had also strongly stained (H). There was definite staining in the nucleus of the epidermal cells as in the stalk trichome cell. Epidermal cells were more uniformly stained than normal and the basal cell of the rosette were also strongly stained (G). Leaf tears were carried out to help establish what specific cells have DMACA staining (I to K). This instance the lower epidermis (outside surface topmost) has been separated from the mesophyll layer. The epidermal cells (apart from specialised cells such as stomata and trichomes) had little activity compared to the mesophyll cell layer. The mesophyll cells showed definite strong staining throughout the cell with definite sub localization into specific vacuole-like organelles, which are obviously multiple per cell. There is therefore compartmentalization of the DMACA staining within the mesophyll cells.

White Clover HPLC/LCMS Analysis

The applicant's biochemical analysis of the transgenic tissue transformed with M14ApHZBAR provided indisputable evidence that over expression of TaMYB14 leads to the accumulation of condensed tannin monomers, dimers and trimers in foliar tissue in white clover and tobacco. It is also possible that longer chain tannins are present but resolving these are beyond the scope of our equipment.

Figure 17:
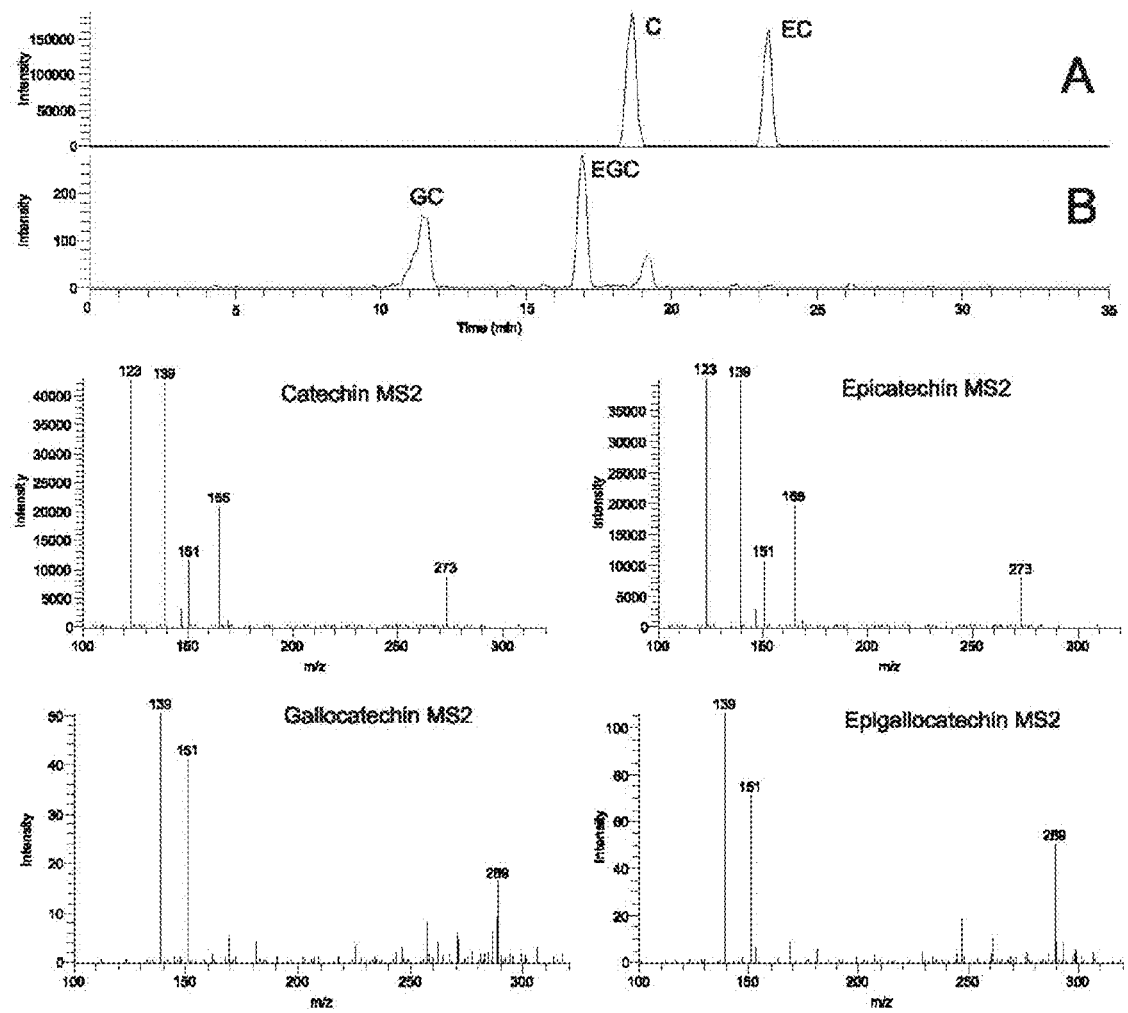
FIG. 17 shows Grape Seed Extract Monomers—The SRM chromatograms of the monomers in a grape seed extract are shown below. Trace A is a sum of the product ions 123, 139 and 165 m/z of the SRM of 291.3 m/z (catechin (C) and epicatechin (EC)). Trace B is a sum of the product ions 139 and 151 m/z of the SRM of 307.3 m/z (gallocatechin (GC) and epigallocatechin (EGG)).
Figure 18:
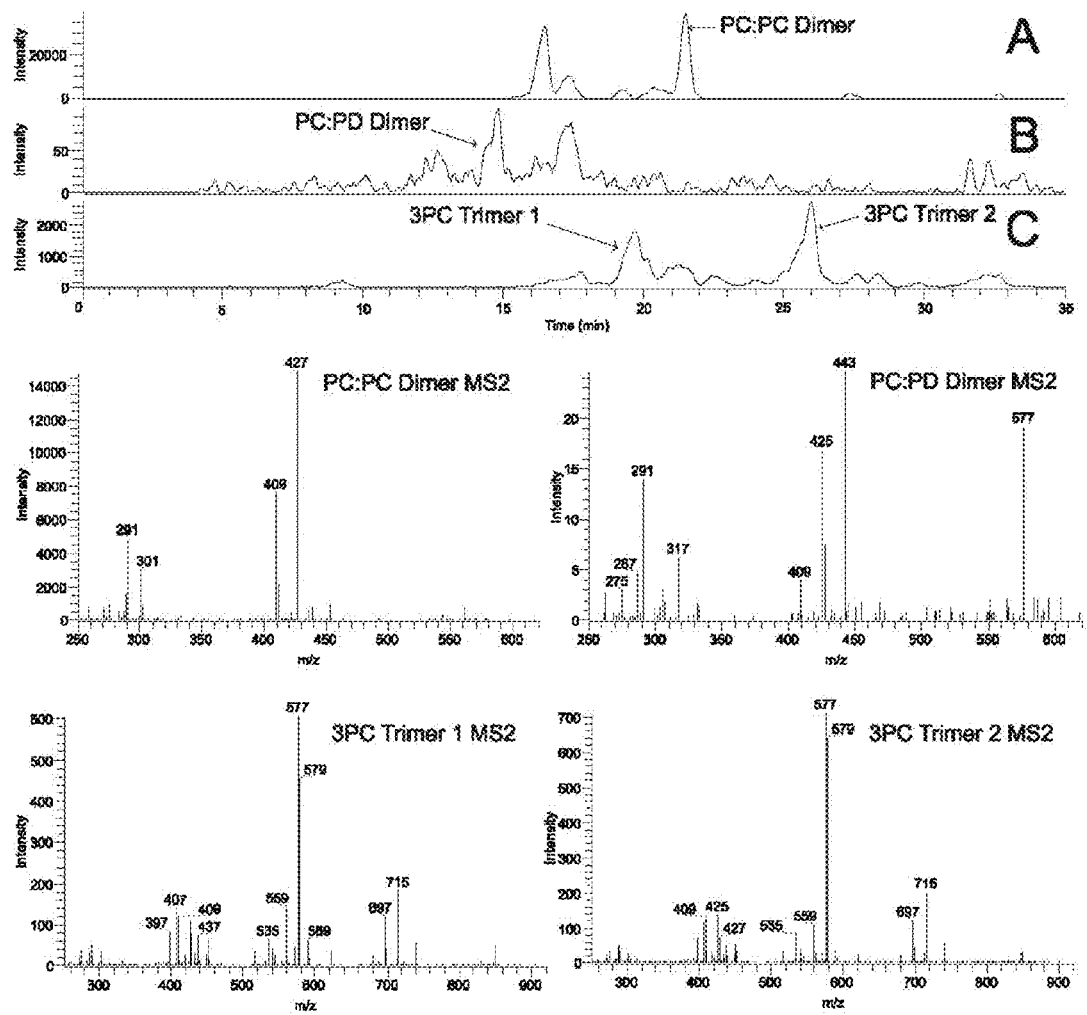
FIG. 18 shows Grape Seed Extract Dimers and Trimers. The SRM chromatograms of the dimers and trimers in a grape seed extract are shown below. Trace A is a sum of the product ions 291, 409 and 427 m/z of the SRM of 579.3 m/z (PC:PC dimer). Trace B is a sum of the product ions 291, 307, 427 and 443 m/z of the SRM of 595.3 m/z (PC:PD dimer). Trace C is a sum of the product ions 291, 577 and 579 m/z of the SRM of 867.3 m/z (3PC trimer). The MS2 spectra of a PC:PC dimer, a PC:PD dimer, and two 3PC trimers are provided as evidence of identification of these metabolites.

Purified grape seed extract was used as the standard for all LCMSMS HPLC measurements because its tannin profile has been well characterised and is shown in FIGS. 17 and 18. This extract allows definite identification of catechin (C), epicatechin (EC), gallocatechin (GC) and epigallocatechin (EGC) as well as detection of PC:PC dimers, a PC:PD dimers and two 3PC trimers.

The MS2 spectra of all four monomers are provided as evidence of identification of these metabolites.

Figure 19:
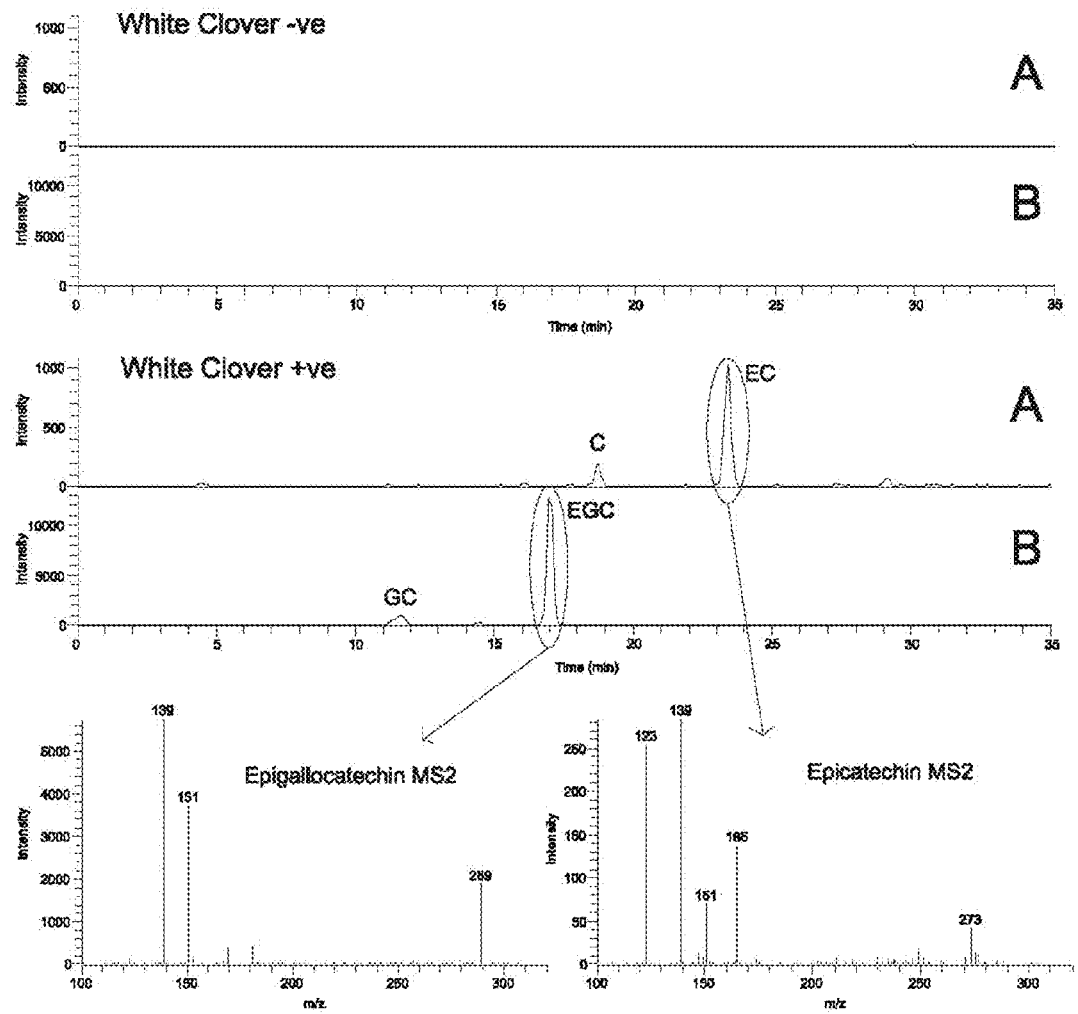
FIG. 19 shows the SRM chromatograms of monomers for the control (White Clover –ve) and transgenic (White Clover +ve) plants expressing MYB14 are shown below. Trace A is a sum of the product ions 123, 139 and 165 m/z of the SRM of 291.3 m/z (PC; catechin and epicatechin). Trace B is a sum of the product ions 139 and 151 m/z of the SRM of 307.3 m/z (PD; gallocatechin and epigallocatechin). The chromatogram scales are fixed to show the appearance of monomers in the modified plant. No monomers were detected in the control plant. The MS2 spectra of epicatechin (EC) and epigallocatechin (EGC) are provided from the modified plant as evidence of identification of these metabolites.
Figure 20:
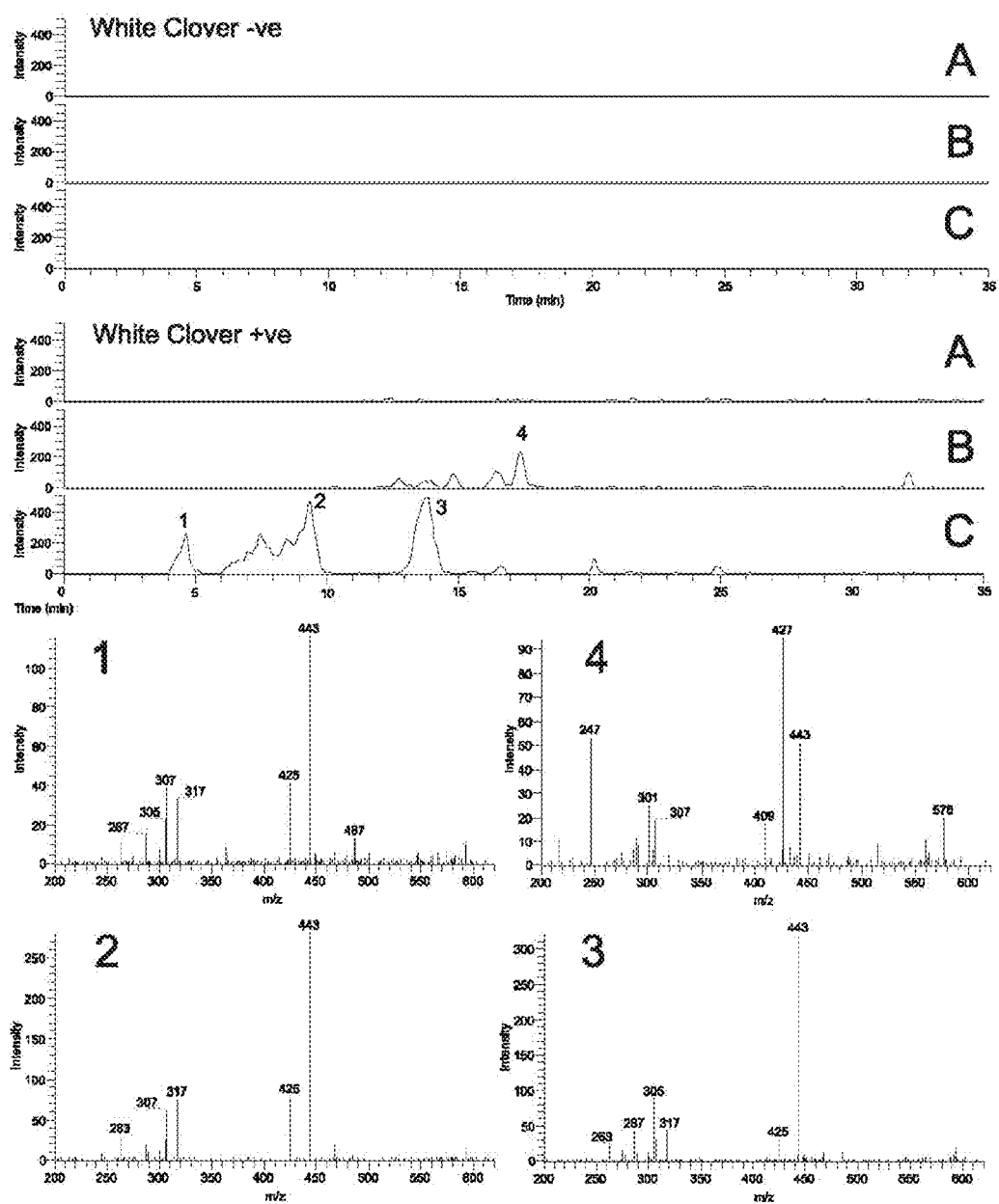
FIG. 20 shows the SRM chromatograms of dimers for the control (White Clover –ve) and transgenic (White Clover +ve) plants expressing MYB14 are shown below. Trace A is a sum of the product ions 291, 409 and 427 m/z of the SRM of 579.3 m/z (PC:PC dimer). Trace B is a sum of the product ions 291, 307, 427 and 443 m/z of the SRM of 595.3 m/z (PC:PD dimer). Trace C is a sum of the product ions 307 and 443 m/z of the SRM of 611.3 m/z (PD:PD dimer). The chromatogram scales are fixed to show the appearance of dimers in the modified plant. No dimers were detected in the control plant. The MS2 spectra of three PD:PD dimers (1-3) and one PC:PD mixed dimer (4) are provided from the modified plant as evidence of identification of these metabolites.
Figure 21:
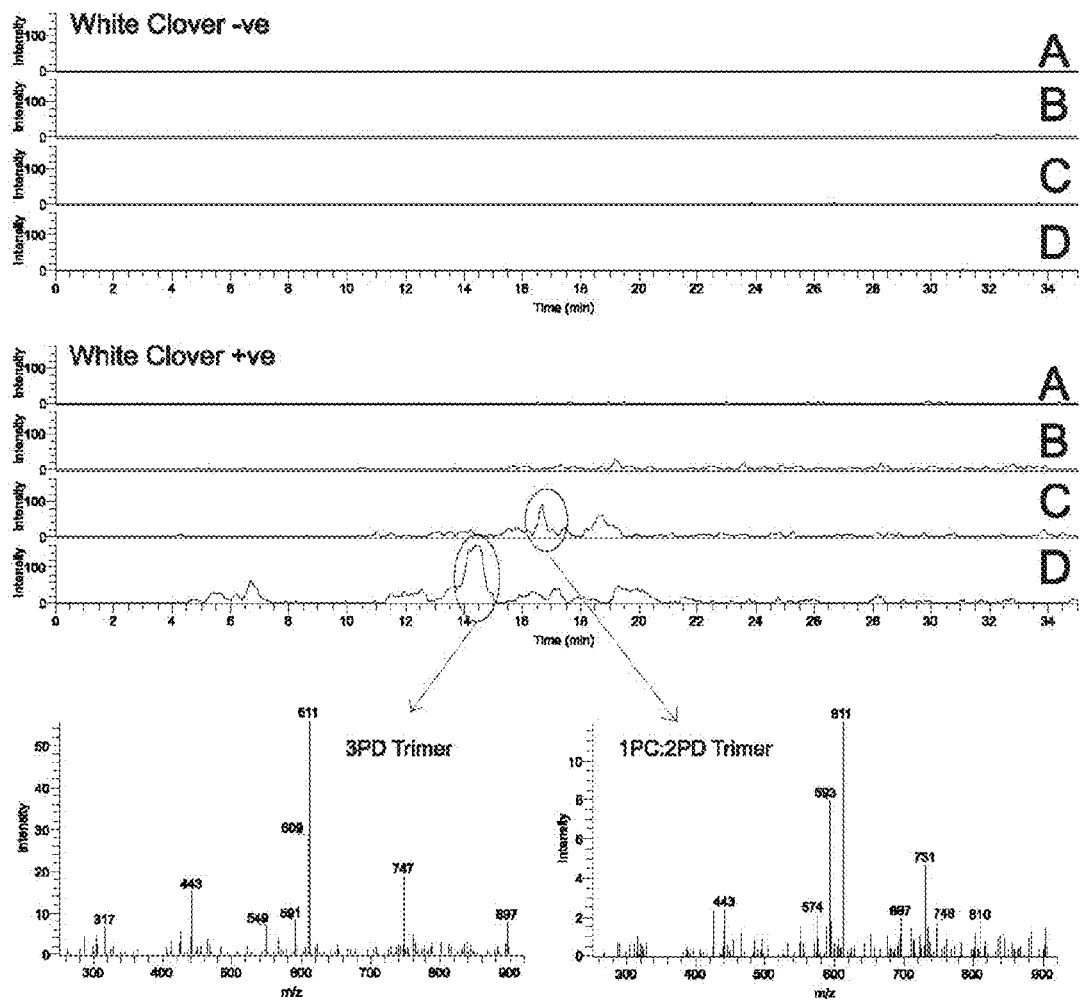
FIG. 21 shows the SRM chromatograms of trimers for the control (White Clover –ve) and transgenic (White Clover +ve) plants expressing MYB14 are shown below. Trace A is a sum of the product ions 291, 577 and 579 m/z of the SRM of 867.3 m/z (3PC trimer). Trace B is a sum of the product ions 291, 307, 427, 443, 577, 579, 593, 595 and 757 m/z of the SRM of 883.3 m/z (PC:PD trimer). Trace C is a sum of the product ions 291, 307, 443, 593, 595, 611, 731, 757 and 773 m/z of the SRM of 899.3 m/z (1PC:2PD trimer). Trace D is a sum of the product ions 307, 443, 609, 611, 747, 773 and 789 m/z of the SRM of 915.3 m/z (3PD trimer). The chromatogram scales are fixed to show the appearance of trimers in the modified plant. No trimers were detected in the control plant. The MS2 spectra of a 3PD trimer and a 1 PC:2PD mixed trimer are provided from the modified plant as evidence of identification of these metabolites.

Flavonoids were extracted from transgenic and wild type control white clover plants, and processed via HPLC/LCMS. Results of these analyses confirmed the presence of CT in leaf extracts from the transgenic clover samples. The majority of monomers detected were epicatechin and epigallocatechin with traces of gallocatechin. This is consistent as clover tannins are delphinidin derived. No monomers were detected in wild type white clover leaf tissue (FIG. 19). Dimers and trimers were also detected (FIGS. 20, 21).

EXAMPLE 3

Use of the MYB14 Nucleic Acid Sequence of the Invention to Produce Condensed Tannins in Tobacco (*Nicotiana tabacum*)

Materials and Methods

Genetic Construct Used in Transformation Protocols.

The NotI fragment from the plasmid M14ApHZBAR (FIG. 6) was isolated and cloned into pART27 (Gleave, 1992) for transformation of tobacco. This binary vector contains the nptII selection gene for kanamycin resistance under the control of the CaMV 35S promoter.

Tobacco Transformation

Tobacco was transformed via the leaf disk transformation-regeneration method (Horsch et al. 1985). Leaf disks from sterile wild type W38 tobacco plants were inoculated with an *Agrobacterium tumefaciens* strain containing the binary vector, and were cultured for 3 days. The leaf disks were then transferred to MS selective medium containing 100 mg/L of kanamycin and 300 mg/L of cefotaxime. Shoot regeneration occurred over a month, and the leaf explants were placed on hormone free medium containing kanamycin for root formation.

Results

Molecular Analysis, DMACA Screen and Biochemistry of Transgenic Tobacco

Tobacco Molecular Analysis

Figure 22:
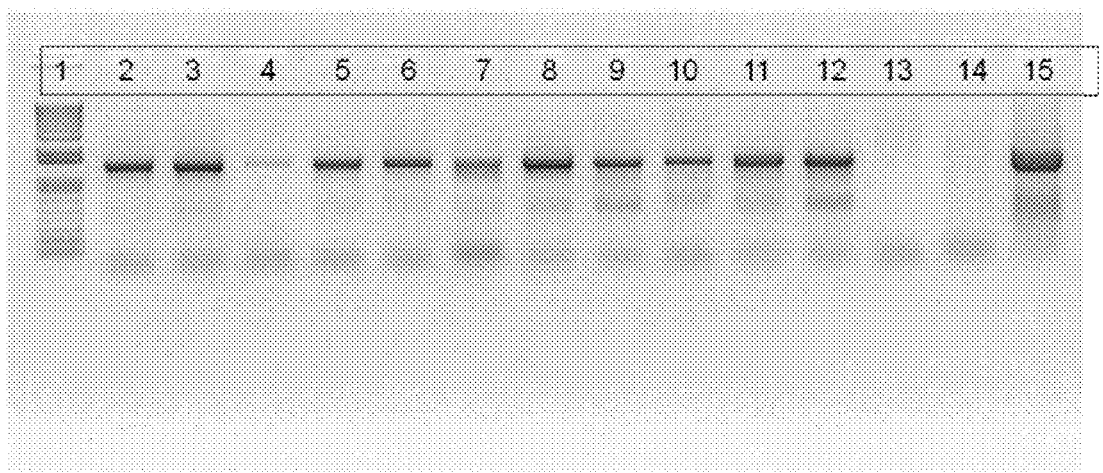
FIG. 22 shows the PCR reaction for the presence of M14ApHZBAR from genomic DNA isolated from putatively transformed tobacco plantlets. Lanes; A1, Ladder; A2-10 transformed tobacco, A13, 14, tobacco controls, A15 plasmid control. Primers were 35S (promoter) and PMYBR (to 3' end of gene) amplifying a 1,244 bp fragment.

DNA extracted from transgenic tobacco plants was tested for integration of the M14ApHZBAR binary vector. PCR reactions were performed using primer sets designed to amplify a portion of the 35S promoter and the majority of the gene. Results of this analysis indicated integration of the binary vector containing the TaMyb14A gene (SEQ ID NO:2) into the white clover genome (FIG. 22).

Tobacco DMACA Analysis

Figure 23:
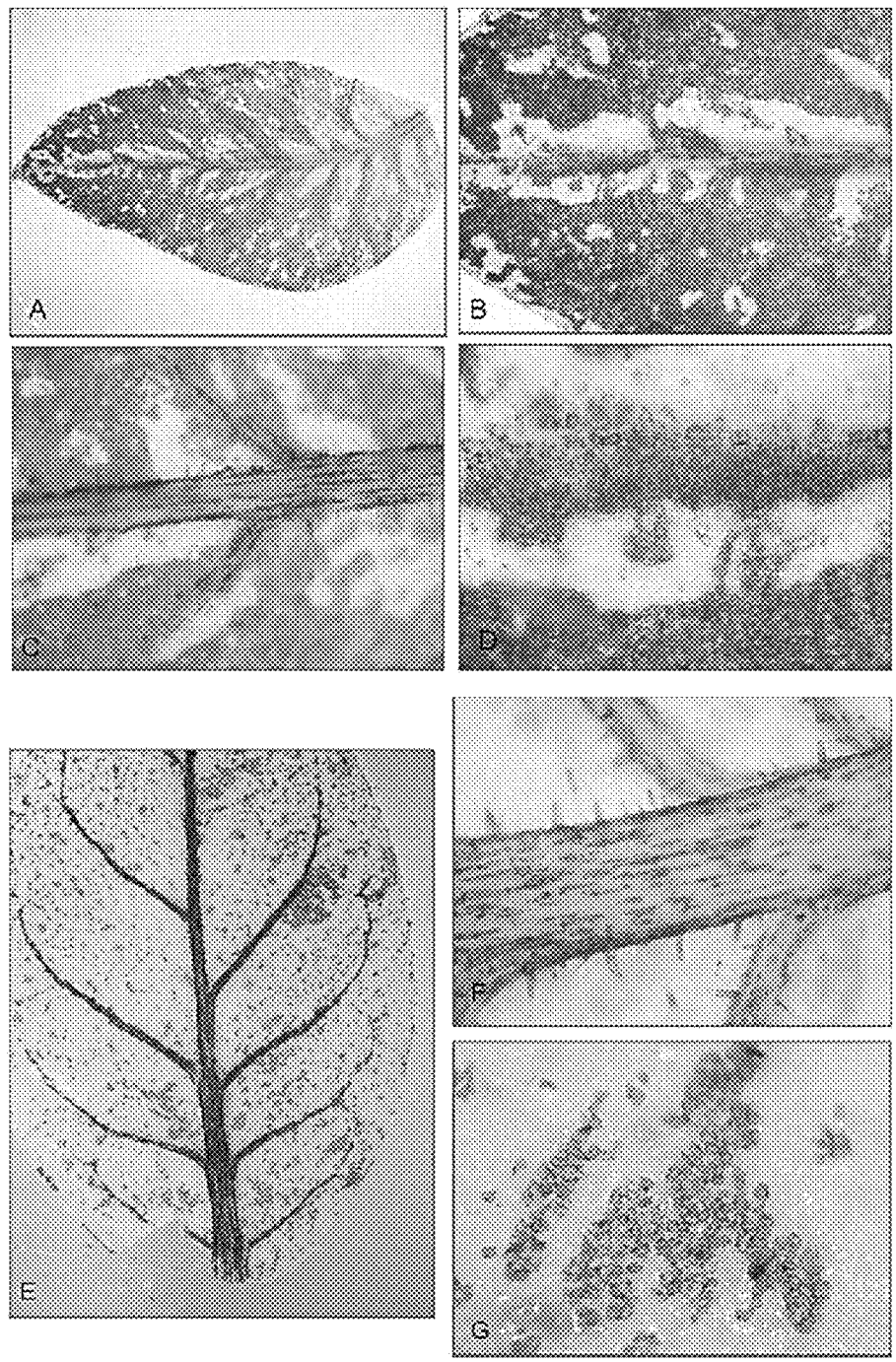
FIG. 23 shows the results of DMACA screening of transgenic (A to G) tobacco (*Nicotiana tabacum*) leaves, transformed with M14ApHZBAR construct.

DMACA analysis was performed on the tobacco plants, as described for clover in Example 1. Transgenic tobacco plantlets expressing TaMYB14A (under the control of the cauliflower mosaic virus 35S promoter) showed no significant differences in growth compared to wild-type plants. Moreover, CT was detected in leaf tissue of transgenic tobacco plantlets derived from cells of either the wild type or the transgenic tobacco (already accumulating anthocyanin) compared to wild type untransformed tobacco that does not accumulate CT in vegetative tissues. This indicates that the *T. arvense* MYB14 gene is able to activate all the genes of the CT pathway in tobacco, on its own. Examples of the DMACA staining of transgenic tobacco leaves are shown (FIG. 23). The CT specific stain, DMACA, heavily stained the leaf blade of the transgenic tobacco leaves (A to G) compared to wild type leaves, which are always devoid of CT.

Tobacco HPLC/LCMS Analysis

Figure 24:
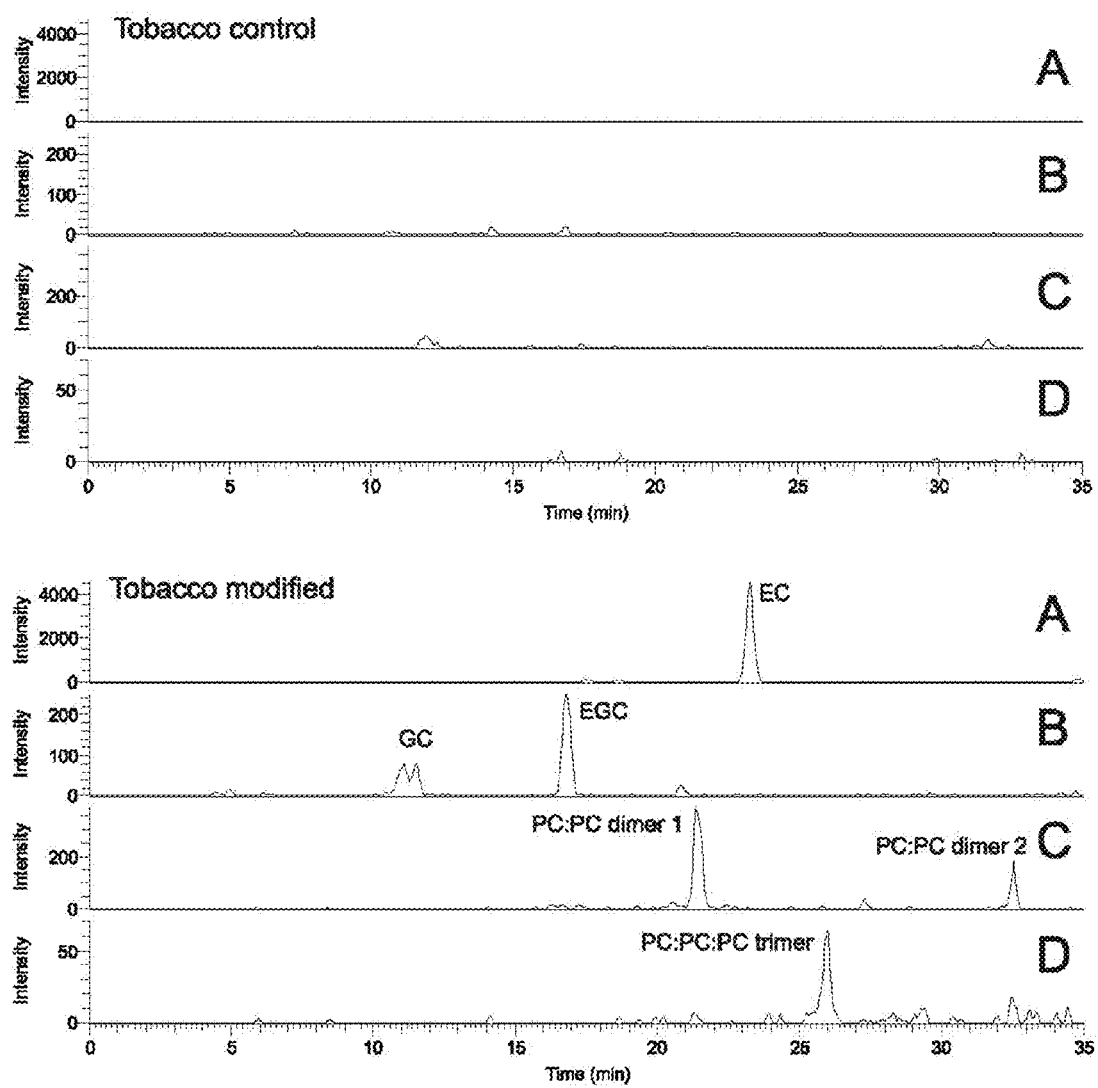
FIG. 24 shows the SRM chromatograms for the control (wild type) and modified (transgenic) plants expressing MYB14 are shown below. Trace A is a sum of the product ions 123, 139 and 165 m/z of the SRM of 291.3 m/z (PC; catechin and epicatechin). Trace B is a sum of the product ions 139 and 151 m/z of the SRM of 307.3 m/z (PD; gallocatechin and epigallocatechin). Trace C is a sum of the product ions 291, 409 and 427 m/z of the SRM of 579.3 m/z (PC:PC dimer). Trace D is a sum of the product ions 291, 577 and 579 m/z of the SRM of 867.3 m/z (PC:PC:PC timer). The chromatogram scales are fixed to show the appearance of monomers, dimers and trimers in the modified plant. Note, no mixed PC:PD or 100% PD dimers or trimers were detected.
Figure 25:
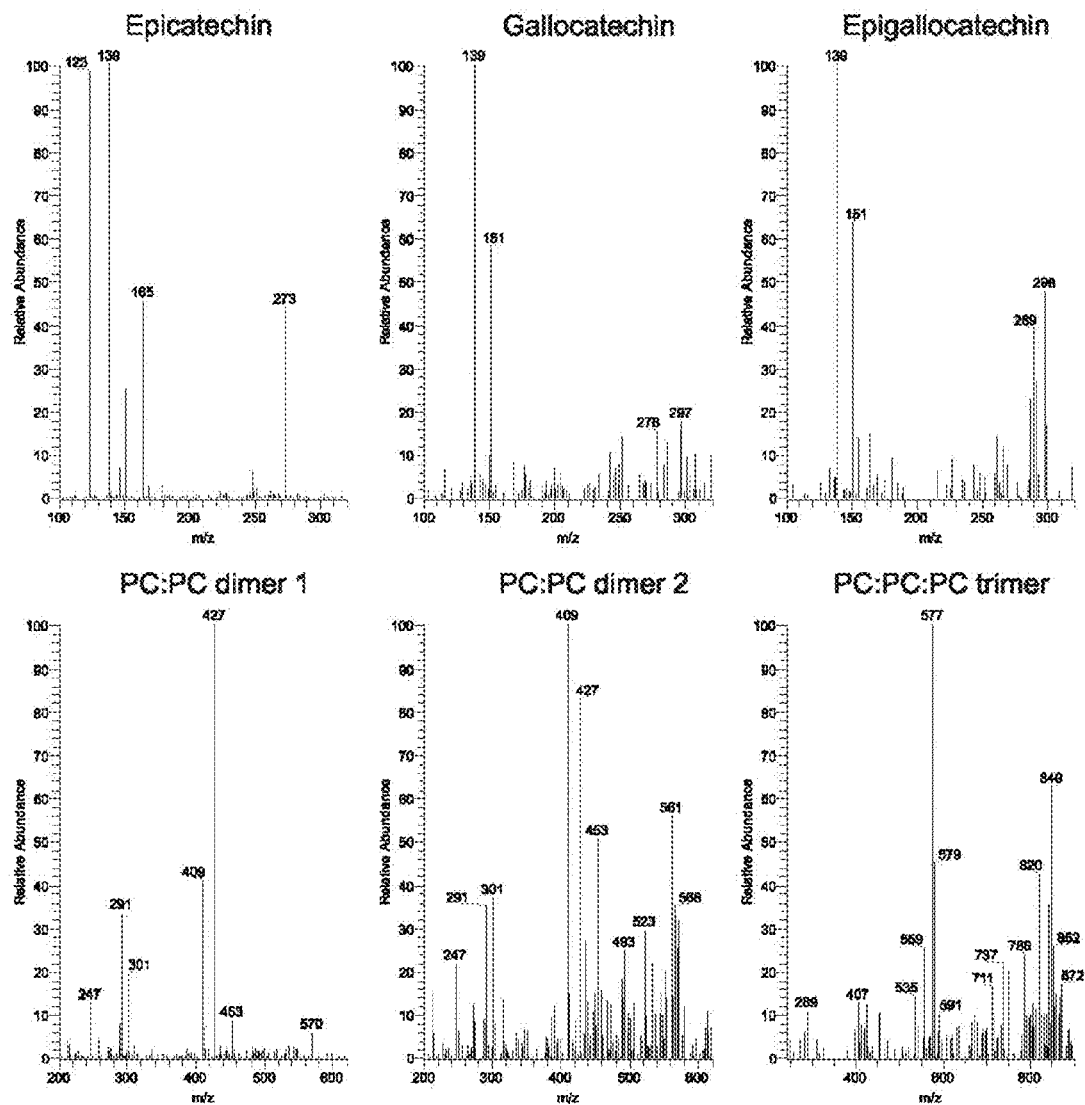
FIG. 25 shows the MS2 spectra of epicatechin (EC), gallocatechin (GC), epigallocatechin (EGC), PC:PC dimer 1 and 2, and the PC:PC:PC trimer are provided from the modified (transgenic) plants expressing MYB14, as evidence of identification of these metabolites.

HPLC/LCMS analysis was performed for tobacco as described for clover in Example 2. Flavonoids were extracted from transgenic and wild type control tobacco plants, and processed via HPLC. Results of these analyses confirmed the presence of CT in leaf extracts from the transgenic tobacco samples. The tobacco control samples were devoid of CT units. The majority of monomers detected were epicatechin, with small amounts of epigallocatechin and gallocatechin monomers (FIG. 24). Dimers and trimers were also detected (FIG. 25).

EXAMPLE 4

Use of the MYB14 Nucleic Acid Sequence of the Invention to Reduce Production Condensed Tannins in *Trifolium arvense*

Figure 13:
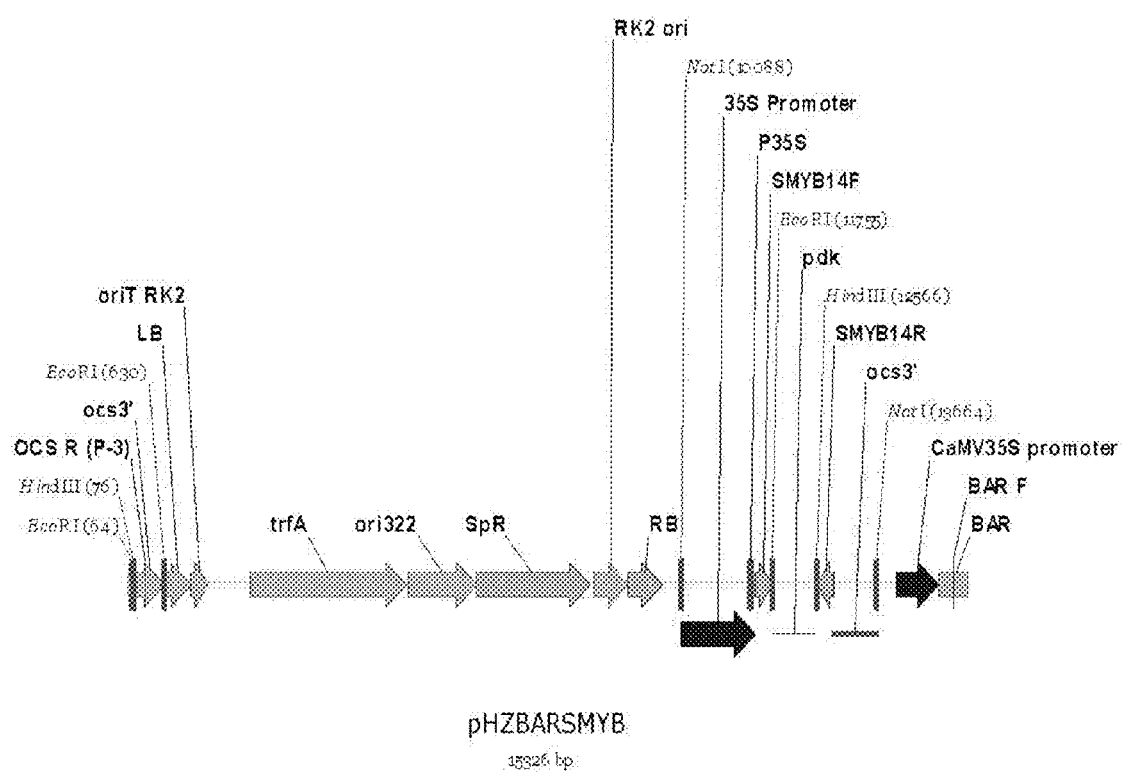
FIG. 13 shows the Vector NTI map of the construct pHZbarSMYB containing the NotI fragment from MYB14pHANNIBAL, which contains a segment of TaMYB14 cDNA from *T. arvense* in sense (SMYB14F) and antisense (SMYB14R) orientation flanking the pdk intron.

Materials and Methods
Genetic Construct Used in Silencing Protocol pHANNIBAL (Helliwell and Waterhouse, 2003), a hairpin RNAi plant vector, was used to transform *T. arvense* cotyledons with a construct expressing self-complementary portions of a sequence homologous to a portion of the cDNA of TaMYB14. The entire cDNA for the MYB14 (previously isolated from a leaf library) was used to amplify a 299 bp long fragment of the cDNA from the 3' end of the gene (caatgctggttgatggtgtggctagtgattcatg agtaacaacg aaatgg aacacggttatgg atttttgtcattttg cgatgaagag a aagaactatccgcagatttgctagaa- gattttaacatcgcggatgatatttgcttatctgaacttttgaactctga tttctcaaat- gcgtgca atttcgattacaatgatctattgtcaccttgttcggaccaaactcaaat gttctctgatgatgagattctcaagaattggacacaatgtaact ttgctgatgaga- caaatgtgtcc—SEQ ID NO:65). The primers were designed to allow the cloning of the fragments into the silencing vector pHANNIBAL (Table 5). The fragment was cloned into XhoI site in the sense direction in front of the pdk intron or the XbaI sites, after the pdk intron, in the antisense direction. Direction of the cloning was determined by PCR to ensure the fragment was in the correct orientation. The NotI fragment from MYB14pHANNIBAL containing the hpRNA cassette was subcloned into pHZBar (designated pHZBARSMYB (FIG. 13) and used in transformation experiments.

TABLE 8

Primers modified to include either an XbaI restriction enzyme site (highlighted with italics) or a XhoI restriction enzyme site (highlighted with bold) at the 5'end of the primers to allow cloning.

| Primer | Sequence |
|---|---|
| MYB14F1 | *TCTAGA*CAATGCTGGTTGATGGTGTGGC (SEQ ID NO: 66) |
| MYB14R | *TCTAGA*GGACACATTTGTCTCATCAGC (SEQ ID NO: 67) |
| MYB14F | CTCGAGCAATGCTGGTTGATGGTGTGGC (SEQ ID NO: 68) |
| MYB14R1 | CTCGAGGGACACATTTGTCTCATCAGC (SEQ ID NO: 69) |

*T. arvense* Transformation:

Cultivars of *T. arvense* were transformed with the pHZbarSMYB silencing binary vector, essentially as described for *T. repens*, with some minor modifications (Voisey et al., 1994). The ammonium glufosinate level was decreased to 1.25 mg/L; and plants were placed onto CR5 media for only a fortnight prior to placement onto CR0 medium for root regeneration.

Figure 26:
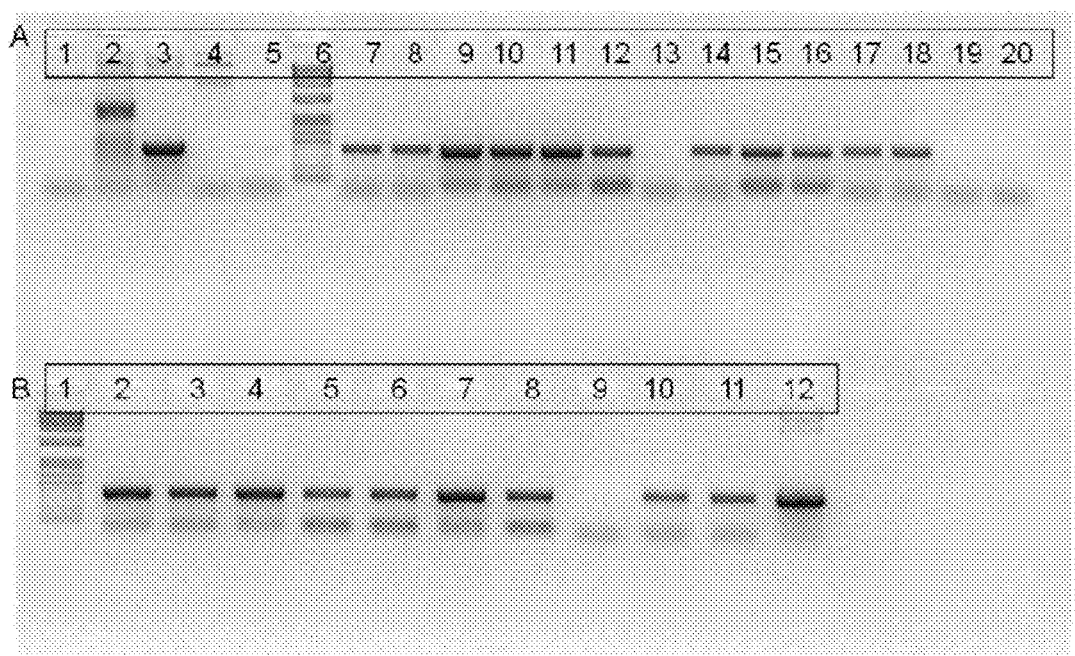
FIG. 26 shows the PCR reaction for the presence of M14pHANNIBAL in genomic DNA isolated from putatively transformed *T. arvense*. Lanes; A1 pHANNIBAL negative control vector, A2 M14ApHZBAR containing 35S and genomic gene construct—control amplifying a 1,244 bp fragment; A3 M14pHANNIBAL positive plasmid control containing hpRNA construct, A4 pHANNIBAL containing MYB fragment in antisense orientation upstream of ocs terminator (negative control), A5 pHZBARSMYB positive plasmid control, A6 Ladder, A7-18 transformed *T. arvense*, A19 genomic DNA wild type *T. arvense*, A20 water control.

Results
Molecular analysis, DMACA Screen and Biochemistry of Transgenic *Trifolium arvense*.
*T. arvense* Molecular Analysis DNA extracted from transgenic *T. arvense* plants was tested for integration of the M14pHANNIBAL binary vector. PCR reactions were performed using primer sets designed to amplify a portion of the 35S promoter and the 3' end of the cDNA gene fragment. Results of this analysis indicated integration of the binary vector containing the hpRNA gene construct into the genome (FIG. 26).

*T. arvense* DMACA Analysis

Plant material from control *T. arvense* and some of the transformed plantlets have been stained using DMACA (FIG. 27) as described in Example 1. The transformed plants were compared to the wild type mature leaves also regenerated through tissue culture as tissue culture affects leaf regeneration and the onset of tannin production compared to naturally soil grown plants derived from seeds. Wild type *T. arvense* callus does not produce tannin (A), but cells start to accumulate tannin in tissue resembling leaves (B to D-purple colour). The transgenic plants also do not produce tannin in callus, but leaf tissue similarly stained with DMACA showed only a light blue stain (E-L), indicating the levels of CT were dramatically reduced in plants expressing the silencing construct.

*T. arvense* HPLC/LCMS Analysis

Flavonoids were extracted from transgenic and wild type control *T. arvense* plants, and processed via HPLC/LCMS, as described in Example 2. Wild type (non-transformed) *T. arvense* plantlets had high detectable levels of CT monomers. The majority of these monomers were catechin, with small amounts of gallocatechin monomers (FIG. 28). Dimers were also detected (FIG. 29). In contrast, only traces of these compounds were detected in the transformed plantlets, if at all. Therefore HPLC analysis of silenced *T. arvense* plantlets confirmed CT accumulation had been significantly reduced. These results confirm the absence of CT in leaf extracts from the transgenic *T. arvense* plants is associated with the presence of the vector designed to silence expression of TaMYB14.

EXAMPLE 5

Use of the MYB14 Nucleic Acid Sequence of the Invention to Produce Condensed Tannins in Alfalfa (*Medicago sativa*)

Materials and Methods
Alfalfa Transformation by Microprojectile Bombardment

The cultivar Regen-SY was used for all transformation experiments (Bingham 1991). The transformation protocol was adapted from Samac et al (1995). Callus cultures were initiated from petiole explants and grown in the dark on Schenk and Hildebrandt media (Schenk and Hildebrandt, 1972) supplemented with 2, 4-Dichlorophenoxyacetic acid and Kinetin (SHDK). Developing cultures were passaged by regular subculture onto fresh media at four weekly intervals. Eight to twelve week old Regen Sy callus was transformed by microprojectile bombardment in a Bio-Rad PDS1000/He Biolistic® Particle Delivery System apparatus. Callus cultures were incubated for a minimum of four hours on SHDK medium supplemented with a 0.7M concentration of sorbitol and mannitol to induce cell plasmolysis. Plasmid DNA (1 µg/µl) of p35STaMyb14A (containing the NotI fragment from M14ApHZBAR) and pCW122 (which contains an nptII gene for conferring resistance to the antibiotic kanamycin; Walter et al, 1998) were precipitated to tungsten particles (M17, Bio-Rad) as described by the manufacturer. Standard parameters (27"Hg vacuum, 1100 psi rupture, and 100 mm target distance) were used for transformation according to the instruction manual. Transformed tissues were rested overnight before transfer to SHDK medium. After two days, cultures were transferred to SHDK medium containing antibiotic selection (kanamycin 50 mg/L) for selection of transformed cells. This material was sub-cultured up to three times at three weekly intervals before transfer to hormone-free SH medium or Blaydes medium (Blaydes, 1966) and placed in the light for regeneration. Germinating somatic embryos were dissected from the callus mass and transferred to a half-strength Murashige and Skoog medium (Murashige and Skoog, 1962) for root and shoot development.

Aim

Transformation experiments were undertaken to introduce a plasmid containing the TaMyb14 gene under the control of the CaMV35S promoter into alfalfa. The objective was to generate plants expressing TaMyb14 and to screen for the accumulation of condensed tannins in foliar tissues.

Results

Molecular analysis, DMACA Screen and biochemistry of transgenic Alfalfa.

Alfalfa Molecular Analysis

DNA extracted from transgenic alfalfa was tested for integration of the P35STaMyb14A vector. Primer sets designed to amplify product from either the nptII gene or TaMyb14A gene (SEQ ID NO:2) were used. Results of this analysis indicated integration of both plasmid constructs into the alfalfa genome (FIG. 30).

Alfalfa DMACA Analysis

To test for accumulation of condensed-tannins, DMACA analysis can be conducted for the Alfalfa plants as described for clover in Example 1.

Alfalfa HPLC/LCMS Analysis

HPLC/LCMS analysis as described for clover in Example 2 above can be used to accurately detect the presence of tannin monomers, dimers and trimers in transgenic alfalfa. To conduct the analysis, flavonoids are extracted from transgenic and wild type control alfalfa plants, as described for clover. Wild type alfalfa accumulates (in the seed coat) mainly cyanidin derived tannins and small amounts of delphinidin derived tannins (Pang et al., 2007). The leaves of transgenic medicago lines expressing TaMYB14 can be tested for production of epicatechin, catechin and epigallocatechin, and gallocatechin monomers as well as dimer and trimer combinations of these base units.

EXAMPLE 6

Use of the MYB14 Nucleic Acid Sequence of the Invention to Produce Condensed Tannins in brassica (Brassica oleracea)

Materials and Methods
Transformation of Brassica Lines

Seeds of Brassica oleracea var. acephala cv. Coleor (red forage kale) and Gruner (green forage kale) were germinated in vitro as described in Christey et al. (1997, 2006). Hypocotyl and cotyledonary petiole explants from 4-5 day old seedlings were co-cultivated briefly with a culture of Agrobacterium tumefaciens grown overnight in LB medium containing antibiotics prior to 1:10 dilution in antibiotic-free minimal medium (7.6 mM $(NH_4)_2SO_4$, 1.7 mM sodium citrate, 78.7 mM $K_2HPO_4$, 0.33 M $KH_2PO_4$, 1 mM $MgSO_4$, 0.2% sucrose) with growth for a further 4 hrs. Explants were cultured on Murashige-Skoog (MS, Murashige and Skoog, 1962) based medium with B5 vitamins and 2.5 mg/L BA and solidified with 10 gm/L Danisco standard agar. After 3 days co-cultivation, explants were transferred to the same medium with the addition of 300 mg/L Timentin (SmithKline Beecham) and 15/L kanamycin. Explants were transferred every 3-4 weeks to fresh selection medium. Green shoots were transferred as they appeared to hormone-free Linsmaier-Skoog based medium (L S, Linsmaier and Skoog, 1965) containing 50 mg/L kanamycin and solidified with 10 gm/L Danisco standard agar. Explants were cultured in tall Petri dishes (9 cm diameter, 2 cm tall) sealed with Micropore (3M) surgical tape. Shoots were cultured in clear plastic tubs (98 mm, 250 ml, Vertex). All plant culture manipulations were conducted at 25° C. with a 16 h/day photoperiod, provided by Cool White fluorescent lights, 20 $uE/mm^2/s$.

Results

Molecular Analysis, DMA CA Screen and Biochemistry of Transgenic Brassica

Brassica Molecular Analysis

DNA extracted from transgenic brassica plants was tested for integration of the M14ApHZ8AR binary vector. PCR reactions were performed using primer sets designed to amplify a portion of the 35S promoter and the majority of the gene. Results of this analysis indicated integration of the binary vector containing the TaMyb14A gene (SEQ ID NO:2) into the brassica genome (shown in FIG. 31).

Brassica DMACA Analysis

DMACA analysis was performed on the Brassica plants as described for clover in Example 1. Transgenic brassica plantlets expressing TaMYB14A (under the control of the cauliflower mosaic virus 35S promoter) were indistinguishable from the wild-type plants. Wild type untransformed cabbage of either cultivar that does not naturally accumulate CT in vegetative tissues, remained unstained. However, CT was detected in leaf tissue of transgenic brassica plantlets derived from the accumulating anthocyanin cultivars, as evidenced by the positive DMACA staining. The staining was not as intense as that noted for tobacco and clovers. In contrast transgenic plantlets derived from wild type green cultivar never stained with DMACA.

This indicates that the T. arvense MYB14 gene is able to activate a portion of the genes of the CT pathway in brassica, but may require an active anthocyanin pathway for CT production. Examples of the DMACA staining of transgenic brassica leaves are shown in the pictures below (FIG. 32). The CT specific stain, DMACA, stained the leaf blade of the transgenic brassica (B to D) compared to wild type leaves (A), which are always devoid of CT.

Brassica HPLC/LCMS Analysis

Flavonoids were extracted from transgenic and wild type control Brassica plants, and processed via HPLC as described for clover in Example 2. Results of these analyses confirmed the presence of CT in leaf extracts from one transgenic brassica sample. The brassica transformation was done with both normal green coloured brassica as well as with a brassica line accumulating anthocyanin. The HPLC analysis detected epicatechin in green coloured brassica but no tannin monomers in the anthocyanin accumulating lines. The transgenic brassica overexpressing TaMYB14 that accumulated CTs in the leaf was derived from an anthocyanin accumulating line. Only epicatechin monomers were detected in this transgenic line as shown in FIG. 33.

EXAMPLE 6

To Demonstrate Modification of Condensed Tannin Poluation by MYB14 Variant

Any variant MYB sequences, which may be identified by methods described herein, can be texsted for their ability to alter condensed tannins in plants using the methods described in Examples 2 to 5.

Briefly the coding sequences (such as but not limited to those of SEQ ID NO: 56-64) of the variant sequences can be cloned into a suitable expression consistent (e.g. pHZBar, as described in Example 2) and transformed into a plant cell or plant. A particularly convenient and relatively simple approach is to use tobacco as a test plant as described in Example 3. DMACA analysis can be used as a quick and convenient test for alternations in condensed tannin production as described in Example 1.

In this way the function of MYB14 variants in regulating condense tannin production can be quickly confirmed.

More detailed analysis of the condensed tannins can also be performed using HPLC/LCMS analysis as described in Example 2.

Summary of Examples

The examples clearly demonstrate that the MYB14 gene of the invention is useful for manipulating the production of flavonoids, specifically condensed tannins in a range of plant genera, including tobacco (*Nicotiana tabacum*; Solanaceae Family), and in the legumes white clover (*Trifolium repens*; Fabaceae Family) and brassica (*Brassica oleracea*, Brassicaceae Family).

The applicants have demonstrated both increase and decrease in the production of condensed tannins using the methods and polynucloetides of the invention.

It is not the intention to limit the scope of the invention to the above mentioned examples only. As would be appreciated by a skilled person in the art, many variations are possible without departing from the scope of the invention.

References

Abrahams S, Lee E, Walker A R, Tanner G J, Larkin P J, Ashton A R (2003). The *Arabidopsis* TDS4 gene encodes leucoanthocyanidin dioxygenase (LDOX) and is essential for proanthocyanidin synthesis and vacuole development. Plant Journal 35: 624-636.

Abrahams S, Tanner G J, Larkin P J, Ashton A R (2002). Identification and biochemical characterization of mutants in the proanthocyanidin pathway in *Arabidopsis*. Plant Physiology 130: 561-576.

Aerts, R J, Barry, T N and McNabb, W C (1999). Polyphenols and agriculture: beneficial effects of proanthocyanidins in forages. Agric. Ecosyst. Env. 75: 1-12.

Baudry A, Heim M A, Dubreucq B, Caboche M, Weisshaar B, Lepiniec L (2004). TT2, TT8, and TTG1 synergistically specify the expression of BANYULS and proanthocyanidin biosynthesis in *Arabidopsis thaliana*. Plant J 39: 366-380.

Bingham, E T (1991). Registration of Alfalfa Hybrid Regen-Sy Germplasm for Tissue Culture and Transformation Research. Crop Science 31: 1098.

Blaydes, D F (1966). Interaction of kinetin and various inhibitors in the growth of soybean tissue. Physiologia Plantarum 19:748-753.

Blaxter, K. L., Clapperton, J. L. (1965). Prediction of the amount of methane produced by ruminants. British Journal of Nutrition 19: 511-522.

Bogs J, Downey M, Harvey J S, Ashton A R, Tanner G J, Robinson S P (2005). Proanthocyanidin synthesis and expression of genes encoding leucoanthocyanidin reductase and anthocyanidin reductase in developing grape berries and grapevine leaves. Plant Physiology 139: 652-663.

Bogs J, Jaffe F W, Takos A M, Walker A R, Robinson S P (2007). The grapevine transcription factor VvMYBPA1 regulates proanthocyanidin synthesis during fruit development. Plant Physiology 143:1347-1361.

Broun P. (2005). Transcriptional control of flavonoid biosynthesis: a complex network of conserved regulators involved in multiple aspects of differentiation in *Arabidopsis*. Current Opinion in Plant Biology 8:272-279.

Burggraaf, V. T., Woodward, S. L., Woodfield, D. R., Thom, E. R., Waghorn, G. C. and Kemp, P. D. (2006). Morphology and agronomic performance of white clover with increased flowering and condensed tannin concentration. New Zealand Journal of Agricultural Research 49: 147-155.

Caradus, J. R., Woodfield, D. R., Easton, H. S (2000). Improved grazing value of pasture cultivars for temperate environments. Asian-Australasian Journal of Animal Sciences 13 (SUPPL. 1), pp. 5-8.

Christey, M. C., Sinclair, B. K., Braun, R. H. and Wyke, L. (1997). Regeneration of transgenic vegetable brassicas (*Brassica oleracea* and *B. campestris*) via R1-mediated transformation. Plant Cell Reports 16: 587-593.

Christey M C, Braun R H, Conner E L, Reader J K, White D W R, Voisey C R (2006). Cabbage white butterfly and diamond-back moth resistant *Brassica oleracea* plants transgenic for cry1Ba1 or cry1Ca5. Acta Horticulturae 706: 247-253.

Clark, H. (2001). Ruminant Methane Emissions: A Review of the Methodology Used for National Inventory Estimations. A Report Prepared for the Ministry of Agriculture and Forestry, New Zealand.

Choreo and Goodman, Acc. Chem. REs., (1993) 26 266-273.

Dairylnsight: Strategic Framework for Dairy Farming's Future, 2005-2015.

Damiani F, Paolocci F, Cluster P D, Arcioni S, Tanner G J, Joseph R G, Li Y G, de Majnik J, Larkin P J (1999). The maize transcription factor Sn alters proanthocyanidin synthesis in transgenic *Lotus corniculatus* plants Australian Journal Of Plant Physiology 26: 159-169.

Davies K M, Schwinn K E (2003). Transcriptional regulation of secondary metabolism. Functional Plant Biology 30:913-925.

de Majnik, J. Weinman, J., Djordjevic, M. Rolfe, M B. Tanner, G. Joseph, R G. Larkin P J (2000). Anthocyanin regulatory gene expression in transgenic white clover can result in an altered pattern of pigmentation. Australian Journal of Plant Physiology 27:659-667.

I, Nesi N, Perez P, Devic M, Grandjean O, Caboche M, Lepiniec L (2003). Proanthocyanidin-accumulating cells in *Arabidopsis* testa: regulation of differentiation and role in seed development. Plant Cell 15: 2514-2531.

Debeaujon I, Peeters A J M, Leon-Kloosterziel K M, Koornneef M (2001). The TRANSPARENT TESTA12 gene of *Arabidopsis* encodes a multidrug secondary transporter-like protein required for flavonoid sequestration in vacuoles of the seed coat endothelium. Plant Cell 13: 853-871.

Ditta, G., Stanfield, S., Corbin, D., and Helsinki, S. R. (1980). Broad host range cloning system for gram-negative bacteria: construction of a gene bank of *Rhizobium meliloti*. Proceedings of the National Academy of Sciences USA 77: 7347-7351.

Dixon R A, Lamb C J, Masoud S, Sewalt V J H, Paiva N L (1996). Metabolic engineering: prospects for crop improvement through the genetic manipulation of phenylpropanoid biosynthesis and defense responses—a review. Gene 179: 61-71.

Dixon R A, Xie D Y, Sharma S B (2005).Proanthocyanidins—a final frontier in flavonoid research? New Phytologist 165: 9-28.

Douglas G B, Wang Y, Waghorn G C, Barry T N, Purchas R W, Foote A G, Wilson G F (1995). Liveweight Gain And Wool Production Of Sheep Grazing *Lotus*-Corniculatus And Lucerne (Medicago-Sativa). New Zealand Journal Of Agricultural Research 38: 95-104.

Ellison, N. W., Liston, A., Steiner, J. J., Williams, W. M., Taylor, N. L (2006). Molecular phylogenetics of the clover genus (Trifolium-Leguminosae) Molecular Phylogenetics and Evolution 39; 688-705.

Fay M F, Dale P J (1993). Condensed Tannins in *Trifolium* species and their significance for taxonomiy and plant breeding. Genetic resources and Crop Evolution 40:7-13.

Freidinger, R. M., Perlow, D. S., Veber, D. F., *J. Org. Chem.* 1982, 59, 104-109.

Gallop, M. A., Barrett, R. W., Dower, W. J., Fodor, S. P. A. and Hogan, Jr., J. C. (1997). Nature Biotechnology, 15 328-330.

Gleave A P (1992). A versatile binary vector system with a T-DNA organisational structure conducive to efficient integration of cloned DNA into the plant genome. Plant Molecular Biology 20: 1203-1207.

Helliwell, C and Waterhouse, P (2003). Constructs and methods for high-throughput gene silencing in plants. Methods 30: 289-295.

Horsch R B, Fry J E, Hoffmann N L, Eichholtz D, Rogers S G, Fraley R T. (1985). A simple and general method for transferring genes into plants. Science; 227:1229-1231.

Jones, W. T., Broadhurst, R. B. and Lyttleton, J. W. (1976). The condensed tannins of pasture legume species. Phytochemistry 15: 1407-1409.

Kingston-Smith A H, Thomas H M (2003). Strategies of plant breeding for improved rumen function Annals of Applied Biology 142:13-24.

Li, Y G and Tanner G, Larkin P (1996). The DMACA-HCl Protocol and the Threshold Proanthocyanidin Content for Bloat Safety in Forage Legumes. Journal of the Science of Food and Agriculture 70 (1996) 98-101.

Linsmaier, E. M. and Skoog, F. (1965). Organic growth factor requirements of tobacco tissue cultures. Physiologia Plantarum. 18:100-127.

McKenna, P. B (1994). The occurrence of anthelminitic resistant sheep nematodes in the southern North Island of New Zealand. NZ Veterinary. Journal. 42: 151-152.

McMahon L R, McAllister T A, Berg B P, Majak W, Acharya S N, Popp J D, Coulman B E, Wang Y, Cheng K J (2000). A review of the effects of forage condensed tannins on ruminal fermentation and bloat in grazing cattle. Canadian Journal of Plant Science 80: 469-485.

Marten, G. C., Ehle, F. R. & Ristau, E. A. (1987). Performance and photosensitization of cattle related to forage quality of four legumes. Crop Science 27: 138-145.

Mehrtens F, Kranz H, Bednarek P, Weisshaar B (2005). The *Arabidopsis* transcription factor MYB12 is a flavonol-specific regulator of phenylpropanoid biosynthesis. Physiologia Plantarum. 138: 1083-1096.

Miyake K, Ito T, Senda M, Ishikawa R, Harada T, Niizeki M, Akada S (2003). Isolation of a subfamily of genes for R2R3-MYB transcription factors showing up-regulated expression under nitrogen nutrient-limited conditions. Plant Molecular Biology 53: 237-245.

Molan. A. L. Waghorn, G. C., McNabb, W. C. (2001). Effect of condensed tannins on egg hatching and larval development of *Trichostrongylus colobriformis* in vitro. The Veterinary Record 150: 65-69.

Murashige T and Skoog F (1962). A revised medium for rapid growth and bioassays with tobacco tissue cultures. Physiologia Plantarum 15(3): 473-497.

Nagai, U., Sato, K. *Tetrahedron Lett.* 1985, 26, 647-650.

Nesi N, Debeaujon I, Jond C, Pelletier G, Caboche M, Lepiniec L (2000). The TT8 gene encodes a basic helix-loop-helix domain protein required for expression of DFR and BAN genes in *Arabidopsis siliques*. Plant Cell 12: 1863-1878.

Nesi N, Debeaujon I, Jond C, Stewart A J, Jenkins G I, Caboche M, Lepiniec L (2002). The TRANSPARENT TESTA16 locus encodes the ARABIDOPSIS BSISTER MADS domain protein and is required for proper development and pigmentation of the seed coat. Plant Cell 14: 2463-2479.

Nesi N, Jond C, Debeaujon I, Caboche M, Lepiniec L (2001). The *Arabidopsis* TT2 gene encodes an R2R3 MYB domain protein that acts as a key determinant for proanthocyanidin accumulation in developing seed. Plant Cell 13: 2099-2114.

Niezen, J. H., Waghorn, T. S., Charleston, W. A. G. and Waghorn, G. C. (1995). Growth and gastrointestinal nematode parasitism in lambs grazing either lucerne (*Medicago sativa*) or sulla (*Hedysarum coronarium*) which contains condensed tannins. *J. Agric. Sci.* (*Cam*) 125, pp. 281-289.

Niezen, J. H., Waghorn, T. S., Waghorn, G. C. and Charleston, W. A. G. (1993) Internal parasites and lamb production—a role for plants containing condensed tannins?. *Proc. NZL. Soc. Anim. Prod.* 53, pp. 235-238.

Olson et al., (1993) J. Med. Chem., 36 3039-3049.

Pang Y, Peel G J, Wright E, Wang Z, Dixon R A (2007). Early steps in proanthocyanidin biosynthesis in the model legume *Medicago truncatula*. Plant Physiology 145(3): 601-615.

Pfeiffer J, Kuhnel C, Brandt J, Duy D, Punyasiri P A N, Forkmann G, Fischer T C (2006). Biosynthesis of flavan 3-ols by leucoanthocyanidin 4-reductases and anthocyanidin reductases in leaves of grape (*Vitis vinifera* L.), apple (*Malus×domestica* Borkh.) and other crops. Plant Physiology and Biochemistry 44: 323-334.

Puchala, R., Min, B. R., Goetsch, A. L. and Sahlu, T. (2005). The effect of a condensed tannin-containing forage on methane emission by goats. Journal of Animal Science 83:182-186.

Ray H, Yu M, Auser P, Blahut-Beatty L, McKersie B, Bowley S, Westcott N, Coulman B, Lloyd A, Gruber M Y (2003). Expression of Anthocyanins and Proanthocyanidins after Transformation of Alfalfa with Maize Lc. Plant Physiology, 132: 1448-1463.

Robbins M P, Paolocci F, Hughes J W, Turchetti V, Allison G, Arcioni S, Morris P, Damiani F (2003). Sn, a maize bHLH gene, modulates anthocyanin and condensed tannin pathways in *Lotus corniculatus*. Journal of Experimental Botany 54:381: 239-248, DOI: 10.1093/jxb/erg022

Rumbaugh, M. D. (1985). Breeding bloat-safe cultivars of bloat-causing legumes. In: Barnes, R. F., Ball, P. R., Bringham, R. W., Martin, G. C., Minson, D. J. (Eds.), Forage Legumes for Energy-Efficient Animal Production. USDA, Washington. Proc. Bilateral Workshop, Palmerston North, NZ, April 1984, pp. 238-245.

Samac, D A (1995), Strain specificity in transformation of alfalfa by *Agrobacterium tumefaciens*. Plant Cell, Tissue and Organ Culture 43: 271-277.

Sanger F, Nicklen S, Coulson A R (1977). DNA sequencing with chain-terminating inhibitors. Proceedings of the National Academy of Sciences USA 74: 5463-5467.

Schenk, R U and Hildebrandt, A C (1972). Medium and techniques for induction and growth of monocotyledonous and dicotyledonous plant cell cultures. Canadian Journal of Botany 50: 199-204.

Sharma, S. B. and Dixon, R. A. (2005). Metabolic engineering of proanthocyanidins by ectopic expression of transcription factors in *Arabidopsis thaliana*. Plant Journal 44:62-75.

Debeaujon Smythe, M. L., von Itzstein, M., *J. Am. Chem. Soc.* 1994, 116, 2725-2733.

Stracke R, Werber M, Weisshaar B (2001). The R2R3-MYB gene family in *Arabidopsis thaliana*. Current Opinion in Plant Biology 4: 447-456.

Sykes. A. R and Coop. R. L (2001). Interaction between nutrition and gastrointestinal parasitism in sheep New Zealand Veterinary Journal. 49: 222-226.

Tanner G J, Francki K T, Abrahams S, Watson J M, Larkin P J, Ashton A R (2003). Proanthocyanidin biosynthesis in plants—Purification of legume leucoanthocyanidin reductase and molecular cloning of its cDNA. Journal of Biological Chemistry 278:31647-31656.

Tanner G J, Moore A E, Larkin P J (1994). Proanthocyanidins Inhibit Hydrolysis Of Leaf Proteins By Rumen Microflora In-Vitro British Journal Of Nutrition 71: 947-958.

Voisey, C. R.; White, D. W. R.; Dudas, B.; Appleby, R. D.; Ealing, P. M.; Scott, A. G. (1994). *Agrobacterium*-mediated transformation of white clover using direct shoot organogenesis. Plant Cell Reports 13: 309-314.

Waghorn, G. C., Douglas, G. B., Niezen, J. H., McNabb, W. and Foote, A. G. (1998). Forages with condensed tannins—their management and nutritive value for ruminants. Proceedings of the New Zealand Grasslands Association 60: 89-98.

Walker A R, Davison P A, Bolognesi-Winfield A C, James C M, Srinivasan N, Blundel T L, Esch J J, Marks M D, Gray J C (1999). The TRANSPARENT TESTA GLABRA1 locus, which regulates trichome differentiation and anthocyanin biosynthesis in *Arabidopsis*, encodes a WD40 repeat protein. Plant Cell 11: 1337-1349.

Walter C, Grace L J, Wagner A, White D W R, Walden A R, Donaldson S S, Hinton H, Gardner R C, Smith D R (1998). Stable transformation and regeneration of transgenic plants of *Pinus radiata* D. Don. Plant Cell Reports 17: 460-469.

Wei Y L, Li J N, Lu J, Tang Z L, Pu D C, Chai Y R (2007). Molecular cloning of *Brassica napus* TRANSPARENT TESTA 2 gene family encoding potential MYB regulatory proteins of proanthocyanidin biosynthesis. Molecular Biology Reports 34:105-120.

Winkel-Shirley B (2001). Flavonoid biosynthesis: a colorful model for genetics, biochemistry, cell biology, and biotechnology. Plant Physiology 126: 485-493.

Winkel-Shirley, B. (2002). A mutational approach to dissection of flavonoid biosynthesis in *Arabidopsis*. In Recent Advances in Phytochemistry: Proceedings of the Annual Meeting of the Phytochemical Society of North America, Vol. 36, J. T. Romeo, ed (New York: Elsevier), pp. 95-110.

Woodfield, D., McNabb, W., Kennedy, L., Cousins, G. and Caradus, J. (1998). Floral and foliar content in white clover. Proceedings of the 15th *Trifolium* Conference, P. 19.

Woodward, S. L., Waghorn, G. C., Ulyatt, M. J. and Lassey. K. R. (2001). Early indications that feeding *Lotus* will reduce methane emission from ruminants. Proceedings New Zealand Society of Animal Production 61:23-26.

Xie D Y, Sharma S B, Dixon R A (2004). Anthocyanidin reductases from *Medicago truncatula* and *Arabidopsis thaliana*. Archives Of Biochemistry and Biophysics 422: 91-102.

Xie D Y, Sharma S B, Paiva N L, Paiva N L, Ferreira D, Dixon R A (2003). Role of anthocyanidin reductase, encoded by BANYULS in plant flavonoid biosynthesis. Science 299: 396-399.

Xie D Y, Sharma S B, Wright E, Wang Z Y, Dixon R A (2006). Metabolic engineering of proanthocyanidins through co-expression of anthocyanidin reductase and the PAP1 MYB transcription factor. Plant Journal 45: 895-907.

Yoshida, K, Iwasaka, R, Kaneko T, Sato s, Tabata, S. Sakuta M (2008). Functional differentiation of *Lotus japonicus* TT2s, R2R3 MYB transcription factors comprising a multigene family. Plant Cell Physiology 49:157-169.

---

The invention claimed is:

1. A host cell which has been altered from the wild-type to include an isolated nucleic acid molecule encoding a MYB polypeptide comprising a sequence with at least 95% identity to SEQ ID NO: 14, wherein percent identity is calculated over the entire length of SEQ ID NO: 14, and wherein the MYB polypeptide regulates at least one of:
   (a) the production of condensed tannins in plants, and
   (b) at least one gene in the condensed tannin biosynthetic pathway in a plant.

2. The host cell of claim 1, wherein the polypeptide comprises the sequence of SEQ ID NO: 14.

3. The host cell of claim 1, wherein the polypeptide comprises an amino acid sequence with the sequence of SEQ ID NO: 17.

4. The host cell of claim 1, wherein the nucleic acid molecule is selected from the group consisting of:
   a) SEQ ID NO: 1, 2 or 55; and
   b) a polynucleotide with at least 95% identity to the coding sequence of any one of the sequence(s) in a), wherein the polynucleotide regulates at least one of:
      (i) the production of condensed tannins in plants, and
      (ii) at least one gene in the condensed tannin biosynthetic pathway in a plant.

5. The host cell of claim 1 wherein the nucleic acid molecule is part of a construct.

6. The host cell of claim 5 wherein the construct includes:
   at least one promoter; and
   the nucleic acid molecule;
   and wherein the promoter is operatively linked to the nucleic acid molecule to control the expression of the nucleic acid molecule.

7. The host cell of claim 1, wherein the host cell is a plant cell.

8. The host cell of claim 6 that is a plant cell.

9. A plant or seed wherein the plant or seed comprises the plant cell of claim 7.

10. A composition which includes a plant of claim 9, or a part thereof, containing the nucleic acid molecule encoding the MYB polypeptide.

11. A part, seed, fruit, harvested material, propagule or progeny of a plant, wherein the part, seed, fruit, harvested material, propagule or progeny is altered from the wild-type to comprise an isolated nucleic acid molecule encoding a polypeptide comprising a sequence with at least 95% identity to SEQ ID NO: 14, wherein percent identity is calculated over the entire length of SEQ ID NO: 14.

12. The part, seed, fruit, harvested material, propagule or progeny of a plant of claim 11, wherein the isolated nucleic acid molecule is part of a construct.

13. A plant or seed wherein the plant or seed comprises the plant cell of claim 8.

* * * * *